United States Patent
Gomtsian et al.

(10) Patent No.: US 10,112,911 B2
(45) Date of Patent: Oct. 30, 2018

(54) SUBSTITUTED CYANOGUANIDINES AS ORAL ANTI-VIRALS

(71) Applicant: Abbvie Inc, North Chicago, IL (US)

(72) Inventors: Artour Gomtsian, Vernon Hills, IL (US); Tatyana Dekhtyar, Libertyville, IL (US); Kristine E. Frank, Grayslake, IL (US); Michael M. Friedman, Brookline, MA (US); Nathan Josephsohn, Boston, MA (US); M-Akhteruzzaman Molla, Gurnee, IL (US); Anil Vasudevan, Union Grove, WI (US); Iok Chan Ng, Arlington Heights, IL (US); Mikhail Chafeev, Toronto (CA)

(73) Assignee: ABBVIE INC., North Chicago, IL (US)

(*) Notice: Subject to any disclaimer, the term of this patent is extended or adjusted under 35 U.S.C. 154(b) by 0 days.

(21) Appl. No.: 14/410,952

(22) PCT Filed: Jun. 28, 2013

(86) PCT No.: PCT/US2013/048789
§ 371 (c)(1),
(2) Date: Dec. 23, 2014

(87) PCT Pub. No.: WO2014/005129
PCT Pub. Date: Jan. 3, 2014

(65) Prior Publication Data
US 2015/0322045 A1    Nov. 12, 2015

Related U.S. Application Data

(60) Provisional application No. 61/665,797, filed on Jun. 28, 2012.

(51) Int. Cl.
| | | |
|---|---|---|
| A61K 31/495 | (2006.01) | |
| A61K 31/497 | (2006.01) | |
| C07D 241/04 | (2006.01) | |
| C07D 241/26 | (2006.01) | |
| A61K 31/498 | (2006.01) | |

(Continued)

(52) U.S. Cl.
CPC .......... C07D 241/26 (2013.01); A61K 31/496 (2013.01); A61K 31/497 (2013.01); A61K 31/498 (2013.01); A61K 31/499 (2013.01); A61K 31/4985 (2013.01); A61K 31/517 (2013.01); A61K 31/519 (2013.01); A61K 31/5377 (2013.01); C07C 335/30 (2013.01); C07D 231/40 (2013.01); C07D 241/44 (2013.01); C07D 317/66 (2013.01); C07D 401/04 (2013.01); C07D 401/14 (2013.01); C07D 403/04 (2013.01); C07D 403/14 (2013.01); C07D 405/04 (2013.01); C07D 405/14 (2013.01); C07D 413/04 (2013.01);

(Continued)

(58) Field of Classification Search
CPC ... A61K 31/495; A61K 31/497; C07D 241/04
USPC .............................. 514/249, 252.13; 544/336
See application file for complete search history.

(56) References Cited

FOREIGN PATENT DOCUMENTS

| | | |
|---|---|---|
| EP | 1067123 A1 | 1/2001 |
| EP | 1418175 A1 | 5/2004 |

(Continued)

OTHER PUBLICATIONS

Nisius, et al. Journal of Chemical Information and Modeling, 49(2), 2009, 247-256.*

(Continued)

*Primary Examiner* — Douglas M Willis
(74) *Attorney, Agent, or Firm* — Neal, Gerber & Eisenberg LLP

(57) ABSTRACT

This disclosure relates to: (a) compounds and salts of formula (I), formula (II), formula (III), and formula (IV), that, inter alia, inhibit RSV infection and/or replication; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

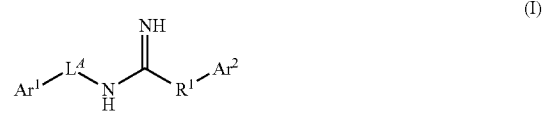

(I)

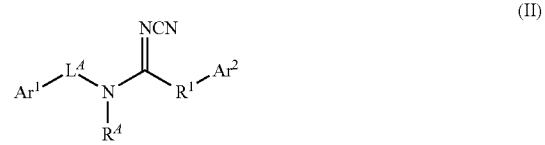

(II)

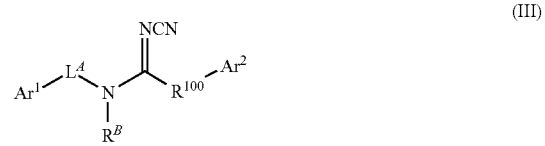

(III)

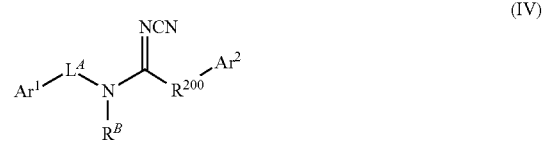

(IV)

18 Claims, No Drawings

(51) Int. Cl.
| | |
|---|---|
| C07D 413/04 | (2006.01) |
| A61K 31/496 | (2006.01) |
| A61K 31/517 | (2006.01) |
| C07D 487/04 | (2006.01) |
| A61K 31/519 | (2006.01) |
| C07D 405/14 | (2006.01) |
| C07D 403/14 | (2006.01) |
| A61K 31/499 | (2006.01) |
| A61K 31/5377 | (2006.01) |
| A61K 31/4985 | (2006.01) |
| C07D 401/14 | (2006.01) |
| C07D 401/04 | (2006.01) |
| C07D 403/04 | (2006.01) |
| C07D 405/04 | (2006.01) |
| C07D 417/04 | (2006.01) |
| C07D 241/44 | (2006.01) |
| C07D 471/04 | (2006.01) |
| C07D 317/66 | (2006.01) |
| C07D 231/40 | (2006.01) |
| C07C 335/30 | (2006.01) |

(52) U.S. Cl.
CPC ......... *C07D 417/04* (2013.01); *C07D 471/04* (2013.01); *C07D 487/04* (2013.01)

(56) References Cited

FOREIGN PATENT DOCUMENTS

| | | |
|---|---|---|
| WO | WO-2004002983 A2 | 1/2004 |
| WO | WO-2008005368 A2 | 1/2008 |
| WO | WO-2009021169 A2 | 2/2009 |

OTHER PUBLICATIONS

Allen L.V., et al., Ansel's Pharmaceutical Dosage forms and Drug Delivery Systems, TROY D.B., et al., eds., 8th Edition, Lippincott Williams & Wilkins, 2005.

Bunnelle W.H., et al., "Structure-Activity Studies and Analgesic Efficacy of N-(3-pyridinyl)-Bridged Bicyclic Diamines, Exceptionally Potent Agonists at Nicotinic Acetylcholine Receptors," Journal of Medicinal Chemistry, 2007, vol. 50, pp. 3627-3644.

Campbell S.F., et. Al., "2,4-Diamino-6,7-Dimethoxyquinazolines. 1. 2-[4-(1,4-Benzodioxan-2-ylcarbonyl)pierazi n-l-yl] Derivatives as alpha-1 Adrenoceptor Antagonists and Antihypertensive Agents," Journal of Medicinal Chemistry, 1987, vol. 30 (1), pp. 49-57.

Cappelli A., et al., "Structure-Affinity Relationship Studies on Arylpiperazine Derivatives Related to Quipazine as Serotonin Transporter Ligands. Molecular Basis of the Selectivity SERT/5HT3 Receptor," Bioorganic & Medicinal Chemistry, 2005, vol. 13 (10), pp. 3455-3460.

Gerdes J.M., et al., "Serotonin Transporter Inhibitors: Synthesis and Binding Potency of 2'-Methyl- and 3'-Methyl-6-Nitroquipazine," Bioorganic and Medicinal Chemistry Letters, 2000, vol. 10, pp. 2643-2646.

Greene T.W., et al., "Protective Groups," in: Organic Synthesis, 3rd Edition, John Wiley and Sons, Inc., 1999.

Harrison B.A., et al., "Novel Class of LIM-Kinase 2 Inhibitors for the Treatment of Ocular Hypertension and Associated Glaucoma," Journal of Medicinal Chemistry, 2009, vol. 52 (21), pp. 6515-6518.

Hoover J.E., Remington's Pharmaceutical Sciences, 15th Edition, 1975, Mack Publishing Co.

International Search Report for Application No. PCT/US2013/048789, dated Aug. 22, 2013, 6 pages.

Lumma W.C., Jr., et al., "Piperazinylquinoxalines with Central Serotoninmimetic Activity," Journal of Medicinal Chemistry, 1981, vol. 24 (1), pp. 93-101.

Patane M.A., et al., "4-Amino-2-[4-[1-(Benzyloxycarbonyl)-2(S)-[[(1,1-Dimethylethyl)Amino]Carbonyl]-Piperazinyl]-6,7-Dimethoxyquinazoline (L-765,314): A Potent and Selective Alpha1b Adrenergic Receptor Antagonist," Journal of Medicinal Chemistry, 1998, vol. 41 (8), pp. 1205-1208.

Shen H.C., et al., "Discovery of Orally Bioavailable and Novel Urea Agonists of the High Affinity Niacin Receptor GPR109A," Bioorganic & Medicinal Chemistry Letters, 2007, vol. 17 (24), pp. 6723-6728.

Written Opinion for PCT/US2013/048789, 11 pages, dated Dec. 28, 2014.

Wobig D., "Reaktionen Von Cyanimidodithiocarbonaten und Cyanthioharnstoffen Mit Gamma-Bromocrotonsaurederivaten," Liebigs Annalen Der Chemie, 1978, vol. 1978 (7), pp. 1118-1122.

Zhou D., et al., "Synthesis, Potency, and in Vivo Evaluation of 2-Piperazin-1-Ylquinoline Analogues as Dual Serotonin Reuptake Inhibitors and Serotonin 5-Ht1a Receptor Antagonists," Journal of Medicinal Chemistry, 2009, vol. 52 (15), pp. 4955-4959.

* cited by examiner

SUBSTITUTED CYANOGUANIDINES AS ORAL ANTI-VIRALS

TECHNICAL FIELD

This disclosure is directed to: (a) compounds and salts thereof that, inter alia, are useful for inhibiting respiratory syncytial virus (RSV) infection and/or replication; (b) intermediates useful for the preparation of such compounds and salts; (c) compositions comprising such compounds and salts; (d) methods for preparing such intermediates, compounds, salts, and compositions; (e) methods of use of such compounds, salts, and compositions; and (f) kits comprising such compounds, salts, and compositions.

BACKGROUND

Respiratory syncytial virus (RSV) is a pneumovirus in the Paramyxoviridae family. It is an enveloped, nonsegmented, negative-stranded RNA virus. Its 15.2 kb genome has been completely sequenced and it contains 10 mRNAs encoding 11 distinct proteins. RSV has three transmembrane surface proteins (F, G, SH) essential for attachment and entry, two nonstructural proteins (NS1, NS2), a matrix (M) protein, a nucleocapsid (N) protein that encapsidates the viral RNA genome, a phosphoprotein (P), and an RNA polymerase (L). In addition, the RSV M2 mRNA encodes both the M2-1 and M2-2 proteins.

RSV is the leading cause of serious lower respiratory tract infection in infants and young children. Most infected infants and children suffer only mild symptoms, but 25-40% of them develop lower respiratory signs indicative of a viral bronchiolitis or pneumonia. Severe lower respiratory tract RSV infection can lead to consequences of different severity, ranging from increased risk of developing childhood asthma to death. Following RSV infection, immunity is incomplete and re-infections can occur throughout life. It is estimated that RSV causes approximately 60 million infections and 160,000 deaths worldwide each year. RSV infection results in up to 125,000 hospitalizations of infants annually in the United States, which is equivalent to approximately 0.1-0.2% of hospital admission of infants from this age group. The infants most at risk of severe RSV disease are those born prematurely, and those with bronchopulmonary dysplasia, congenital heart disease, or immunodeficiency. Hospital admission rates with these conditions range between 5% and 30%. The mortality rate among children admitted to hospital is approximately 3% for those with heart and lung diseases and up to 1% for those without these risk factors. RSV infection is also a significant cause of morbidity in the elderly and immunocompromised populations. In the hospitalized elderly, mortality can be as high as 10-20%, and in the severely immunocompromised patients with RSV pneumonia, the rate is approximately 50%.

RSV epidemics occur every winter in temperate climates. There are currently two known groups (also referred to as subgroups) of RSV: A and B. Both groups A and B may co-circulate within an epidemic, but their relative proportion may vary from year to year. The predominant epidemic group may also change in different years, with group A having a somewhat higher incidence of being the predominant group. The sequence homology between the two groups varies in the different viral proteins. For example, the F and N proteins are highly conserved with 91% and 96% amino acid identity between the two groups, respectively. The sequence of the G protein, on the other hand, is significantly different between the two groups, with the amino acid identity being only 53%. There is conflicting data regarding the virulence differences between the two groups of RSV. Some studies found no difference in the clinical severity of the illness caused by the two groups, while others reported that group A appeared to be associated with more severe disease.

At present, there is no clinically approved vaccine or effective antiviral therapy for the treatment of RSV. Attempts to develop a safe and efficacious RSV vaccine have failed thus far due to challenges associated with at-risk subjects (including infants, the elderly and the immunocompromised) who usually have low tolerance to the side effects of a vaccine and who tend to mount reduced immune responses due to their weaker immune systems.

Ribavirin has been used to treat RSV infection but requires a prolonged aerosol administration, and there are doubts as to its safety and its efficacy in the treatment of RSV infection. In addition, ribavirin is associated with undesirable side effects such as anemia, fatigue, irritability, skin rash, nasal stuffiness, sinusitis, cough and even birth defects.

Palivizumab/Synagis® is a humanized murine monoclonal antibody directed against the RSV F protein that has been used as passive immunoprophylaxis to prevent the spread of the virus to the lower respiratory tract. Although palivizumab has been used successfully to reduce the frequency of hospitalizations for RSV infection in high risk populations, the antibody has only been approved for prophylactic use in infants who are at risk of developing serious symptoms from RSV infection, such as those born prematurely, and/or with congenital heart or lung disease.

Therefore, there is a significant need for compounds for the prevention and treatment of RSV and for therapies that extend safe and effective treatment to at-risk adults and children with acute RSV infections.

SUMMARY

Disclosed herein are compounds of formula (I), and methods of making such compounds,

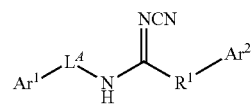

wherein:

Ar$^1$ is phenyl or monocyclic heteroaryl having a structure corresponding to a formula selected from the group consisting of:

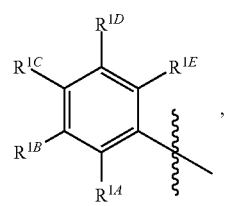

-continued

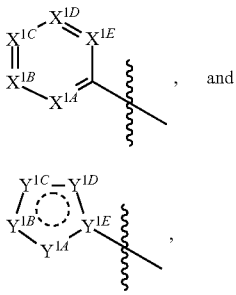
(i-2)

(i-3)

wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2$$R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl;

$R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl; or $R^{1B}$ and $R^{1C}$, or $R^{1C}$ and $R^{1D}$, or $R^{1D}$ and $R^{1E}$ taken together are —O—CH$_2$—O—;

$X^{1A}$, $X^{1B}$, $X^{1C}$, $X^{1D}$ and $X^{1E}$ are $CR^{1AX}$, $CR^{1BX}$, $CR^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2$$R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$R^{1BX}$, $R^{1CX}$, $R^{1DX}$ and $R^{1EX}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl;

$Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S;

$Y^{1E}$ is N or C;

wherein 1, 2, 3, or 4 ring atoms of (i-3) is a heteroatom;

$R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2$$R^{1'}$, wherein $L^1$ is a bond or alkylene, and $R^{2'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$L^A$ is bond or $CR^aR^b$, wherein $R^a$ and $R^b$ are independently hydrogen or alkyl;

$R^1$ is selected from the group consisting of:

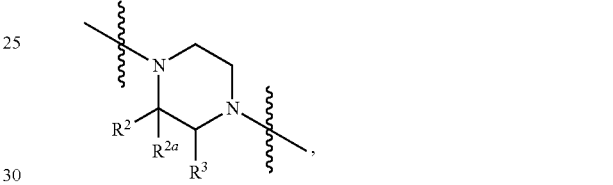
(ii-1)

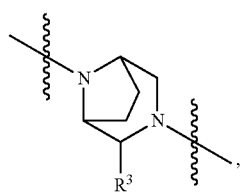
(ii-2)

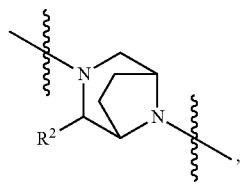
(ii-3)

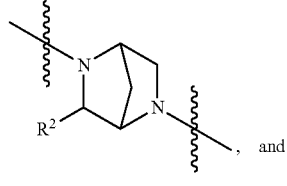
(ii-4)
, and

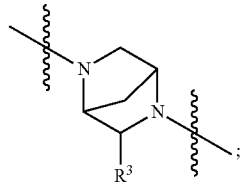
(ii-5)
;

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl-; or $R^2$, $R^{2a}$, and the carbon atom to which they are attached form a $C_3$-$C_6$cycloalkyl and $R^3$ is hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, —N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-CO$_2$H, -$L^c$-CO$_2R^f$, -$L^c$-N($R^f$)C(O)N($R^f$)$_2$, -$L^c$-S—$R^f$, -$L^c$-S(O)$_2R^f$, -$L^c$-S(O)$R^f$, -$L^c$-SO$_2$N($R^e$)($R^f$), -$L^c$-N($R^e$)($R^f$), -$L^c$-N($R^f$)S(O)$_2R^f$, and -$L^c$-N($R^f$)C(O)O($R^f$);

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

$R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^f$ is at each occurrence independently selected from the group consisting of hydrogen, $C_1$-$C_6$alkyl, and $C_1$-$C_6$haloalkyl;

$Ar^2$ is selected from the group consisting of:

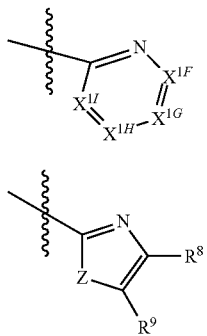

$X^{1F}$, $X^{1G}$, $X^{1H}$, and $X^{1I}$ are $CR^4$, $CR^5$, $CR^6$ and $CR^7$, respectively, or N; wherein 0, 1 or 2 of $X^{1F}$, $X^{1G}$, $X^{1H}$, and $X^{1I}$ are N; wherein $R^4$, $R^5$, $R^6$ and $R^7$ are each independently selected from the group consisting of hydrogen, cyano, halo, $C_1$-$C_6$alkyl, alkoxy, amino, alkylamino, cycloalkylamino, dialkylamino, cycloalkyl, heterocyclyl, haloalkoxy, haloalkyl, —O$R^f$, and —CO$_2R^f$; or $R^4$ and $R^5$; $R^5$ and $R^6$; or $R^6$ and $R^7$ and the atoms to which they are attached taken together form a fused phenyl ring, pyrrole, pyridine, or pyrazine optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —O$R^f$, and —CO$_2R^f$;

wherein Z is selected from the group consisting of O, S, and $NR^e$; and $R^8$ and $R^9$ are each independently selected from the group consisting of hydrogen, cyano, halo, $C_1$-$C_6$alkyl, amino, alkylamino, dialkylamino, cycloalkyl, heterocyclyl, haloalkoxy, haloalkyl, —O$R^f$ and —CO$_2R^f$; or $R^8$ and $R^9$ and the atoms to which they are attached taken together form a fused phenyl ring optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —O$R^f$, and —CO$_2R^f$.

Disclosed herein are compounds of formula (II), and methods of making such compounds,

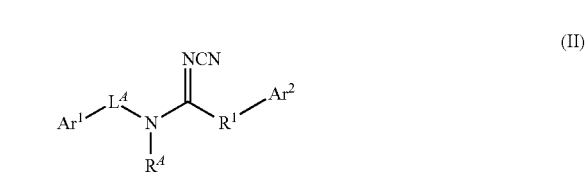

(II)

wherein:

$Ar^1$ is phenyl or monocyclic heteroaryl having a structure corresponding to a formula selected from the group consisting of:

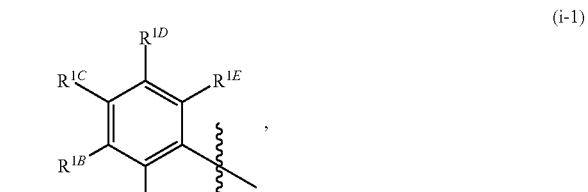

(i-1)

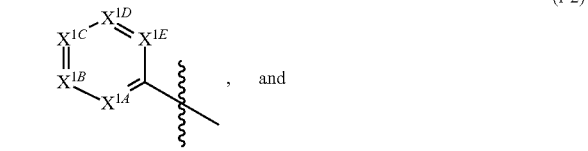

(i-2)

, and

(i-3)

, wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl;

$R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl; or $R^{1B}$ and $R^{1C}$, or $R^{1C}$ and $R^{1D}$, or $R^{1D}$ and $R^{1E}$ taken together are —O—CH$_2$—O—;

$X^{1A}$, $X^{1B}$, $X^{1C}$, $X^{1D}$ and $X^{1E}$ are $CR^{1AX}$, $CR^{1BX}$, $CR^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2$$R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl;

$Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S;

$Y^{1E}$ is N or C;

wherein 1, 2, 3, or 4 ring atoms of (i-3) is a heteroatom;

$R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2$$R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$L^A$ is a bond or $CR^aR^b$, wherein $R^a$ and $R^b$ are independently hydrogen or alkyl;

$R^d$ is $C_1$-$C_6$alkyl, hydroxy$C_1$-$C_6$alkyl or halo$C_1$-$C_6$alkyl;

$R^1$ is selected from the group consisting of:

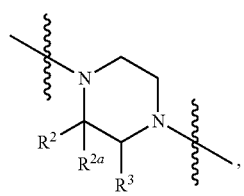

(ii-1)

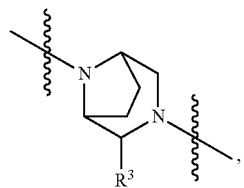

(ii-2)

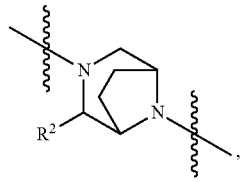

(ii-3)

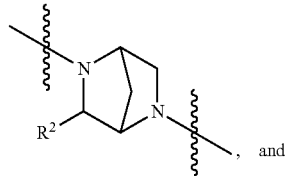

, and (ii-4)

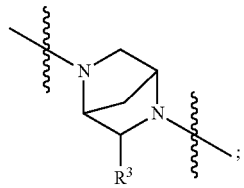

;

(ii-5)

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl-; or $R^2$, $R^{2a}$, and the carbon atom to which they are attached form a $C_3$-$C_6$cycloalkyl and $R^3$ is hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-CO$_2$H, -$L^c$-CO$_2R^f$, -$L^c$-N($R^f$)C(O)N($R^f$)$_2$, -$L^c$-S—$R^f$, -$L^c$-S(O)$_2R^f$, - $L^c$-S(O)$R^f$, -$L^c$-SO$_2$N($R^e$)($R^f$), -$L^c$-N($R^e$)($R^f$), -$L^c$-N($R^f$)S(O)$_2R^f$, and -$L^c$-N($R^f$)C(O)O($R^f$);

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

$R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^f$ is at each occurrence independently selected from the group consisting of hydrogen, $C_1$-$C_6$alkyl, and $C_1$-$C_6$haloalkyl;

$Ar^2$ is selected from the group consisting of:

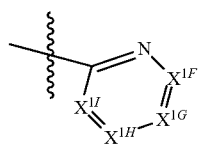

(iii-1)

(iii-2)

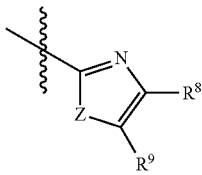

$X^{1F}$, $X^{1G}$, $X^{1H}$, and $X^{1I}$ are $CR^4$, $CR^5$, $CR^6$ and $CR^7$, respectively, or N; wherein 0, 1 or 2 of $X^{1F}$, $X^{1G}$, $X^{1H}$, and $X^{1I}$ are N; wherein $R^4$, $R^5$, $R^6$ and $R^7$ are each independently selected from the group consisting of hydrogen, cyano, halo, $C_1$-$C_6$alkyl, alkoxy, amino, alkylamino, cycloalkylamino, dialkylamino, cycloalkyl, heterocyclyl, haloalkoxy, haloalkyl, —$OR^f$, and —$CO_2R^f$; or $R^4$ and $R^5$; $R^5$ and $R^6$; or $R^6$ and $R^7$ and the atoms to which they are attached taken together form a fused phenyl ring, pyrrole, pyridine, or pyrazine optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —$OR^f$, and —$CO_2R^f$;

wherein Z is selected from the group consisting of O, S, and $NR^e$; and $R^8$ and $R^9$ are each independently selected from the group consisting of hydrogen, cyano, halo, $C_1$-$C_6$alkyl, amino, alkylamino, dialkylamino, cycloalkyl, heterocyclyl, haloalkoxy, haloalkyl, —$OR^f$ and —$CO_2R^f$; or $R^8$ and $R^9$ and the atoms to which they are attached taken together form a fused phenyl ring optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —$OR^f$, and —$CO_2R^f$.

Disclosed herein are compounds of formula (III), and methods of making such compounds, (III)

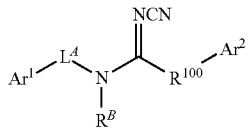

wherein:

$Ar^1$ is phenyl or monocyclic heteroaryl having a structure corresponding to a formula selected from the group consisting of:

(i-1)

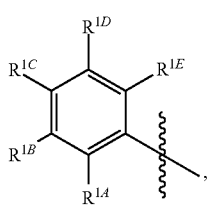

(i-2)

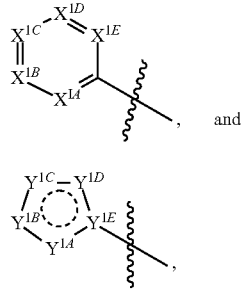

and (i-3)

wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl;

$R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl; or $R^{1B}$ and $R^{1C}$, or $R^{1C}$ and $R^{1D}$, or $R^{1D}$ and $R^{1E}$ taken together are —O—$CH_2$—O—;

$X^{1A}$, $X^{1B}$, $X^{1C}$, $X^{1D}$ and $X^{1E}$ are $CR^{1AX}$, $CR^{1BX}$, $Cr^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein L is a bond or alkylene, $R^{3'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl;

$Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$ and $Y^{1D}$ is O or S;

$Y^{1E}$ is N or C;

wherein 1, 2, 3, or 4 ring atoms of (i-3) is a heteroatom;

$R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—OR$^{1'}$ or -$L^1$-S(O)$_2$R$^{1'}$, wherein $L^1$ is a bond or alkylene, and R$^{1'}$ is hydrogen, $C_1$-$C_6$alkyl or hydroxyalkyl; -$L^2$-O—C(O)—R$^{2'}$, wherein $L^2$ is a bond or alkylene, and R$^{2'}$ is $C_1$-$C_6$alkyl or hydroxyalkyl; -$L^3$-C(O)—NR$^{3'}$R$^{4'}$, wherein $L^3$ is a bond or alkylene, and R$^{3'}$ and R$^{4'}$ are each independently selected from the group consisting of hydrogen, $C_1$-$C_6$alkyl, and hydroxyalkyl; -$L^4$-NR$^{5'}$—C(O)—R$^{6'}$, wherein $L^4$ is a bond or alkylene, R$^{5'}$ is hydrogen or $C_1$-$C_6$alkyl, and R$^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$L^A$ is a bond or CR$^a$R$^b$, wherein R$^a$ and R$^b$ are independently hydrogen or alkyl;

$R^B$ is hydrogen, $C_1$-$C_6$alkyl, hydroxy$C_1$-$C_6$alkyl or halo$C_1$-$C_6$alkyl;

$R^{100}$ is (vii-1):

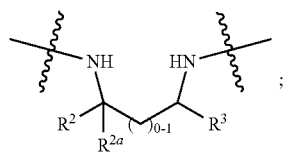

(vii-1)

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, G$^1$, G$^2$, and G$^2$alkyl-; or $R^2$, $R^{2a}$, and the carbon atom to which they are attached form a $C_3$-$C_6$cycloalkyl and $R^3$ is hydrogen;

G$^1$ is aryl or heteroaryl, and G$^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—R$^f$, —CN, —N(R$^f$)C(O)R$^f$, —CON(R$^e$)(R$^f$), —C(O)R$^f$, —OC(O)R$^f$, —CO$_2$R$^f$, —N(R$^f$)C(O)N(R$^f$)$_2$, —S—R$^f$, —S(O)$_2$R$^f$, —S(O)R$^f$, —SO$_2$N(R$^e$)(R$^f$), —N(R$^e$)(R$^f$), —N(R$^f$)S(O)$_2$R$^f$, N(R$^f$)C(O)O(R$^f$), -$L^c$-O—R$^f$, -$L^c$-CN, -$L^c$-N(R$^f$)C(O)R$^f$, -$L^c$-CON(R$^e$)(R$^f$), -$L^c$-C(O)R$^f$, -$L^c$-OC(O)R$^f$, -$L^c$-CO$_2$H, -$L^c$-CO$_2$R$^f$, -$L^c$-N(R$^f$)C(O)N(R$^f$)$_2$, -$L^c$-S—R$^f$, -$L^c$-S(O)$_2$R$^f$, - $L^c$-S(O)R$^f$, -$L^c$-SO$_2$N(R$^e$)(R$^f$), -$L^c$-N(R$^e$)(R$^f$), -$L^c$-N(R$^f$)S(O)$_2$R$^f$, and -$L^c$-N(R$^f$)C(O)O(R$^f$);

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

$R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^f$ is at each occurrence independently selected from the group consisting of hydrogen, $C_1$-$C_6$alkyl, and $C_1$-$C_6$haloalkyl;

Ar$^2$ is selected from the group consisting of:

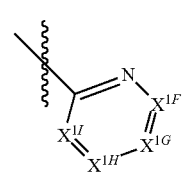

(iii-1)

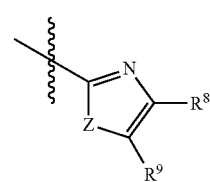

(iii-2)

$X^{1F}$, $X^{1G}$, $X^{1H}$, and $X^{1I}$ are CR$^4$, CR$^5$, CR$^6$ and CR$^7$, respectively, or N; wherein 0, 1 or 2 of $X^{1F}$, $X^{1G}$, $X^{1H}$, and $X^{1I}$ are N; wherein R$^4$, R$^5$, R$^6$ and R$^7$ are each independently selected from the group consisting of hydrogen, cyano, halo, $C_1$-$C_6$alkyl, alkoxy, amino, alkylamino, cycloalkylamino, dialkylamino, cycloalkyl, heterocyclyl, haloalkoxy, haloalkyl, —OR$^f$, and —CO$_2$R$^f$; or R$^4$ and R$^5$; R$^5$ and R$^6$; or R$^6$ and R$^7$ and the atoms to which they are attached taken together form a fused phenyl ring, pyrrole, pyridine, or pyrazine optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —OR$^f$, and —CO$_2$R$^f$;

wherein Z is selected from the group consisting of O, S, and NR$^e$; and

R$^8$ and R$^9$ are each independently selected from the group consisting of hydrogen, cyano, halo, $C_1$-$C_6$alkyl, amino, alkylamino, dialkylamino, cycloalkyl, heterocyclyl, haloalkoxy, haloalkyl, —OR$^f$ and —CO$_2$R$^f$; or R$^8$ and R$^9$ and the atoms to which they are attached taken together form a fused phenyl ring optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —OR$^f$, and —CO$_2$R$^f$.

Disclosed herein are compounds of formula (IV), and methods of making such compounds,

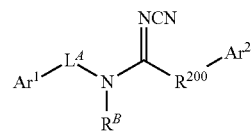

(IV)

wherein:

Ar$^1$ is phenyl or monocyclic heteroaryl having a structure corresponding to a formula selected from the group consisting of:

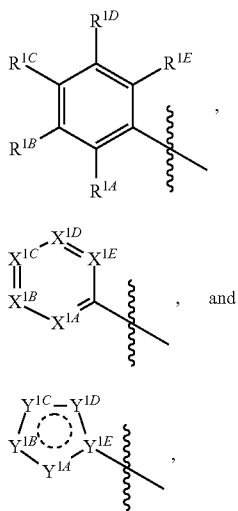

(i-1)

(i-2) and (i-3)

wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl;

$R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl; or $R^{1B}$ and $R^{1C}$, or $R^{1C}$ and $R^{1D}$, or $R^{1D}$ and $R^{1E}$ taken together are —O—CH$_2$—O—;

$X^{1A}$, $X^{1B}$, $X^{1C}$, $X^{1D}$ and $X^{1E}$ are $CR^{1AX}$, $CR^{1BX}$, $CR^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl;

$Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S;

$Y^{1E}$ is N or C;

wherein 1, 2, 3, or 4 ring atoms of (i-3) is a heteroatom;

$R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{3'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$L^A$ is a bond or $CR^aR^b$, wherein $R^a$ and $R^b$ are independently hydrogen or alkyl;

$R^B$ is hydrogen, $C_1$-$C_6$alkyl, hydroxy$C_1$-$C_6$alkyl or halo$C_1$-$C_6$alkyl;

$R^{200}$ is (vi-1):

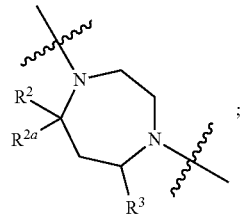

(vi-1)

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl-; or $R^2$, $R^{2a}$, and the carbon atom to which they are attached form a $C_3$-$C_6$cycloalkyl and $R^3$ is hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^e$)C(O)$R^f$, —CON($R^e$)($R^f$), —C(O)$R^f$, —OC(O)$R^f$, —CO$_2R^f$, —N($R^e$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-CO$_2$H, -$L^c$-CO$_2R^f$, -$L^c$-N($R^f$)C(O)N($R^f$)$_2$, -$L^c$-S—$R^f$, -$L^c$-S(O)$_2R^f$, - $L^c$-S(O)$R^f$, -$L^c$-SO$_2$N($R^e$)($R^f$), -$L^c$-N($R^e$)($R^f$), -$L^c$-N($R^f$)S(O)$_2R^f$ and -$L^c$-N($R^f$)C(O)O($R^f$);

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

$R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^f$ is at each occurrence independently selected from the group consisting of hydrogen, $C_1$-$C_6$alkyl, and $C_1$-$C_6$haloalkyl;

$Ar^2$ is selected from the group consisting of:

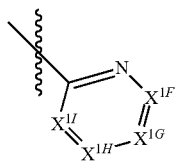

(iii-1)

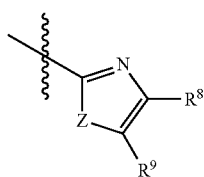

(iii-2)

$X^{1F}$, $X^{1G}$, $X^{1H}$, and $X^{1I}$ are $CR^4$, $CR^5$, $CR^6$ and $CR^7$, respectively, or N; wherein 0, 1 or 2 of $X^{1F}$, $X^{1G}$, $X^{1H}$, and $X^{1I}$ are N; wherein $R^4$, $R^5$, $R^6$ and $R^7$ are each independently selected from the group consisting of hydrogen, cyano, halo, $C_1$-$C_6$alkyl, alkoxy, amino, alkylamino, cycloalkylamino, dialkylamino, cycloalkyl, heterocyclyl, haloalkoxy, haloalkyl, —$OR^f$, and —$CO_2R^f$; or $R^4$ and $R^5$; $R^5$ and $R^6$; or $R^6$ and $R^7$ and the atoms to which they are attached taken together form a fused phenyl ring, pyrrole, pyridine, or pyrazine optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —$OR^f$, and —$CO_2R^f$; wherein Z is selected from the group consisting of O, S, and $NR^e$; and $R^8$ and $R^9$ are each independently selected from the group consisting of hydrogen, cyano, halo, $C_1$-$C_6$alkyl, amino, alkylamino, dialkylamino, cycloalkyl, heterocyclyl, haloalkoxy, haloalkyl, —$OR^f$ and —$CO_2R^f$; or $R^8$ and $R^9$ and the atoms to which they are attached taken together form a fused phenyl ring optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —$OR^f$, and —$CO_2R^f$.

This disclosure also relates to pharmaceutical compositions comprising therapeutically effective amount of one or more compound(s) described herein or pharmaceutically acceptable salts, solvates, or salts of solvates thereof, in combination with one or more pharmaceutically acceptable carrier(s).

This disclosure also is directed to compositions (including pharmaceutical compositions) that comprise one or more of the disclosed compounds and/or salts, and, optionally, one or more additional therapeutic agents.

This disclosure also is directed to kits that comprise one or more of the disclosed compounds and/or salts, and, optionally, one or more additional therapeutic agents.

This disclosure also is directed to methods of use of the compounds, salts, compositions, and/or kits to, for example, inhibit replication of an RNA virus (including RSV) or treat an RSV infection.

This disclosure also is directed to a use of one or more of the disclosed compounds and/or salts to prepare a medicament. The medicament optionally can comprise one or more additional therapeutic agents. In some embodiments, the medicament is useful for treating RSV infection.

The compounds, compositions comprising the compounds, pharmaceutically acceptable salts, solvates, or salts of the solvates thereof, and methods for treating or preventing conditions and disorders by administering the compounds or compositions thereof, are further described herein.

These and other objectives are described further in the following paragraphs. These objectives should not be deemed to narrow the scope of the disclosure.

DETAILED DESCRIPTION

This detailed description is intended only to acquaint others skilled in the art with the disclosed embodiments, their principles, and their practical application so that others skilled in the art may adapt and apply the embodiments in their numerous forms, as they may be best suited to the requirements of particular uses. This description and its specific examples are intended for purposes of illustration only. This disclosure, therefore, is not limited to the embodiments described in this patent application, and may be variously modified.

The present disclosure describes compounds of formula (I), formula (II), formula (III), and formula (IV), and methods of preparing such compounds,

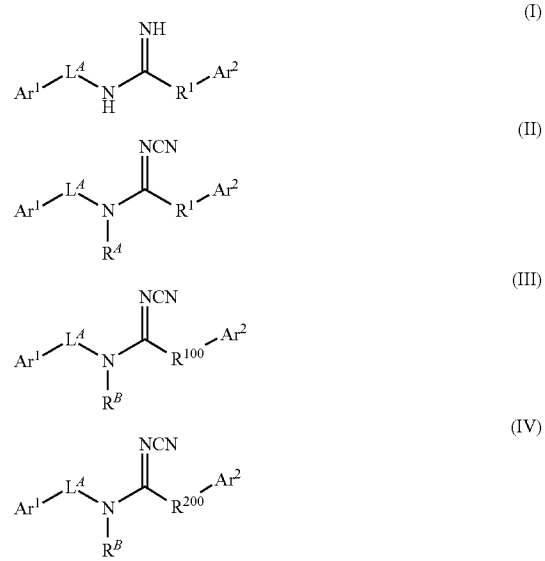

wherein $Ar^1$, $Ar^2$, $L^A$, $R^A$, $R^B$, $R^1$, $R^{100}$, and $R^{200}$ are as defined above in the Summary and below in the Detailed Description. Compositions comprising such compounds and methods for treating conditions and disorders using such compounds and compositions are also disclosed.

In various embodiments, compounds described herein may contain variables that occur more than one time in any substituent or in the compound described or any other formulae herein. Definition of a variable on each occurrence is independent of its definition at another occurrence. Further, combinations of variables are permissible only if such combinations result in stable compounds. Stable compounds are compounds that can be isolated from a reaction mixture.

Definitions

, when found within the ring of a chemical structure, indicates that the ring is aromatic.

"Alkenyl" is a straight or branched hydrocarbon chain containing at least one carbon-carbon double bond. The term "$C_2$-$C_{10}$ alkenyl" means an alkenyl group containing 2-10 carbon atoms. Non-limiting examples of alkenyl include buta-2,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

"Alkenylene" is a divalent group derived from a straight or branched chain hydrocarbon and contains at least one carbon-carbon double. "$C_2$-$C_6$ alkenylene" means an alkenylene group containing 2-6 carbon atoms. Representative examples of alkenylene include, but are not limited to, —C(=$CH_2$)—, —CH=CH— and —$CH_2$CH=CH—.

"Alkoxy" is RO— where R is alkyl. Non-limiting examples of alkoxy groups include a $C_1$-$C_{10}$ alkoxy group, a $C_1$-$C_6$ alkoxy group, or a $C_1$-$C_3$ alkoxy group methoxy, ethoxy and propoxy.

"Alkoxyalkyl" refers to an alkyl moiety substituted with an alkoxy group. Embodiments can be named by combining the designations of alkoxy and alkyl. So for example, there can be ($C_1$-$C_6$)alkoxy-($C_1$-$C_{10}$)alkyl and the like. Examples of alkoxyalkyl groups include methoxymethyl, methoxyethyl, methoxypropyl, ethoxyethyl, and so on.

"Alkyl" is a straight or branched, saturated hydrocarbon chain. For example "$C_1$-$C_{10}$ alkyl" means a straight or branched chain, saturated hydrocarbon containing 1 to 10 carbon atoms. For example "$C_1$-$C_3$ alkyl" means a straight or branched chain, saturated hydrocarbon containing 1 to 3 carbon atoms. Examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

"Alkylamino" is RNH— and "dialkylamino" is $R_2$N—, where the R groups are alkyl as defined herein and are the same or different. In various embodiments, R is a $C_1$-$C_{10}$ alkyl group or a $C_1$-$C_6$ alkyl group. Examples of alkylamino groups include methylamino, ethylamino, propylamino, and butylamino. Examples of dialkylamino groups include dimethylamino, diethylamino, methylethylamino, and methylpropylamino.

"Alkylthio" is —SR and "alkylseleno" is —SeR, where R is alkyl as defined herein.

"Alkylene" is a divalent group derived from a straight or branched, saturated hydrocarbon chain. Examples of alkylene include, but are not limited to, —$CH_2$—, —$CH_2CH_2$—, —$CH_2CH_2CH_2$—, —$CH_2CH_2CH_2CH_2$—, —CH($CH_3$)—, and —$CH_2$CH($CH_3$)$CH_2$—.

"Alkynyl" is a straight or branched chain hydrocarbon group containing at least one carbon-carbon triple bond. The term "$C_2$-$C_{10}$ alkynyl" means an alkynyl group containing from 2 to 10 carbon atoms. Representative examples of alkynyl include, but are not limited, to acetylenyl, 1-propynyl, 2-propynyl, 3-butynyl, 2-pentynyl, and 1-butynyl.

"Amino" (alone or in combination with another term(s)) means —$NH_2$.

"Aminoalkyl" is an alkyl group substituted with an amino group —$NH_2$. "N-alkylaminoalkyl" means aminoalkyl in which there is an alkyl group substituted for one of the hydrogens of the amino group. "Dialkylaminoalkyl" or "N,N-dialkylaminoalkyl" means aminoalkyl in which there is an alkyl group substituted for both of the hydrogens of the amino group. The two substituted alkyl groups can be the same or different. "Trialkylammoniumalkyl" or "N,N,N-trialkylammoniumalkyl" means aminoalkyl in which there are three alkyl group substituted on the nitrogen of the amino group resulting in a net positive charge. The three substituted alkyl groups can be the same of different. Examples of alkylaminoalkyl groups include methylaminomethyl and ethylaminomethyl. Examples of N,N-dialkylaminoalkyl groups include dimethylaminomethyl and diethylaminomethyl. Examples of N,N,N-trialkyammoniumalkyl include trimethylammoniummethyl and diethylmethylammoniummethyl.

"Aryl" is phenyl or a bicyclic aryl. For example, "$C_6$-$C_{10}$aryl" refers to an aryl group that may have from six to ten carbon atoms. The bicyclic aryl is naphthyl, or a phenyl fused to a monocyclic cycloalkyl, or a phenyl fused to a monocyclic cycloalkenyl. Non-limiting examples of the aryl groups include dihydroindenyl, indenyl, naphthyl, dihydronaphthalenyl, and tetrahydronaphthalenyl. The aryl groups can be unsubstituted or substituted, and the bicyclic aryl is attached to the parent molecular moiety through any substitutable carbon atom contained within the bicyclic ring system.

"Cyano" means —CN, which also may be depicted as —C≡N.

"Cycloalkenyl" or "cycloalkene" is a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two, or three double bonds. Representative examples of monocyclic cycloalkenyl groups include, but are not limited to, cyclobutenyl, cyclopentenyl, cyclohexenyl, cycloheptenyl, and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two, or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl, and 1,6-dihydro-pentalene. The monocyclic and bicyclic cycloalkenyl can be attached to the parent molecular moiety through any substitutable atom contained within the ring systems, and can be unsubstituted or substituted.

"Cycloalkyl" or "cycloalkane" is a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring. Tricyclic cycloalkyls are exemplified by a bicyclic cycloalkyl fused to a monocyclic cycloalkyl. The monocyclic or bicyclic cycloalkyl ring may contain one or two alkylene bridges, each consisting of one, two, or three carbon atoms, each linking two non-adjacent carbon atoms of the ring system. Non-limiting examples of such bridged cycloalkyl ring systems include bicyclo[3.1.1] heptane, bicyclo[2.2.1]heptane, bicyclo[2.2.2]octane, bicyclo[3.2.2]nonane, bicyclo[3.3.1]nonane, bicyclo[4.2.1] nonane, tricyclo[3.3.1.0$^{3,7}$]nonane (octahydro-2,5-methanopentalene or noradamantane), and tricyclo [3.3.1.1$^{3,7}$]decane (adamantane).

The monocyclic, bicyclic, and tricyclic cycloalkyls can be unsubstituted or substituted, and are attached to the parent molecular moiety through any substitutable atom contained within the ring system.

"Cycloalkylamino" is an amino group substituted with a cycloalkyl group. Examples of cycloalkylamino include cyclopropylamino and cyclohexylamine.

"Halo" or "halogen" means Cl, Br, I, or F.

"Haloalkoxy" refers to an alkoxy group substituted with one or more halo groups. Examples of haloalkoxy groups include, but are not limited to, —OCF$_3$, —OCHF$_2$ and —OCH$_2$F.

"Haloalkyl" refers to an alkyl group, as defined herein, in which one, two, three, four, five or six hydrogen atoms are replaced by halogen. The term "C$_1$-C$_{10}$haloalkyl" means a C$_1$-C$_{10}$ alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, trifluorobutyl (such as, but not limited to, 4,4,4-trifluorobutyl), and trifluoropropyl (such as, but not limited thereto, 3,3,3-trifluoropropyl).

"Haloalkenyl" refers to an alkenyl group, as defined herein, substituted by one, two, three, or four halogen atoms.

"Haloalkynyl" refers to an alkynyl group, as defined herein, substituted by one, two, three, or four halogen atoms.

"Heterocycle", "heterocyclyl", or "heterocyclic" means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond and one heteroatom selected from the group consisting of O, N, and S. The five-membered ring contains zero or one double bond and one, two, or three heteroatoms selected from the group consisting of O, N, and S. The six-membered ring contains zero, one, or two double bonds and one, two, or three heteroatoms selected from the group consisting of O, N, and S. The seven- and eight-membered rings contain zero, one, two, or three double bonds and one, two, or three heteroatoms selected from the group consisting of O, N, and S. Non-limiting examples of monocyclic heterocycles include azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl (including, but not limited thereto, pyrrolidin-1-yl, pyrrolidin-2-yl, pyrrolidin-3-yl), tetrahydrofuranyl (including, but not limited thereto, tetrahydrofuran-3-yl), tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Non-limiting examples of bicyclic heterocycles include benzopyranyl, benzothiopyranyl, 2,3-dihydrobenzofuranyl, 2,3-dihydrobenzothienyl, benzo[d][1,3]dioxolyl and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle. The monocyclic and the bicyclic heterocycles may contain an alkenylene bridge of two, three, or four carbon atoms, or one or two alkylene bridges of 1, 2, 3, or 4 carbon atoms, or combinations thereof, wherein each bridge links two non-adjacent atoms of the ring system. Non-limiting examples of such bridged heterocycles include octahydro-2,5-epoxypentalene, azabicyclo[2.2.1]heptyl (including 2-azabicyclo [2.2.1]hept-2-yl), hexahydro-2H-2,5-methanocyclopenta[b] furan, hexahydro-1H-1,4-methanocyclopenta[c]furan, aza-admantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles can be unsubstituted or substituted, and are connected to the parent molecular moiety through any substitutable carbon atom or any substitutable nitrogen atom contained within the rings. The nitrogen and sulfur heteroatoms in the heterocycle rings may optionally be oxidized and the nitrogen atoms may optionally be quaternized. The term "N-heterocyclyl" refers to a nitrogen-containing heterocyclic group attached to the parent molecular moiety through a nitrogen atom.

"Heteroaryl" means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or one sulfur atom. The six-membered ring contains three double bonds and one, two, three or four nitrogen atoms. Representative examples of monocyclic heteroaryl include, but are not limited to, furanyl (including, but not limited thereto, furan-2-yl), imidazolyl (including, but not limited thereto, 1H-imidazol-1-yl), isoxazolyl, isothiazolyl, oxadiazolyl, 1,3-oxazolyl, pyridinyl (e.g. pyridin-4-yl, pyridin-2-yl, pyridin-3-yl), pyridazinyl, pyrimidinyl, pyrazinyl, pyrazolyl, pyrrolyl, tetrazolyl, thiadiazolyl, 1,3-thiazolyl, thienyl (including, but not limited thereto, thien-2-yl, thien-3-yl), triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryl groups include benzofuranyl, benzothienyl, benzoxazolyl, benzimidazolyl, benzoxadiazolyl, 6,7-dihydro-1,3-benzothiazolyl, furo[3,2-c] pyridazinyl, furo[3,2-d]pyrimidinyl, furo[2,3-b]pyrazinyl, furo[2,3-c]pyridazinyl, furo[2,3-d]pyrimidinyl, furo[3,2-b] pyridinyl, furo[3,2-c]pyridinyl, furo[2,3-c]pyridinyl, furo[2, 3-b]pyridine, imidazo[2,1-b]oxazolyl, imidazo[1,2-a]pyridinyl, imidazo[2,1-b][1,3,4]thiadiazolyl, imidazo[2,1-b][1,3, 4]thiadiazolyl, imidazo[1,2-d][1,2,4]thiadiazolyl, imidazo [2,1-b]thiazolyl, indazolyl, 4,5,6,7-tetrahydro-1H-indazolyl, indolizinyl, indolyl, isoindolyl, isoquinolinyl, naphthyridinyl, pyrazolo[1,5-a]pyridinyl, pyrazolo[1,5-c]pyrimidinyl, pyrazolo[1,5-a]pyrimidinyl, pyrazolo[5,1-c][1,2,4]triazinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups can be substituted or unsubstituted and are connected to the parent molecular moiety through any substitutable carbon atom or any substitutable nitrogen atom contained within the ring systems.

"Heteroatom" refers to a nitrogen, oxygen, or sulfur atom.

"Hydroxyl" or "hydroxy" is a —OH group.

"Hydroxyalkyl" is an alkyl group as defined herein substituted with at least one hydroxy group. Examples of hydroxyalkyl groups include, but are not limited to, hydroxymethyl, hydroxyethyl, hydroxypropyl and hydroxybutyl.

"Oxo" means a =O group.

"Oxoalkyl" is a substituted alkyl group wherein at least one of the carbon atoms of an alkyl group is substituted with an oxo group, being a double bond to an oxygen, also known as a carbonyl. An oxoalkyl group thus has ketone or aldehyde functionality. If the oxo substitution is on the first atom bonded to the respective ring, the group can be called as "alkanoyl" or "acyl," being the group RC(O)— where R is an alkyl group as defined herein. In various embodiments, "oxoalkyl" is a $C_1$-$C_{10}$ oxoalkyl group, a $C_1$-$C_6$ oxoalkyl group, or a $C_1$-$C_3$ oxoalkyl group.

"Sulfate" is —O—S($O_2$)—OH or its salt form.

"Sulfamoyl" is —S(O)$_2$—NH$_2$. "N-(alkyl)sulfamoyl" is RNH—S(O)$_2$—; and "N,N-(alkyl)$_2$sulfamoyl" or "N,N-(dialkyl)sulfamoyl" is R$_2$N—S(O)$_2$—, where the R groups are alkyl as defined herein and are the same or different. In various embodiments, R is a $C_1$-$C_{10}$ alkyl group or a $C_1$-$C_6$ alkyl group.

"Sulfonamide" as used herein, means a $Z^1$S(O)$_2$NZ$^2$— group, as defined herein, wherein $Z^1$ is an optionally substituted alkyl, aryl, haloalkyl, or heteroaryl as defined herein, and $Z^2$ is hydrogen or alkyl. Representative examples of sulfonamide include, but are not limited to, methanesulfonamide, trifluoromethanesulfonamide, and benzenesulfonamide.

"Thioalkyl" is an alkyl group as defined herein substituted with a thio group —SH.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent, therefore, may be identical to or different from the other substituent(s).

When words are used to describe a substituent, the rightmost-described component of the substituent is the component that has the free valence.

When a chemical formula is used to describe a substituent, the dash on the left side of the formula indicates the portion of the substituent that has the free valence.

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X-L-Y and L is described as —C(O)—N(H)—, then the chemical would be X—C(O)—N(H)—Y.

Compounds of formula (I), formula (II), formula (III) and formula (IV) are as described herein.

Particular values of variable groups in compounds of formula (I), formula (II), formula (III) and formula (IV) are as follows. Such values may be used where appropriate with any of the other values, definitions, claims or embodiments defined herein.

In certain embodiments, $Ar^1$ is phenyl or monocyclic heteroaryl having a structure corresponding to a formula selected from the group consisting of:

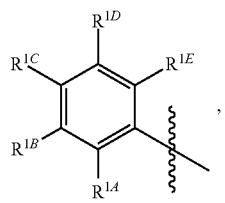
(i-1)

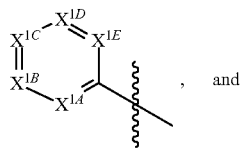
(i-2) and

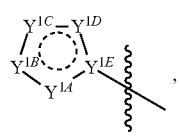
(i-3)

wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl; $R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl; or $R^{1B}$ and $R^{1C}$, or $R^{1C}$ and $R^{1D}$, or $R^{1D}$ and $R^{1E}$ taken together are —O—CH$_2$—O—; $X^{1A}$, $X^{1B}$, $X^{1C}$, $X^{1D}$ and $X^{1E}$ are $CR^{1AX}$, $CR^{1BX}$, $CR^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl; $R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl; $Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$ and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S; $Y^{1E}$ is N or C; wherein 1, 2, 3, or 4 ring atoms of (i-3) is a heteroatom; $R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl.

In certain embodiments, $Ar^1$ is phenyl

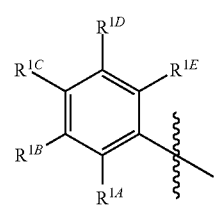
(i-1)

wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—

NR³'R⁴', wherein L³ is a bond or alkylene, and R³' and R⁴' are each independently selected from the group consisting of hydrogen, alkyl, and hydroxyalkyl; -L⁴-NR⁵'—C(O)—R⁶', wherein L⁴ is a bond or alkylene, R⁵' is hydrogen or alkyl, and R⁶' is alkyl or hydroxyalkyl; sulfamoyl; N-(alkyl)sulfamoyl; N,N-(dialkyl)sulfamoyl; sulfonamide; alkylthio; and thioalkyl; $R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl; or $R^{1B}$ and $R^{1C}$, or $R^{1C}$ and $R^{1D}$, or $R^{1D}$ and $R^{1E}$ taken together are —O—CH₂—O—.

In certain embodiments, $Ar^1$ is phenyl

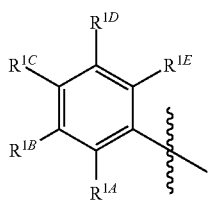
(i-1)

wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -L¹-C(O)—OR¹' or -L¹-S(O)₂R¹', wherein L¹ is a bond or alkylene, and R¹' is hydrogen, $C_1$-$C_6$alkyl or hydroxyalkyl; -L²-O—C(O)—R²', wherein L² is a bond or alkylene, and R²' is $C_1$-$C_6$alkyl or hydroxyalkyl; -L³-C(O)—NR³'R⁴', wherein L³ is a bond or alkylene, and R³' and R⁴' are each independently selected from the group consisting of hydrogen, alkyl, and hydroxyalkyl; -L⁴-NR⁵'—C(O)—R⁶', wherein L⁴ is a bond or alkylene, R⁵' is hydrogen or alkyl, and R⁶' is alkyl or hydroxyalkyl; sulfamoyl; N-(alkyl)sulfamoyl; N,N-(dialkyl)sulfamoyl; sulfonamide; alkylthio; and thioalkyl; and $R^{1B}$, $R^{1C}$, $R^{1D}$ and $R^{1E}$ are each independently selected from the group consisting of hydrogen, halo, $C_1$-$C_6$alkyl, and haloalkyl; or $R^{1B}$ and $R^{1C}$, or $R^{1C}$ and $R^{1D}$, or $R^{1D}$ and $R^{1E}$ taken together are —O—CH₂—O—.

In certain embodiments, $Ar^1$ is phenyl

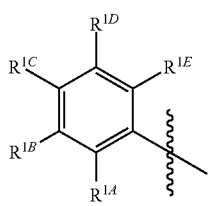
(i-1)

wherein, $R^{1A}$ is selected from the group consisting of hydrogen; halo; $C_1$-$C_6$alkyl; $C_1$-$C_6$alkoxy; and haloalkoxy; and $R^{1B}$, $R^{1C}$, $R^{1D}$ and $R^{1E}$ are each independently selected from the group consisting of hydrogen, halo, $C_1$-$C_6$alkyl, and haloalkyl; or $R^{1B}$ and $R^{1C}$, or $R^{1C}$ and $R^{1D}$, or $R^{1D}$ and $R^{1E}$ taken together are —O—CH₂—O—.

In certain embodiments, $Ar^1$ is phenyl

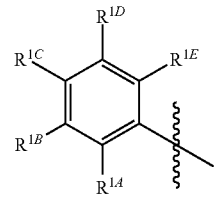
(i-1)

wherein, $R^{1A}$ is selected from the group consisting of hydrogen; $C_1$-$C_6$alkyl; halo; $C_1$-$C_6$alkoxy; haloalkyl and haloalkoxy; and $R^{1B}$, $R^{1C}$, $R^{1D}$ and $R^{1E}$ are each independently hydrogen; $C_1$-$C_6$alkyl; halo; or haloalkyl.

In certain embodiments, $Ar^1$ is phenyl

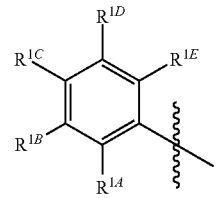
(i-1)

wherein, $R^{1A}$ is selected from the group consisting of hydrogen; halo; $C_1$-$C_6$alkyl; $C_1$-$C_6$alkoxy; and haloalkoxy; and $R^{1B}$, $R^{1C}$, $R^{1D}$ and $R^{1E}$ are each hydrogen.

In certain embodiments, $Ar^1$ is phenyl

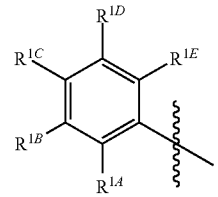
(i-1)

wherein, $R^{1A}$ is selected from halo or $C_1$-$C_6$alkyl; and $R^{1B}$, $R^{1C}$, $R^{1D}$ and $R^{1E}$ are each hydrogen.

In certain embodiments, $Ar^1$ is phenyl

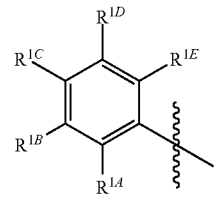
(i-1)

wherein, $R^{1A}$ is halo; and $R^{1B}$, $R^{1C}$, $R^{1D}$ and $R^{1E}$ are each hydrogen.

In certain embodiments, $Ar^1$ is phenyl

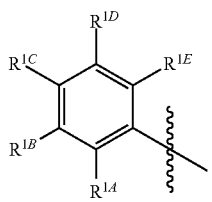

(i-1)

wherein, $R^{1A}$ is $C_1$-$C_6$alkyl; and $R^{1B}$, $R^{1C}$, $R^{1D}$ and $R^{1E}$ are each hydrogen.

In certain embodiments, $Ar^1$ is monocyclic heteroaryl having a structure corresponding to a formula selected from the group consisting of:

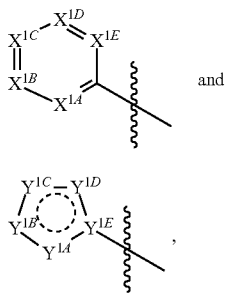

(i-2)

and (i-3)

wherein $X^{1A}$, $X^{1B}$, $X^{1C}$, $X^{1D}$ and $X^{1E}$ are $CR^{1AX}$, $CR^{1BX}$, $CR^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl; $R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl; $Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S; $Y^{1E}$ is N or C; wherein 1, 2, 3, or 4 ring atoms of (i-3) is a heteroatom; $R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl.

In certain embodiments, $Ar^1$ is monocyclic heteroaryl having a structure corresponding to a formula (i-2):

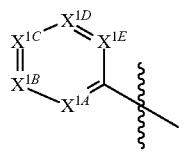

(i-2)

wherein, $X^{1A}$, $X^{1B}$, $X^{1C}$, $X^{1D}$ and $X^{1E}$ are $CR^{1BX}$, $CR^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl; $R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl.

In certain embodiments, $Ar^1$ is monocyclic heteroaryl having a structure corresponding to a formula (i-2):

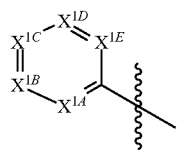

(i-2)

wherein, $X^{1A}$, $X^{1C}$, $X^{1D}$ and $X^{1E}$ are $CR^{1AX}$, $CR^{1CX}$, $CR^{1DX}$ and $CR^{1EX}$, respectively; $X^{1B}$ is N; wherein $R^{1AX}$ is selected from the group consisting of hydrogen and $C_1$-$C_6$alkyl; $R^{1CX}$ and $R^{1DX}$ are both hydrogen; and $R^{1EX}$ is hydrogen or $C_1$-$C_6$alkyl.

In certain embodiments, $Ar^1$ is monocyclic heteroaryl having a structure corresponding to a formula (i-2):

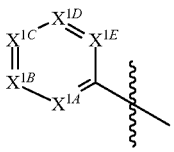

(i-2)

wherein, $X^{1A}$ is $CR^{1AX}$, $X^{1C}$ is $CR^{1CX}$, $X^{1E}$ is $CR^{1EX}$, wherein, $R^{1AX}$ is $C_1$-$C_6$alkyl and $R^{1CX}$ and $R^{1EX}$ are each hydrogen; one of $X^{1B}$ and $X^{1D}$ is N, and the other is $CR^{1BX}$ or $CR^{1DX}$, respectively, wherein $R^{1BX}$ and $R^{1DX}$ are hydrogen.

In certain embodiments, $Ar^1$ is monocyclic heteroaryl having a structure corresponding to a formula (i-3):

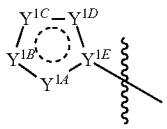

(i-3)

wherein $Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S; $Y^{1E}$ is N or C; wherein 1, 2, 3, or 4 ring atoms of (i-3) is a heteroatom; $R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2$$R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{3'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl.

In certain embodiments, $Ar^1$ is monocyclic heteroaryl having a structure corresponding to a formula (i-3):

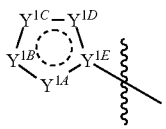

(i-3)

wherein $Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$ and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S; $Y^{1E}$ is N or C; wherein 1, 2, 3, or 4 ring atoms of (i-3) is a heteroatom; $R^{1AY}$, $R^{1BY}$, $R^{1CY}$, and $R^{1DY}$ are each independently selected from the group consisting of hydrogen;

cyano; halo; $C_1$-$C_6$alkyl; $C_1$-$C_6$alkenyl; $C_1$-$C_6$alkynyl; haloalkyl; haloalkoxy; oxoalkyl; and alkoxy; alkoxyalkyl.

In certain embodiments, $L^A$ is bond or $CR^aR^b$, wherein $R^a$ and $R^b$ are independently hydrogen or alkyl.

In certain embodiments, $L^A$ is bond.

In certain embodiments, $L^A$ is $CR^aR^b$, wherein $R^a$ and $R^b$ are independently hydrogen or alkyl.

In certain embodiments, $L^A$ is $CR^aR^b$, wherein $R^a$ and $R^b$ are each alkyl.

In certain embodiments, $L^A$ is $CH_2$.

In certain embodiments, $R^1$ is selected from the group consisting of,

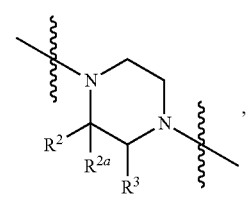

(ii-1)

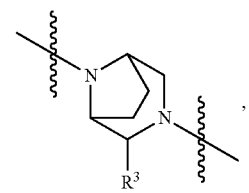

(ii-2)

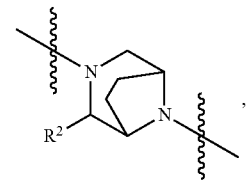

(ii-3)

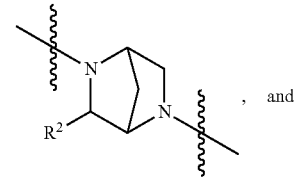

(ii-4)

, and

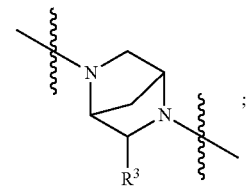

(ii-5)

;

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl-; or $R^2$, $R^{2a}$, and the carbon atom to which they are attached form a $C_3$-$C_6$cycloalkyl and $R^3$ is hydrogen; $G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2$R$^f$, —S(O)R$^f$, —SO$_2$N(R$^e$)(R$^f$), —N(R$^e$)(R$^f$), —N(R$^f$)S(O)$_2$R$^f$, N(R$^f$)C(O)O(R$^f$), -L$^c$-O—R$^f$, -L$^c$-CN, -L$^c$-N(R$^f$)C(O)R$^f$, -L$^c$-CON(R$^e$)(R$^f$), -L$^c$-C(O)R$^f$, -L$^c$-OC(O)R$^f$, -L$^c$-CO$_2$H, -L$^c$-CO$_2$R$^f$, -L$^c$-N(R$^f$)C(O)N(R$^f$)$_2$, -L$^c$-S—R$^f$, -L$^c$-S(O)$_2$R$^f$, -L$^c$-S(O)R$^f$, -L$^c$-SO$_2$N(R$^e$)(R$^f$), -L$^c$-N(R$^e$)(R$^f$), -L$^c$-N(R$^f$)S(O)$_2$R$^f$ and -L$^c$-N(R$^f$)C(O)O(R$^f$); L$^c$, at each occurrence, is independently C$_1$-C$_6$alkylene or C$_3$-C$_8$cycloalkyl, wherein L$^c$ at each occurrence, is optionally substituted with 1, 2, 3, or 4 halogen or 1 or 2 hydroxy; R$^e$, at each occurrence, is independently selected form the group consisting of hydrogen, C$_1$-C$_6$alkyl, C$_1$-C$_6$haloalkyl, and C$_3$-C$_8$cycloalkyl, wherein the C$_3$-C$_8$cycloalkyl is optionally substituted with 1, 2, 3, or 4 substituents selected from the group consisting of halogen, oxo, C$_1$-C$_3$alkyl, and C$_1$-C$_3$haloalkyl; and R$^f$ is at each occurrence independently selected from the group consisting of hydrogen, C$_1$-C$_6$alkyl, and C$_1$-C$_6$haloalkyl.

In certain embodiments, R$^1$ is

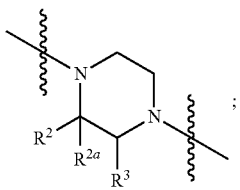

(ii-1)

wherein R$^2$, R$^{2a}$, and R$^3$ are each independently selected from the group consisting of hydrogen, C$_1$-C$_6$alkyl, C$_1$-C$_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, G$^1$, G$^2$, and G$^2$alkyl-; or R$^2$, R$^{2a}$, and the carbon atom to which they are attached form a C$_3$-C$_6$cycloalkyl and R$^3$ is hydrogen; G$^1$ is aryl or heteroaryl, and G$^2$ is C$_3$-C$_6$cycloalkyl, wherein the aryl, the heteroaryl and the C$_3$-C$_6$cycloalkyl are optionally substituted with 1, 2, 3, 4, or 5 substituents selected from the group consisting of halogen, C$_1$-C$_6$alkyl, C$_1$-C$_6$haloalkyl, —O—R$^f$, —CN, —N(R$^f$)(O)R$^f$, —CON(R$^e$)(R$^f$), —C(O)R$^f$, —OC(O)R$^f$, —CO$_2$R$^f$, —N(R$^f$)C(O)N(R$^f$)$_2$, —S—R$^f$, —S(O)$_2$R$^f$, —S(O)R$^f$, —SO$_2$N(R$^e$)(R$^f$), —N(R$^e$)(R$^f$), —N(R$^f$)S(O)$_2$R$^f$, N(R$^f$)C(O)O(R$^f$), -L$^c$-O—R$^f$, -L$^c$-CN, -L$^c$-N(R$^f$)C(O)R$^f$, -L$^c$-CON(R$^f$)(R$^f$), -L$^c$-C(O)R$^f$, -L$^c$-OC(O)R$^f$, -L$^c$-CO$_2$H, -L$^c$-CO$_2$R$^f$, -L$^c$-N(R$^f$)C(O)N(R$_2$, -L$^c$-S—R$^f$, -L$^c$-S(O)$_2$R$^f$, -L$^c$-S(O)R$^f$, -L$^c$- SO$_2$N(R$^e$)(R$^f$), -L$^c$-N(R$^e$)(R$^f$), -L$^c$-N(R$^f$)S(O)$_2$R$^f$, and -L$^c$-N(R$^f$)C(O)O(R$^f$); L$^c$, at each occurrence, is independently C$_1$-C$_6$alkylene or C$_3$-C$_8$cycloalkyl, wherein L$^c$ at each occurrence, is optionally substituted with 1, 2, 3, or 4 halogen or 1 or 2 hydroxy; R$^e$, at each occurrence, is independently selected form the group consisting of hydrogen, C$_1$-C$_6$alkyl, C$_1$-C$_6$haloalkyl, and C$_3$-C$_8$cycloalkyl, wherein the C$_3$-C$_8$cycloalkyl is optionally substituted with 1, 2, 3, or 4 substituents selected from the group consisting of halogen, oxo, C$_1$-C$_3$alkyl, and C$_1$-C$_3$haloalkyl; and R$^f$ is at each occurrence independently selected from the group consisting of hydrogen, C$_1$-C$_6$alkyl, and C$_1$-C$_6$haloalkyl.

In certain embodiments, R$^1$ is,

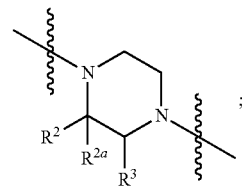

(ii-1)

wherein R$^2$ is selected from the group consisting of C$_1$-C$_6$alkyl, G$^2$, and G$^2$alkyl-; wherein, G$^2$ is optionally substituted C$_3$-C$_6$cycloalkyl; R$^2$ is hydrogen and R$^3$ is hydrogen.

In certain embodiments, R$^1$ is,

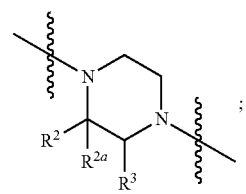

(ii-1)

wherein R$^2$ is hydrogen, R$^{2a}$ is hydrogen and R$^3$ is C$_1$-C$_6$alkyl.

In certain embodiments, R$^1$ is,

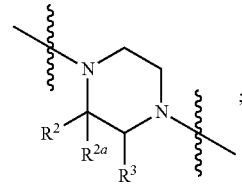

(ii-1)

wherein R$^2$, R$^{2a}$, and the carbon atom to which they are attached form a C$_3$-C$_6$cycloalkyl and R$^3$ is hydrogen.

In certain embodiments, R$^1$ is,

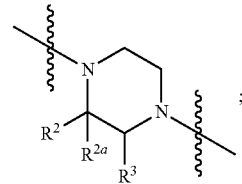

(ii-1)

wherein R$^2$, R$^{2a}$ and R$^3$ are each hydrogen.

In certain embodiments, R$^1$ is selected from the group consisting of,

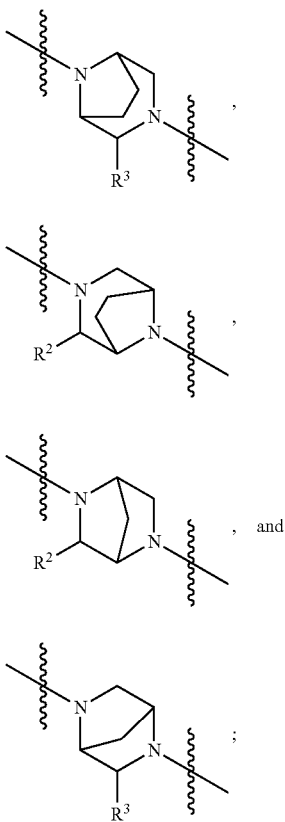

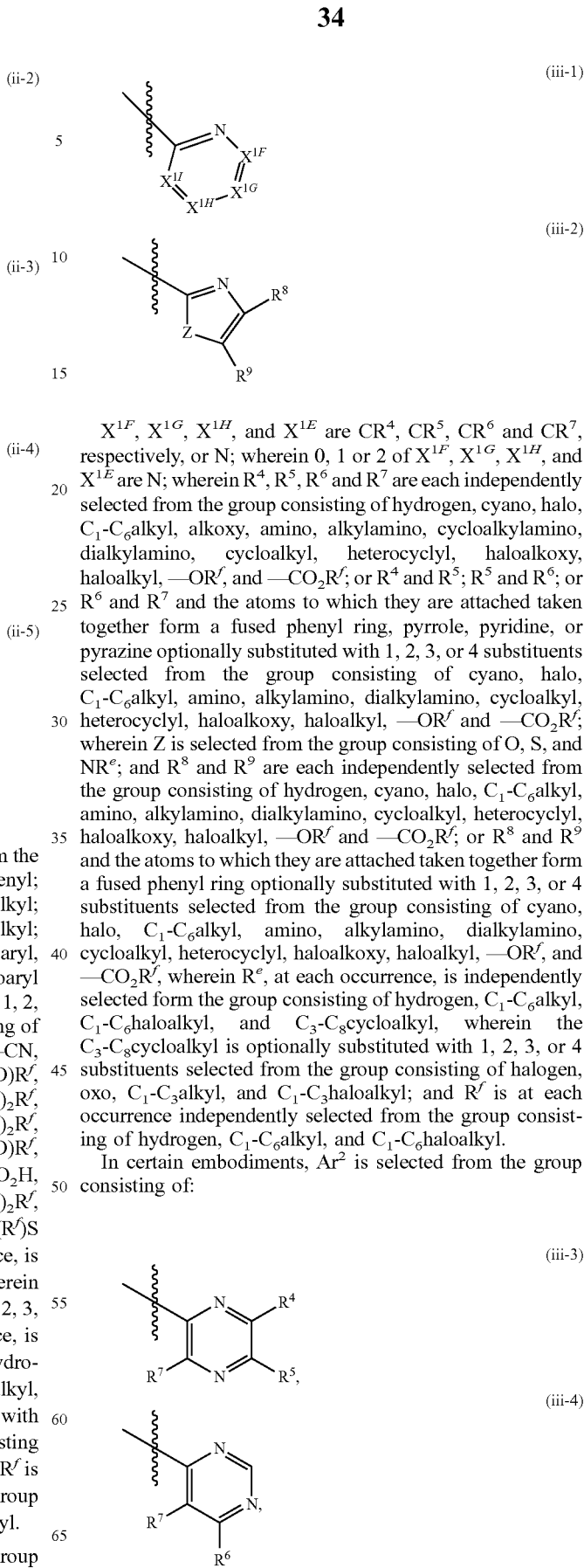

wherein $R^2$ and $R^3$ are each independently selected from the group consisting of hydrogen; $C_1$-$C_6$alkyl; $C_1$-$C_6$alkenyl; haloalkyl; alkynyl; oxoalkyl; hydroxyalkyl; alkoxyalkyl; aminoalkyl; N-alkylaminoalkyl; N,N-dialkylaminoalkyl; thioalkyl; and $G^1$, $G^2$, and $G^2$alkyl-; $G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, —N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$- OC(O)$R^f$, -$L^c$-CO$_2$H, -$L^c$-CO$_2R^f$, -$L^c$-N($R^f$)C(O)N($R^f$)$_2$, -$L^c$-S—$R^f$, -$L^c$-S(O)$_2R^f$, -$L^c$-S(O)$R^f$, - $L^c$-SO$_2$N($R^e$)($R^f$), -$L^c$-N($R^e$)($R^f$), -$L^c$-N($R^f$)S(O)$_2R^f$, and -$L^c$-N($R^f$)C(O)O($R^f$); $L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy; $R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl; and $R^f$ is at each occurrence independently selected from the group consisting of hydrogen, $C_1$-$C_6$alkyl, and $C_1$-$C_6$haloalkyl.

In certain embodiments, $Ar^2$ is selected from the group consisting of:

$X^{1F}$, $X^{1G}$, $X^{1H}$, and $X^{1E}$ are $CR^4$, $CR^5$, $CR^6$ and $CR^7$, respectively, or N; wherein 0, 1 or 2 of $X^{1F}$, $X^{1G}$, $X^{1H}$, and $X^{1E}$ are N; wherein $R^4$, $R^5$, $R^6$ and $R^7$ are each independently selected from the group consisting of hydrogen, cyano, halo, $C_1$-$C_6$alkyl, alkoxy, amino, alkylamino, cycloalkylamino, dialkylamino, cycloalkyl, heterocyclyl, haloalkoxy, haloalkyl, —$OR^f$, and —$CO_2R^f$; or $R^4$ and $R^5$; $R^5$ and $R^6$; or $R^6$ and $R^7$ and the atoms to which they are attached taken together form a fused phenyl ring, pyrrole, pyridine, or pyrazine optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —$OR^f$ and —$CO_2R^f$; wherein Z is selected from the group consisting of O, S, and $NR^e$; and $R^8$ and $R^9$ are each independently selected from the group consisting of hydrogen, cyano, halo, $C_1$-$C_6$alkyl, amino, alkylamino, dialkylamino, cycloalkyl, heterocyclyl, haloalkoxy, haloalkyl, —$OR^f$ and —$CO_2R^f$; or $R^8$ and $R^9$ and the atoms to which they are attached taken together form a fused phenyl ring optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —$OR^f$, and —$CO_2R^f$, wherein $R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl; and $R^f$ is at each occurrence independently selected from the group consisting of hydrogen, $C_1$-$C_6$alkyl, and $C_1$-$C_6$haloalkyl.

In certain embodiments, $Ar^2$ is selected from the group consisting of:

-continued

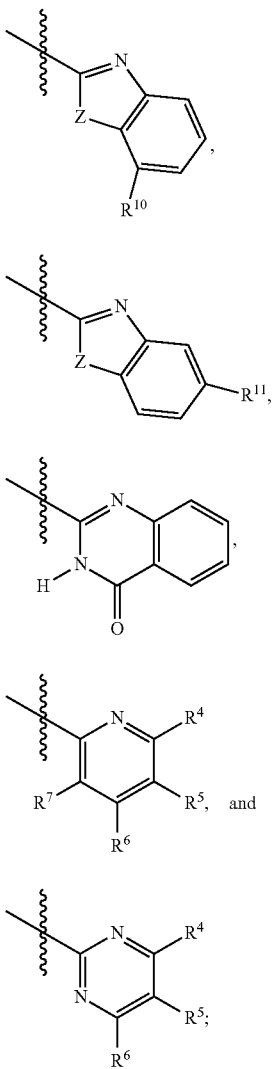

wherein for (iii-3), $R^4$ and $R^5$ are hydrogen and $R^7$ is cyano; or $R^4$ and $R^7$ are hydrogen and $R^5$ is —$CO_2CH_3$; or $R^4$ is heterocyclyl and $R^5$ and $R^7$ are hydrogen; or $R^4$ and $R^5$ and the atoms to which they are attached taken together form a fused phenyl ring optionally substituted with 1, 2, or 3 $C_1$-$C_6$alkyl, halo, or halo$C_1$-$C_6$alkyl; and $R^7$ is hydrogen, $C_1$-$C_6$alkyl, or halo$C_1$-$C_6$alkyl; wherein for (iii-4), $R^6$ and $R^7$ and the atoms to which they are attached taken together form a fused phenyl or pyrrole ring; wherein for (iii-5) and (iii-6), Z is selected from the group consisting of O, S, NH, and $NCH_3$; $R^{10}$ is hydrogen or halogen; $R^{11}$ is $C_1$-$C_6$ alkyl; wherein for (iii-8), $R^4$ and $R^5$ and the atoms to which they are attached taken together form a fused phenyl ring, a fused pyridine ring, or a fused pyrazine ring each optionally substituted with 1, 2, or 3 $C_1$-$C_6$alkyl, halo, or halo$C_1$-$C_6$alkyl; $R^6$ and $R^7$ are independently hydrogen, $C_1$-$C_6$alkyl, or halo$C_1$-$C_6$alkyl; and wherein for (iii-9), $R^4$ is hydrogen or $C_3$-$C_6$cycloalkylamino, $R^5$ and $R^6$ are independently hydrogen or $C_1$-$C_6$alkyl; or $R^4$ and $R^5$ and the atoms to which they are attached taken together form a fused phenyl ring, and $R^6$ is hydrogen.

In certain embodiments, $Ar^2$ is

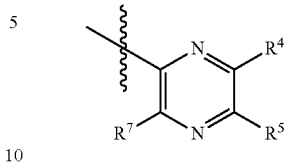

(iii-3)

wherein $R^4$ and $R^5$ are hydrogen and $R^7$ is cyano; or $R^4$ and $R^7$ are hydrogen and $R^5$ is —$CO_2CH_3$; or $R^4$ is heterocyclyl, and $R^5$ and $R^7$ are hydrogen.

In certain embodiments, $Ar^2$ is

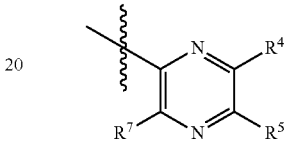

(iii-3)

wherein $R^4$ and $R^5$ and the atoms to which they are attached taken together form a fused phenyl ring optionally substituted with 1, 2, or 3 $C_1$-$C_6$alkyl, halo, or halo$C_1$-$C_6$alkyl; and $R^7$ is hydrogen, $C_1$-$C_6$alkyl, or halo$C_1$-$C_6$alkyl.

In certain embodiments, $Ar^2$ is selected from the group consisting of:

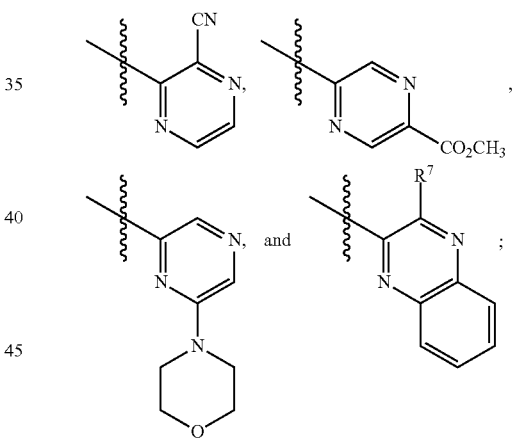

wherein $R^7$ is hydrogen, $C_1$-$C_6$alkyl, or halo$C_1$-$C_6$alkyl; and the phenyl ring of the quinoxaline is optionally substituted with 1, 2, or 3 $C_1$-$C_6$alkyl, halo, or halo$C_1$-$C_6$alkyl.

In certain embodiments, $Ar^2$ is

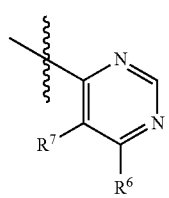

(iii-4)

wherein for (iii-4), $R^6$ and $R^7$ and the atoms to which they are attached taken together form a fused phenyl or pyrrole ring.

In certain embodiments Ar² is

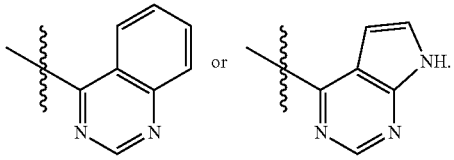 [SMILES: *c1ncnc2ccccc12 ; *c1ncnc2[nH]ccc12]

In certain embodiments Ar² is (iii-5)

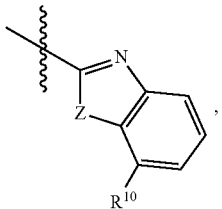

wherein Z is selected from the group consisting of O, S, NH and NCH₃; and $R^{10}$ is hydrogen or halogen.

In certain embodiments, Ar² is selected from the group consisting of,

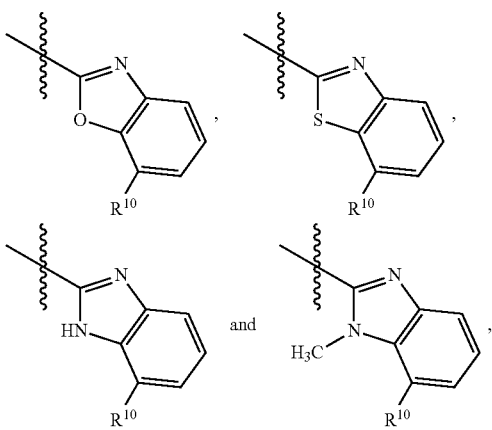

wherein $R^{10}$ is hydrogen or halogen.

In certain embodiments, Ar² is (iii-6)

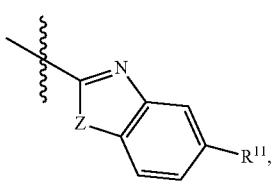

wherein Z is selected from the group consisting of O, S, NH and NCH₃; and $R^{11}$ is $C_1$-$C_6$ alkyl.

In certain embodiments, Ar² is selected from the group consisting of,

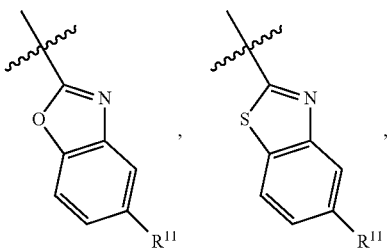

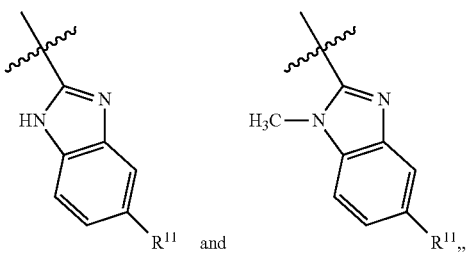

wherein $R^{11}$ is $C_1$-$C_6$ alkyl.

In certain embodiments, Ar² is (iii-7)

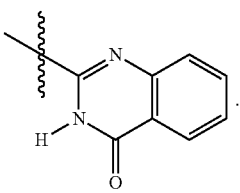

In certain embodiments, Ar² is (iii-8)

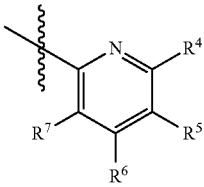

wherein for, $R^4$ and $R^5$ and the atoms to which they are attached taken together form a fused phenyl ring, a fused pyridine ring, or a fused pyrazine ring each optionally substituted with 1, 2, or 3 $C_1$-$C_6$alkyl, halo, or halo$C_1$-$C_6$alkyl; and $R^6$ and $R^7$ are independently hydrogen, $C_1$-$C_6$alkyl, or halo$C_1$-$C_6$alkyl.

In certain embodiments, Ar² is selected from the group consisting of,

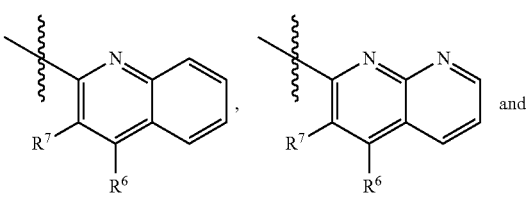

and

-continued

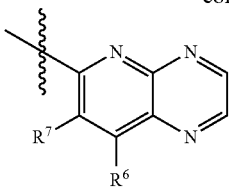

wherein the fused phenyl ring, the fused pyridine ring, or the fused pyrazine ring are each optionally substituted with 1, 2, or 3 $C_1$-$C_6$alkyl, halo, or halo$C_1$-$C_6$alkyl; and $R^6$ and $R^7$ are independently hydrogen, $C_1$-$C_6$alkyl, or halo$C_1$-$C_6$alkyl.

In certain embodiments, $Ar^2$ is

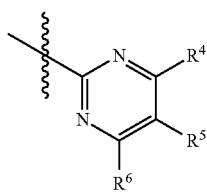

(iii-9)

wherein $R^4$ is hydrogen or $C_3$-$C_6$cycloalkylamino, $R^5$ and $R^6$ are independently hydrogen or $C_1$-$C_6$alkyl; or $R^4$ and $R^5$ and the atoms to which they are attached taken together form a fused phenyl ring, and $R^6$ is hydrogen.

In certain embodiments, $Ar^2$ is

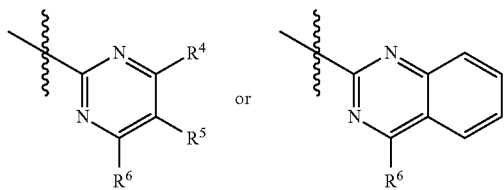

or wherein $R^4$ is hydrogen or $C_3$-$C_6$cycloalkylamino, $R^5$ and $R^6$ are independently hydrogen or $C_1$-$C_6$alkyl; and $R^6$ on the quinazoline is hydrogen.

In certain embodiments, $R^A$ is $C_1$-$C_6$alkyl, hydroxy$C_1$-$C_6$alkyl or halo$C_1$-$C_6$alkyl.

In certain embodiments, $R^A$ is $C_1$-$C_6$alkyl.

In certain embodiments, $R^B$ is hydrogen, $C_1$-$C_6$alkyl, hydroxy$C_1$-$C_6$alkyl or halo$C_1$-$C_6$alkyl.

In certain embodiments, $R^B$ is hydrogen.

In certain embodiments, $R^B$ is $C_1$-$C_6$alkyl, hydroxy$C_1$-$C_6$alkyl or halo$C_1$-$C_6$alkyl.

In certain embodiments, $R^{100}$ is

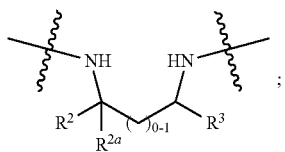

(vii-1)

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl-; or $R^2$, $R^{2a}$, and the carbon atom to which they are attached form a $C_3$-$C_6$cycloalkyl and $R^3$ is hydrogen; $G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(o)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-CO$_2$H, -$L^c$-CO$_2R^f$-$L^c$-N($R^f$)C(O)N($R^f$), -$L^c$-S—$R^f$, -$L^c$-S(O)$_2R^f$, -$L^c$-S(O)$R^f$, -$L^c$- SO$_2$N($R^e$)($R^f$), -$L^c$-N($R^e$)($R^f$), -$L^c$-N($R^f$)S(O)$_2R^f$, and -$L^c$-N($R^f$)C(O)O($R^f$); $L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy; $R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl; and $R^f$ is at each occurrence independently selected from the group consisting of hydrogen, $C_1$-$C_6$alkyl, and $C_1$-$C_6$haloalkyl.

In certain embodiments, $R^{100}$ is

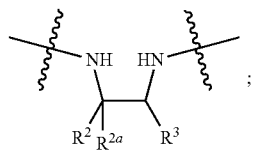

wherein $R^2$ is $C_1$-$C_6$alkyl, $R^{2a}$ is hydrogen, and $R^3$ is hydrogen.

In certain embodiments, $R^{200}$ is

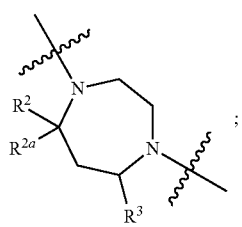

(vi-1)

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl-; or $R^2$, $R^{2a}$, and the carbon atom to which they are attached form a $C_3$-$C_6$cycloalkyl and $R^3$ is hydrogen; $G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, N($R^f$)C(O)O($R^f$), -$L^c$-O—$R^f$, -$L^c$-CN, -$L^c$-

N(R$^f$)C(O)R$^f$, -L$^c$-CON(R$^e$)(R$^f$), -L$^c$-C(O)R$^f$, -L$^c$-OC(O)R$^f$, -L$^c$-CO$_2$H, -L$^c$-CO$_2$R$^f$, -L$^c$-N(R$^f$)C(O)N(R$^f$)$_2$, -L$^c$-S—R$^f$, -L$^c$-S(O)$_2$R$^f$, -L$^c$-S(O)R$^f$, -L$^c$-SO$_2$N(R$^e$)(R$^f$), -L$^c$-N(R$^e$)(R$^f$), -L$^c$-N(R$^f$)S(O)$_2$R$^f$ and -L$^c$-N(R$^f$)C(O)O(R$^f$); L$^c$, at each occurrence, is independently C$_1$-C$_6$alkylene or C$_3$-C$_8$cycloalkyl, wherein L$^c$ at each occurrence, is optionally substituted with 1, 2, 3, or 4 halogen or 1 or 2 hydroxy; R$^e$, at each occurrence, is independently selected form the group consisting of hydrogen, C$_1$-C$_6$alkyl, C$_1$-C$_6$haloalkyl, and C$_3$-C$_8$cycloalkyl, wherein the C$_3$-C$_8$cycloalkyl is optionally substituted with 1, 2, 3, or 4 substituents selected from the group consisting of halogen, oxo, C$_1$-C$_3$alkyl, and C$_1$-C$_3$haloalkyl; and R$^f$ is at each occurrence independently selected from the group consisting of hydrogen, C$_1$-C$_6$alkyl, and C$_1$-C$_6$haloalkyl.

In certain embodiments, R$^{200}$ is

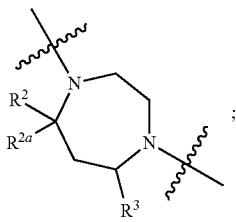
(vi-1)

wherein R$^2$ is C$_1$-C$_6$alkyl and R$^{2a}$ and R$^3$ are each hydrogen.

In one aspect of the disclosure are compounds of formula (I) wherein:

Ar$^1$ is phenyl or monocyclic heteroaryl having a structure corresponding to a formula selected from the group consisting of:

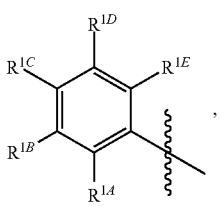
(i-1)

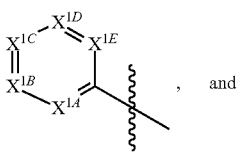
(i-2)
, and

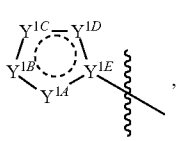
(i-3)
, wherein, R$^{1A}$ is selected from the group consisting of hydrogen; amino; hydroxyl; cyano; halo; C$_1$-C$_6$alkyl; C$_1$-C$_6$alkenyl; C$_1$-C$_6$alkynyl; C$_1$-C$_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -L$^1$-C(O)—OR$^{1'}$ or -L$^1$-S(O)$_2$R$^{1'}$, wherein L$^1$ is a bond or alkylene, and R$^{1'}$ is hydrogen, C$_1$-C$_6$alkyl or hydroxyalkyl; -L$^2$-O—C(O)—R$^{2'}$, wherein L$^2$ is a bond or alkylene, and R$^{2'}$ is C$_1$-C$_6$alkyl or hydroxyalkyl; -L$^3$-C(O)—NR$^{3'}$R$^{4'}$, wherein L$^3$ is a bond or alkylene, and R$^{3'}$ and R$^{4'}$ are each independently selected from the group consisting of hydrogen, alkyl, and hydroxyalkyl; -L$^4$-NR$^{5'}$—C(O)—R$^{6'}$, wherein L$^4$ is a bond or alkylene, R$^{5'}$ is hydrogen or alkyl, and R$^{6'}$ is alkyl or hydroxyalkyl; sulfamoyl; N-(alkyl)sulfamoyl; N,N-(dialkyl)sulfamoyl; sulfonamide; alkylthio; and thioalkyl;

R$^{1B}$, R$^{1C}$, R$^{1D}$ and R$^{1E}$ are each independently hydrogen, C$_1$-C$_6$alkyl, halo, or haloalkyl;

X$^{1A}$, X$^{1B}$, X$^{1C}$, X$^{1D}$ and X$^{1E}$ are CR$^{1AX}$, CR$^{1BX}$, CR$^{1CX}$, CR$^{1DX}$ and CR$^{1EX}$, respectively, or N; wherein 1, 2 or 3 of X$^{1A}$, X$^{1B}$, X$^{1C}$, X$^{1D}$ and X$^{1E}$ are N; wherein R$^{1AX}$ is selected from the group consisting of hydrogen; amino; hydroxyl; cyano; halo; C$_1$-C$_6$alkyl; C$_1$-C$_6$alkenyl; C$_1$-C$_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -L$^1$-C(O)—OR$^{1'}$ or -L$^1$-S(O)$_2$R$^{1'}$, wherein L$^1$ is a bond or alkylene, and R$^{1'}$ is selected from the group consisting of hydrogen, C$_1$-C$_6$alkyl and hydroxyalkyl; -L$^2$-O—C(O)—R$^{2'}$, wherein L$^2$ is a bond or alkylene, and R$^{2'}$ is C$_1$-C$_6$alkyl or hydroxyalkyl; -L$^3$-C(O)—NR$^{3'}$R$^{4'}$, wherein L$^3$ is a bond or alkylene, and R$^{3'}$ and R$^{4'}$ are each independently selected from the group consisting of hydrogen, C$_1$-C$_6$alkyl, and hydroxyalkyl; -L$^4$-NR$^{5'}$—C(O)—R$^{6'}$, wherein L$^4$ is a bond or alkylene, R$^{3'}$ is hydrogen or alkyl, and R$^{6'}$ is C$_1$-C$_6$alkyl or hydroxyalkyl; sulfamoyl; N-(alkyl)sulfamoyl; N,N-(dialkyl)sulfamoyl; sulfonamide; alkylthio; and thioalkyl;

R$^{1BX}$, R$^{1CX}$, R$^{1DX}$ and R$^{1EX}$ are each hydrogen;

Y$^{1A}$, Y$^{1B}$, Y$^{1C}$, and Y$^{1D}$ are CR$^{1AY}$ or NR$^{1AY}$, CR$^{1BY}$ or NR$^{1BY}$, CR$^{1CY}$ or NR$^{1CY}$, CR$^{1DY}$ or NR$^{1DY}$, respectively, or N, O or S; wherein 0, 1, 2, 3 or 4 of Y$^{1A}$, Y$^{1B}$, Y$^{1C}$, and Y$^{1D}$ are NR$^{1AY}$, NR$^{1BY}$, NR$^{1CY}$, or NR$^{1DY}$, respectively or N; wherein 0 or 1 of Y$^{1A}$, Y$^{1B}$, Y$^{1C}$, and Y$^{1D}$ is O or S;

Y$^{1E}$ is N or C;

wherein 1, 2, 3, or 4 ring atoms of (i-3) is a heteroatom;

R$^{1AY}$, R$^{1BY}$, R$^{1CY}$, and R$^{1DY}$ are each independently selected from the group consisting of hydrogen; amino; hydroxyl; cyano; halo; C$_1$-C$_6$alkyl; C$_1$-C$_6$alkenyl; C$_1$-C$_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -L$^1$-C(O)—OR$^{1'}$ or -L$^1$-S(O)$_2$R$^{1'}$, wherein L$^1$ is a bond or alkylene, and R$^{1'}$ is selected from the group consisting of hydrogen, C$_1$-C$_6$alkyl and hydroxyalkyl; -L$^2$-O—C(O)—R$^{2'}$, wherein L$^2$ is a bond or alkylene, and R$^{2'}$ is C$_1$-C$_6$alkyl or hydroxyalkyl; -L$^3$-C(O)—NR$^{3'}$R$^{4'}$, wherein L$^3$ is a bond or alkylene, and R$^{3'}$ and R$^{4'}$ are each independently selected from the group consisting of hydrogen, C$_1$-C$_6$alkyl, and hydroxyalkyl; -L$^4$-NR$^{5'}$—C(O)—R$^{6'}$, wherein L$^4$ is a bond or alkylene, R$^{5'}$ is hydrogen or C$_1$-C$_6$alkyl, and R$^{6'}$ is C$_1$-C$_6$alkyl or hydroxyalkyl; sulfamoyl; N-(alkyl)sulfamoyl; N,N-(dialkyl)sulfamoyl; sulfonamide; alkylthio; and thioalkyl;

L$^A$ is bond or CR$^a$R$^b$, wherein R$^a$ and R$^b$ are each hydrogen;

R$^1$ is selected from the group consisting of:

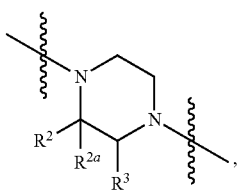
(ii-1)
,

-continued

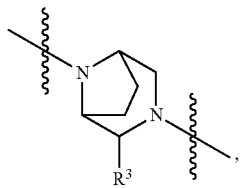
(ii-2)

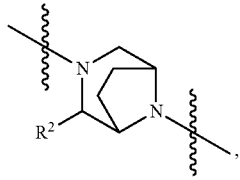
(ii-3)

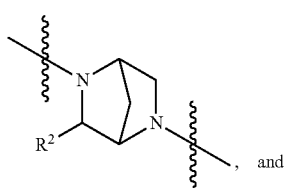
(ii-4), and

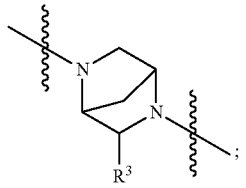
(ii-5);

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl- wherein
when both $R^2$ and $R^3$ are present, one or both of $R^2$ and $R^3$ are hydrogen; or
$R^2$, $R^{2a}$, and the carbon atom to which they are attached form a $C_3$-$C_6$cycloalkyl and $R^3$ is hydrogen;
$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-CO$_2$H, -$L^c$-CO$_2R^f$, -$L^c$-N($R^f$)C(O)N($R^f$)$_2$, -$L^c$-S—$R^f$, -$L^c$-S(O)$_2R^f$, -$L^c$-S(O)$R^f$, -$L^c$-SO$_2$N($R^e$)($R^f$), -$L^c$-N($R^e$)($R^f$), -$L^c$-N($R^f$)S(O)$_2R^f$, and -$L^c$-N($R^f$)C(O)O($R^f$);
$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;
$R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;
$R^f$ is at each occurrence independently selected from the group consisting of hydrogen, $C_1$-$C_6$alkyl, and $C_1$-$C_6$haloalkyl;

$Ar^2$ is selected from the group consisting of:

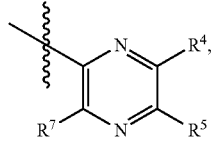
(iii-3)

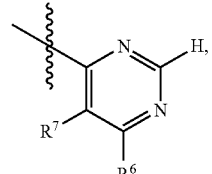
(iii-4)

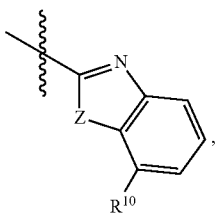
(iii-5)

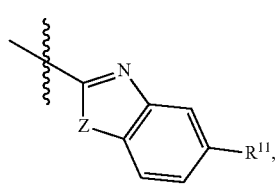
(iii-6)

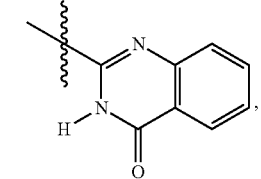
(iii-7)

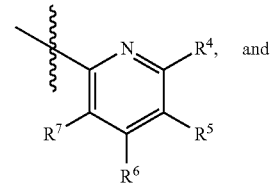
(iii-8) and

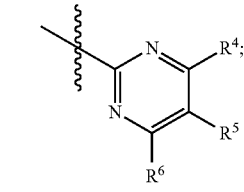
(iii-9)

wherein for (iii-3), $R^4$ and $R^5$ are hydrogen and $R^7$ is cyano; or
$R^4$ and $R^7$ are hydrogen and $R^5$ is —CO$_2$CH$_3$; or
$R^4$ is heterocyclyl, and $R^6$ and $R^7$ are hydrogen; or
$R^4$ and $R^5$ and the atoms to which they are attached taken together form a fused phenyl ring optionally substituted with 1, 2, or 3 $C_1$-$C_6$alkyl, halo, or halo$C_1$-$C_6$alkyl; and $R^7$ is hydrogen, $C_1$-$C_6$alkyl, or halo$C_1$-$C_6$alkyl;

wherein for (iii-4), $R^6$ and $R^7$ and the atoms to which they are attached taken together form a fused phenyl or pyrrole ring;

wherein for (iii-5) and (iii-6), Z is selected from the group consisting of O, S, NH, and $NCH_3$;

$R^{10}$ is hydrogen or halogen;

$R^{11}$ is $C_1$-$C_6$ alkyl;

wherein for (iii-8), $R^4$ and $R^5$ and the atoms to which they are attached taken together form a fused phenyl ring, a fused pyridine ring, or a fused pyrazine ring each optionally substituted with 1, 2, or 3 $C_1$-$C_6$alkyl, halo, or halo$C_1$-$C_6$alkyl;

$R^6$ and $R^7$ are independently hydrogen, $C_1$-$C_6$alkyl, or halo$C_1$-$C_6$alkyl; and wherein for (iii-9), $R^4$ is hydrogen or $C_3$-$C_6$cycloalkylamino, $R^5$ and $R^6$ are independently hydrogen or $C_1$-$C_6$alkyl; or $R^4$ and $R^5$ and the atoms to which they are attached taken together form a fused phenyl ring, and $R^6$ is hydrogen.

In one aspect of the disclosure are compounds of formula (I) wherein:

$Ar^1$ is (i-1):

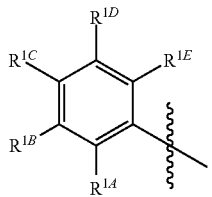

(i-1)

wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-$S(O)_2R^{1'}$, wherein $L^1$ is a bond or alkylene, and $R^{1'}$ is selected from the group consisting of hydrogen, alkyl and hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl;

$R^{1B}$, $R^{1C}$, $R^{1D}$ and $R^{1E}$ are each independently hydrogen, $C_1$-$C_6$alkyl, halo, or haloalkyl;

$L^A$ is bond or $CR^aR^b$, wherein $R^a$ and $R^b$ are each hydrogen;

$R^1$ is

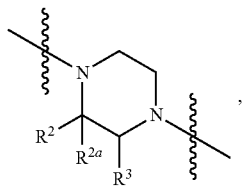

(ii-1)

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, $G^2$alkyl-; wherein when both $R^2$ and $R^3$ are present, one or both of $R^2$ and $R^3$ are hydrogen; or $R^2$, $R^{2a}$, and the carbon atom to which they are attached form a $C_3$-$C_6$cycloalkyl and $R^3$ is hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —$CO_2R^f$, —N($R^f$)C(O)N($R^f$)$_2$, —S—$R^f$, —S(O)$_2R^f$—S(O)$R^f$, —$SO_2$N($R^e$)($R^f$), —N($R^e$)($R^f$), —N($R^f$)S(O)$_2R^f$, —N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-$CO_2$H, -$L^c$-$CO_2R^f$, -$L^c$-N($R^f$)C(O)N($R^f$)$_2$, -$L^c$-S—$R^f$, -$L^c$-S(O)$_2R^f$, - $L^c$-S(O)$R^f$, -$L^c$-$SO_2$N($R^e$)($R^f$), -$L^c$-N($R^e$)($R^f$), -$L^c$-N($R^f$)S(O)$_2R^f$, and -$L^c$-N($R^f$)C(O)O($R^f$);

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

$R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^f$ is at each occurrence independently selected from the group consisting of hydrogen, $C_1$-$C_6$alkyl, and $C_1$-$C_6$haloalkyl;

$Ar^2$ is selected from the group consisting of:

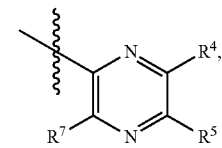

(iii-3)

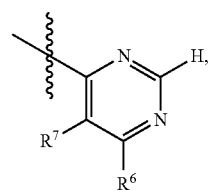

(iii-4)

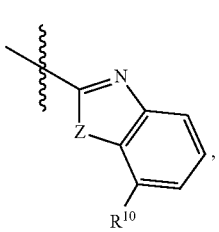

(iii-5)

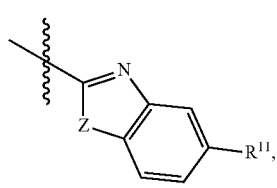

(iii-6)

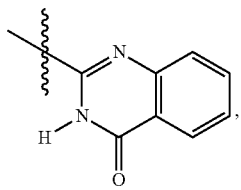
(iii-7)

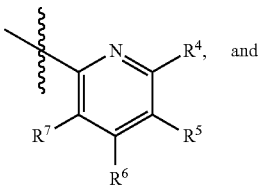
(iii-8)

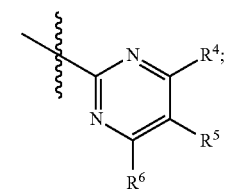
(iii-9)

wherein for (iii-3), $R^4$ and $R^5$ are hydrogen and $R^7$ is cyano; or $R^4$ and $R^7$ are hydrogen and $R^5$ is —CO$_2$CH$_3$; or $R^4$ is heterocyclyl, and $R^5$ and $R^7$ are hydrogen; or $R^4$ and $R^5$ and the atoms to which they are attached taken together form a fused phenyl ring optionally substituted with 1, 2, or 3 C$_1$-C$_6$alkyl, halo, or haloC$_1$-C$_6$alkyl; and $R^7$ is hydrogen, C$_1$-C$_6$alkyl, or haloC$_1$-C$_6$alkyl;

wherein for (iii-4), $R^6$ and $R^7$ and the atoms to which they are attached taken together form a fused phenyl or pyrrole ring;

wherein for (iii-5) and (iii-6), Z is selected from the group consisting of O, S, NH, and NCH$_3$;

$R^{10}$ is hydrogen or halogen;

$R^{11}$ is C$_1$-C$_6$ alkyl;

wherein for (iii-8), $R^4$ and $R^5$ and the atoms to which they are attached taken together form a fused phenyl ring, a fused pyridine ring, or a fused pyrazine ring each optionally substituted with 1, 2, or 3 C$_1$-C$_6$alkyl, halo, or haloC$_1$-C$_6$alkyl;

$R^6$ and $R^7$ are independently hydrogen, C$_1$-C$_6$alkyl, or haloC$_1$-C$_6$alkyl; and wherein for (iii-9), $R^4$ is hydrogen or C$_3$-C$_6$cycloalkylamino, $R^5$ and $R^6$ are independently hydrogen or C$_1$-C$_6$alkyl; or $R^4$ and $R^5$ and the atoms to which they are attached taken together form a fused phenyl ring, and $R^6$ is hydrogen.

In one aspect of the disclosure are compounds of formula (I) wherein:

Ar$^1$ is (i-1):

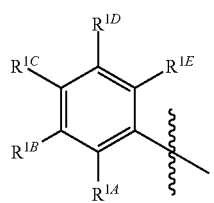
(i-1)

wherein, $R^{1A}$ is hydrogen, C$_1$-C$_6$alkyl, halo, haloalkyl, or haloalkoxy;

$R^{1B}$, $R^{1C}$, $R^{1D}$ and $R^{1E}$ are each independently hydrogen, C$_1$-C$_6$alkyl, halo, or haloalkyl;

$R^1$ is

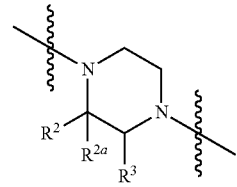
(ii-1)

wherein $R^2$ is C$_1$-C$_6$alkyl;

$R^{2a}$ and $R^3$ is hydrogen;

Ar$^2$ is selected from the group consisting of:

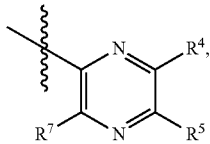
(iii-3)

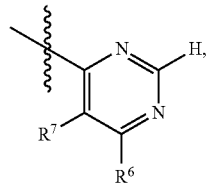
(iii-4)

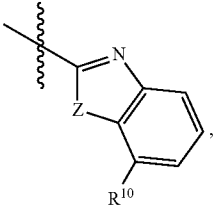
(iii-5)

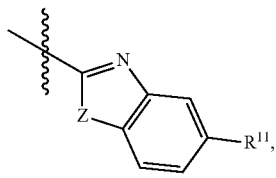
(iii-6)

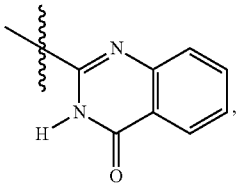
(iii-7)

-continued

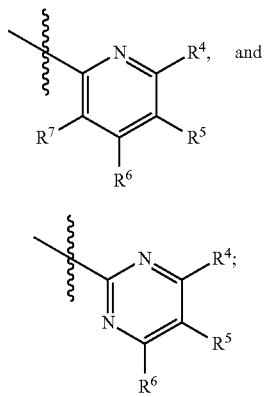

wherein for (iii-3), R⁴ and R⁵ are hydrogen and R⁷ is cyano; or

R⁴ and R⁷ are hydrogen and R⁵ is —CO₂CH₃; or

R⁴ is heterocyclyl, and R⁵ and R⁷ are hydrogen; or

R⁴ and R⁵ and the atoms to which they are attached taken together form a fused phenyl ring optionally substituted with 1, 2, or 3 C₁-C₆alkyl, halo, or haloC₁-C₆alkyl; and R⁷ is hydrogen, C₁-C₆alkyl, or haloC₁-C₆alkyl;

wherein for (iii-4), R⁶ and R⁷ and the atoms to which they are attached taken together form a fused phenyl or pyrrole ring;

wherein for (iii-5) and (iii-6), Z is selected from the group consisting of O, S, NH, and NCH₃;

R¹⁰ is hydrogen or halogen;

R¹¹ is C₁-C₆ alkyl;

wherein for (iii-8), R⁴ and R⁵ and the atoms to which they are attached taken together form a fused phenyl ring, a fused pyridine ring, or a fused pyrazine ring each optionally substituted with 1, 2, or 3 C₁-C₆alkyl, halo, or haloC₁-C₆alkyl;

R⁶ and R⁷ are independently hydrogen, C₁-C₆alkyl, or haloC₁-C₆alkyl; and wherein for (iii-9), R⁴ is hydrogen or C₃-C₆cycloalkylamino, R⁵ and R⁶ are independently hydrogen or C₁-C₆alkyl; or R⁴ and R⁵ and the atoms to which they are attached taken together form a fused phenyl ring, and R⁶ is hydrogen.

In one aspect of the disclosure are compounds of formula (I) wherein:

Ar¹ is phenyl

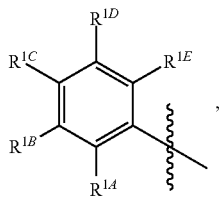

wherein, R¹ᴬ is selected from the group consisting of hydrogen, halo, C₁-C₆alkyl, C₁-C₆alkoxy, and haloalkoxy; R¹ᴮ, R¹ᶜ, R¹ᴰ and R¹ᴱ are each independently hydrogen, halo haloalkyl; C₁-C₆alkyl; or R¹ᴮ and R¹ᶜ, or R¹ᶜ and R¹ᴰ, or R¹ᴰ and R¹ᴱ taken together are —O—CH₂—O—;

L⁴ is a bond or —CH₂—

R¹ is

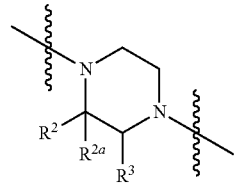

wherein R² is hydrogen, C₁-C₆alkyl, G², and G²alkyl-; wherein G² is C₃-C₆cycloalkyl; R²ᵃ is hydrogen; and R³ is hydrogen or C₁-C₆alkyl; or R², R²ᵃ, and the carbon atom to which they are attached form a C₃-C₆cycloalkyl and R³ is hydrogen; and Ar² is

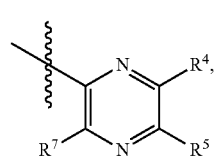

wherein R⁴ and R⁵ are hydrogen and R⁷ is cyano; or R⁴ and R⁷ are hydrogen and R⁵ is —CO₂CH₃; or R⁴ is heterocyclyl and R⁵ and R⁷ are hydrogen; or R⁴ and R⁵ and the atoms to which they are attached taken together form a fused phenyl ring optionally substituted with 1, 2, 3, or 4 substituents selected from the group consisting of cyano, halo, C₁-C₆alkyl, amino, alkylamino, dialkylamino, cycloalkyl, heterocyclyl, haloalkoxy, haloalkyl, —ORᶠ, and —CO₂Rᶠ; and R⁷ is hydrogen, cyano, halo, C₁-C₆alkyl, alkoxy, amino, alkylamino, cycloalkylamino, dialkylamino, cycloalkyl, heterocyclyl, haloalkoxy, haloalkyl, —ORᶠ, and —CO₂Rᶠ, wherein Rᶠ is at each occurrence independently selected from the group consisting of hydrogen, C₁-C₆alkyl, and C₁-C₆haloalkyl.

In one aspect of the disclosure are compounds of formula (I) wherein:

Ar¹ is monocylic heteroaryl of formula (i-2) or (i-3)

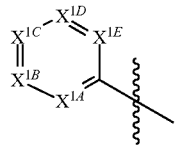

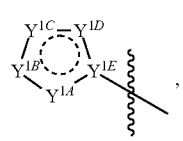

wherein, X¹ᴬ, X¹ᴮ, X¹ᶜ, X¹ᴰ and X¹ᴱ are CR¹ᴬˣ, CR¹ᴮˣ, CR¹ᶜˣ, CR¹ᴰˣ and CR¹ᴱˣ, respectively, or N; wherein 1, 2 or 3 of X¹ᴬ, X¹ᴮ, X¹ᶜ, X¹ᴰ and X¹ᴱ are N; wherein R¹ᴬˣ is selected from the group consisting of hydrogen; amino; hydroxyl; cyano; halo; C₁-C₆alkyl; C₁-C₆alkenyl; C₁-C₆alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -L¹-C(O)—ORᶠ or -L¹-S(O)₂R¹', wherein L¹ is a bond or alkylene, and R$^{1'}$ is selected from the group consisting of hydrogen, C$_1$-C$_6$alkyl and hydroxyalkyl; -L$^2$-O—C(O)—R$^{2'}$, wherein L$^2$ is a bond or alkylene, and R$^{2'}$ is C$_1$-C$_6$alkyl or hydroxyalkyl; -L$^3$-C(O)—NR$^{3'}$R$^{4'}$, wherein L$^3$ is a bond or alkylene, and R$^{3'}$ and R$^{4'}$ are each independently selected from the group consisting of hydrogen, C$_1$-C$_6$alkyl, and hydroxyalkyl; -L$^4$-NR$^{5'}$—C(O)—R$^{6'}$, wherein L$^4$ is a bond or alkylene, R$^{5'}$ is hydrogen or alkyl, and R$^{6'}$ is C$_1$-C$_6$alkyl or hydroxyalkyl; sulfamoyl; N-(alkyl)sulfamoyl; N,N-(dialkyl)sulfamoyl; sulfonamide; alkylthio; and thioalkyl;

R$^{1BX}$, R$^{1CX}$, R$^{1DX}$ and R$^{1EX}$ are each hydrogen;

Y$^{1A}$, Y$^{1B}$, Y$^{1C}$, and Y$^{1D}$ are CR$^{1AY}$ or NR$^{1AY}$, CR$^{1BY}$ or NR$^{1BY}$, CR$^{1CY}$ or NR$^{1CY}$, CR$^{1DY}$ or NR$^{1DY}$, respectively, or N, O or S; wherein 0, 1, 2, 3 or 4 of Y$^{1A}$, Y$^{1B}$, Y$^{1C}$, and Y$^{1D}$ are NR$^{1AY}$, NR$^{1BY}$, NR$^{1CY}$, or NR$^{1DY}$, respectively or N; wherein 0 or 1 of Y$^{1A}$, Y$^{1B}$, Y$^{1C}$, and Y$^{1D}$ is O or S;

Y$^{1E}$ is N or C;

wherein 1, 2, 3, or 4 ring atoms of (i-3) is a heteroatom;

R$^{1AY}$, R$^{1BY}$, R$^{1CY}$, and R$^{1DY}$ are each independently selected from the group consisting of hydrogen; amino; hydroxyl; cyano; halo; C$_1$-C$_6$alkyl; C$_1$-C$_6$alkenyl; C$_1$-C$_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -L$^1$-C(O)—OR$^{1'}$ or -L$^1$-S(O)$_2$R$^{1'}$, wherein L$^1$ is a bond or alkylene, and R$^{1'}$ is selected from the group consisting of hydrogen, C$_1$-C$_6$alkyl and hydroxyalkyl; -L$^2$-O—C(O)—R$^{2'}$, wherein L$^2$ is a bond or alkylene, and R$^{2'}$ is C$_1$-C$_6$alkyl or hydroxyalkyl; -L$^3$-C(O)—NR$^{3'}$R$^{4'}$, wherein L$^3$ is a bond or alkylene, and R$^{3'}$ and R$^{4'}$ are each independently selected from the group consisting of hydrogen, C$_1$-C$_6$alkyl, and hydroxyalkyl; -L$^4$-NR$^{5'}$—C(O)—R$^{6'}$, wherein L$^4$ is a bond or alkylene, R$^{5'}$ is hydrogen or C$_1$-C$_6$alkyl, and R$^{6'}$ is C$_1$-C$_6$alkyl or hydroxyalkyl; sulfamoyl; N-(alkyl)sulfamoyl; N,N-(dialkyl)sulfamoyl; sulfonamide; alkylthio; and thioalkyl;

L$^A$ is a bond or —CH$_2$—

R$^1$ is

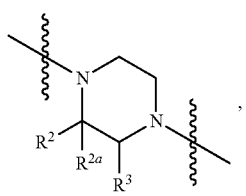

(ii-1)

wherein R$^2$ is hydrogen, C$_1$-C$_6$alkyl, G$^2$, and G$^2$alkyl-; wherein G$^2$ is C$_3$-C$_6$cycloalkyl; R$^{2a}$ is hydrogen; and R$^3$ is hydrogen or C$_1$-C$_6$alkyl; or R$^2$, R$^{2a}$, and the carbon atom to which they are attached form a C$_3$-C$_6$cycloalkyl and R$^3$ is hydrogen; and Ar$^2$ is

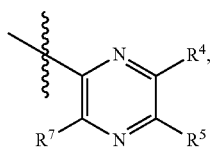

(iii-3)

wherein R$^4$ and R$^5$ are hydrogen and R$^7$ is cyano; or R$^4$ and R$^7$ are hydrogen and R$^5$ is —CO$_2$CH$_3$; or R$^4$ is heterocyclyl and R$^5$ and R$^7$ are hydrogen; or R$^4$ and R$^5$ and the atoms to which they are attached taken together form a fused phenyl ring optionally substituted with 1, 2, 3, or 4 substituents selected from the group consisting of cyano, halo, C$_1$-C$_6$alkyl, amino, alkylamino, dialkylamino, cycloalkyl, heterocyclyl, haloalkoxy, haloalkyl, —OR$^f$, and —CO$_2$R$^f$; and R$^7$ is hydrogen, cyano, halo, C$_1$-C$_6$alkyl, alkoxy, amino, alkylamino, cycloalkylamino, dialkylamino, cycloalkyl, heterocyclyl, haloalkoxy, haloalkyl, —OR$^f$, and —CO$_2$R$^f$ wherein R$^f$ is at each occurrence independently selected from the group consisting of hydrogen, C$_1$-C$_6$alkyl, and C$_1$-C$_6$haloalkyl.

In one aspect of the disclosure are compounds of formula (I) wherein:

Ar$^1$ is phenyl

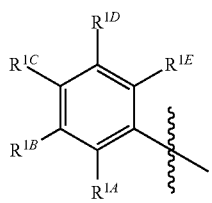

(i-1)

wherein, R$^{1A}$ is selected from the group consisting of halo, C$_1$-C$_6$alkyl, C$_1$-C$_6$alkoxy; R$^{1B}$, R$^{1C}$, R$^{1D}$ and R$^{1E}$ are independently selected from the group consisting of hydrogen, C$_1$-C$_6$alkyl;

L$^A$ is a bond;

R$^1$ is

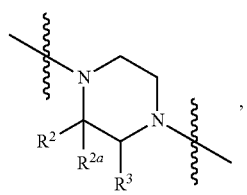

(ii-1)

wherein R$^2$ is C$_1$-C$_6$alkyl and R$^{2a}$ and R$^3$ are each hydrogen; and Ar$^2$ is

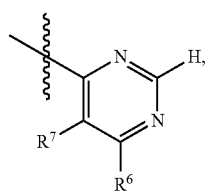

(iii-4)

wherein R$^6$ and R$^7$ and the atoms to which they are attached taken together form a fused phenyl or pyrrole ring.

In one aspect of the disclosure are compounds of formula (I) wherein:

Ar¹ is phenyl

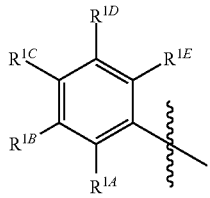
(i-1)

wherein, $R^{1A}$ is selected from the group consisting of halo and $C_1$-$C_6$alkyl; $R^{1B}$, $R^{1C}$, $R^{1D}$ and $R^{1E}$ are each hydrogen;

$L^A$ is a bond;

$R^1$ is

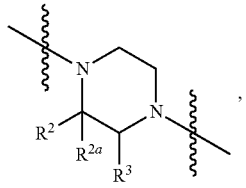
(ii-1)

wherein $R^2$ is $C_1$-$C_6$alkyl and $R^{2a}$ and $R^3$ are each hydrogen; and $Ar^2$ is

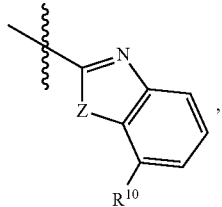
(iii-5)

wherein Z is selected from the group consisting of O, S, NH, and $NCH_3$; and $R^{10}$ is hydrogen or halogen.

In one aspect of the disclosure are compounds of formula (I) wherein:

Ar¹ is phenyl

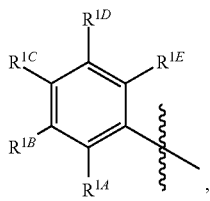
(i-1)

wherein, $R^{1A}$ is selected from the group consisting of halo and $C_1$-$C_6$alkyl; $R^{1B}$, $R^{1C}$, $R^{1D}$ and $R^{1E}$ are each hydrogen;

$L^A$ is a bond;

$R^1$ is

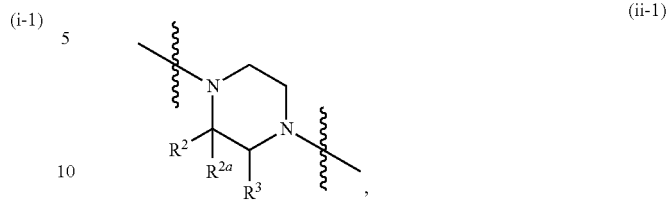
(ii-1)

wherein $R^2$ is $C_1$-$C_6$alkyl and $R^{2a}$ and $R^3$ are each hydrogen; and $Ar^2$ is

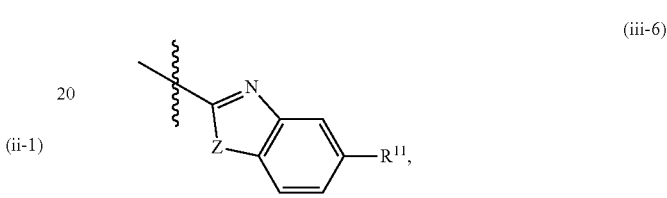
(iii-6)

wherein Z is selected from the group consisting of O, S, NH, and $NCH_3$; and $R^{11}$ is $C_1$-$C_6$ alkyl.

In one aspect of the disclosure are compounds of formula (I) wherein:

Ar¹ is phenyl

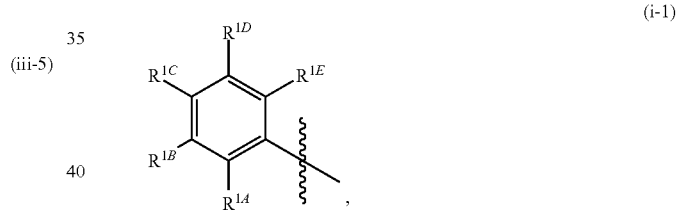
(i-1)

wherein, $R^{1A}$ is selected from the group consisting of halo and $C_1$-$C_6$alkyl; $R^{1B}$, $R^{1C}$, $R^{1D}$ and $R^{1E}$ are each hydrogen;

$L^A$ is a bond;

$R^1$ is

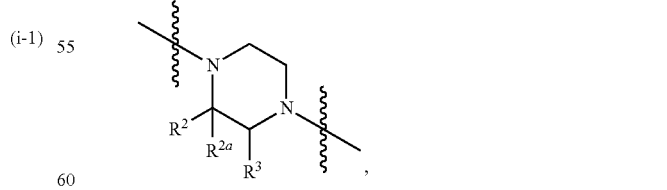
(ii-1)

wherein $R^2$ is $C_1$-$C_6$alkyl and $R^{2a}$ and $R^3$ are each hydrogen; and $Ar^2$ is

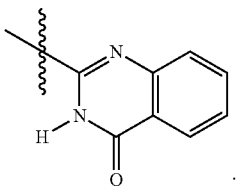

In one aspect of the disclosure are compounds of formula (I) wherein:

Ar$^1$ is phenyl

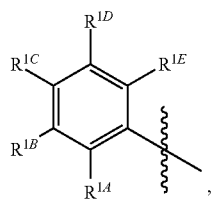

wherein, R$^{1A}$ is selected from the group consisting of halo and C$_1$-C$_6$alkyl; R$^{1B}$, R$^{1C}$, R$^{1D}$ and R$^{1E}$ are each hydrogen; L$^A$ is a bond;
R$^1$ is

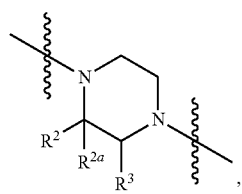

wherein R$^2$ is C$_1$-C$_6$alkyl and R$^{2a}$ and R$^3$ are each hydrogen; and Ar$^2$ is

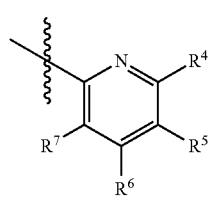

wherein, R$^4$ and R$^5$ and the atoms to which they are attached taken together form a fused phenyl ring, a fused pyridine ring, or a fused pyrazine ring each optionally substituted with 1, 2, or 3 C$_1$-C$_6$alkyl, halo, or haloC$_1$-C$_6$alkyl;

R$^6$ and R$^7$ are independently hydrogen, C$_1$-C$_6$alkyl, or haloC$_1$-C$_6$alkyl;

In one aspect of the disclosure are compounds of formula (I) wherein:

Ar$^1$ is phenyl

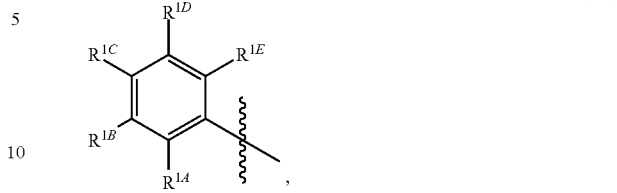

wherein, R$^{1A}$ is selected from the group consisting of halo and C$_1$-C$_6$alkyl; R$^{1B}$, R$^{1C}$, R$^{1D}$ and R$^{1E}$ are each hydrogen; L$^A$ is a bond;
R$^1$ is

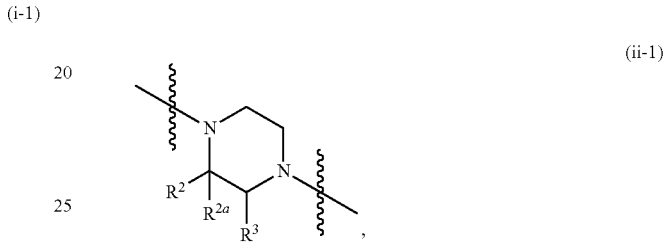

wherein R$^2$ is C$_1$-C$_6$alkyl and R$^{2a}$ and R$^3$ are each hydrogen; and Ar$^2$ is

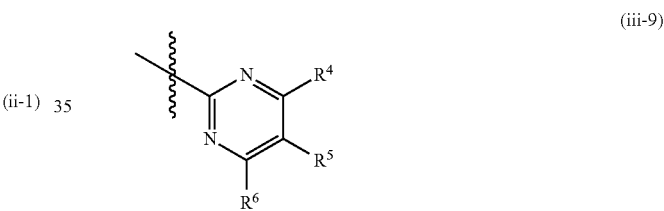

wherein for (iii-9), R$^4$ is hydrogen or C$_3$-C$_6$cycloalkylamino, R$^5$ and R$^6$ are independently hydrogen or C$_1$-C$_6$alkyl; or R$^4$ and R$^5$ and the atoms to which they are attached taken together form a fused phenyl ring, and R$^6$ is hydrogen.

In one aspect of the disclosure are compounds of formula (II) wherein:

Ar$^1$ is phenyl or monocyclic heteroaryl having a structure corresponding to a formula selected from the group consisting of:

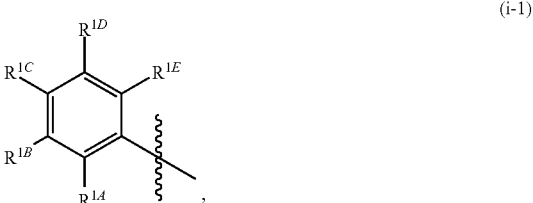

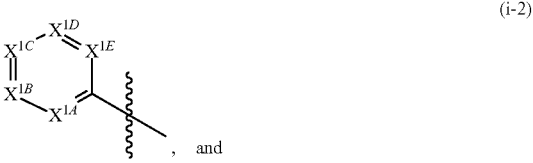

, and

-continued (i-3)

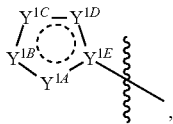

wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl;

$R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl; or $R^{1B}$ and $R^{1C}$, or $R^{1C}$ and $R^{1D}$, or $R^{1D}$ and $R^{1E}$ taken together are —O—CH$_2$—O—;

$X^{1A}$, $X^{1B}$, $X^{1C}$, $X^{1D}$ and $X^{1E}$ are $CR^{1AX}$, $CR^{1BX}$, $CR^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl;

$Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S;

$Y^{1E}$ is N or C;

wherein 1, 2, 3, or 4 ring atoms of (i-3) is a heteroatom;

$R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$L^A$ is a bond or $CR^aR^b$, wherein $R^a$ and $R^b$ are independently hydrogen or alkyl;

$R^A$ is $C_1$-$C_6$alkyl, hydroxy$C_1$-$C_6$alkyl or halo$C_1$-$C_6$alkyl;

$R^1$ is selected from the group consisting of:

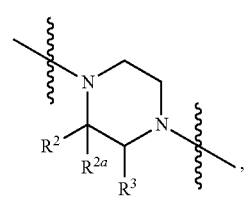

(ii-1)

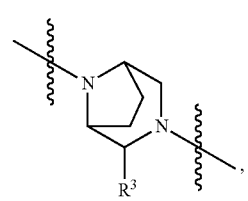

(ii-2)

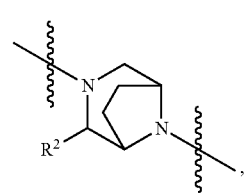

(ii-3)

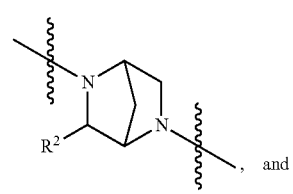

(ii-4)

, and

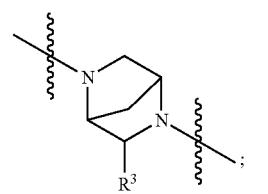

(ii-5)

;

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl-; wherein when both $R^2$ and $R^3$ are present, one or both of $R^2$ and $R^3$ are hydrogen; or $R^2$, $R^{2a}$, and the carbon atom to which they are attached form a $C_3$-$C_6$cycloalkyl and $R^3$ is hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-CO$_2$H, -$L^c$-CO$_2R^f$, -$L^c$-N($R^f$)C(O)N($R^f$)$_2$, -$L^c$-S—$R^f$, -$L^c$-S(O)$_2R^f$, - $L^c$-S(O)$R^f$, -$L^c$-SO$_2$N($R^e$)($R^f$), -$L^c$-N($R^e$)($R^f$), -$L^c$-N($R^f$)S(O)$_2R^f$, and -$L^c$-N($R^f$)C(O)O($R^f$);

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

$R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^f$ is at each occurrence independently selected from the group consisting of hydrogen, $C_1$-$C_6$alkyl, and $C_1$-$C_6$haloalkyl;

$Ar^1$ is selected from the group consisting of:

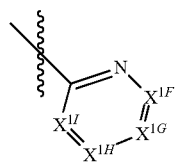

(iii-1)

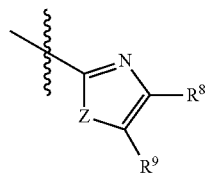

(iii-2)

$X^{1F}$, $X^{1G}$, $X^{1H}$, and $X^{1I}$ are $CR^4$, $CR^5$, $CR^6$ and $CR^7$, respectively, or N; wherein 0, 1 or 2 of $X^{1F}$, $X^{1G}$, $X^{1H}$, and $X^{1I}$ are N; wherein $R^4$, $R^5$, $R^6$ and $R^7$ are each independently selected from the group consisting of hydrogen, cyano, halo, $C_1$-$C_6$alkyl, alkoxy, amino, alkylamino, cycloalkylamino, dialkylamino, cycloalkyl, heterocyclyl, haloalkoxy, haloalkyl, —OR$^f$, and —CO$_2R^f$; or $R^4$ and $R^5$; $R^5$ and $R^6$; or $R^6$ and $R^7$ and the atoms to which they are attached taken together form a fused phenyl ring, pyrrole, pyridine, or pyrazine optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —OR$^f$, and —CO$_2R^f$;

wherein Z is selected from the group consisting of O, S, and N$R^e$; and $R^8$ and $R^9$ are each independently selected from the group consisting of hydrogen, cyano, halo, $C_1$-$C_6$alkyl, amino, alkylamino, dialkylamino, cycloalkyl, heterocyclyl, haloalkoxy, haloalkyl, —OR$^f$ and —CO$_2R^f$; or $R^8$ and $R^9$ and the atoms to which they are attached taken together form a fused phenyl ring optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —OR$^f$, and —CO$_2R^f$.

In one aspect of the disclosure are compounds of formula (III) wherein:

$Ar^1$ is phenyl or monocyclic heteroaryl having a structure corresponding to a formula selected from the group consisting of:

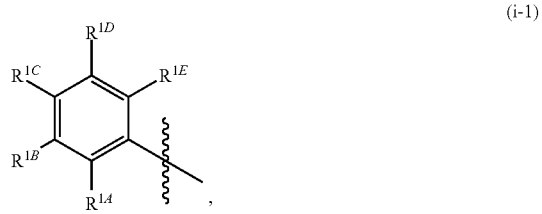

(i-1)

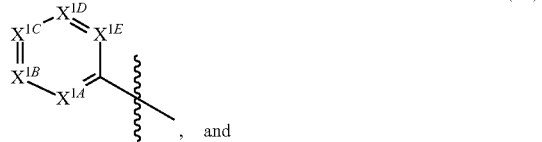

(i-2)

, and

(i-3)

, wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—OR$^{1'}$ or -$L^1$-S(O)$_2R^{1'}$, wherein $L^1$ is a bond or alkylene, and $R^{1'}$ is alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—NR$^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-NR$^{5'}$—C(O)—R$^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl;

$R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl; or $R^{1B}$ and $R^{1C}$, or $R^{1C}$ and $R^{1D}$, or $R^{1D}$ and $R^{1E}$ taken together are —O—CH$_2$—O—;

$X^{1A}$, $X^{1B}$, $X^{1C}$, $X^{1D}$ and $X^{1E}$ are $CR^{1AX}$, $CR^{1BX}$, $CR^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—OR$^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—NR$^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-NR$^{5'}$—C(O)—R$^{6'}$, wherein $L^4$ is a bond or alkylene, $R^{3'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl;

$Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S;

$Y^{1E}$ is N or C;

wherein 1, 2, 3, or 4 ring atoms of (i-3) is a heteroatom; $R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$L^A$ is a bond or $CR^aR^b$, wherein $R^a$ and $R^b$ are independently hydrogen or alkyl;

$R^B$ is hydrogen, $C_1$-$C_6$alkyl, hydroxy$C_1$-$C_6$alkyl or halo$C_1$-$C_6$alkyl;

$R^{100}$ is (vii-1):

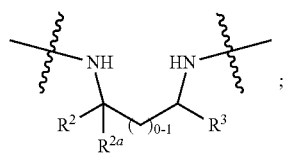

(vii-1)

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl-; wherein when both $R^2$ and $R^3$ are present, one or both of $R^2$ and $R^3$ are hydrogen; or $R^2$, $R^{2a}$, and the carbon atom to which they are attached form a $C_3$-$C_6$cycloalkyl and $R^3$ is hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —$N(R^f)C(O)R^f$, —$CON(R^e)(R^f)$, —$C(O)R^f$, —$OC(O)R^f$, —$CO_2R^f$—$N(R^f)C(O)N(R^f)_2$, —S—$R^f$, —$S(O)_2R^f$—$S(O)R^f$, —$SO_2N(R^e)(R^f)$, —$N(R^e)(R^f)$, —$N(R^f)S(O)_2R^f$, $N(R^f)C(O)R^f)$, -$L^c$-O—$R^f$, -$L^c$-CN, -$L^c$-$N(R^f)(R^f)$, -$L^c$-$CON(R^e)(R^f)$, -$L^c$-$C(O)R^f$, -$L^c$-OC(O)$R^f$, -$L^c$-$CO_2H$, -$L^c$-$CO_2R^f$, -$L^c$-$N(R^f)C(O)N(R^f)_2$, -$L^c$-S—$R^f$, -$L^c$-$S(O)_2R^f$, - $L^c$-$S(O)R^f$, -$L^c$-$SO_2N(R^e)(R^f)$, -$L^c$-$N(R^f)(R^f)$, -$L^c$-$N(R^f)S(O)_2R^f$, and -$L^c$-$N(R^f)C(O)O(R^f)$;

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

$R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^f$ is at each occurrence independently selected from the group consisting of hydrogen, $C_1$-$C_6$alkyl, and $C_1$-$C_6$haloalkyl;

$Ar^2$ is selected from the group consisting of:

(iii-1)

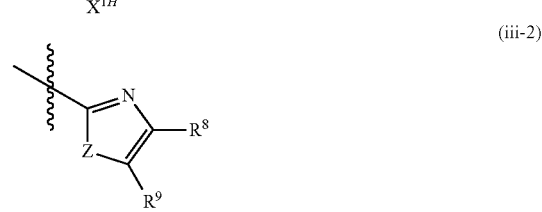

(iii-2)

$X^{1F}$, $X^{1G}$, $X^{1H}$, and $X^{1I}$ are $CR^4$, $CR^5$, $CR^6$ and $CR^7$, respectively, or N; wherein 0, 1 or 2 of $X^{1F}$, $X^{1G}$, $X^{1H}$, and $X^{1I}$ are N; wherein $R^4$, $R^5$, $R^6$ and $R^7$ are each independently selected from the group consisting of hydrogen, cyano, halo, $C_1$-$C_6$alkyl, alkoxy, amino, alkylamino, cycloalkylamino, dialkylamino, cycloalkyl, heterocyclyl, haloalkoxy, haloalkyl, —$OR^f$, and —$CO_2R^f$; or $R^4$ and $R^5$; $R^5$ and $R^6$; or $R^6$ and $R^7$ and the atoms to which they are attached taken together form a fused phenyl ring, pyrrole, pyridine, or pyrazine optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —$OR^f$, and —$CO_2R^f$;

wherein Z is selected from the group consisting of O, S, and $NR^e$; and $R^8$ and $R^9$ are each independently selected from the group consisting of hydrogen, cyano, halo, $C_1$-$C_6$alkyl, amino, alkylamino, dialkylamino, cycloalkyl, heterocyclyl, haloalkoxy, haloalkyl, —$OR^f$ and —$CO_2R^f$; or $R^8$ and $R^9$ and the atoms to which they are attached taken together form a fused phenyl ring optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —$OR^f$, and —$CO_2R^f$.

In one aspect of the disclosure are compounds of formula (IV) wherein:

$Ar^1$ is phenyl or monocyclic heteroaryl having a structure corresponding to a formula selected from the group consisting of:

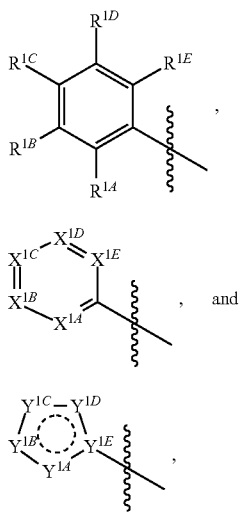

(i-1)

(i-2) and (i-3)

wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2$$R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl;

$R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl; or $R^{1B}$ and $R^{1C}$, or $R^{1C}$ and $R^{1D}$, or $R^{1D}$ and $R^{1E}$ taken together are —O—$CH_2$—O—;

$X^{1A}$, $X^{1B}$, $X^{1C}$, $X^{1D}$ and $X^{1E}$ are $CR^{1AX}$, $CR^{1BX}$, $CR^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2$$R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl;

$Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S; $Y^{1E}$ is N or C;

wherein 1, 2, 3, or 4 ring atoms of (i-3) is a heteroatom;

$R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2$$R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$L^A$ is a bond or $CR^aR^b$, wherein $R^a$ and $R^b$ are independently hydrogen or alkyl;

$R^B$ is hydrogen, $C_1$-$C_6$alkyl, hydroxy$C_1$-$C_6$alkyl or halo$C_1$-$C_6$alkyl;

$R^{200}$ is (vi-1):

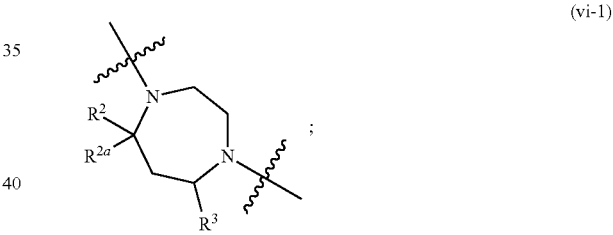

(vi-1)

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl-; wherein when both $R^2$ and $R^3$ are present, one or both of $R^2$ and $R^3$ are hydrogen; or $R^2$, $R^{2a}$, and the carbon atom to which they are attached form a $C_3$-$C_6$cycloalkyl and $R^3$ is hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2$$R^f$, —N($R^f$)C(O)N($R^f$)$_2$, —S—$R^f$, —S(O)$_2$$R^f$, —S(O)$R^f$, —SO$_2$N($R^e$)($R^f$), —N($R^e$)($R^f$), —N($R^f$)S(O)$_2$$R^f$, N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-CO$_2$H, -$L^c$-CO$_2$$R^f$, -$L^c$-N($R^f$)C(O)N($R^f$)$_2$, -$L^c$-S—$R^f$, -$L^c$-S(O)$_2$$R^f$, - $L^c$-S(O)$R^f$, -$L^c$-SO$_2$N($R^e$)($R^f$), -$L^c$-N($R^e$)($R^f$), -$L^c$-N($R^f$)S(O)$_2$$R^f$, and -$L^c$-N($R^f$)C(O)O($R^f$);

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

$R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^f$ is at each occurrence independently selected from the group consisting of hydrogen, $C_1$-$C_6$alkyl, and $C_1$-$C_6$haloalkyl;

$Ar^2$ is selected from the group consisting of:

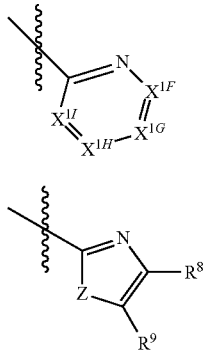

(iii-1)

(iii-2)

$X^{1F}$, $X^{1G}$, $X^{1H}$, and $X^{1I}$ are $CR^4$, $CR^5$, $CR^6$ and $CR^7$, respectively, or N; wherein 0, 1 or 2 of $X^{1F}$, $X^{1G}$, $X^{1H}$, and $X^{1I}$ are N; wherein $R^4$, $R^5$, $R^6$ and $R^7$ are each independently selected from the group consisting of hydrogen, cyano, halo, $C_1$-$C_6$alkyl, alkoxy, amino, alkylamino, cycloalkylamino, dialkylamino, cycloalkyl, heterocyclyl, haloalkoxy, haloalkyl, —$OR^f$, and —$CO_2R^f$; or $R^4$ and $R^5$; $R^5$ and $R^6$; or $R^6$ and $R^7$ and the atoms to which they are attached taken together form a fused phenyl ring, pyrrole, pyridine, or pyrazine optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —$OR^f$, and —$CO_2R^f$;

wherein Z is selected from the group consisting of O, S, and $NR^e$; and $R^8$ and $R^9$ are each independently selected from the group consisting of hydrogen, cyano, halo, $C_1$-$C_6$alkyl, amino, alkylamino, dialkylamino, cycloalkyl, heterocyclyl, haloalkoxy, haloalkyl, —$OR^f$, and —$CO_2R^f$; or $R^8$ and $R^9$ and the atoms to which they are attached taken together form a fused phenyl ring optionally substituted with 1, 2, 3, or 4 substituents selected from the group consisting of cyano, halo, $C_1$-$C_6$alkyl, amino, alkylamino, dialkylamino, cycloalkyl, heterocyclyl, haloalkoxy, haloalkyl, —$OR^f$, and —$CO_2R^f$.

Exemplary compounds include, but are not limited to:

N'-cyano-4-(3-cyanopyrazin-2-yl)-2-isopropyl-N-(2-methylphenyl)piperazine-1-carboximidamide;

methyl 5-{4-[N-(2-chlorophenyl)-N'-cyanocarbamimidoyl]-3-isopropylpiperazin-1-yl}pyrazine-2-carboxylate;

N'-cyano-2-isopropyl-N-(2-methylphenyl)-4-(quinoxalin-2-yl)piperazine-1-carboximidamide;

4-(1,3-benzoxazol-2-yl)-N'-cyano-2-isopropyl-N-(2-methylphenyl)piperazine-1-carboximidamide;

4-(7-chloro-1,3-benzoxazol-2-yl)-N'-cyano-2-isopropyl-N-(2-methylphenyl)piperazine-1-carboximidamide;

4-(1,3-benzothiazol-2-yl)-N'-cyano-2-isopropyl-N-(2-methylphenyl)piperazine-1-carboximidamide;

N'-cyano-2-isopropyl-4-(5-methyl-1,3-benzoxazol-2-yl)-N-(2-methylphenyl)piperazine-1-carboximidamide;

N'-cyano-2-isopropyl-N-(2-methylphenyl)-4-(quinazolin-4-yl)piperazine-1-carboximidamide;

4-(1H-benzimidazol-2-yl)-N'-cyano-2-isopropyl 1N-(2-methylphenyl)piperazine-1-carboximidamide;

N'-cyano-2-isopropyl-N-(2-methylphenyl)-4-(4-oxo-3,4-dihydroquinazolin-2-yl)piperazine-1-carboximidamide;

N'-cyano-2-isopropyl-N-(2-methylphenyl)-4-(7H-pyrrolo[2,3-d]pyrimidin-4-yl)piperazine-1-carboximidamide;

(2R)-cyano-2-isopropyl-N-(2-methylphenyl)-4-(quinoxalin-2-yl)piperazine-1-carboximidamide;

(2S)-cyano-2-isopropyl-N-(2-methylphenyl)-4-(quinoxalin-2-yl)piperazine-1-carboximidamide;

N-(1,3-benzodioxol-5-yl)-N'-cyano-2-isopropyl-4-(quinoxalin-2-yl)piperazine-1-carboximidamide;

N-(4-chlorophenyl)-N'-cyano-2-isopropyl-4-(quinoxalin-2-yl)piperazine-1-carboximidamide;

N'-cyano-2-isopropyl-N-(4-methylphenyl)-4-(quinoxalin-2-yl)piperazine-1-carboximidamide;

N'-cyano-N-(2,6-dimethylphenyl)-2-isopropyl-4-(quinoxalin-2-yl)piperazine-1-carboximidamide;

N'-cyano-2-isopropyl-N-(2-methoxyphenyl)-4-(quinoxalin-2-yl)piperazine-1-carboximidamide;

N-(2-chlorophenyl)-N'-cyano-2-isopropyl-4-(quinoxalin-2-yl)piperazine-1-carboximidamide;

N'-cyano-N-(3-fluorophenyl)-2-isopropyl-4-(quinoxalin-2-yl)piperazine-1-carboximidamide;

N'-cyano-N-(2-fluorophenyl)-2-isopropyl-4-(quinoxalin-2-yl)piperazine-1-carboximidamide;

N'-cyano-2-isopropyl-N-(3-methylphenyl)-4-(quinoxalin-2-yl)piperazine-1-carboximidamide;

N'-cyano-N-(4-fluorophenyl)-2-isopropyl-4-(quinoxalin-2-yl)piperazine-1-carboximidamide;

N'-cyano-2-isopropyl-4-(quinoxalin-2-yl)-N-[4-(trifluoromethyl)phenyl]piperazine-1-carboximidamide;

N'-cyano-2-isopropyl-4-(quinoxalin-2-yl)-N-[3-(trifluoromethyl)phenyl]piperazine-1-carboximidamide;

N'-cyano-2-isopropyl-N-(2-isopropylphenyl)-4-(quinoxalin-2-yl)piperazine-1-carboximidamide;

N'-cyano-2-isopropyl-4-(quinoxalin-2-yl)-N-[2-(trifluoromethoxy)phenyl]piperazine-1-carboximidamide;

N-(3-chlorophenyl)-N'-cyano-2-isopropyl-4-(quinoxalin-2-yl)piperazine-1-carboximidamide;

N'-cyano N-(3-fluoro-2-methylphenyl)-2-isopropyl-4-(quinoxalin-2-yl)piperazine-1-carboximidamide;

N-(2-chloro-4-fluorophenyl)-N'-cyano-2-isopropyl-4-(quinoxalin-2-yl)piperazine-1-carboximidamide;

N'-cyano-N-(5-fluoro-2-methylphenyl)-2-isopropyl-4-(quinoxalin-2-yl)piperazine-1-carboximidamide;

N'-cyano-N-(4-fluoro-2-methylphenyl)-2-isopropyl-4-(quinoxalin-2-yl)piperazine-1-carboximidamide;

N'-cyano-N-(2-fluoro-6-methylphenyl)-2-isopropyl-4-(quinoxalin-2-yl)piperazine-1-carboximidamide;

N'-cyano-N-(4,5-difluoro-2-methylphenyl)-2-isopropyl-4-(quinoxalin-2-yl)piperazine-1-carboximidamide;

N'-cyano-2-isopropyl-N-(2-methylbenzyl)-4-(quinoxalin-2-yl)piperazine-1-carboximidamide;

N-(3-tert-butyl-1-methyl-1H-pyrazol-5-yl)-N'-cyano-2-isopropyl-4-(quinoxalin-2-yl)piperazine-1-carboximidamide;

N'-cyano-2-isopropyl-N-(2-methylphenyl)-4-(quinoxalin-2-yl)piperazine-1-carboximidamide;

N'-cyano-2-isopropyl-N-(3-methylphenyl)-4-(quinoxalin-2-yl)piperazine-1-carboximidamide;

N'-cyano-N-(2-fluorophenyl)-2-isobutyl-4-(quinoxalin-2-yl)piperazine-1-carboximidamide;
N'-cyano-N-(3-fluorophenyl)-2-isobutyl-4-(quinoxalin-2-yl)piperazine-1-carboximidamide;
N-(2-chlorophenyl)-N'-cyano-2-isobutyl-4-(quinoxalin-2-yl)piperazine-1-carboximidamide;
N'-cyano-2-methyl-N-(2-methylphenyl)-4-(quinoxalin-2-yl)piperazine-1-carboximidamide;
N'-cyano-N-(2-methylphenyl)-8-(quinoxalin-2-yl)-5,8-diazaspiro[3.5]nonane-5-carboximidamide;
N'-cyano-2-ethyl-N-(2-methylphenyl)-4-(quinoxalin-2-yl)piperazine-1-carboximidamide;
N'-cyano-N-(2-methylphenyl)-7-(quinoxalin-2-yl)-4,7-diazaspiro[2.5]octane-4-carboximidamide;
2-tert-butyl-N'-cyano-N-(2-methylphenyl)-4-(quinoxalin-2-yl)piperazine-1-carboximidamide;
2-sec-butyl-N'-cyano-N-(2-methylphenyl)-4-(quinoxalin-2-yl)piperazine-1-carboximidamide;
N'-cyano-2-cyclohexyl-N-(2-methylphenyl)-4-(quinoxalin-2-yl)piperazine-1-carboximidamide;
N'-cyano-2-(cyclohexylmethyl)-N-(2-methylphenyl)-4-(quinoxalin-2-yl)piperazine-1-carboximidamide;
N'-cyano-4-(6,7-dimethylquinoxalin-2-yl)-2-isopropyl-N-(2-methylphenyl)piperazine-1-carboximidamide;
N'-cyano-4-(6,7-difluoroquinoxalin-2-yl)-2-isopropyl-N-(2-methylphenyl)piperazine-1-carboximidamide;
N'-cyano-2-isopropyl-N-(2-methylphenyl)-4-(3-methylquinoxalin-2-yl)piperazine-1-carboximidamide;
N'-cyano-2-isopropyl-N-(2-methylphenyl)-4-[3-(trifluoromethyl)quinoxalin-2-yl]piperazine-1-carboximidamide;
N'-cyano-4-(6-fluoroquinoxalin-2-yl)-2-isopropyl-N-(2-methylphenyl)piperazine-1-carboximidamide;
4-(7-chloroquinoxalin-2-yl)-N'-cyano-2-isopropyl-N-(2-methylphenyl)piperazine-1-carboximidamide;
N'-cyano-2-isopropyl-N-(2-methylphenyl)-4-(7-methylquinoxalin-2-yl)piperazine-1-carboximidamide;
N'-cyano-2-isopropyl-N-(2-methylphenyl)-4-[6-(trifluoromethyl)quinoxalin-2-yl]piperazine-1-carboximidamide;
N'-cyano-4-(6,7-dichloroquinoxalin-2-yl)-2-isopropyl-N-(2-methylphenyl)piperazine-1-carboximidamide;
N'-cyano-2-isopropyl-N-(2-methylphenyl)-4-[8-(trifluoromethyl)quinoxalin-2-yl]piperazine-1-carboximidamide;
N'-cyano-4-(7-fluoroquinoxalin-2-yl)-2-isopropyl-N-(2-methylphenyl)piperazine-1-carboximidamide;
N'-cyano-2-isopropyl-N-(2-methylphenyl)-4-(quinolin-2-yl)piperazine-1-carboximidamide;
N'-cyano-2-isopropyl-N-(2-methylphenyl)-4-(quinazolin-2-yl)piperazine-1-carboximidamide;
N'-cyano-2-isopropyl-N-(2-methylphenyl)-4-[6-(morpholin-4-yl)pyrazin-2-yl]piperazine-1-carboximidamide;
N'-cyano-4-[4-(cyclohexylamino)-5,6-dimethylpyrimidin-2-yl]-2-isopropyl-N-(2-methylphenyl)piperazine-1-carboximidamide;
N'-cyano-2-isopropyl-N-(2-methylphenyl)-4-(pyrido[2,3-b]pyrazin-6-yl)piperazine-1-carboximidamide;
N'-cyano-2-isopropyl-N-(2-methylphenyl)-4-(1,8-naphthyridin-2-yl)piperazine-1-carboximidamide;
(2S)—N'-cyano-4-(6-fluoroquinoxalin-2-yl)-2-isopropyl-N-(2-methylphenyl)piperazine-1-carboximidamide;
N'-cyano-2-isopropyl-4-(7-methyl-1,8-naphthyridin-2-yl)-N-(2-methylphenyl)piperazine-1-carboximidamide;
N'-cyano-2-isopropyl-4-(1-methyl-1H-benzimidazol-2-yl)-N-(2-methylphenyl)piperazine-1-carboximidamide;
N'-cyano-3-isopropyl-N-(2-methylphenyl)-4-(quinoxalin-2-yl)piperazine-1-carboximidamide;
(2S)—N-(2-chlorophenyl)-N'-cyano-4-(6-fluoroquinoxalin-2-yl)-2-isopropylpiperazine-1-carboximidamide;
N'-cyano-2-isopropyl-N-(4-methylpyridin-3-yl)-4-(quinoxalin-2-yl)piperazine-1-carboximidamide;
N'-cyano-2-isopropyl-N-(2-methylpyridin-3-yl)-4-(quinoxalin-2-yl)piperazine-1-carboximidamide;
N'-cyano-N-(2-methylphenyl)-4-(quinoxalin-2-yl)piperazine-1-carboximidamide;
N'-cyano-2-isopropyl-N-methyl-N-(2-methylphenyl)-4-(quinoxalin-2-yl)piperazine-1-carboximidamide;
2-cyano-1-(2-methylphenyl)-3-[3-methyl-1-(quinoxalin-2-ylamino)butan-2-yl]guanidine; or
N'-cyano-7-isopropyl-N-(2-methylphenyl)-4-(quinoxalin-2-yl)-1,4-diazepane-1-carboximidamide.

Isomers

The present disclosure contemplates various stereoisomers and mixtures thereof, and these are specifically included within the scope of this disclosure. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, or (2) direct separation of the mixture of optical enantiomers on chiral chromatographic columns.

Geometric isomers may exist in the disclosed compounds. The present disclosure contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or a heterocycle are designated as being of cis or trans configuration. An example of a carbon-nitrogen double bond is the cyanoguanidine moiety.

It is to be understood that compounds disclosed herein may exhibit the phenomenon of tautomerism. For example, subgroup (iii-7) can be represented by either tautomeric form or a mixture thereof shown below:

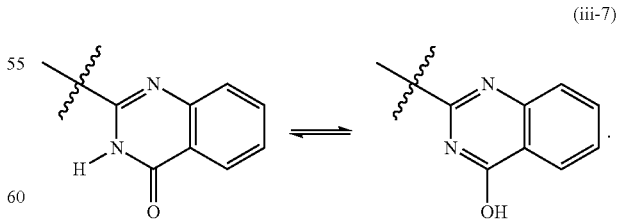

(iii-7)

Thus, it is to be understood that the disclosed compounds encompass any tautomeric or stereoisomeric forms, and mixtures thereof, and are not to be limited merely to any one tautomeric or stereoisomeric form utilized within the naming of the compounds or formulae drawings.

Isotopes

The disclosure also include isotopically-labeled compounds, which are identical to disclosed compounds, but for the fact that one or more atoms are replaced by an atom having an atomic mass or mass number different from the atomic mass or mass number usually found in nature. Examples of isotopes suitable for inclusion in the disclosed compounds are hydrogen, carbon, nitrogen, oxygen, phosphorus, fluorine, and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be employed in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of the present disclosure can generally be prepared by conventional techniques known to those skilled in the art or by processes analogous to those described in the accompanying Examples using appropriate isotopically-labeled reagent in place of non-isotopically-labeled reagent.

Salts

This disclosure is also directed, in part, to all salts of the disclosed compounds. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt may be pharmaceutically acceptable and/or physiologically compatible. The term "pharmaceutically acceptable" is used adjectivally in this disclosure to mean that the modified noun is appropriate for use as a pharmaceutical product or as a part of a pharmaceutical product. Pharmaceutically acceptable salts include, for example, salts commonly used to form alkali metal salts and to form addition salts of free acids or free bases. In general, these salts typically may be prepared by conventional means by reacting, for example, the appropriate acid or base with a disclosed compound.

Pharmaceutically acceptable acid addition salts of the disclosed compounds can be prepared from an inorganic or organic acid. Examples of suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the disclosed compounds include, for example, metallic salts and organic salts. Metallic salts may include alkali metal (group Ia) salts, alkaline earth metal (group IIa) salts, and other physiologically acceptable metal salts. Such salts may be made from aluminum, calcium, lithium, magnesium, potassium, sodium, and zinc. Organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Purity

The disclosed compounds (and salts thereof) with any level of purity (including pure and substantially pure) are within the scope of the present disclosure. The term "substantially pure" in reference to a compound/salt/isomer, means that the preparation/composition containing the compound/salt/isomer contains more than about 85% by weight of the compound/salt/isomer, more than about 90% by weight of the compound/salt/isomer, more than about 95% by weight of the compound/salt/isomer, more than about 97% by weight of the compound/salt/isomer, and more than about 99% by weight of the compound/salt/isomer.

Compositions

The disclosure is also directed, in part, to compositions comprising one or more of the disclosed compounds and/or salts thereof. In some embodiments, the compositions comprise one or more substantially phase pure crystalline forms. The compositions may be pharmaceutical compositions.

In some embodiments, the compositions further comprise one or more additional therapeutic agents. Such therapeutic agents may include, for example, one or more therapeutic agents used to treat respiratory syncytial virus (e.g., ribavirin).

The components of the compositions may depend on the method of administration, and may comprise one or more conventional pharmaceutically acceptable carriers, adjuvants, and/or vehicles (together referred to as "excipients"). Formulation of drugs is generally discussed in, for example, Hoover, J., *Remington's Pharmaceutical Sciences* (Mack Publishing Co., 1975) and Ansel's *Pharmaceutical Dosage Forms and Drug Delivery Systems* (Lippincott Williams & Wilkins, 2005).

The disclosed pharmaceutical compositions may be administered to a patient in need thereof via a variety of routes, such as orally, parenterally, sublingually, rectally, topically or by inhalation. Topical administration may involve the use of transdermal administration such as transdermal patches or iontophoresis devices. Parenteral administration includes, but is not limited to, subcutaneous, intravenous, intramuscular or intrasternal injections, and infusion techniques.

Solid dosage forms for oral administration include, for example, capsules, tablets, pills, powders, and granules. In such solid dosage forms, the disclosed compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions may also comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the present disclosure can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration may be prepared by, for example, mixing a compound or salt of the present disclosure with a suitable nonirritating excipient that is solid at ordinary temperatures, but liquid at the rectal temperature, and will, therefore, melt in the rectum to release the drug. Suitable excipients include, for example, cocoa butter, synthetic mono-, di-, or triglycerides, fatty acids, and/or polyethylene glycols.

Topical administration includes the use of transdermal administration, such as transdermal patches or iontophoresis devices.

The disclosed compounds or pharmaceutical compositions may be formulated to be suitable for inhalation. The pharmaceutical composition may be in the form of a solution, suspension, powder or other suitable form for pulmonary administration. These compositions may be administered to the lungs by any suitable delivery method such as, for example, in an aerosol, atomized, nebulized, or vaporized form through devices known in the art to affect such delivery. The amount of the disclosed pharmaceutical composition may be controlled by providing a valve to deliver a metered amount such as in a metered dose inhalers (MDI) that delivers a fixed dose in a spray with each actuation of the device. The pharmaceutical compositions may be formulated with one or more suitable propellants, such as, for example, dichlorodifluoromethane, trichlorofluoromethane, dichlorotetrafluoroethane, carbon dioxide or other suitable gas. Capsules and cartridges for use in an inhaler or insufflator may be formulated containing a powder mix of the disclosed compounds or pharmaceutical compositions and a suitable powder base such as lactose or starch.

The pharmaceutical compositions may be formulated with one or more binding agent as a dry powder for inhalation.

The disclosed compounds or pharmaceutical compositions may be in the form of sustained- or controlled-delivery formulations. Techniques for making such sustained- and controlled-delivery formulations are well-known to those skilled in the art. Among these are delivery methods that use liposome carriers, bio-erodible microparticles, porous beads, and semi-permeable polymer matrices.

Other excipients and modes of administration known in the pharmaceutical art also may be used.

The total daily dose of the disclosed compounds or salts thereof (administered in single or divided doses) may be from about 0.001 to about 100 mg/kg, from about 0.001 to about 30 mg/kg, or from about 0.01 to about 10 mg/kg (i.e., mg of the compound or salt per kg body weight). Dosage unit compositions may contain such amounts or submultiples thereof to make up the daily dose. In many instances, the administration of the disclosed compounds or salts thereof will be repeated a plurality of times. Multiple doses per day typically may be used to increase the total daily dose, if desired.

Factors affecting the dosage regimen include the type, age, weight, sex, diet, and condition of the patient; the severity of the pathological condition; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the dosage regimen set forth above.

Kits

This disclosure is also directed, in part, to kits comprising one or more of the disclosed compounds and/or salts thereof. The kits may optionally contain one or more additional therapeutic agents and/or instructions for, for example, using the kit.

Methods of Use.

This disclosure is directed, in part, to a method for inhibiting infection and/or replication of an RNA virus. The method comprises exposing the virus to one or more of the disclosed compounds and/or salts thereof. In embodiments, infection and/or replication of the RNA virus is inhibited in vitro. In embodiments, infection and/or replication of the RNA virus is inhibited in vivo. In embodiments, the RNA virus whose infection and/or replication is being inhibited is a single-stranded, negative sense RNA virus. In embodiments, the RNA virus whose infection and/or replication is being inhibited is a virus from the Paramyxoviridae family. In embodiments, the RNA virus whose infection and/or replication is being inhibited is RSV.

The term "inhibiting" means reducing the level of infection and/or RNA virus replication either in vitro or in vivo. The inhibition may act on any stage of viral infection and/or replication, such as (but not exclusively) attachment, penetration, uncoating, genome replication, assembly, maturation or egress from infected cells. The target of the compound may be either a viral or host component (or rarely both) involved in viral infection and/or replication. For example, if a disclosed compound/salt reduces the level of infection and/or RNA virus replication by at least about 10% compared to the level of RNA virus replication before the virus is exposed to the compound/salt, then the compound/salt inhibits RNA virus replication. In some embodiments, the compound/salt can inhibit RNA virus replication by at least about 20%, at least about 30%, at least about 40%, at least about 50%, at least about 60%, at least about 70%, at least about 80%, at least about 90%, or at least about 95%.

This disclosure also is directed, in part, to a method for treating RSV infection in a subject in need of such treatment. These methods comprise administering to the subject one or more of the disclosed compounds and/or salts thereof, and, optionally, one or more additional therapeutic agents. In some embodiments, a therapeutically effective amount of the compound(s) and/or salt(s) thereof is administered to the subject. "Treating" means ameliorating, suppressing, eradicating, preventing, reducing the risk of, and/or delaying the onset of the infection or disease being treated. For example, the disclosed compounds and/or salts thereof may be used for prophylaxis to prevent infection of uninfected subjects, and/or the spread of the virus to the lower respiratory tract in patients already infected with the virus. The term "treating" encompasses administration of the disclosed compounds and/or salts thereof to a patient at risk for RSV infection. Patients at risk for RSV infection may include premature infants, children with bronchopulmonary dysplasia, children with congenital heart or lung disease, the elderly and immunocompromised and other patients who are unable to mount a sufficient immune responses due to their immature or weaker immune systems. The disclosed compounds and/or salts thereof may be administered to patients with a low tolerance to the side effects of current therapies.

The methods of treatment are particularly suitable for use with humans, but may be used with other animals. A "therapeutically effective amount" or "effective amount" is an amount that will substantially achieve the goal of treating the targeted condition.

In embodiments, the disclosed methods comprise combination therapy, wherein the disclosed compound(s) and/or salt(s) is/are co-administered with a second compound, such as, for example, another therapeutic agent used to treat RSV such as, for example, the current standard of therapy, and other antivirals. In these co-administration embodiments, the disclosed compound(s) and/or salt(s) and the second, etc. therapeutic agent(s) may be administered in a substantially simultaneous manner (e.g., within at least about 5 minutes of each other), in a sequential manner, or both. For example, the disclosed compound(s) and/or salt(s) may be administered to a patient before, during or after treatment with the current standard of therapy, if such an administration is deemed medically necessary and/or appropriate.

This disclosure also is directed, in part, to uses of one or more of the disclosed compounds and/or salts, and, optionally, in combination with one or more additional therapeutic agents to prepare a medicament. In some embodiments, the medicament is for co-administration with one or more additional therapeutic agents.

In some embodiments, the medicament is for inhibiting replication of an RNA virus.

In some embodiments, the medicament is for treating RSV.

In embodiments, one or more of the disclosed compounds and/or salts may be used to prevent and/or treat RSV infections caused by one or both groups A or B RSV virus.

In embodiments, one or more of the disclosed compounds and/or salts may be used to inhibiting infection and/or replication of one or both of group A or group B RSV virus.

This disclosure also is directed, in part, to one or more of the disclosed compounds and/or salts of the present disclosure, and, optionally, in combination with one or more additional therapeutic agents, for use in inhibiting replication of an RNA virus and/or for use in treating RSV infection.

BIOLOGICAL ASSAYS

Cells and Virus

HEp-2 cells and RSV (Group A, Long Strain) were obtained from the American Type Culture Collection (Manassas, Va.).

Antiviral Assay

A cytopathetic effect (CPE) protection assay was performed to determine the ability of a compound to protect the cells from viral infection and thus the CPE induced by viral infection. 96-Well plates were first seeded with 3×10 HEp-2 cells per well in Dulbecco's modified Eagle's medium (DMEM) containing 10% fetal bovine serum (FBS). One day after the cells were seeded, they were preincubated with serial dilutions of compounds prepared in 100 µL assay medium (DMEM mixed with F12 medium at a 1:1 ratio, supplemented with 2% FBS and 1 mM sodium pyruvate) for 1 hour at 37° C. 100 µL of assay medium containing 0.2 multiplicity of infection (MOI) of RSV was then added to each well of cells. In addition to wells containing infected cells incubated with compounds, each plate also contained replicates of two kinds of controls: (1) Virus control contained cells infected with 0.2 MOI of RSV in assay medium, (2) Uninfected cell control contained cells incubated with assay medium only. After 4 days of incubation at 37° C., the viability of cells was assessed using MTT (Thiazolyl blue tetrazolium bromide, Sigma). A stock solution of MTT, at a concentration of 4 mg/mL in phosphate-buffered saline, was added to all wells at 25 µL per well. Plates were further incubated for 4 hours, and each well was then treated with 50 µL of a solution containing 20% sodium dodecyl sulfate (SDS) and 0.02 N HCl. After an overnight incubation, the plates were measured on a BioTek® microtiter plate reader at wavelengths of 570 nm and 650 nm. The MTT detection is based on the fact that viable (uninfected) cells can reduce the tetrazolium salts into colored formazan products, which can then be quantitated by spectrometry. Based on the spectrometric absorbance of each sample, the percent of protection from CPE, which is an indicator of protection from viral infection, can be calculated for each compound and the 50% effective concentrations ($EC_{50}$) can be calculated using a nonlinear regression curve fitting equation provided by the GraphPad Prism® 4 software. Using the above-described assay, compounds of the present disclosure showed obvious inhibitory activities against RSV replication. Results are shown in Table 1.

TABLE 1

| Example | RSV $EC_{50}$ (µM) |
|---|---|
| 1.1 | 0.89 |
| 1.2 | 1.13 |

TABLE 1-continued

| Example | RSV EC$_{50}$ (µM) |
|---|---|
| 1.3 | 0.25 |
| 1.4 | 1.14 |
| 1.5 | 0.81 |
| 1.6 | 1.59 |
| 1.7 | 0.83 |
| 1.8 | 0.45 |
| 1.9 | 4.09 |
| 1.10 | 0.43 |
| 1.11 | 1.41 |
| 1.12 | >32 |
| 1.13 | 0.20 |
| 1.14 | >10 |
| 1.15 | >10 |
| 1.16 | >10 |
| 1.17 | 0.54 |
| 1.18 | 1.16 |
| 1.19 | 0.15 |
| 1.20 | >10 |
| 1.21 | 2.07 |
| 1.22 | 0.40 |
| 1.23 | >10 |
| 1.24 | >6.68 |
| 1.25 | >7.29 |
| 1.26 | >10 |
| 1.27 | >10 |
| 1.28 | 3.1 |
| 1.29 | >3.16 |
| 1.30 | >10 |
| 1.31 | 2 |
| 1.32 | >10 |
| 1.33 | 0.3 |
| 1.34 | >3.1 |
| 1.35 | >10 |
| 1.36 | >6.6 |
| 1.37 | 0.4 |
| 1.38 | >3.1 |
| 1.39 | >10 |
| 1.40 | >10 |
| 1.41 | 1.22 |
| 1.42 | >10 |
| 1.43 | >10 |
| 1.44 | 0.12 |
| 1.45 | >10 |
| 1.46 | >10 |
| 1.47 | >1.38 |
| 1.48 | 1.34 |
| 1.49 | >3.2 |
| 1.50 | >3.2 |
| 1.51 | 0.69 |
| 1.52 | >10 |
| 1.53 | >10 |
| 1.54 | 0.26 |
| 1.56 | 1.6 |
| 1.57 | 0.29 |
| 1.58 | >3.2 |
| 1.59 | >3.2 |
| 1.60 | 1.05 |
| 1.61 | >6.6 |
| 1.62 | >32 |
| 1.63 | >10 |
| 1.64 | >10 |
| 1.65 | 5.9 |
| 1.66 | 1.5 |
| 1.67 | 0.36 |
| 1.68 | >10 |
| 1.69 | 2.99 |
| 1.70 | >10 |
| 1.72 | >5.37 |
| 1.73 | >10 |
| 1.74 | >61.7 |
| 1.75 | 3.4 |
| 2.1 | >10 |
| 3.1 | >32 |

Cytotoxicity Assay

Cytotoxicity of the compounds was determined in experiments done in parallel with the antiviral assays. To do this, 100 µL of assay medium was added to the wells of HEp-2 cells pretreated with 100 µL serially diluted compounds as described above. After 4 days of incubation, the viability of the cells was determined by the MT assay in the same way as detailed in the "Antiviral Assay" method. Results were expressed as 50% toxicity dose (TD$_{50}$) values. Results are shown in Table 2.

Compound Testing Strategy

Compounds were tested to determine both their antiviral and toxicity to determine their therapeutic window. Determination of the EC$_{50}$ and TD$_{50}$ of these active compounds were repeated one additional time to confirm the window. Results are shown in Table 2.

TABLE 2

| Example | RSV EC$_{50}$ (µM) | MTT TD$_{50}$ (µM) | Window (TD$_{50}$/EC$_{50}$) |
|---|---|---|---|
| 1.1 | 0.89 | >100 | >112 |
| 1.2 | 1.13 | >100 | >88 |
| 1.3 | 0.25 | >32 | >128 |
| 1.4 | 1.14 | 28.85 | 25 |
| 1.5 | 0.81 | >10 | >12.3 |
| 1.6 | 1.87 | >10 | >5.3 |
| 1.7 | 0.83 | >10 | >12 |
| 1.8 | 0.3 | >100 | >333 |
| 1.9 | 4.09 | >100 | >24 |
| 1.10 | 0.43 | >100 | >233 |
| 1.11 | 1.91 | >100 | >52 |
| 1.13 | 0.20 | >38.6 | >193 |
| 1.19 | 0.15 | >27.49 | >183 |
| 1.44 | 0.12 | 42.06 | 351 |
| 1.54 | 0.26 | >29.31 | >113 |

General Synthesis

Additional information about the preparation of compounds of formula (I), formula (II), formula (III), and formula (IV) (and their salts) is provided in the general discussion and/or specific synthesis examples below. In the discussion below, Ar$^1$ and Ar$^2$ have the meaning discussed above unless otherwise stated. LG means a leaving group such as halogen.

The disclosed compounds may be made by methods known in the art including the methods described below and variations thereof.

In the Schemes below, compounds are shown wherein an aromatic ring (e.g., phenyl) is substituted with groups in a particular regiochemistry (e.g., ortho). A starting material or intermediate with ortho-substitution provides a final product with ortho-substitution in the Schemes. It is understood by one of skill in the art that substitution in the Schemes of a starting material or intermediate with a different regiochemistry (e.g., meta) would provide a final product with a different regiochemistry. For example, replacement of an ortho-substituted starting material or intermediate in the Schemes with a meta substituted starting material or intermediate would lead to a meta-substituted product.

If a moiety described herein (e.g., —NH$_2$ or —OH) is not compatible with the synthetic methods, the moiety may be protected with a suitable protecting group that is stable to the reaction conditions used in the methods. The protecting group may be removed at any suitable point in the reaction sequence to provide a desired intermediate or target compound. Suitable protecting groups and methods for protecting or deprotecting moieties are well known in the art, examples of which can be found in Greene TW and Wuts PGM, *Protective Groups in Organic Synthesis*, (3$^{rd}$ ed., John Wiley & Sons, NY (1999)). Optimum reaction conditions and reaction times for each individual step may vary depending on the particular reactants employed and substituents present in the reactants used. Solvents, temperatures and other reaction conditions may be readily selected by one of ordinary skill in the art based on the present disclosure.

Other disclosed compounds can be similarly prepared according to the Schemes below as well as the procedures described in the following disclosure of intermediates, procedures, and examples as appreciated by those skilled in the art. It should be understood that the above-described embodiments and schemes and the following intermediates, general procedures, and examples disclosure are given by way of illustration, not limitation. Various changes and modifications within the scope of the present disclosure will become apparent to those skilled in the art from the present description.

Intermediate Compounds

This disclosure also is directed, in part, to intermediates that correspond in structure to formula (V) that can be used to prepare the compounds of formula (I), formula (II), formula (III) and formula (IV) (and their salts):

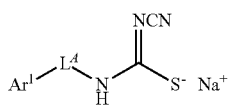
(V)

In formula (V), $Ar^1$ and $L^a$ are as discussed above for the compounds of formula (I), formula (II), formula (III) and formula (IV).

In various embodiments, the compounds of formula (V) correspond in structure to formula (Va).

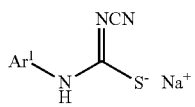
(Va)

In various embodiments, the compounds of formula (V) correspond in structure to formula (Vb).

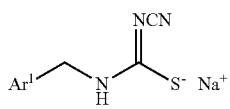
(Vb)

In some embodiments of the compounds of formula (V):
$Ar^1$ is phenyl or monocyclic heteroaryl having a structure corresponding to a formula selected from the group consisting of:

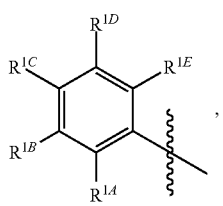
(i-1)

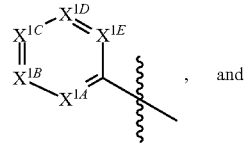
(i-2)

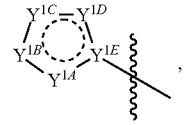
(i-3)

wherein, $R^{1A}$ is selected from the group consisting of hydrogen; amino; hydroxyl; cyano; halo; $C_1$-$C_6$alkyl; $C_1$-$C_6$alkenyl; $C_1$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-$NR^{5'}$—C(O)—$R^{6'}$, wherein $L^4$ is a bond or alkylene, $R^{3'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl;

$R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl; or $R^{1B}$ and $R^{1C}$, or $R^{1C}$ and $R^{1D}$, or $R^{1D}$ and $R^{1E}$ taken together are —O—$CH_2$—O—;

$X^{1A}$, $X^{1B}$, $X^{1C}$, $X^{1D}$ and $X^{1E}$ are $CR^{1AX}$, $CR^{1BX}$, $CR^{1CX}$, $CR^{1DX}$ and $CR^{1EX}$, respectively, or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl;

$Y^{1A}$, $Y^{1B}$, $Y^{1C}$, and $Y^{1D}$ are $CR^{1AY}$ or $NR^{1AY}$, $CR^{1BY}$ or $NR^{1BY}$, $CR^{1CY}$ or $NR^{1CY}$, $CR^{1DY}$ or $NR^{1DY}$, respectively, or N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S;

$Y^{1E}$ is N or C;

wherein 1, 2, 3, or 4 ring atoms of (i-3) is a heteroatom;

$R^{1AY}$, $R^{1BY}$, $R^{1CY}$, and $R^{1DY}$ are each independently selected from the group consisting of hydrogen; amino; hydroxyl; cyano; halo; $C_1$-$C_6$alkyl; $C_1$-$C_6$alkenyl; $C_1$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—OR$^{1'}$ or -$L^1$-S(O)$_2$R$^{1'}$, wherein $L^1$ is a bond or alkylene, and $R^{1'}$ is hydrogen, $C_1$-$C_6$alkyl or hydroxyalkyl; -$L^2$-O—C(O)—R$^{2'}$, wherein $L^2$ is a bond or alkylene, and $R^{2'}$ is $C_1$-$C_6$alkyl or hydroxyalkyl; -$L^3$-C(O)—NR$^{3'}$R$^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-NR$^{5'}$—C(O)—R$^{6'}$, wherein $L^4$ is a bond or alkylene, $R^{5'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl; and $L^A$ is a bond or CR$^a$R$^b$, wherein $R^a$ and $R^b$ are independently hydrogen or alkyl.

This disclosure also is directed, in part, to intermediates that correspond in structure to formula (VI) that can be used to prepare the compounds of formula (I) and formula (II) (and their salts):

    (VI)

In formula (VI), $R^1$ and Ar$^2$ are as discussed above for the compounds of formula (I) and formula (II).

In some embodiments of the compounds of formula (VI):

$R^1$ is selected from the group consisting of:

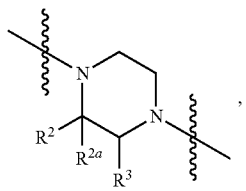    (ii-1)

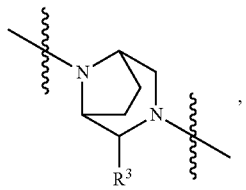    (ii-2)

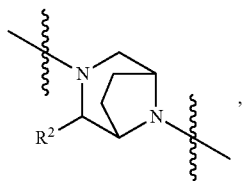    (ii-3)

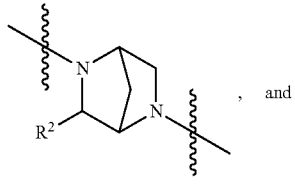    (ii-4) , and

-continued

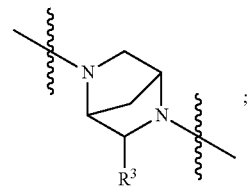    (ii-5)

wherein $R^2$, $R^{2a}$, and $R^3$ are each independently selected from the group consisting of hydrogen, $C_1$-$C_6$alkyl, $C_1$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$alkyl-; wherein when both $R^2$ and $R^3$ are present, one or both of $R^2$ and $R^3$ are hydrogen; or $R^2$, $R^{2a}$, and the carbon atom to which they are attached form a $C_3$-$C_6$cycloalkyl and $R^3$ is hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—R$^f$, —CN, —N(R$^f$)C(O)R$^f$, —CON(R$^e$)(R$^f$), —C(O)R$^f$, —OC(O)R$^f$, —CO$_2$R$^f$—N(R$^f$)C(O)N(R$^f$), —S—R$^f$, —S(O)$_2$R$^f$—S(O)R$^f$, —SO$_2$N(R$^e$)(R$^f$), —N(R$^e$)(R$^f$), —N(R$^f$)S(O)$_2$R$^f$, N(R$^f$)C(O)O(R$^f$), -L$^c$-O—R$^f$, -L$^c$-CN, -L$^c$-N(R$^f$)C(O)R$^f$, -L$^c$-CON(R$^e$)(R$^f$), -L$^c$-C(O)R$^f$, -L$^c$-OC(O)R$^f$, -L$^c$-CO$_2$H, -L$^c$-CO$_2$R$^f$, -L$^c$-N(R$^f$)C(O)N(R$^f$)$_2$, -L$^c$-S—R$^f$, -L$^c$-S(O)$_2$R$^f$, - L$^c$-S(O)R$^f$, -L$^c$-SO$_2$N(R$^e$)(R$^f$), -L$^c$-N(R$^e$)(R$^f$), -L$^c$-N(R$^f$)S(O)$_2$R$^f$, and -L$^c$-N(R$^f$)C(O)O(R$^f$);

L$^c$, at each occurrence, is independently $C_1$-$C_6$alkylene or $C_3$-$C_8$cycloalkyl, wherein L$^c$ at each occurrence, is optionally substituted with 1, 2, 3, or 4 halogen or 1 or 2 hydroxy;

R$^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

R$^f$ is at each occurrence independently selected from the group consisting of hydrogen, $C_1$-$C_6$alkyl, and $C_1$-$C_6$haloalkyl;

Ar$^2$ is selected from the group consisting of:

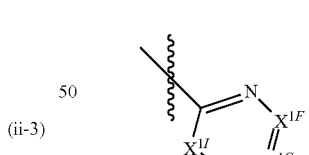    (iii-1)

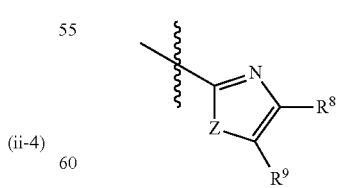    (iii-2)

$X^{1F}$, $X^{1G}$, $X^{1H}$, and $X^{1I}$ are CR$^4$, CR$^5$, CR$^6$ and CR$^7$, respectively, or N; wherein 0, 1 or 2 of $X^{1F}$, $X^{1G}$, $X^{1H}$, and $X^{1I}$ are N; wherein $R^4$, $R^5$, $R^6$ and $R^7$ are each independently selected from the group consisting of hydrogen, cyano, halo, $C_1$-$C_6$alkyl, alkoxy, amino, alkylamino, cycloalkylamino, dialkylamino, cycloalkyl, heterocyclyl, haloalkoxy, haloalkyl, —OR$^f$, and —CO$_2$R$^f$; or R$^4$ and R$^5$; R$^5$ and R$^6$; or R$^6$ and R$^7$ and the atoms to which they are attached taken together form a fused phenyl ring, pyrrole, pyridine, or pyrazine optionally substituted with 1, 2, 3, or 4 substituents selected from the group consisting of cyano, halo, C$_1$-C$_6$alkyl, amino, alkylamino, dialkylamino, cycloalkyl, heterocyclyl, haloalkoxy, haloalkyl, —OR$^f$, and —CO$_2$R$^f$;

wherein Z is selected from the group consisting of O, S, and NR$^e$; and

R$^8$ and R$^9$ are each independently selected from the group consisting of hydrogen, cyano, halo, C$_1$-C$_6$alkyl, amino, alkylamino, dialkylamino, cycloalkyl, heterocyclyl, haloalkoxy, haloalkyl, —OR$^f$, and —CO$_2$R$^f$; or R$^8$ and R$^9$ and the atoms to which they are attached taken together form a fused phenyl ring optionally substituted with 1, 2, 3, or 4 substituents selected from the group consisting of cyano, halo, C$_1$-C$_6$alkyl, amino, alkylamino, dialkylamino, cycloalkyl, heterocyclyl, haloalkoxy, haloalkyl, —OR$^f$, and —CO$_2$R$^f$.

In various embodiments, the compounds of formula (VI) correspond in structure to formula (VII).

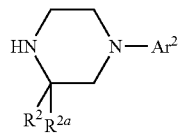

(VII)

In formula (VII), Ar$^2$ is as discussed above for the compounds of formula (I) and formula (II).

In some embodiments of the compounds of formula (VII): wherein R$^2$ and R$^{2a}$ are each independently selected from the group consisting of hydrogen, C$_1$-C$_6$alkyl, C$_1$-C$_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, G$^1$, G$^2$, and G$^2$alkyl-; or R$^2$, R$^{2a}$, and the carbon atom to which they are attached form a C$_3$-C$_6$cycloalkyl;

G$^1$ is aryl or heteroaryl, and G$^2$ is C$_3$-C$_6$cycloalkyl, wherein the aryl, the heteroaryl and the C$_3$-C$_6$cycloalkyl are optionally substituted with 1, 2, 3, 4, or 5 substituents selected from the group consisting of halogen, C$_1$-C$_6$alkyl, C$_1$-C$_6$haloalkyl, —O—R$^f$, —CN, —N(R$^f$)C(O)R$^f$, —CON(R$^e$)(R$^f$), —C(O)R$^f$, —OC(O)R$^f$, —CO$_2$R$^f$, —N(R$^f$)C(O)N(R$^f$)$_2$, —S—R$^f$, —S(O)$_2$R$^f$, —S(O)R$^f$, —SO$_2$N(R$^e$)(R$^f$), —N(R$^e$)(R$^f$), —N(R$^f$)S(O)$_2$R$^f$, N(R$^f$)C(O)O(R$^f$), -L$^c$-O—R$^f$, -L$^c$-CN, -L$^c$-N(R$^f$)C(O)R$^f$, -L$^c$-CON(R$^e$)(R$^f$), -L$^c$-C(O)R$^f$, -L$^c$-OC(O)R$^f$, -L$^c$-CO$_2$H, -L$^c$-CO$_2$R$^f$, -L$^c$-N(R$^f$)C(O)N(R$^f$)$_2$, -L$^c$-S—R$^f$, -L$^c$-S(O)$_2$R$^f$, -L$^c$-S(O)R$^f$, -L$^c$-SO$_2$N(R$^e$)(R$^f$), -L$^c$-N(R$^e$)(R$^f$), -L$^c$-N(R$^f$)S(O)$_2$R$^f$, and -L$^c$-N(R$^f$)C(O)O(R$^f$);

L$^c$, at each occurrence, is independently C$_1$-C$_6$alkylene or C$_3$-C$_8$cycloalkyl, wherein L at each occurrence, is optionally substituted with 1, 2, 3, or 4 halogen or 1 or 2 hydroxy;

R$^e$, at each occurrence, is independently selected form the group consisting of hydrogen, C$_1$-C$_6$alkyl, C$_1$-C$_6$haloalkyl, and C$_3$-C$_8$cycloalkyl, wherein the C$_3$-C$_8$cycloalkyl is optionally substituted with 1, 2, 3, or 4 substituents selected from the group consisting of halogen, oxo, C$_1$-C$_3$alkyl, and C$_1$-C$_3$haloalkyl;

R$^f$ is at each occurrence independently selected from the group consisting of hydrogen, C$_1$-C$_6$alkyl, and C$_1$-C$_6$haloalkyl; and Ar$^2$ is selected from the group consisting of:

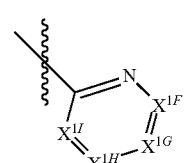

(iii-1)

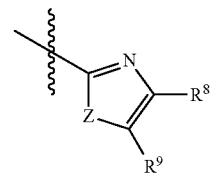

(iii-2)

X$^{1F}$, X$^{1G}$, X$^{1H}$, and X$^{1I}$ are CR$^4$, CR$^5$, CR$^6$ and CR$^7$, respectively, or N; wherein 0, 1 or 2 of X$^{1F}$, X$^{1G}$, X$^{1H}$, and X$^{1I}$ are N; wherein R$^4$, R$^5$, R$^6$ and R$^7$ are each independently selected from the group consisting of hydrogen, cyano, halo, C$_1$-C$_6$alkyl, alkoxy, amino, alkylamino, cycloalkylamino, dialkylamino, cycloalkyl, heterocyclyl, haloalkoxy, haloalkyl, —OR$^f$, and —CO$_2$R$^f$; or R$^4$ and R$^5$; R$^5$ and R$^6$; or R$^6$ and R$^7$ and the atoms to which they are attached taken together form a fused phenyl ring, pyrrole, pyridine, or pyrazine optionally substituted with 1, 2, 3, or 4 substituents selected from the group consisting of cyano, halo, C$_1$-C$_6$alkyl, amino, alkylamino, dialkylamino, cycloalkyl, heterocyclyl, haloalkoxy, haloalkyl, —OR$^f$, and —CO$_2$R$^f$;

wherein Z is selected from the group consisting of O, S, and NR$^e$; and

R$^8$ and R$^9$ are each independently selected from the group consisting of hydrogen, cyano, halo, C$_1$-C$_6$alkyl, amino, alkylamino, dialkylamino, cycloalkyl, heterocyclyl, haloalkoxy, haloalkyl, —OR$^f$, and —CO$_2$R$^f$; or R$^8$ and R$^9$ and the atoms to which they are attached taken together form a fused phenyl ring optionally substituted with 1, 2, 3, or 4 substituents selected from the group consisting of cyano, halo, C$_1$-C$_6$alkyl, amino, alkylamino, dialkylamino, cycloalkyl, heterocyclyl, haloalkoxy, haloalkyl, —OR$^f$, and —CO$_2$R$^f$.

EXAMPLES

Abbreviations: APCI for atmospheric pressure chemical ionization; Cbz-O-Su for N-(benzyloxycarbonyloxy)succinimide; DIAD for diisopropylazodicarboxylate; DMF for N,N-dimethylformamide; DMSO for dimethyl sulfoxide; EDCI for N-(3-dimethylaminopropyl)-N''-ethylcarbodiimide hydrochloride; ESI for electrospray ionization; Et for ethyl; EtOH for ethanol; HOAc for acetic acid; HPLC for high performance liquid chromatography; iPr for isopropyl; LCMS for liquid chromatography mass spectroscopy; PG for protecting group; Ph for phenyl; PhthH for phthalimide; PPh$_3$ for triphenylphosphine; psi for pounds per square inch; RP-HPLC for reverse-phase HPLC; and R$_t$ for retention time.

Synthetic Details

Analytical data is included either in the illustrations of the general procedures or in the tables of examples. Unless otherwise stated, all $^1$H or $^{13}$C NMR data were collected on a Varian Mercury Plus 400 MHz or a Bruker DRX 400 MHz instrument; chemical shifts are quoted in parts per million (ppm). High performance liquid chromatography (HPLC) analytical data are either detailed within the experimental or referenced to the Table of HPLC and LCMS conditions, using the lower case method letter (Table 3).

TABLE 3

HPLC and LCMS conditions

| Method | Conditions<br>Unless indicated otherwise, mobile phase A was 10 mM ammonium acetate, mobile phase B was HPLC grade acetonitrile for purification methods described in Table 4. |
|---|---|
| a | 30% to 95% B over 2.0 minutes; 95% B for 1.5 minutes at 1.0 mL/minute; UV λ = 210-360 nm; Vydac® Genesis® C8, 4 μm, 30 × 4.6 mm column; ESI +ve/−ve. |
| b | 10-100% acetonitrile/0.1% aqueous trifluoroacetic acid at 2 mL/minute; C8, 2 × 50 mm column at 55° C.; APCI +ve. |

List of General Procedures
General Procedure A: Heteroarylamine formation from a haloheteroarene
General Procedure B: Cyanoguanidine formation from an isothiocyanate
General Procedure C: Cyanoguanidine formation from N'-cyano-carbamimidate
General Procedure D: Heteroarylamine formation from a haloheteroarene and a N'-cyanoguanidine-amine The general synthetic schemes that were utilized to construct compounds disclosed in this application are described below in (Schemes 1 and 2).

The general procedure letter codes constitute a synthetic route to the final product.
General Procedure A: Heteroarylamine Formation from a Haloheteroarene The haloheteroarene (1.0-1.5 equivalents, preferably 1.0 equivalent) is added to the amine (1 equivalent) in an organic solvent (for example tetrahydrofuran, dichloromethane, N,N-dimethylformamide, acetonitrile or 1-propanol, preferably 1-propanol). The mixture is stirred at 25-170° C. (preferably at ambient temperature). An oil bath or a microwave oven can be used for heating if necessary for 0.3-18 hours (preferably 0.3 or 6 hours). The product is purified by chromatography or by filtration of the precipitate.

Illustration of General Procedure A

Preparation of
2-(3-isopropylpiperazin-1-yl)-1,3-benzoxazole

At ambient temperature, 2-chlorobenzoxazole (1.81 mL, 15.60 mmol) was added to a solution of 2-isopropylpiperazine (2.00 g, 15.60 mmol) in dichloromethane (20 mL). The reaction was stirred at ambient temperature for 0.5 hour before it was diluted with brine. The organic layer was separated and was dried with sodium sulfate. The solvent was removed in vacuo before the product was purified by silica gel chromatography using 3% methanol in dichloromethane to give the titled compound (1.69 g, 6.89 mmol): $^1$HNMR (DMSO-$d_6$, 400 MHz) δ ppm 7.38 (m, 1H), 7.27 (m, 1H), 7.14 (m, 1H), 7.00 (m, 1H), 3.97 (m, 2H), 3.00 (m, 2H), 2.79 (t, 1H), 2.68 (m, 1H), 2.36 (m, 1H), 1.60 (m, 1H), 0.95 (m, 6H); RP-HPLC (Method a)$R_t$ 1.00 minute; MS (ESI) m/z 246 (M+H).

General Procedure B: Cyanoguanidine Formation from an Isothiocyanate

At ambient temperature, the isothiocyanate (1.0-1.2 equivalents, preferably 1.0 equivalent) is added to a suspension of the sodium hydrogen cyanamide (1.0-1.2 equivalents, preferably 1.0 equivalent) in an organic solvent (for example tetrahydrofuran, N,N-dimethylformamide or ethanol, preferably N,N-dimethylformamide). The mixture is allowed to stir at ambient temperature for 0.2-4.0 hours (preferably 0.5 hours) before the addition of zinc dichloride (0-1 equivalents, preferably 1 equivalent or 0 equivalents). At ambient temperature, N-(3-dimethylaminopropyl)-N'-ethylcarbodiimide hydrochloride (1.0-1.2 equivalents, preferably 1.1 equivalents) is premixed with the amine (1.0 equivalent) in an organic solvent (for example tetrahydrofuran, N,N-dimethylformamide or ethanol, preferably N,N-dimethylformamide) before it is added to the reaction dropwise. The reaction is allowed to stir at ambient temperature for 1-18 hours (preferably 6 hours). For reactions containing zinc dichloride, the reaction is partitioned with organic solvent (for example dichloromethane or ethyl acetate, preferably dichloromethane) and brine. The organic layer is dried with sodium sulfate or magnesium sulfate before it is filtered. The solvent is removed in vacuo before the product(s) are purified by chromatography.

Illustration of General Procedure B

Example 1.4 Preparation of 4-(1,3-benzoxazol-2-yl)-N'-cyano-2-isopropyl-N-(2-methylphenyl)piperazine-1-carboximidamide Sodium hydrogen cyanamide (0.026 g, 0.41 mmol) was dissolved in N,N-dimethylformamide (1 mL) and the solution of 1-isothiocyanato-2-methylbenzene (0.061 g, 0.41 mmol) in N,N-dimethylformamide (1 mL) was added at ambient temperature. The mixture was stirred under a continuous nitrogen flow for 20 minutes, and the solution of N-(3-dimethylaminopropyl)-N'-ethylcarbodiimide hydrochloride (0.079 g, 0.41 mmol) and 2-(3-isopropylpiperazin-1-yl)-1,3-benzoxazole (0.1 g, 0.41 mmol) in N,N-dimethylformamide (1 mL) was added dropwise. Stirring at ambient temperature was continued for another 3 hours; the mixture was concentrated, and the residue was subjected to purification by reverse-phase HPLC on a Hyperprep™ HS C18 column, 8 μm, 250×21.2 mm; 20% acetonitrile-50 mM ammonium acetate over 1 minute, 40-70% acetonitrile-50 mM ammonium acetate for 30 minutes, 60-100% acetonitrile for 1 minute, 100% acetonitrile for 5 minutes, 25 mL/minute. The product was isolated by lyophilization of the desired fractions to give the titled compound (0.027 mg, 0.067 mmol) as an off-white solid: $^1$HNMR (DMSO-$d_6$, 400 MHz) δ ppm 7.42 (d, 1H), 7.30 (d, 1H), 7.23-7.02 (m, 6H), 4.27 (d, 1H), 4.12 (m, 3H), 3.3 (m, 3H), 2.23 (s, 3H), 2.12 (m, 1H), 1.03 (d, 3H), 0.90 (d, 3H), RP-HPLC (Method a) $R_t$ 1.97 minutes; MS (ESI) m/z 403 (M+H)$^+$.
General Procedure C: Cyanoguanidine Formation from an N-cyano-carbamimidate A mixture of a cyclic diamine (1.0 equivalent) and N-(benzyloxycarbonyloxy)succinimide (1.0 equivalent) is stirred in an organic solvent (for example dichloromethane or tetrahydrofuran) for 4-24 hours. The organic phase is washed with saturated aqueous sodium bicarbonate and brine, dried over anhydrous magnesium sulfate, filtered and concentrated to yield the mono-protected cyclic amine.

The mono-protected cyclic amine (1.0 equivalent) and phenyl N'-cyano-N—Ar$^1$-carbamimidate (WO 2008005368) (1 equivalent) are dissolved in an organic solvent (for example acetonitrile). The reaction mixture is stirred at room temperature for 8-24 hours (preferably 16 hours) and then heated at 60-75° C. (preferably 70° C.) for 24-96 hours (preferably 72 hours). The reaction mixture is concentrated and the residue purified by silica gel chromatography.

The carboxybenzyl-protected compound is dissolved in ethanol, 10% palladium on carbon is added, and the mixture is hydrogenated under 20-60 psi (preferably 50 psi) of hydrogen pressure for 4-24 hours (preferably 16 hours). The catalyst is removed by filtration through a pad of diatomaceous earth, and the filtrate is concentrated to yield the crude deprotected amine. The crude material may be purified or preferably used as is.

Illustration of General Procedure C

Preparation of N'-cyano-2-isopropyl-N-(o-tolyl) piperazine-1-carboximidamide

A mixture of 2-isopropylpiperazine (8 g, 62.4 mmol) and N-(benzyloxycarbonyloxy)succinimide (15.55 g, 62.4 mmol) was stirred in dichloromethane (200 mL) for 16 hours. The organic phase was washed with saturated aqueous sodium bicarbonate (2×100 mL) and brine (1×150 mL), dried over anhydrous magnesium sulfate, filtered and concentrated to yield benzyl 3-isopropylpiperazine-1-carboxylate as an amorphous solid.

Benzyl 3-isopropylpiperazine-1-carboxylate (4.75 g) and phenyl N'-cyano-N-o-tolylcarbamimidate (WO 2008005368) (4.96 g, 18.92 mmol) were dissolved in acetonitrile (100 mL). The reaction mixture was stirred at room temperature for 16 hours and then heated at 70° C. for 72 hours. It was concentrated and purified by silica gel column chromatography (ethyl acetate:heptane=1:2 to ethyl acetate:heptane=2:3 over 40 minutes) to yield benzyl 4-(N'-cyano-N-o-tolylcarbamimidoyl)-3-isopropylpiperazine-1-carboxylate (4.4 g, 55% yield) as an off-white solid: LCMS (Method b) $R_t$=2.04 minutes; MS (APCI) m/z 420 (M+H)$^+$.

4-(N'-Cyano-N-o-tolylcarbamimidoyl)-3-isopropylpiperazine-1-carboxylate (4.2 g, 10 mmol) was dissolved in ethanol (150 mL), 10% palladium on carbon (0.6 g) was added, and the mixture was hydrogenated under 50 psi of hydrogen pressure for 16 hours. The catalyst was removed by filtration through a pad of diatomaceous earth, and the filtrate was concentrated to yield the titled compound (2.8 g, 99% yield) as an amorphous solid: LCMS (Method a) $R_t$=1.14 minutes; MS (ESI) m/z 284 (M–H)$^-$.

General Procedure D: Heteroarylamine Formation from a Haloheteroarene and a N-cyanoguanidine-amine The haloheteroarene (1.0-1.5 equivalents, preferably 1.0 equivalent) is added to the amine (1 equivalent) in an organic solvent (for example tetrahydrofuran, dichloromethane, N,N-dimethylformamide, acetonitrile or 1-propanol, preferably 1-propanol) and in the presence of a non-nucleophilic amine (for example triethylamine or N,N-diisopropylethylamine). The mixture is stirred at 25-120° C. (preferably at 78° C.). An oil bath or a microwave oven can be used for heating if necessary for 0.3-18 hours (preferably 10 hours). The product is purified by chromatography.

Illustration of General Procedure D

Example 1.10 Preparation of N'-cyano-2-isopropyl-N-(2-methylphenyl)-4-(4-oxo-3,4-dihydroquinazolin-2-yl)piperazine-1-carboximidamide The mixture of N'-cyano-2-isopropyl-N-o-tolylpiperazine-1-carboximidamide (0.339 g, 1.19 mmol), 2-chloroquinazolin-4-ol (0.215 g, 1.19 mmol) and triethylamine (0.83 mL, 5.95 mmol) was heated in ethanol at reflux for 10 hours. The reaction mixture was concentrated and the residue purified by reverse-phase HPLC on a Hyperprep™ HS C18 column, 8 µm, 250×21.2 mm; 20% acetonitrile-50 mM ammonium acetate over 1 minute, 30-60% acetonitrile-50 mM ammonium acetate for 30 minutes, 60-100% acetonitrile for 1 minute, 100% acetonitrile for 5 minutes, 25 mL/minute. The product was isolated by lyophilization of the desired fractions to give the titled compound (0.027 g, 3.3%) as a white solid: LCMS (Method a) $R_t$=1.51 minutes; MS (ESI) m/z 430 (M+H)$^+$.

Preparation of Intermediates

Preparation of 2-isopropylpiperazine

2-Isopropylpyrazine (50 g, 409.3 mmol) was dissolved in ethanol (200 mL), palladium on carbon (10% by weight, 4 g) was added, and the reaction mixture was hydrogenated at 50 psi over 48 hours. The reaction mixture was filtered through a pad of diatomaceous earth and concentrated under reduced pressure to yield the titled compound (45.4 g, 86.5%) as an off-white solid: $^1$H NMR (DMSO-d$_6$) δ ppm 2.74 (m, 2H), 2.64 (m, 1H), 2.57 (m, 1H), 2.41 (m, 1H), 2.15 (m, 2H), 1.41 (m, 1H), 0.84 (dd, 6H).

Preparation of 2-chloroquinazolin-4-ol 2,4-Dichloroquinazoline (0.6 g, 3.01 mmol) was triturated in 2% NaOH (20 mL) and stirred at ambient temperature for 3 hours. The insoluble residue was removed by filtration, and the filtrate was neutralized by the slow addition of acetic acid. The precipitate was collected by filtration and dried under reduced pressure to yield the titled compound (0.45 g, 84% yield) as a white solid. LCMS (Method a) $R_t$=1.14 minutes; MS (ESI) m/z 179 (M–H)$^-$.

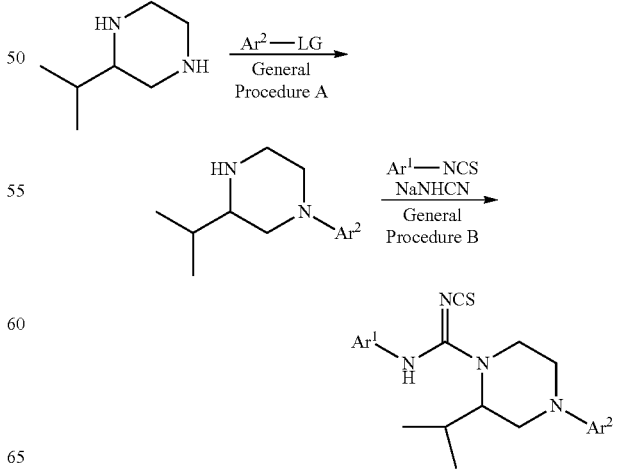

Scheme 1: 2-Isopropyl-heteroarenes

Scheme 2: 2-Isopropyl-heteroarenes

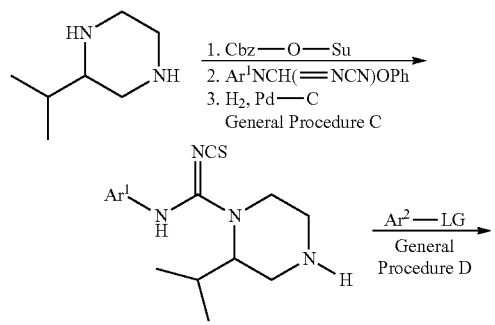

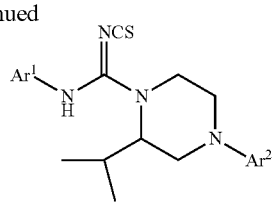

The compounds in Table 4 were made according to general procedure A followed by general procedure B as illustrated in Scheme 1 or according to general procedure C followed by general procedure D as illustrated in Scheme 2.

TABLE 4

2-Isopropylpiperazine-heteroarenes

| Ex# | Ar²—LG | Ar¹—NCS or Ar¹NHC(=NCN)OPh | Product (Preparation Scheme) | Rt/min (method) | m/z |
|---|---|---|---|---|---|
| 1.1 | 3-chloro-2-cyanopyrazine | 2-methylphenyl NCS | (1) | 1.93 (a) | 387 (M − H)⁻ |
| 1.2 | methyl 5-chloropyrazine-2-carboxylate | 2-chlorophenyl NCS | (1) | 1.56 (b) | 442 (M + H)⁺ |
| 1.3 | 2-chloroquinoxaline | 2-methylphenyl NCS | (1) | 1.91 (a) | 412 (M − H)⁻ |
| 1.4 | 2-chlorobenzoxazole | 2-methylphenyl NCS | (1) | 1.97 (a) | 403 (M + H)⁺ |
| 1.5 | 2,7-dichlorobenzoxazole | 2-methylphenyl NCS | (1) | 2.36 (a) | 437 (M + H)⁺ |

TABLE 4-continued
2-Isopropylpiperazine-heteroarenes
| Ex# | Ar²—LG | Ar¹—NCS or Ar¹NHC(=NCN)OPh | Product (Preparation Scheme) | Rt/min (method) | m/z |
|---|---|---|---|---|---|
| 1.6 | 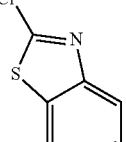 | 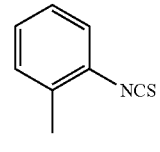 | 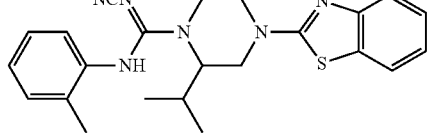<br>(1) | 2.20 (a) | 417 (M − H)⁻ |
| 1.7 | 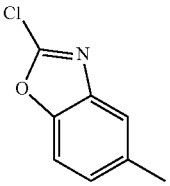 | 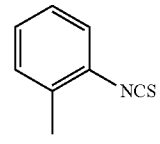 | 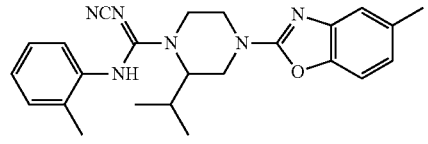<br>(1) | 2.17 (a) | 417 (M + H)⁺ |
| 1.8 | 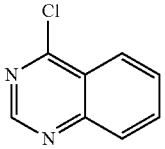 | 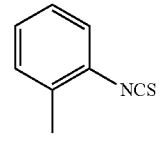 | 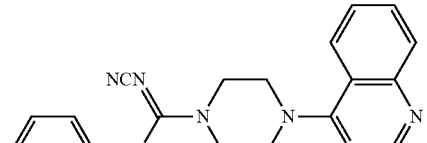<br>(1) | 1.95 (a) | 412 (M − H)⁻ |
| 1.9 | 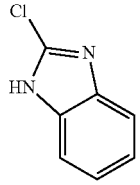 | 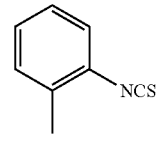 | 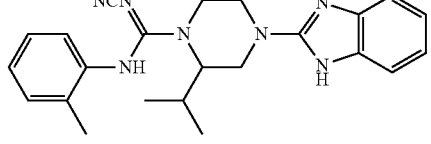<br>(1) | 2.11 (a) | 400 (M − H)⁻ |
| 1.10 | 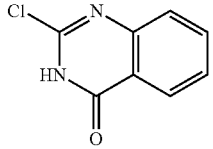 | 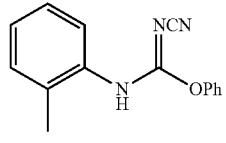 | 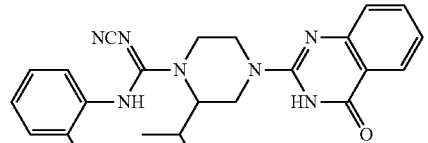<br>(2) | 1.37 (b) | 430 (M + H)⁺ |
| 1.11 | 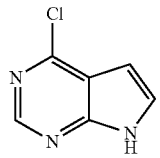 | 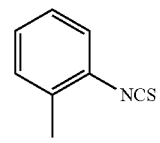 | 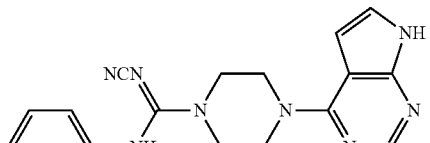<br>(1) | 1.65 (a) | 401 (M − H)⁻ |

N'-cyano-4-(3-cyanopyrazin-2-yl)-2-isopropyl-N-(2-methylphenyl)piperazine-1-carboximidamide $^1$H NMR (400 MHz, DMSO-d$_6$) δ ppm 10.98 (br s, 1H), 8.91 (br s, 1H), 8.00-7.84 (m, 1H), 7.66-7.54 (m, 1H), 7.34-7.03 (m, 6H), 4.65 (d, J=14.0 Hz, 1H), 4.41 (d, J=13.0 Hz, 1H), 4.20-3.81 (m, 2H), 3.25-3.15 (m, 1H), 3.15-2.99 (m, 2H), 2.23 (s, 3H), 2.03 (s, 1H), 1.02 (d, J=4.4 Hz, 3H), 0.88 (d, J=6.4 Hz, 3H).

Example 1.2 methyl 5-{4-[N-(2-chlorophenyl)-N'-cyanocarbamimidoyl]-3-isopropylpiperazin-1-yl}pyrazine-2-carboxylate $^1$H NMR (400 MHz, DMSO-d$_6$) δ ppm 9.28 (s, 1H), 8.67 (d, J=1.1 Hz, 1H), 8.46 (d, J=1.1 Hz, 1H), 7.55-7.44 (m, 1H), 7.31 (m, 3H), 4.72 (d, J=13.8 Hz, 1H), 4.45 (d, J=11.7 Hz, 1H), 3.82 (s, 3H), 3.41-3.14 (m, 5H), 2.06 (m, 1H), 1.04 (d, J=6.5 Hz, 3H), 0.90 (d, J=6.7 Hz, 3H).

Example 1.3

N'-cyano-2-isopropyl-N-(2-methylphenyl)-4-(quinoxalin-2-yl)piperazine-1-carboximidamide $^1$H NMR (400 MHz, DMSO-d$_6$) δ ppm 8.90 (br s, 1H), 8.87 (s, 1H), 7.84 (d, J=8.1 Hz, 1H), 7.60 (d, J=3.7 Hz, 2H), 7.46-7.36 (m, 1H), 7.29-7.04 (m, 4H), 4.81 (d, J=14.2 Hz, 1H), 4.58 (d, J=12.2 Hz, 1H), 4.24-3.85 (m, 2H), 3.30-3.22 (m, 1H), 3.22-3.10 (m, 2H), 2.24 (s, 3H), 2.15-1.98 (m, 1H), 1.04 (d, J=6.5 Hz, 3H), 0.89 (d, J=6.7 Hz, 3H).

Example 1.4

4-(1,3-benzoxazol-2-yl)-N'-cyano-2-isopropyl-N-(2-methylphenyl)piperazine-1-carboximidamide $^1$H NMR (400 MHz, DMSO-d$_6$) δ ppm 9.16-8.78 (m, 1H), 7.42 (d, J=8.0 Hz, 1H), 7.30 (d, J=7.8 Hz, 1H), 7.23 (d, J=7.2 Hz, 1H), 7.21-7.09 (m, 3H), 7.08-6.99 (m, 2H), 4.27 (d, J=13.5 Hz, 1H), 4.21-3.96 (m, 3H), 3.31-3.15 (m, 3H), 2.23 (s, 3H), 2.21-2.03 (m, 1H), 1.03 (d, J=6.5 Hz, 3H), 0.90 (d, J=6.7 Hz, 3H).

Example 1.5

4-(7-chloro-1,3-benzoxazol-2-yl)-N'-cyano-2-isopropyl-N-(2-methylphenyl)piperazine-1-carboximidamide $^1$H NMR (400 MHz, DMSO-d$_6$) δ ppm 9.06 (br s, 1H), 7.31-7.05 (m, 7H), 4.27 (d, J=13.9, 1H), 4.13 (m, 3H), 3.42-3.21 (m, 3H), 2.23 (s, 3H), 2.20-2.08 (m, 1H), 1.03 (d, J=6.5, 3H), 0.90 (d, J=6.7, 3H).

Example 1.6

4-(1,3-benzothiazol-2-yl)-N'-cyano-2-isopropyl-N-(2-methylphenyl)piperazine-1-carboximidamide $^1$H NMR (400 MHz, DMSO-d$_6$) δ ppm 8.99 (s, 1H), 7.81-7.73 (m, 1H), 7.46 (d, J=8.1 Hz, 1H), 7.32-7.03 (m, 6H), 4.23-3.94 (m, 4H), 3.37-3.32 (m, 3H), 2.23 (s, 3H), 2.20-2.09 (m, 1H), 1.04 (d, J=6.5 Hz, 3H), 0.90 (d, J=6.7 Hz, 3H).

Example 1.7

N'-cyano-2-isopropyl-4-(5-methyl-1,3-benzoxazol-2-yl)-N-(2-methylphenyl)piperazine-1-carboximidamide $^1$H NMR (400 MHz, DMSO-d$_6$) δ ppm 8.92 (br s, 1H), 7.29-7.05 (m, 6H), 6.84 (d, J=8.8 Hz, 1H), 4.25 (d, J=13.6 Hz, 1H), 4.16-3.88 (m, 3H), 3.29-3.18 (m, 3H), 2.33 (s, 3H), 2.23 (s, 3H), 2.19-2.05 (m, 1H), 1.02 (d, J=6.5 Hz, 3H), 0.90 (d, J=6.7 Hz, 3H).

Example 1.8

N'-cyano-2-isopropyl-N-(2-methylphenyl)-4-(quinazolin-4-yl)piperazine-1-carboximidamide Example 1.9

4-(1H-benzimidazol-2-yl)-N'-cyano-2-isopropyl-N-(2-methylphenyl)piperazine-1-carboximidamide Example 1.10

N'-cyano-2-isopropyl-N-(2-methylphenyl)-4-(4-oxo-3,4-dihydroquinazolin-2-yl)piperazine-1-carboximidamide $^1$H NMR (400 MHz, DMSO-d$_6$) δ ppm 10.98 (br s, 1H), 8.91 (br s, 1H), 8.00-7.84 (m, 1H), 7.66-7.54 (m, 1H), 7.34-7.03 (m, 6H), 4.65 (d, J=14.0 Hz, 1H), 4.41 (d, J=13.0 Hz, 1H), 4.20-3.81 (m, 2H), 3.25-3.15 (m, 1H), 3.15-2.99 (m, 2H), 2.23 (s, 3H), 2.03 (s, 1H), 1.02 (d, J=4.4 Hz, 3H), 0.88 (d, J=6.4 Hz, 3H).

Example 1.11

N'-cyano-2-isopropyl-N-(2-methylphenyl)-4-(7H-pyrrolo[2,3-d]pyrimidin-4-yl)piperazine-1-carboximidamide List of General Procedures
General Procedure E: Formation of sodium aryl and heteroaryl carbamimidothioates from an isothiocyanate
General Procedure F: Formation of phenyl N'-cyano-N-arylcarbamimidate or phenyl N'-cyano-N-heteroarylcarbamimidate
General Procedure G: Formation of (piperazin-1-yl)heteroaryl from a piperazine and haloheteroaryl
General Procedure H: Cross-coupling of a piperazine and haloheteroaryl to form a (piperazin-1-yl)heteroaryl
General Procedure I: Formation of (piperazin-1-yl)benzimidazoles from 2-chlorobenzimidazoles and piperazines with microwave irradiation
General Procedure J: Formation of (2-Substituted piperazin-1-yl)heteroaryls
General Procedure K: Formation of cyanoguanidines from aryl or heteroaryl carbamimidothioc acid sodium salts reacted with (piperazin-1-yl)heteroaryl The general synthetic schemes that were utilized to construct compounds disclosed in this application are described below in (Schemes 3 through 11).
General Procedure E: Formation of Sodium Aryl and Heteroaryl Carbamimidothioates from an Isothiocyanate At ambient temperature, sodium (1.0-1.2 equivalents, preferably 1.0 equivalent) is dissolved in ethanol. Then cyanamide (1.0-1.2 equivalents, preferably 1.0 equivalent)

and the isothiocyanate (1.0-1.2 equivalents, preferably 1.0 equivalent) are added. The mixture is allowed to stir at ambient temperature for 8-36 hours (preferably 15 hours). Concentration to dryness supplies the aryl or heteroaryl carbamimidothioc acid sodium salts.

Illustrations of General Procedure E

Preparation of sodium N'-cyano-N-(2-methylphenyl)carbamimidothioate (Example E1)

Sodium (0.16 g, 6.7 mmol) was dissolved in ethanol (15 mL), and then cyanamide (0.28 g, 6.7 mmol) and 1-isothiocyanato-2-methylbenzene (1 g, 6.7 mmol) were added. The reaction mixture was stirred at ambient temperature overnight. The reaction mixture was then concentrated to dryness to afford 1.43 g, 100% of the titled compound as a white solid. The product was used for the next step without purification.

Preparation of Intermediates

Preparation of 3-tert-butyl-5-isothiocyanato-1-methyl-1H-pyrazole

To a suspension of 3-tert-butyl-1-methyl-1H-pyrazol-5-amine (0.78 g, 5.1 mmol) and potassium carbonate (2.1 g, 15.3 mmol) in acetone (40 mL) was added thiophosgene (1.47 g, 12.8 mmol). The resulting mixture was stirred at ambient temperature overnight. The reaction mixture was cooled to 0° C., and then water (70 mL) and ethyl acetate (70 mL) were added. The organic layer was separated and washed with brine and concentrated. The residue was purified by silica gel column chromatography eluting with mixture of hexane:ethyl acetate (10:1) to afford 580 mg, 58% of the titled compound as yellow oil. $^1$H NMR (300 MHz, CDCl$_3$) δ ppm 1.27 (s, 9H), 3.76 (s, 3H), 6.09 (s, 1H).

Scheme 3: Aryl and heteroaryl carbamimidothioc acid sodium salts and arylalkyl and heteroarylalkyl carbamimidothioc acid sodium salts

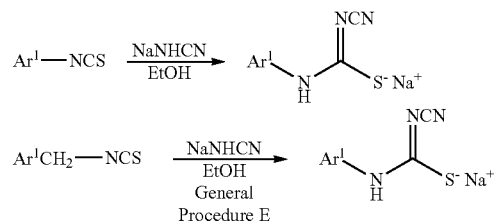

The compounds in Table 5 were made according to general procedure E as illustrated in Scheme 3.

TABLE 5

Aryl and heteroaryl carbamimidothioc acid sodium salts and arylalkyl and heteroarylalkyl carbamimidothioc acid sodium salts

| Ex# | Ar$^1$—NCS or Ar$^1$CH$_2$—NCS | Ar$^1$NHC(NCN)—S$^-$Na$^+$ or Ar$^1$CH$_2$NHC(NCN)—S$^-$Na$^+$ | Name |
|---|---|---|---|
| E1 | (2-methylphenyl NCS) | (2-methylphenyl NHC(NCN)S$^-$Na$^+$) | sodium N'-cyano-N-(2-methylphenyl)carbamimidothioate |
| E2 | (1,3-benzodioxol-5-yl NCS) | (1,3-benzodioxol-5-yl NHC(NCN)S$^-$Na$^+$) | sodium N-1,3-benzodioxol-5-yl-N'-cyanocarbamimidothioate |
| E3 | (4-chlorophenyl NCS) | (4-chlorophenyl NHC(NCN)S$^-$Na$^+$) | sodium N-(4-chlorophenyl)-N'-cyanocarbamimidothioate |
| E4 | (4-methylphenyl NCS) | (4-methylphenyl NHC(NCN)S$^-$Na$^+$) | sodium N'-cyano-N-(4-methylphenyl)carbamimidothioate |
| E5 | (2,6-dimethylphenyl NCS) | (2,6-dimethylphenyl NHC(NCN)S$^-$Na$^+$) | sodium N'-cyano-N-(2,6-dimethylphenyl)carbamimidothioate |

TABLE 5-continued

Aryl and heteroaryl carbamimidothioc acid sodium salts and arylalkyl and heteroarylalkyl carbamimidothioc acid sodium salts

| Ex# | Ar¹—NCS or Ar¹CH₂—NCS | Ar¹NHC(NCN)—S⁻Na⁺ or Ar¹CH₂NHC(NCN)—S⁻Na⁺ | Name |
|---|---|---|---|
| E6 | | | sodium N'-cyano-N-(2-methoxyphenyl)carbamimidothioate |
| E7 | | | sodium N-(2-chlorophenyl)-N'-cyanocarbamimidothioate |
| E8 | | | sodium N'-cyano-N-(3-fluorophenyl)carbamimidothioate |
| E9 | | | sodium N'-cyano-N-(2-fluorophenyl)carbamimidothioate |
| E10 | | | sodium N'-cyano-N-(3-methylphenyl)carbamimidothioate |
| E11 | | | sodium N'-cyano-N-(4-fluorophenyl)carbamimidothioate |
| E12 | | | sodium N'-cyano-N-[4-(trifluoromethyl)phenyl]carbamimidothioate |
| E13 | | | sodium N'-cyano-N-[3-(trifluoromethyl)phenyl]carbamimidothioate |
| E14 | | | sodium N'-cyano-N-(2-isopropylphenyl)carbamimidothioate |
| E15 | | | sodium N-(2-tert-butoxyphenyl)-N'-cyanocarbamimidothioate |

TABLE 5-continued

Aryl and heteroaryl carbamimidothioc acid sodium salts and arylalkyl and heteroarylalkyl carbamimidothioc acid sodium salts

| Ex# | Ar¹—NCS or Ar¹CH₂—NCS | Ar¹NHC(NCN)—S⁻Na⁺ or Ar¹CH₂NHC(NCN)—S⁻Na⁺ | Name |
|---|---|---|---|
| E16 | 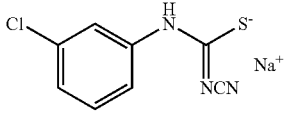 | | sodium N-(3-chlorophenyl)-N'-cyanocarbamimidothioate |
| E17 | 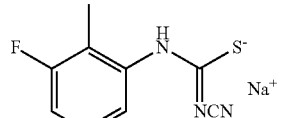 | | sodium N'-cyano-N-(3-fluoro-2-methylphenyl)carbamimidothioate |
| E18 | 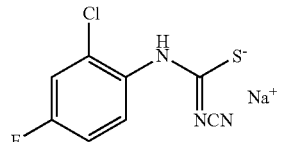 | | sodium N-(2-chloro-4-fluorophenyl)-N'-cyanocarbamimidothioate |
| E19 | 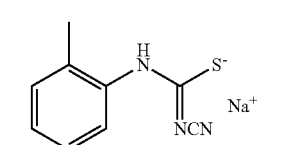 | | sodium N'-cyano-N-(5-fluoro-2-methylphenyl)carbamimidothioate |
| E20 | 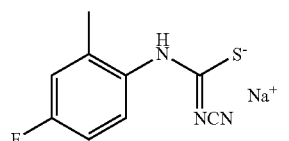 | | sodium N'-cyano-N-(4-fluoro-2-methylphenyl)carbamimidothioate |
| E21 | 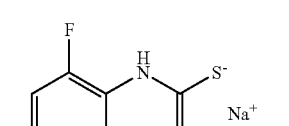 | | sodium N'-cyano-N-(2-fluoro-6-methylphenyl)carbamimidothioate |
| E22 | 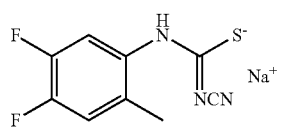 | | sodium N'-cyano-N-(4,5-difluoro-2-methylphenyl)carbamimidothioate |
| E23 | 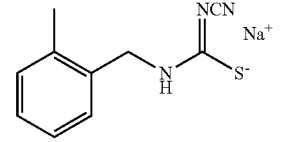 | | sodium N'-cyano-N-(2-methylbenzyl)carbamimidothioate |
| E24 | 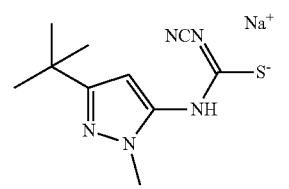 | | sodium N-(3-tert-butyl-1-methyl-1H-pyrazol-5-yl)-N'-cyanocarbamimidothioate |

General Procedure F: Formation of phenyl N'-cyano-N-arylcarbamimidate or phenyl N'-cyano-N-heteroarylcarbamimidate To a mixture of heteroarylamine or arylamine (1.0-1.5 equivalents, preferably 1.0 equivalent) and diphenyl cyanoimidocarbonate (1.0-1.5 equivalents, preferably 1.0 equivalent) are added a solvent (for example acetonitrile) and an optional tertiary amine base (for example triethylamine or diisopropylethylamine, 0.0-1.5 equivalents, preferably 1.0 equivalent). The mixture is stirred at 25-100° C. (preferably at 81° C.) for 4-36 hours (preferably 15 hours). The reaction mixture is concentrated and the residue is purified by chromatography.

Illustration of General Procedure F

Preparation of phenyl N'-cyano-N-(4-methylpyridin-3-yl)imidocarbamate (Example F1)

To a mixture of 4-methylpyridin-3-amine (3 g, 27.7 mmol) and diphenyl cyanoimidocarbonate (6.6 g, 27.7 mmol) was added acetonitrile (30 mL) and triethylamine (2.8 g, 27.7 mmol). The mixture was refluxed overnight and then concentrated. The residue was purified by silica gel column chromatography eluting with mixture dichloromethane:methanol (100:1) to afford 2.7 g, 38% of the titled compound as a white solid. $^1$H NMR (300 MHz, DMSO-$d_6$) δ ppm 2.33 (s, 3H), 7.17-7.53 (m, 6H), 8.36-8.45 (m, 1H), 8.56 (s, 1H), 10.63 (bs, 1H).

Scheme 4: Formation of phenyl N'-cyano-N-arylcarbamimidate or phenyl N'-cyano-N-heteroarylcarbamimidate

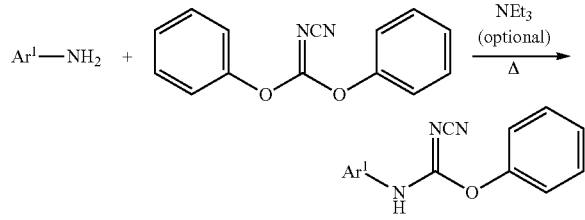

The compounds in Table 6 were made according to general procedure F as illustrated in Scheme 4.

TABLE 6 phenyl N'-cyano-N-arylcarbamimidates and phenyl N'-cyano-N-heteroarylcarbamimidates

| Ex# | Ar$^1$—NH$_2$ | Ar$^1$—NH—C(=NCN)OPh |
|---|---|---|
| F1 | | |
| F2 | | |
| F3 | | |

Example F1 phenyl N'-cyano-N-(4-methylpyridin-3-yl)carbamimidate $^1$H NMR (300 MHz, DMSO-$d_6$) δ ppm 2.33 (s, 3H), 7.17-7.53 (m, 6H), 8.36-8.45 (m, 1H), 8.56 (s, 1H), 10.63 (bs, 1H).

Example F2 phenyl N'-cyano-N-(2-methylpyridin-3-yl)carbamimidate $^1$H NMR (300 MHz, DMSO-$d_6$) δ ppm 2.51 (s, 3H), 7.18-7.54 (m, 6H), 7.84 (d, J=8 Hz, 1H), 8.42 (d, J=4 Hz, 1H), 10.65 (bs, 1H).

Example F3 phenyl N'-cyano-N-(2-methylphenyl)carbamimidate (prepared without a tertiary amine base)

$^1$H NMR (400 MHz, DMSO-$d_6$) δ ppm 2.31 (s, 3H), 7.19-7.28 (m, 4H), 7.28-7.33 (m, 2H), 7.34-7.40 (m, 1H), 7.44 (t, J=7.7 Hz, 2H), 10.49 (s, 1H); MS (ESI) m/z 252 (M+1)$^+$.

General Procedure G: Formation of (piperazin-1-yl)heteroaryl from a Piperazine and Haloheteroaryl The haloheteroaryl (1.0-1.5 equivalents, preferably 1.0 equivalent), tertiary amine base (for example diisopropylethylamine or triethylamine, preferably diisopropylethylamine) (1.0-1.5 equivalents, preferably 1.0 equivalent), and piperazine (1 equivalent) are combined in an organic solvent (for example tetrahydrofuran, dichloromethane, N,N-dimethylformamide, acetonitrile or 1-propanol, preferably N,N-dimethylformamide), and the mixture is stirred at 25-170° C. (preferably at ambient temperature) for 4-36 hours (preferably 15 hours). The volatiles are removed in vacuo, and water is added. The product is purified by chromatography or by filtration of the precipitate.

Illustration of General Procedure G

Preparation of 2-(3-isopropylpiperazin-1-yl)quinoxaline (Example G1)

2-Chloroquinoxaline (0.38 g, 1.5 mmol), 2-isopropylpiperazine (200 mg, 1.5 mmol) and diisopropylethylamine (200 mg, 1.5 mmol) were mixed in dimethylformamide (20 mL), and the reaction mixture was stirred at ambient temperature overnight. Then the volatiles were removed under reduced pressure, and water (100 mL) was added. The precipitate was collected by filtration and washed with diethyl ether to afford 250 mg, 65% of the titled compound as a light-grey solid. MS (ESI) m/z 257.1 (M+H)$^+$.

Preparation of Intermediates

Preparation of 2-sec-butylpiperazine

Step A: methyl N-(tert-butoxycarbonyl)glycylisoleucinate

To a suspension of methyl isoleucinate hydrochloride (360 mg, 2 mmol) in tetrahydrofuran (5 mL), N-(tert-butoxycarbonyl)glycine (385 mg, 2.2 mmol), triethylamine (0.9 mL, 0.9 mmol) and TBTU (770 mg, 2.4 mmol) were added. The reaction mixture was stirred at ambient temperature overnight and then concentrated to dryness. To the residue was taken into a mixture of ethyl acetate:hexane (1:1, 20 mL) and then washed sequentially with 5% aqueous solution of citric acid, aqueous potassium carbonate and finally with brine. The organic layer was passed through a short silica gel column eluting with mixture of hexane:ethyl acetate (1:1). Fractions containing the titled compound were combined and concentrated to dryness to afford 550 mg, 92% of the titled compound as a light-brown solid. $^1$H NMR (300 MHz, DMSO-$d_6$) δ ppm 0.70-0.92 (m, 6H), 1.10-1.19 (m, 1H); 1.30-1.42 (m, 1H), 1.40 (s, 9H), 1.75-1.85 (m, 1H), 3.55-3.65 (m, 1H), 3.55-3.74 (m, 3H), 4.24-4.40 (m, 1H); 6.90-7.00 (m, 1H); 7.90-8.00 (m, 1H).

Step B: methyl glycylisoleucinate hydrochloride

To a solution of methyl N-(tert-butoxycarbonyl)glycylisoleucinate (550 mg, 1.82 mmol) in methanol (10 mL), a 33% solution of hydrochloric acid in water (1 mL) was added. The reaction mixture was stirred at 45° C. for 2 hours and then it was concentrated under reduced pressure to dryness. The titled compound was obtained as white solid 430 mg, 98%. $^1$H NMR (300 MHz, DMSO-$d_6$) δ ppm 0.74-0.94 (m, 6H), 1.15-1.23 (m, 1H), 1.32-1.38 (m, 1H), 1.80-1.89 (m, 1H), 3.50-3.75 (m, 5H), 4.28-4.42 (m, 1H), 8.20 (bs, 3H), 8.72-8.80 (m, 1H).

Step C: 3-Sec-butylpiperazine-2,5-dione

Methyl glycylisoleucinate hydrochloride (8.3 g, 0.03 mol) was dissolved in ethanol (50 mL), and triethylamine (15 mL) was added. The reaction mixture was refluxed for 16 hours and then concentrated. The residual solid was washed with water (30 mL) and diethyl ether (50 mL), and dried to afford 2.5 g, 42% of the titled compound as a white solid. $^1$H NMR (300 MHz, DMSO-$d_6$) δ ppm 0.75-0.90 (m, 6H), 1.15-1.22 (m, 1H), 1.35-1.47 (m, 1H), 1.80-1.90 (m, 1H), 3.54-3.74 (m, 2H), 3.76- 3.82 (m, 1H); 7.95-8.02 (m, 1H); 8.10-8.16 (m, 1H).

Step D: 2-sec-butylpiperazine

To a suspension of lithium aluminum hydride (4.6 g, 0.13 mol) in dry tetrahydrofuran (50 mL), 3-sec-butylpiperazine-2,5-dione (2.8 g, 0.016 mol) was added. The reaction mixture was stirred at reflux for 12 hours, cooled down to ambient temperature, and a solution of sodium hydroxide (1 M, 10 mL) was added. The solid was collected by filtration and washed with tetrahydrofuran. The filtrate was concentrated, and the titled compound was obtained as a yellow solid 0.9 g, 80% and used without additional purification. MS (ESI) m/z 144.3 (M+1)$^+$.

Preparation of 2-cyclohexylpiperazine

Step A: methyl {[N-(tert-butoxycarbonyl)glycyl]amino}(cyclohexyl)acetate

The titled compound was synthesized according to the procedure described for preparation of 2 methyl N-(tert-butoxycarbonyl)glycylisoleucinate making non-critical variations using methyl amino(cyclohexyl)acetate hydrochloride instead of methyl isoleucinate hydrochloride. The titled compound was obtained as a white solid, 1.48 g 99%. $^1$H NMR (300 MHz, DMSO-$d_6$) δ ppm 0.95-1.10 (m, 3H); 1.15-1.25 (m, 2H), 1.36 (s, 9H), 1.50-1.58 (m, 1H), 1.55-1.65 (m, 2H), 1.60.-1.75 (m, 3H), 3.50-3.62 (m, 2H), 3.62 (s, 3H), 4.12-4.20 (m, 1H); 6.90-6.95 (m, 1H), 7.90-8.00 (m, 1H).

Step B: methyl cyclohexyl(glycylamino)acetate hydrochloride

The titled compound was synthesized according to the procedure described for preparation of methyl glycylisoleucinate hydrochloride making non-critical variations using methyl {[N-(tert-butoxycarbonyl)glycyl]amino}(cyclohexyl)acetate instead of methyl N-(tert-butoxycarbonyl) glycylisoleucinate. The product was obtained as a white solid, 1.2 g 99%. MS (ESI) m/z 229.4 (M+1)$^+$.

Step C: 3-Cyclohexylpiperazine-2,5-dione

The compound was synthesized according to the procedure described for preparation of 3-sec-butylpiperazine-2,5-dione making non-critical variations using methyl cyclohexyl(glycylamino)acetate hydrochloride instead of methyl glycylisoleucinate hydrochloride. The titled compound was obtained as a white solid, 460 mg, 70%. $^1$H NMR (300 MHz, DMSO-d) δ ppm 1.05-1.25 (m, 5H), 1.50-1.66 (m, 3H), 1.67-1.80 (m, 3H), 3.55-3.65 (m, 2H), 3.80 (d, J=18 Hz, 1H), 7.99 (bs, 1H), 8.17 (bs, 1H).

Step D: 2-cyclohexylpiperazine

The titled compound was synthesized according to the procedure described for preparation of 2-sec-butylpiperazine making non-critical variations using 3-cyclohexylpiperazine-2,5-dione instead of 3-sec-butylpiperazine-2,5-dione. The titled compound was obtained as a white solid, 320 mg, 83%. MS (ESI) m/z 169.2 (M+1)$^+$.

Preparation of 2-(cyclohexylmethyl)piperazine

Step A: methyl N-(tert-butoxycarbonyl)glycyl-3-cyclohexylalaninate

The titled compound was synthesized according to the procedure described for preparation of 2 methyl N-(tert-butoxycarbonyl)glycylisoleucinate making non-critical variations using methyl 3-cyclohexylalaninate hydrochloride instead of methyl isoleucinate hydrochloride. The titled compound was obtained as a white solid, 0.68 g 94%. $^1$H NMR (300 MHz, DMSO-$d_6$) δ ppm 0.80-0.92 (m, 2H); 1.10-1.23 (m, 3H); 1.25-1.32 (m, 1H); 1.38 (s, 9H), 1.50-1.60 (m, 2H); 1.62-1.81 (m, 5H), 3.50-3.60 (m, 2H), 3.63 (s, 3H), 4.30-4.48 (m, 1H), 6.85-6.96 (m, 1H), 8.10-8.15 (m, 1H).

Step B: methyl glycyl-3-cyclohexylalaninate hydrochloride

The titled compound was synthesized according to the procedure described for preparation of methyl glycylisoleucinate hydrochloride making non-critical variations using methyl N-(tert-butoxycarbonyl)glycyl-3-cyclohexylalaninate instead of methyl N-(tert-butoxycarbonyl)glycylisoleucinate. The titled compound was obtained as a white solid, 430 g 99%. $^1$H NMR (300 MHz, DMSO-$d_6$) δ ppm 0.85-0.94 (m, 2H), 1.10-1.26 (m, 3H), 1.30-1.35 (m, 1H), 1.50-1.64 (m, 2H), 1.66-1.80 (m, 5H), 3.50-3.65 (m, 2H), 3.66 (s, 3H), 4.30-4.40 (m, 1H); 8.08 (bs, 3H), 8.75-8.80 (m, 1H).

Step C: 3-(cyclohexylmethyl)piperazine-2,5-dione

The titled compound was synthesized according to the procedure described for preparation of 3-sec-butylpiperazine-2,5-dione making non-critical variations using methyl glycyl-3-cyclohexylalaninate hydrochloride instead of methyl glycylisoleucinate hydrochloride. The titled compound was obtained as a white solid, 460 mg, 70%. $^1$H NMR (300 MHz, DMSO-$d_6$) δ ppm 0.80-0.90 (m, 2H), 1.10-1.28 (m, 3H), 1.42-1.56 (m, 3H), 1.55-1.72 (m, 5H), 3.57-3.64 (m, 1H), 3.68-3.75 (m, 1H), 3.82 (d, J=18 Hz, 1H), 7.94 (bs, 1H), 8.21 (bs, 1H).

Step D: 2-(cyclohexylmethyl)piperazine

The titled compound was synthesized according to the procedure described for preparation of 2-sec-butylpiperazine making non-critical variations using 3-(cyclohexylmethyl)piperazine-2,5-dione instead of 3-sec-butylpiperazine-2,5-dione. The titled compound was obtained as a white solid, 150 mg, 70%. MS (ESI) m/z 183.3 (M+1)$^+$.

Preparation of 2-chloro-8-(trifluoromethyl)quinoxaline 3-(Trifluoromethyl)benzene-1,2-diamine (4.4 g, 25 mmol) and ethyl 2-oxoacetate (2.7 g, 27 mmol) were refluxed in ethanol (50 mL) overnight. The mixture was cooled and the precipitate was collected by filtration. The precipitate was refluxed overnight in phosphorus oxychloride (30 mL), and then the reaction mixture was concentrated. A solution of sodium hydroxide in water (0.5 M, 20 mL) was added, and the reaction mixture was extracted with chloroform. The crude product was purified by silica gel column chromatography eluting with chloroform to afford 1.4 g, 35% of the titled compound as a brown solid. MS (ESI) m/z 233.4 (M+1)$^+$.

Preparation of 2-chloro-7-fluoroquinoxaline

The compound was synthesized according to the procedure described for preparation of 2-chloro-8-(trifluoromethyl)quinoxaline making non-critical variations using 4-fluorobenzene-1,2-diamine instead of 3-(trifluoromethyl)benzene-1,2-diamine. The titled compound was obtained in mixture with by-product 2-chloro-6-fluoroquinoxaline (1:1) as a yellow oil, 1.5 g, 55%. MS (ESI) m/z 183.5 (M+1)$^+$.

Scheme 5: Formation of (piperazin-1-yl)heteroaryl from a piperazine and haloheteroaryl

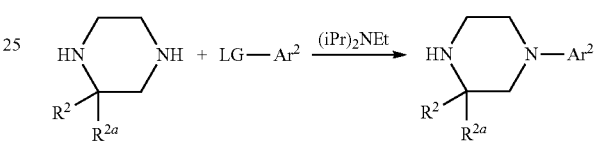

The compounds in Table 7 were made according to general procedure G as illustrated in Scheme 5.

TABLE 7

(piperazin-1-yl)heteroaryl

| Ex# | $R^2$, $R^{2a}$ piperazine | Ar$^2$—LG | Product | m/z (ESI) |
|---|---|---|---|---|
| G1 | 2-isopropylpiperazine | 2-chloroquinoxaline | 2-(2-isopropylpiperazin-1-yl)quinoxaline | 257.1 (M + H)$^+$ |
| G2 | (S)-2-isopropylpiperazine | 2-chloroquinoxaline | (S)-2-(2-isopropylpiperazin-1-yl)quinoxaline | 257.3 (M + H)$^+$ |
| G3 | (R)-2-isopropylpiperazine | 2-chloroquinoxaline | (R)-2-(2-isopropylpiperazin-1-yl)quinoxaline | 257.3 (M + H)$^+$ |

TABLE 7-continued (piperazin-1-yl)heteroaryl

| Ex# | (piperazine structure) | Ar²—LG | (product structure) | m/z (ESI) |
|---|---|---|---|---|
| G4 | | | | 271.2 (M + H)⁺ |
| G5 | | | | |
| G6 | | | | |
| G7 | | | | |
| G8 | | | | |
| G9 | | | | |
| G10 | | | | |
| G11 | | | | |

TABLE 7-continued
(piperazin-1-yl)heteroaryl
| Ex# | 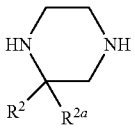 | Ar²—LG |  | m/z (ESI) |
|---|---|---|---|---|
| G12 | 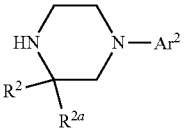 | 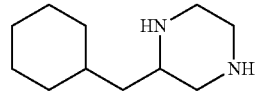 | 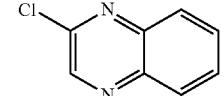 | |
| G13 | 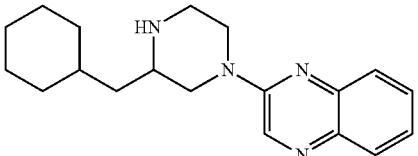 | 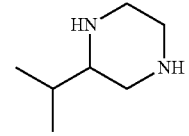 | 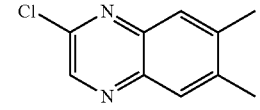 | 285.0 (M + H)⁺ |
| G14 | 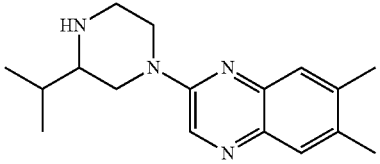 | 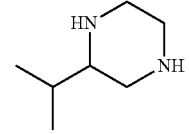 | 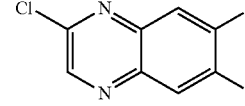 | 293.2 (M + H)⁺ |
| G15 | 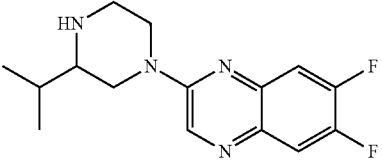 | 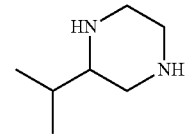 | 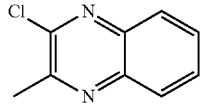 | 271.4 (M + H)⁺ |
| G16 | 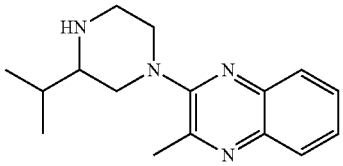 | 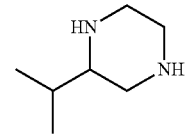 | 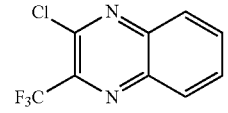 [SMILES: FC(F)(F)c1nc2ccccc2nc1Cl] | 324.1 (M + H)⁺ |
| G17 | 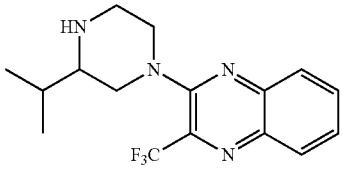 | 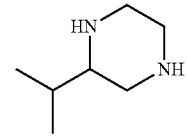 | 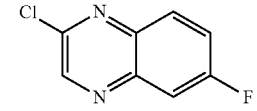 [SMILES: Fc1ccc2nc(Cl)cnc2c1] | 275.3 (M + H)⁺ |
| G18 | 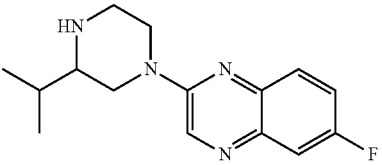 | 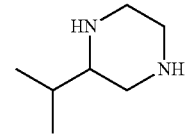 | 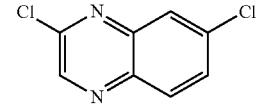 [SMILES: Clc1ccc2ncc(Cl)nc2c1] | 291.4 (M + H)⁺ |
| G19 | 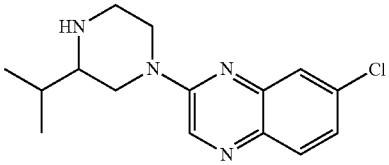 | 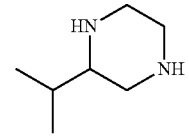 | 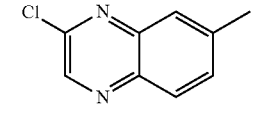 | 271.3 (M + H)⁺ |

TABLE 7-continued (piperazin-1-yl)heteroaryl

| Ex# | R²,R²ᵃ piperazine | Ar²—LG | Product | m/z (ESI) |
|---|---|---|---|---|
| G20 | isopropyl piperazine | 2-chloro-6-CF₃-quinoxaline | | 325.2 (M + H)⁺ |
| G21 | isopropyl piperazine | 2,6,7-trichloroquinoxaline | | 326.8 (M + H)⁺ |
| G22 | isopropyl piperazine | 2-chloro-8-CF₃-quinoxaline | | 325.4 (M + H)⁺ |
| G23 | isopropyl piperazine | 2-chloro-6-fluoroquinoxaline | | 275.5 (M + H)⁺ |
| G24 | (S)-isopropyl piperazine | 2-chloro-6-fluoroquinoxaline | | 275.2 (M + H)⁺ |

Example G1

2-(3-isopropylpiperazin-1-yl)quinoxaline

Example G2

2-[(3R)-3-isopropylpiperazin-1-yl]quinoxaline

Example G3

2-[(3S)-3-isopropylpiperazin-1-yl]quinoxaline

Example G4

2-(3-isobutylpiperazin-1-yl)quinoxaline

Example G5

2-(3-methylpiperazin-1-yl)quinoxaline

¹H NMR (300 MHz, CDCl₃) δ ppm 1.36 (d, J=6.4 Hz, 3H), 3.00-3.12 (m, 1H), 3.18-3.54 (mn, 3H), 4.61 (d, J=13.6 Hz, 2H), 7.40-7.50 (mn, 1H), 7.60-7.70 (mn, 2H), 7.86 (d, J=8.4 Hz, 1H), 8.89 (s, 1H), 9.85 (bs, 1H).

Example G6

2-(5,8-diazaspiro[3.5]non-8-yl)quinoxaline

¹H NMR (300 MHz, CDCl₃) δ ppm 1.70-1.86 (mn, 5H), 2.01-2.12 (mn, 2H), 2.90-3.00 (m, 2H), 3.60-3.78 (m, 4H), 7.30-7.42 (m, 1H), 7.50-7.60 (m, 1H), 7.64-7.70 (m, 1H), 7.80-7.88 (m, 1H), 8.58 (s, 1H).

Example G7

2-(3-ethylpiperazin-1-yl)quinoxaline

¹H NMR (300 MHz, CDCl₃) δ ppm 1.00-1.14 (m, 3H), 1.50-1.62 (m, 2H), 1.75-1.84 (m, 1H), 2.45-2.56 (m, 2H), 2.95-3.04 (m, 1H), 3.10-3.22 (m, 2H), 4.40-4.50 (m, 2H), 7.35-7.45 (m, 1H), 7.55-7.60 (m, 1H), 7.65-7.75 (m, 1H); 7.85-7.93 (m, 1H), 8.59 (s, 1H).

Example G8

2-(4,7-diazaspiro[2.5]oct-7-yl)quinoxaline

¹H NMR (300 MHz, CDCl₃) δ ppm 0.68 (bs, 4H), 1.74 (bs, 1H), 3.08-3.20 (m, 2H), 3.64 (bs, 2H), 3.70-7.85 (m, 2H), 7.35-7.45 (m, 1H), 7.50-7.60 (m, 1H), 7.65-7.72 (m, 1H), 7.82-7.91 (m, 1H), 8.54 (bs, 1H).

Example G9

2-(3-tert-butylpiperazin-1-yl)quinoxaline

¹H NMR (300 MHz, CDCl₃) δ ppm 0.94 (s, 9H), 2.42-2.50 (m, 1H), 2.72-2.81 (m, 1H), 2.90 (bs, 1H), 3.02-3.06 (m, 1H), 3.20-3.28 (m, 1H), 4.35-4.42 (m, 1H), 4.52-4.60 (m, 1H), 7.31-7.38 (m, 1H), 7.46- 7.55 (m, 1H), 7.60-7.68 (m, 1H), 7.76-7.85 (m, 1H), 8.54 (s., 1H).

Example G10

2-(3-sec-butylpiperazin-1-yl)quinoxaline

¹H NMR (300 MHz, CDCl₃) δ ppm 0.95-1.01 (m, 1H), 1.04-1.14 (m, 3H), 1.15-1.20 (m, 1H), 1.58-1.68 (m, 2H), 2.68-1.77 (m, 1H), 2.85-2.92 (m, 1H), 3.16-3.26 (m, 2H), 4.38-4.45 (m, 1H), 4.48-4.56 (m, 1H), 7.35-7.45 (m, 1H), 7.53-7.63 (m, 1H), 7.61-7.70 (m, 1H), 7.85-7.91 (m, 1H), 8.59 (bs, 1H).

Example G11

2-(3-cyclohexylpiperazin-1-yl)quinoxaline

¹H NMR (300 MHz, CDCl₃) δ ppm 1.10-1.25 (m, SH), 1.40.1.78 (m, 1H), 1.70.1.76 (m, 1H), 1.80-1.94 (m, 4H), 2.55-2.63 (m, 1H), 2.85-2.95 (m, 2H), 3.16-3.26 (m, 2H), 4.36-4.44 (m, 1H), 5.30-5.35 (m, 1H), 7.35-7.45 (m, 1H), 7.54-7.61 (m, 1H), 7.62-7.70 (m, 1H), 7.84-7.92 (m, 1H), 8.45-8.53 (s, 1H).

Example G12

2-[3-(cyclohexylmethyl)piperazin-1-yl]quinoxaline

¹H NMR (300 MHz, CDCl₃) δ ppm 0.92-1.04 (m, 2H), 1.22-1.39 (m, 6H), 1.65-1.85 (m, SH), 2.16-2.22 (m, 1H), 2.46-2.53 (m, 1H), 2.88-2.96 (m, 2H), 3.16-3.26 (m, 2H), 4.35-3.76 (m, 2H), 7.35-7.43 (m, 1H), 7.55-7.61 (m, 1H), 7.71-7.80 (m, 1H), 7.86-7.93 (m, 1H), 8.58 (bs., 1H).

Example G13

2-(3-isopropylpiperazin-1-yl)-6,7-dimethylquinoxaline

Example G14

6,7-difluoro-2-(3-isopropylpiperazin-1-yl)quinoxaline

Example G15

2-(3-isopropylpiperazin-1-yl)-3-methylquinoxaline

Example G16

2-(3-isopropylpiperazin-1-yl)-3-(trifluoromethyl)quinoxaline

Example G17

6-fluoro-2-(3-isopropylpiperazin-1-yl)quinoxaline

Example G18

7-chloro-2-(3-isopropylpiperazin-1-yl)quinoxaline

Example G19

2-(3-isopropylpiperazin-1-yl)-7-methylquinoxaline

Example G20

2-(3-isopropylpiperazin-1-yl)-6-(trifluoromethyl)quinoxaline

Example G21

6,7-dichloro-2-(3-isopropylpiperazin-1-yl)quinoxaline

Example G22

2-(3-isopropylpiperazin-1-yl)-8-(trifluoromethyl)quinoxaline

Example G23

7-fluoro-2-(3-isopropylpiperazin-1-yl)quinoxaline

Example G24

6-fluoro-2-[(3S)-3-isopropylpiperazin-1-yl]quinoxaline

General Procedure H: Cross-Coupling of a Piperazine and Haloheteroaryl to Form a (piperazin-1-yl)heteroaryl The haloheteroaryl (1.0 equivalent) and piperazine (1-1.5 equivalents, preferably 1.1 equivalents) are dissolved in a solvent, such as acetonitrile. A base, such as cesium carbonate (1.5-3.0 equivalents, preferably 2.0 equivalents), and a catalyst, such as [1,1'-bis(diphenylphosphino)ferrocene]dichloropalladium(II) (0-5 mol %, preferably 0 or 2.0 mol %), are added, and the mixture is heated from 25-82° C. (preferably 80-82° C.) overnight. The volatiles are removed under reduced pressure, and the residue is partitioned between ethyl acetate and water. The organic phase is concentrated and the residue is purified chromatographically.

Illustration of General Procedure H

Preparation of 2-(3-isopropylpiperazin-1-yl)quinoline (Example H1)

2-Bromoquinoline (300 mg, 1.44 mmol) was dissolved in acetonitrile (10 mL) and 2-isopropylpiperazine (200 mg, 1.58 mmol) was added. Cesium carbonate (940 mg, 2.88 mmol), and [1,1'-bis(diphenylphosphino)ferrocene]dichloropalladium(II) (Pd(dppf)Cl$_2$, 20 mg) were added, and the reaction mixture was stirred at reflux for 12 hours. The solvent was removed under reduced pressure, and the residue was diluted with water (50 mL). The aqueous mixture was extracted with ethyl acetate (2×20 mL). The combined organic extracts were concentrated, and the residue was purified by silica gel column chromatography eluting with chloroform:methanol (19:1) to afford 140 mg. 38% of the titled compound as a brown solid. MS (ESI) m/z 256.2 (M+1)$^+$.

Scheme 6: Formation of (piperazin-1-yl)heteroaryl from a piperazine and haloheteroaryl

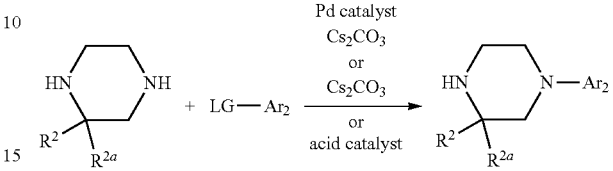

The compounds in Table 8 were made according to general procedure H and general procedure I as illustrated in Scheme 6.

TABLE 8

(piperazin-1-yl)heteroaryl

| Ex# | Experimental procedure variations. | Ar$^2$—LG | $R^2$ $R^{2a}$ | m/z (ESI) |
|---|---|---|---|---|
| H1 | — | | | 256.2 (M + H)$^+$ |
| H2 | No Pd(dppf)Cl$_2$ | | | 257.1 (M + H)$^+$ |
| H3 | — | | | 292.3 (M + H)$^+$ |
| H4 | No Pd(dppf)Cl$_2$ or Cs$_2$CO$_3$. catalyst = 1 drop of 5M HCl in dioxane | | | 332.2 (M + H)$^+$ |
| H5 | No Pd(dppf)Cl$_2$ | | | 258.3 (M + H)$^+$ |

TABLE 8-continued (piperazin-1-yl)heteroaryl

| Ex# | Experimental procedure variations. | Ar²—LG | (structure) | m/z (ESI) |
|---|---|---|---|---|
| H6 | No Pd(dppf)Cl₂ | 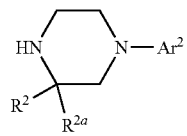 | 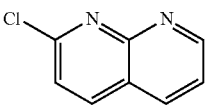 [SMILES: Clc1ccc2cccnc2n1] | 257.3 (M + H)⁺ |
| H7 | No Pd(dppf)Cl₂ | 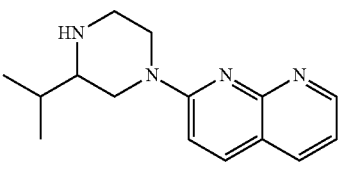 | 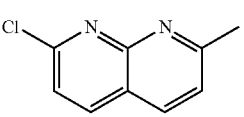 | 271.2 (M + H)⁺ |

Example H1

2-(3-isopropylpiperazin-1-yl)quinoline

Example H2

2-(3-isopropylpiperazin-1-yl)quinazoline

Example H3

4-[6-(3-isopropylpiperazin-1-yl)pyrazin-2-yl]morpholine

Example H4

N-cyclohexyl-2-(3-isopropylpiperazin-1-yl)-5,6-dimethylpyrimidin-4-amine

Example H5

6-(3-isopropylpiperazin-1-yl)pyrido[2,3-b]pyrazine

Example H6

2-(3-isopropylpiperazin-1-yl)-1,8-naphthyridine

Example H7

2-(3-isopropylpiperazin-1-yl)-7-methyl-1,8-naphthyridine

General Procedure I: Formation of (piperazin-1-yl)benzimidazoles from 2-Chlorobenzimidazoles and Piperazines with Microwave Irradiation The 2-halobenzimidazole (1.0 equivalent) and piperazine (1-1.2 equivalents, preferably 1.2 equivalents) are dissolved in a solvent, such as acetonitrile. A base, such as cesium carbonate (1.5-3.0 equivalents, preferably 2.0 equivalents) is added, and the mixture is heated from 100-160° C. (preferably 150° C.) for 1-4 hours. The reaction mixture is partitioned between ethyl acetate and water. The organic phase is concentrated, and the residue is purified chromatographically.

Illustration of General Procedure I

Preparation of 2-(3-isopropylpiperazin-1-yl)-1-methyl-1H-benzimidazole (Example I1)

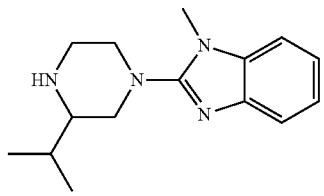 [SMILES: CC(C)C1CN(c2nc3ccccc3n2C)CCN1]

2-Chloro-1-methyl-1H-benzimidazole (250 mg, 1.5 mmol) was dissolved in acetonitrile (10 mL). 2-Isopropylpiperazine (230 mg, 1.8 mmol) and cesium carbonate (980 mg, 3 mmol) were added, and the reaction mixture was stirred in a microwave oven (CEM, Discover®-SP with ActiVent®, 300 W maximum) at 150° C. for 3 hours. Then the reaction mixture was diluted with water (50 mL), and the product was extracted with chloroform (2×20 mL). The crude material was purified with silica gel column chromatography eluting with mixture of chloroform:methanol (20:1) to afford 100 mg, 26% of the titled compound as a light yellow solid. MS (ESI) m/z 259.6 (M+1)⁺.

Preparation of Intermediates

Preparation of 2-chloro-1-methyl-1H-benzimidazole

2-Chloro-1H-benzimidazole (7.5 g, 49 mmol) was dissolved in dimethylformamide (20 mL), and the reaction mixture was cooled to 0° C. Sodium hydride (60% dispersion in mineral oil 2.16 g, 5.4 mmol) was carefully added. The reaction mixture was stirred at ambient temperature for 1 hour, and after that iodomethane (8.37 g, 59 mmol) was added. The reaction mixture was stirred at ambient temperature overnight, and then water (200 mL) was added. The solid was collected by filtration to afford 5 g, 61% of the titled compound as a white solid. $^1$H NMR (300 MHz, DMSO-d$_6$) δ ppm 3.79 (s, 3H), 7.21-7.33 (m, 2H), 7.58 (t, J=7.0 Hz, 2H).

Scheme 7: Formation of (2-Substituted piperazine-1-yl)heteroaryls

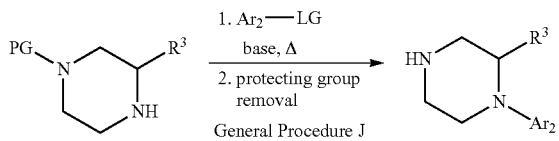

1. Ar$_2$—LG
   base, Δ
2. protecting group removal

General Procedure J

General Procedure J: Formation of (2-Substituted piperazin-1-yl)heteroaryls

To a solution of tert-butyl 3-(substituted)piperazine-1-carboxylate (1 equivalent) and haloheteroaryl (1.0-1.5 equivalents, preferably 1.0 equivalent) in dimethylsulfoxide, a base (preferably cesium fluoride, 1.0-1.5 equivalents, preferably 1.0 equivalent) is added. The reaction mixture is stirred at 25-80° C. (preferably 60° C.) for 8-48 hours, then poured in water and extracted with an organic solvent. The crude product was purified by silica gel column chromatography.

To a solution of tert-butyl 3-substituted-heteroaryl-piperazine-1-carboxylat in methanol, an acid (concentrated hydrochloric acid or trifluoroacetic acid) is added. The reaction mixture is stirred at 25-65° C. for 1-4 hours. The reaction mixture is concentrated and partitioned between aqueous base and an organic solvent. The organic phases are combined and concentrated to provide the titled compound.

Illustration of General Procedure J

Preparation of 2-(2-isopropylpiperazin-1-yl)quinoxaline (Example J1)

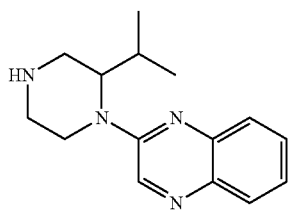 [SMILES: CC(C)C1CNCCN1c1cnc2ccccc2n1]

Step A: 3-isopropyl-4-quinoxalin-2-ylpiperazine-1-carboxylate

To a solution of tert-butyl 3-isopropylpiperazine-1-carboxylate (830 mg, 3.6 mmol) and 2-chloroquinaxaline (600 mg, 3.6 mmol) in dimethyl sulfoxide (5 mL), cesium fluoride (550 mg, 3.6 mmol) was added. The reaction mixture was stirred at 60° C. for 30 hours, and then the reaction mixture was poured into water (70 mL) and extracted with diethyl ether (2×20 mL). The crude product was purified by silica gel column chromatography eluting with mixture hexane:ethyl acetate (4:1) to afford 600 mg, 46% of the titled compound as a light-yellow solid. $^1$H NMR (300 MHz, DMSO-d$_6$) δ ppm 0.84-0.90 (m, 3H), 1.16-1.25 (m, 3H), 1.50 (s, 9H), 2.20-2.30 (m, 1H), 3.00-3.12 (m, 2H), 3.20-3.28 (m, 1H), 4.17-4.23 (m, 1H), 4.30-4.36 (m, 1H), 4.55-4.65 (m, 1H), 7.55-7.62 (m, 1H), 7.72-7.78 (m, 1H), 7.85-7.90 (m, 1H), 8.15-7.23 (m, 1H), 8.58 (s, 1H).

Step B: 2-(2-isopropylpiperazin-1-yl)quinoxaline

To a solution of tert-butyl 3-isopropyl-4-quinoxalin-2-ylpiperazine-1-carboxylate (500 mg 1.4 mmol) in methanol (100 mL), hydrochloric acid (36.5% water solution, 10 mL) was added. The reaction mixture was stirred at 45° C. for 2 hours. The reaction mixture was concentrated under reduced pressure and 10% aqueous potassium carbonate (100 mL) was added. The mixture was extracted with chloroform (2×40 mL) to afford 340 mg, 94% of the titled compound as a yellow solid. $^1$H NMR (300 MHz, CDCl$_3$) δ ppm 0.80-0.90 (m, 3H), 1.00-1.15 (m, 3H), 2.20-2.28 (m, 1H), 2.55-5.65 (m, 1H), 2.70-2.82 (m, 2H), 3.15-3.30 (m, 3H), 4.50-4.60 (m, 1H), 4.55-4.63 (m, 1H), 7.32-7.40 (m, 1H), 7.50-7.60 (m, 1H), 7.61-7.70 (m, 1H), 7.80-7.86 (m, 1H), 8.56 (s., 1H).

General Procedure K: Formation of Cyanoguanidines from Aryl or Heteroaryl Carbamimidothioc Acid Sodium Salts Reacted with (piperazin-1-yl)heteroaryl (Piperazin-1-yl)heteroaryl (1 equivalent), aryl or heteroaryl carbamimidothioc acid sodium salt (1.0-1.5 equivalents, preferably 1.1 equivalents), N-[3-(dimethylamino)propyl]-N'-ethylcarbodiimide hydrochloride (1.0-1.5 equivalents, preferably 1.1 equivalents) and tertiary amine base (preferably diisopropylamine, 1.0-1.5 equivalents, preferably 1.1 equivalents) are mixed in dimethylformamide, and the reaction mixture is stirred at 25-100° C. (preferably 80° C.) for 4-24 hours. Water is added; the precipitate is collected by filtration, washed and dried. The crude product is purified chromatographically.

Illustration of General Procedure K

Preparation of N'-cyano-2-isopropyl-N-(2-methylphenyl)-4-(quinoxalin-2-yl)piperazine-1-carboximidamide trifluoroacetate (Example 1.3)

2-(3-Isopropylpiperazin-1-yl)quinoxaline (250 mg, 1 mmol, Example G1), sodium N'-cyano-N-(2-methylphenyl) carbamimidothioate (200 mg, 1.1 mmol, Example E1), N-[3-(dimethylamino)propyl]-N'-ethylcarbodiimide hydrochloride (200 mg, 1.1 mmol) and diisopropylethylamine (140 mg, 1.1 mmol) were mixed in dimethylformamide (20 mL), and the reaction mixture was stirred at 80° C. overnight. Water (50 mL) was added; the precipitate was collected by filtration, washed by hexane and dried. The crude product was purified by HPLC (column: YMC-PACK ODS-AQ C18, 250 mm×20 mm, 10 m; gradient: 20-50% acetonitrile in 0.02% trifluoroacetic acid/water over 15 minutes; 50-100% acetonitrile in 0.02% trifluoroacetic acid/water over 5 minutes; flow rate: 25 mL/minute; temperature: 25° C.; retention time=6.12 minutes) to afford the titled compound 33 mg. 10% as a white solid. $^1$H NMR (400 MHz, CDCl$_3$) δ ppm 0.90-1.04 (m, 6H), 2.09-2.20 (m, 1H), 2.37 (s, 3H), 2.87-3.26 (m, 3H), 3.55-3.69 (m, 1H), 3.98-4.09 (m, 1H), 4.40-4.54 (m, 2H), 6.56 (s, 1H), 7.11-7.35 (m, 5H), 7.42-7.48 (m, 1H), 7.57-7.72 (m, 2H), 7.87-7.94 (m, 1H), 8.52 (s, 1H); MS (ESI) m/z 415.0 (M+1)$^+$.

Scheme 8: Formation of cyanoguanidines
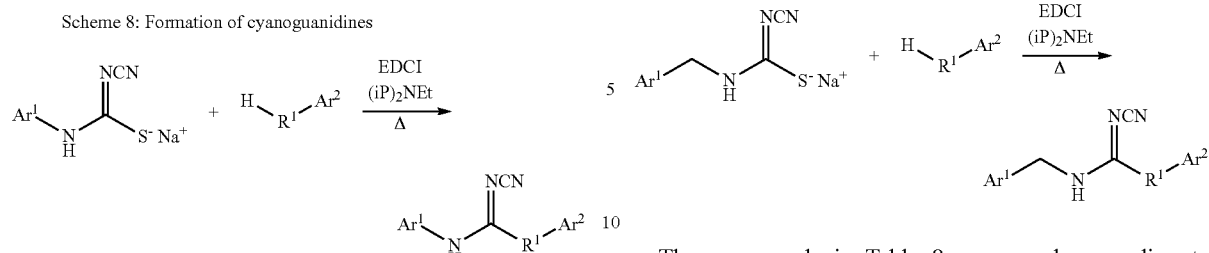
The compounds in Table 8 were made according to general procedure K as illustrated in Scheme 8.
TABLE 8
Cyanoguanidines
| Ex# | Ar¹NHC(NCN)—S⁻ Na⁺ or Ar¹CH₂NHC(NCN)—S⁻ Na | H—R¹—Ar²— | Ar¹—NHC(=NCN)—R¹—Ar² or Ar¹CH₂—NHC(=NCN)—R¹—Ar² | purification |
|---|---|---|---|---|
| 1.3 | (E1) | (G1) | | a |
| 1.12 | (E1) | (G2) | | a |
| 1.13 | (E1) | (G3) | | a |
| 1.14 | (E2) | (G1) | | b |
| 1.15 | (E3) | (G1) | | b |

TABLE 8-continued

Cyanoguanidines

| Ex# | Ar¹NHC(NCN)—S⁻ Na⁺ or Ar¹CH₂NHC(NCN)—S⁻ Na | H—R¹—Ar²— | Ar¹—NHC(=NCN)—R¹—Ar² or Ar¹CH₂—NHC(=NCN)—R¹—Ar² | purification |
|---|---|---|---|---|
| 1.16 | (E4) | (G1) | | b |
| 1.17 | (E5) | (G1) | | b |
| 1.18 | (E6) | (G1) | | b |
| 1.19 | (E7) | (G1) | | b |
| 1.20 | (E8) | (G1) | | b |
| 1.21 | (E9) | (G1) | | b |

TABLE 8-continued

Cyanoguanidines

| Ex# | Ar¹NHC(NCN)—S⁻ Na⁺ or Ar¹CH₂NHC(NCN)—S⁻ Na | H—R¹—Ar²— | Ar¹—NHC(=NCN)—R¹—Ar² or Ar¹CH₂—NHC(=NCN)—R¹—Ar² | purification |
|---|---|---|---|---|
| 1.22 | (E10) | (G1) | | b |
| 1.23 | (E11) | (G1) | | a |
| 1.24 | (E12) | (G1) | | a |
| 1.25 | (E13) | (G1) | | b |
| 1.26 | (E14) | (G1) | | b |
| 1.27 | (E15) | (G1) | | b |

TABLE 8-continued

Cyanoguanidines

| Ex# | Ar¹NHC(NCN)—S⁻ Na⁺ or Ar¹CH₂NHC(NCN)—S⁻ Na | H—R¹—Ar²— | Ar¹—NHC(=NCN)—R¹—Ar² or Ar¹CH₂—NHC(=NCN)—R¹—Ar² | purification |
|---|---|---|---|---|
| 1.28 | (E16) | (G1) | | b |
| 1.29 | (E17) | (G1) | | b |
| 1.30 | (E18) | (G1) | | b |
| 1.31 | (E19) | (G1) | | b |
| 1.32 | (E20) | (G1) | | b |
| 1.33 | (E21) | (G1) | | b |

TABLE 8-continued

Cyanoguanidines

| Ex# | Ar¹NHC(NCN)—S⁻ Na⁺ or Ar¹CH₂NHC(NCN)—S⁻ Na | H—R¹—Ar²— | Ar¹—NHC(=NCN)—R¹—Ar² or Ar¹CH₂—NHC(=NCN)—R¹—Ar² | purification |
|---|---|---|---|---|
| 1.34 | (E22) | (G1) | | b |
| 1.35 | (E23) | (G1) | | b |
| 1.36 | (E24) | (G1) | | a |
| 1.37 | (E1) | (G4) | | b |
| 1.38 | (E10) | (G4) | | b |

TABLE 8-continued

Cyanoguanidines

| Ex# | Ar¹NHC(NCN)—S⁻ Na⁺ or Ar¹CH₂NHC(NCN)—S⁻ Na | H—R¹—Ar²— | Ar¹—NHC(=NCN)—R¹—Ar² or Ar¹CH₂—NHC(=NCN)—R¹—Ar² | purification |
|---|---|---|---|---|
| 1.39 | (E9) | (G4) | | a |
| 1.40 | (E8) | (G4) | | b |
| 1.41 | (E7) | (G4) | | a |
| 1.42 | (E1) | (G5) | | b |
| 1.43 | (E1) | (G6) | | b |

TABLE 8-continued

Cyanoguanidines

| Ex# | Ar¹NHC(NCN)—S⁻ Na⁺ or Ar¹CH₂NHC(NCN)—S⁻ Na | H—R¹—Ar²— | Ar¹—NHC(=NCN)—R¹—Ar² or Ar¹CH₂—NHC(=NCN)—R¹—Ar² | purification |
|---|---|---|---|---|
| 1.44 | (E1) | (G7) | | b |
| 1.45 | (E1) | (G8) | | b |
| 1.46 | (E1) | (G9) | | b |
| 1.47 | (E1) | (G10) | | b |

TABLE 8-continued
Cyanoguanidines
| Ex# | Ar¹NHC(NCN)—S⁻ Na⁺ or Ar¹CH₂NHC(NCN)—S⁻ Na | H—R¹—Ar²— | Ar¹—NHC(=NCN)—R¹—Ar² or Ar¹CH₂—NHC(=NCN)—R¹—Ar² | purification |
|---|---|---|---|---|
| 1.48 | 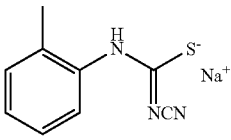 (E1) | 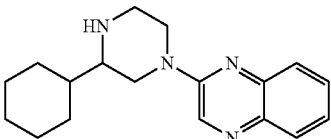 (G11) | 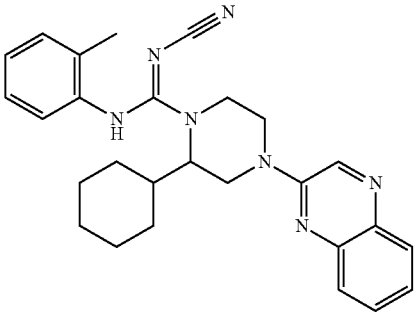 [SMILES: Cc1ccccc1N/C(=N/C#N)N1CCN(c2cnc3ccccc3n2)CC1C1CCCCC1] | b |
| 1.49 | 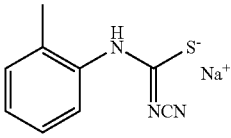 (E1) | 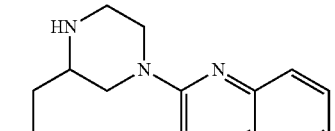 (G12) | 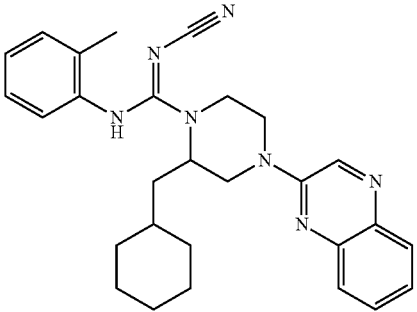 [SMILES: Cc1ccccc1N/C(=N/C#N)N1CCN(c2cnc3ccccc3n2)CC1CC1CCCCC1] | b |
| 1.50 | 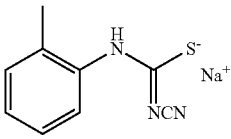 (E1) | 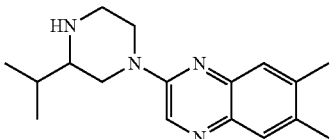 (G13) | 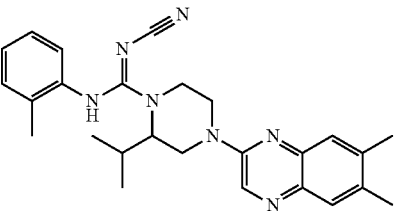 [SMILES: Cc1cc2ncc(N3CCN(/C(=N\C#N)Nc4ccccc4C)C(C(C)C)C3)nc2cc1C] | a |
| 1.51 | 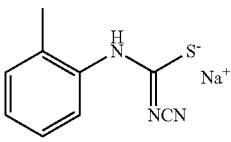 (E1) | 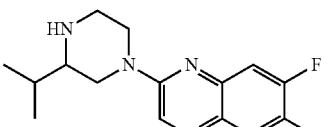 (G14) | 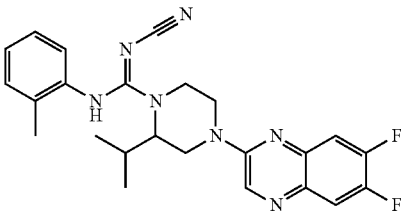 | b |
| 1.52 | 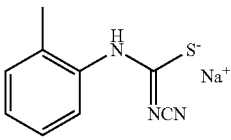 (E1) | 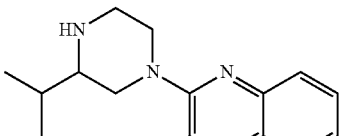 (G15) | 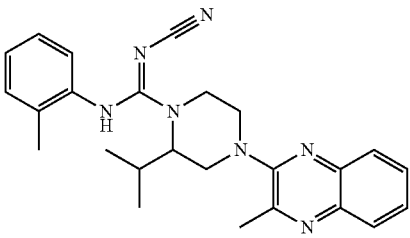 [SMILES: Cc1ccccc1N/C(=N/C#N)N1CCN(c2nc3ccccc3nc2C)CC1C(C)C] | a |

TABLE 8-continued

Cyanoguanidines

| Ex# | Ar¹NHC(NCN)—S⁻ Na⁺ or Ar¹CH₂NHC(NCN)—S⁻ Na | H—R¹—Ar²— | Arʲ—NHC(=NCN)—R¹—Ar² or Ar¹CH₂—NHC(=NCN)—R¹—Ar² | purification |
|---|---|---|---|---|
| 1.53 | (E1) | (G16) | | a |
| 1.54 | (E1) | (G17) | | b |
| 1.55 | (E1) | (G18) | | b |
| 1.56 | (E1) | (G19) | | b |
| 1.57 | (E1) | (G20) | | b |
| 1.58 | (E1) | (G21) | | b |

TABLE 8-continued

Cyanoguanidines

| Ex# | Ar¹NHC(NCN)—S⁻ Na⁺ or Ar¹CH₂NHC(NCN)—S⁻ Na | H—R¹—Ar²— | Ar¹—NHC(=NCN)—R¹—Ar² or Ar¹CH₂—NHC(=NCN)—R¹—Ar² | purification |
|---|---|---|---|---|
| 1.59 | (E1) | (G22) | | b |
| 1.60 | (E1) | (G23) | | c |
| 1.61 | (E1) | (H1) | | b |
| 1.62 | (E1) | (H2) | | b |
| 1.63 | (E1) | (H3) | | b |
| 1.64 | (E1) | (H4) | | b |

TABLE 8-continued

Cyanoguanidines

| Ex# | Ar¹NHC(NCN)—S⁻ Na⁺ or Ar¹CH₂NHC(NCN)—S⁻ Na | H—R¹—Ar²— | Arʲ—NHC(=NCN)—R¹—Ar² or Ar¹CH₂—NHC(=NCN)—R¹—Ar² | purification |
|---|---|---|---|---|
| 1.65 | (E1) | (H5) | | b |
| 1.66 | (E1) | (H6) | | b |
| 1.67 | (E1) | (G24) | | b |
| 1.68 | (E1) | (H7) | | b |
| 1.69 | (E1) | (I1) | | b |
| 1.70 | (E1) | (J1) | | b |

TABLE 8-continued

Cyanoguanidines

| Ex# | Ar¹NHC(NCN)—S⁻ Na⁺ or Ar¹CH₂NHC(NCN)—S⁻ Na | H—R¹—Ar²— | Ar¹—NHC(=NCN)—R¹—Ar² or Ar¹CH₂—NHC(=NCN)—R¹—Ar² | purification |
|---|---|---|---|---|
| 1.71 | (E7) | (G24) | | a | a HPLC (column: YMC-PACK ODS-AQ C18, 250 mm × 20 mm, 10 μm; gradient: 20-50 % acetonitrile in 0.02% trifluoroacetic acid/water over 15 minutes; 50-100% acetonitrile in 0.02% trifluoroacetic acid/water over 5 minutes; flow rate: 25 mL/minute; temperature: 25 ° C.
b Silica gel column chromatography, hexane/ethyl acetate (2:1). Diethyl ether wash.
c Silica gel column chromatography, hexane/ethyl acetate (9:1). Diethyl ether wash.

Example 1.12

(2R)—N'-cyano-2-isopropyl-N-(2-methylphenyl)-4-(quinoxalin-2-yl)piperazine-1-carboximidamide trifluoroacetate $^1$H NMR (400 MHz, CDCl$_3$) δ ppm 1.04-1.18 (m, 6H), 2.21-2.32 (m, 4H), 3.38-3.54 (m, 3H), 4.44-4.61 (m, 2H), 4.89-5.00 (m, 1H), 7.06 (s, 1H), 7.18-7.31 (m, 5H), 7.44-7.50 (m, 1H), 7.59-7.67 (m, 1H), 7.81-7.85 (m, 1H), 7.90-7.96 (m, 1H), 8.61 (s, 1H); MS (ESI) m/z 406.1 (M+1)$^+$.

Example 1.13

(2S)—N'-cyano-2-isopropyl-N-(2-methylphenyl)-4-(quinoxalin-2-yl)piperazine-1-carboximidamide trifluoroacetate $^1$H NMR (400 MHz, CDCl$_3$) δ ppm 1.04-1.18 (m, 6H), 2.21-2.32 (m, 4H), 3.38-3.54 (m, 3H), 4.44-4.61 (m, 2H), 4.89-5.00 (m, 1H), 7.06 (s, 1H), 7.18-7.31 (m, 5H), 7.44-7.50 (m, 1H), 7.59-7.67 (m, 1H), 7.81-7.85 (m, 1H), 7.90-7.96 (m, 1H), 8.61 (s, 1H); MS (ESI) m/z 406.1 (M+1)$^+$.

Example 1.14

N-(1,3-benzodioxol-5-yl)-N'-cyano-2-isopropyl-4-(quinoxalin-2-yl)piperazine-1-carboximidamide $^1$H NMR (300 MHz, DMSO-d$_6$) δ ppm 0.89 (d, J=6.6 Hz, 3H); 1.05 (d, J=6.6 Hz, 3H); 1.99-2.18 (m, 1H), 3.13-3.40 (m, 3H); 4.00-4.16 (m., 2H); 4.51 (d, J=11.8 Hz, 1H); 4.76 (d, J=14.3 Hz, 1H); 6.0 (s, 2H); 6.61 (d, J=8.3 Hz, 1H); 6.71 (s, 1H); 6.85 (d, J=8.1, 1H); 7.35-7.47 (m, 1H); 7.54-7.67 (m, 2H); 7.84 (d, J=8.1 Hz, 1H); 8.80 (s, 1H); 8.95 (s, 1H); MS (ESI) m/z 448.8 (M+1)$^+$.

Example 1.15

N-(4-chlorophenyl)-N'-cyano-2-isopropyl-4-(quinoxalin-2-yl)piperazine-1-carboximidamide $^1$H NMR (300 MHz, DMSO-d$_6$) δ ppm 0.88 (d, J=6.8, 3H); 1.05 (d, J=6.8, 3H); 2.01-2.20 (m, 1H), 3.15-3.45 (m, 3H); 4.02-4.17 (m, 2H); 4.53 (d, J=12.1, 1H); 4.79 (d, J=14.3, 1H); 7.12 (d, J=8.6, 2H); 7.31-7.47 (m, 3H); 7.56-7.66 (m, 2H); 7.84 (d, J=8.1 Hz, 1H); 8.81 (s, 1H); 9.21 (s, 1H); MS (ESI) m/z 434.8 (M+1)$^+$.

Example 1.16

N'-cyano-2-isopropyl-N-(4-methylphenyl)-4-(quinoxalin-2-yl)piperazine-1-carboximidamide $^1$H NMR (300 MHz, CDCl$_3$) δ ppm 0.95 (d, J=5.9 Hz, 3H); 1.02 (d, J=5.9 Hz, 3H); 1.27 (bs, 1H); 2.08-2.22 (bs, 1H), 2.36 (s, 3H); 3.03-3.29 (m, 3H); 3.75-4.10 (m., 1H); 4.45 (d, J=12.1 Hz, 1H); 4.57 (d, J=13.2 Hz, 1H); 6.95 (bs, 1H); 7.04 (d, J=7.8,2 H); 7.20 (d, J=6.2 Hz, 2H); 7.45 (t, J=7.8 Hz, 1H); 7.61 (t, J=7.8 Hz, 1H); 7.70 (d, J=9.4 Hz, 1H); 7.91 (d, J=8.3 Hz, 1H); 8.55 (s, 1H); MS (ESI) m/z 414.9 (M+1)$^+$.

Example 1.17

N'-cyano-N-(2,6-dimethylphenyl)-2-isopropyl-4-(quinoxalin-2-yl)piperazine-1-carboximidamide $^1$H NMR (300 MHz, CDCl$_3$) δ ppm 0.93 (d, J=6.3 Hz, 3H); 0.99 (d, J=6.3 Hz, 3H); 2.15 (bs, 1H), 2.35 (d, J=23.1 Hz, 6H), 2.75 (bs., 1H); 3.07 (t, J=11.6 Hz, 1H); 3.25 (t, J=13.4 Hz, 1H); 3.37-3.56 (bs, 1H), 4.03-4.18 (bs, 1H), 4.45 (d, J=12.6 Hz, 2H), 6.58 (bs, 1H), 7.07-7.24 (m, 3H), 7.45 (t, J=7.5 Hz, 1H), 7.61 (t, J=7.8 Hz, 1H), 7.70 (d, J=8.9 Hz, 1H), 7.91 (d, J=8.1 Hz, 1H), 8.52 (s, 1H); MS (ESI) m/z 428.9 (M+1)$^+$.

Example 1.18

N'-cyano-2-isopropyl-N-(2-methoxyphenyl)-4-(quinoxalin-2-yl)piperazine-1-carboximidamide $^1$H NMR (300 MHz, CDCl$_3$) δ ppm 0.98 (d, J=6.2 Hz, 3H), 1.04 (d, J=6.2 Hz, 3H), 2.09-2.24 (m, 1H), 3.13-3.39 (m, 3H), 3.82-3.89 (bs, 1H), 3.92 (s, 3H), 3.97-4.09 (m, 1H), 4.53 (d, J=12.6 Hz, 1H), 4.62 (d, J=14.8 Hz, 1H), 6.81 (s, 1H), 6.98 (t, J=8.3 Hz, 2H), 7.13-7.25 (m, 2H), 7.47 (t, J=6.7 Hz, 1H), 7.64 (t, J=7.8, 1H); 7.80 (d, J=10.2 Hz, 1H), 7.94 (d, J=8.6 Hz, 1H), 8.59 (s, 1H); MS (ESI) m/z 430.9 (M+1)$^+$.

Example 1.19

N-(2-chlorophenyl)-N'-cyano-2-isopropyl-4-(quinoxalin-2-yl)piperazine-1-carboximidamide $^1$H NMR (300 MHz, CDCl$_3$) δ ppm 0.95 (d, J=6.3 Hz, 3H), 1.04 (d, J=6.3 Hz, 3H), 2.08-2.22 (m, 1H), 3.01-3.20

(m, 2H), 3.27 (t, J=12.1 Hz, 1H), 3.66-3.88 (bs, 1H); 4.00-4.16 (bs, 1H), 4.45 (d, J=12.1 Hz, 2H); 4.61 (d, J=13.4 Hz, 1H), 7.15 (t, J=7.0 Hz, 1H), 7.21-7.33 (m, 3H) 7.44 (t, J=7.8 Hz, 2H), 7.60 (t, J=8.3 Hz, 1H); 7.68 (d, J=8.6 Hz, 1H), 7.89 (d, J=9.4 Hz, 1H), 8.55 (s, 1H); MS (ESI) m/z 435.0 (M+1)⁺.

Example 1.20

N'-cyano-N-(3-fluorophenyl)-2-isopropyl-4-(quinoxalin-2-yl)piperazine-1-carboximidamide ¹H NMR (300 MHz, CDCl₃) δ ppm 0.94 (d, J=7.0 Hz, 3H); 1.06 (d, J=7.0 Hz, 3H); 2.09-2.20 (m, 1H); 3.12-3.38 (m, 3H); 3.87-4.15 (m, 2H); 4.52 (d, J=11.0 Hz, 1H); 4.68 (d, J=15.0 Hz, 1H); 6.77-6.95 (m, 3H); 7.23-7.35 (m, 2H); 7.49 (t, J=7.0 Hz, 1H); 7.66 (t, J=8.3 Hz, 1H); 7.76 (d, J=8.1 Hz, 1H); 7.94 (d, J=6.7 Hz, 1H); 8.63 (s, 1H); MS m/z 418.6 (M+1)⁺.

Example 1.21

N'-cyano-N-(2-fluorophenyl)-2-isopropyl-4-(quinoxalin-2-yl)piperazine-1-carboximidamide ¹H NMR (300 MHz, CDCl₃) δ ppm 0.96 (d, J=6.2 Hz, 3H), 1.05 (d, J=6.2 Hz, 3H), 2.11-2.24 (m, 1H), 3.07-3.22 (m, 2H), 3.25-3.38 (m, 1H), 3.76-3.89 (bs, 1H), 4.09 (d, J=15.0 Hz, 1H), 4.49 (d, J=12.6 Hz, 1H), 4.63 (d, J=14.8 Hz, 1H), 6.86 (s, 1H), 7.13-7.33 (m, 4H), 7.46 (t, J=7.0 Hz, 1H), 7.63 (t, J=7.0 Hz, 1H), 7.72 (d, J=9.4 Hz, 1H), 7.92 (d, J=7.3 Hz, 1H), 8.57 (s, 1H); MS (ESI) m/z 418.6 (M+1)⁺.

Example 1.22

N'-cyano-2-isopropyl-N-(3-methylphenyl)-4-(quinoxalin-2-yl)piperazine-1-carboximidamide ¹H NMR (300 MHz, CDCl₃) δ ppm 0.99 (d, J=28.5 Hz, 6H), 2.08-2.21 (m, 1H), 2.36 (s, 3H), 3.04-3.31 (m, 3H), 3.77-4.07 (m, 2H), 4.45 (d, J=11.3 Hz, 1H), 4.59 (d, J=12.6 Hz, 1H), 6.94 (d, J=7.4 Hz, 2H), 7.02 (d, J=7.8 Hz, 1H), 7.15 (s, 1H), 7.22-7.31 (d, J=9.1 Hz, 1H), 7.45 (t, J=8.1 Hz, 1H), 7.58-7.73 (m, 2H), 7.91 (d, J=7.8 Hz, 1H), 8.50 (s, 1H); MS (ESI) m/z 414.5 (M+1)⁺.

Example 1.23

N'-cyano-N-(4-fluorophenyl)-2-isopropyl-4-(quinoxalin-2-yl)piperazine-1-carboximidamide ¹H NMR (300 MHz, CDCl₃) δ ppm 0.94 (d, J=6.4 Hz, 3H), 1.04 (d, J=6.4 Hz, 3H), 2.07-2.23 (m, 1H), 3.04-3.34 (m, 3H), 3.90 (bs, 1H), 4.05 (bs, 1H), 4.48 (d, J=12.8 Hz, 1H), 4.63 (d, J=13.7 Hz, 1H), 7.02-7.19 (m, 4H), 7.46 (t, J=7.3 Hz, 1H), 7.63 (t, J=7.0 Hz, 2H), 7.71 (d, J=7.5 Hz, 1H), 7.92 (d, J=8.6 Hz, 1H), 8.58 (s, 1H); MS (ESI) m/z 418.4 (M+1)⁺.

Example 1.24

N'-cyano-2-isopropyl-4-(quinoxalin-2-yl)-N-[4-(trifluoromethyl)phenyl]piperazine-1-carboximidamide ¹H NMR (300 MHz, CDCl₃) δ ppm 0.88 (d, J=6.2 Hz, 3H), 1.05 (d, J=6.2 Hz, 3H), 2.07-2.23 (m, 1H), 3.01-3.35 (m, 3H), 3.88-4.27 (bs, 2H), 4.51 (d, J=12.6 Hz, 1H), 4.74 (d, J=13.4 Hz, 1H), 7.05 (d, J=8.3 Hz, 2H), 7.44 (t, J=7.0 Hz, 1H), 7.52 (d, J=8.6 Hz, 2H), 7.61 (t, J=7.0 Hz, 2H), 7.70 (d, J=7.8 Hz, 1H), 7.92 (d, J=8.9 Hz, 1H), 8.57 (s, 1H), 8.99 (s, 1H); MS (ESI) m/z 467.5 (M+1)⁺.

Example 1.25

N'-cyano-2-isopropyl-4-(quinoxalin-2-yl)-N-[3-(trifluoromethyl)phenyl]piperazine-1-carboximidamide ¹H NMR (300 MHz, CDCl₃) δ ppm 0.92 (d, J=7.0 Hz, 3H), 1.05 (d, J=7.0 Hz, 3H), 2.09-2.22 (m, 1H), 3.05-3.34 (m, 3H), 3.84-4.13 (m, 2H), 4.50 (d, J=12.9 Hz, 1H), 4.69 (d, J=14.4 Hz, 1H), 7.23 (s, 1H), 7.34 (t, J=7.3 Hz, 2H), 7.39-7.50 (m, 2H), 7.61 (t, J=7.0 Hz, 1H), 7.71 (d, J=8.1 Hz, 1H), 7.91 (d, J=8.1 Hz, 1H), 8.46 (bs, 1H); 8.56 (s, 1H); MS (ESI) m/z 468.9 (M+1)⁺.

Example 1.26

N'-cyano-2-isopropyl-N-(2-isopropylphenyl)-4-(quinoxalin-2-yl)piperazine-1-carboximidamide ¹H NMR (300 MHz, DMSO-d₆) δ ppm 0.95 (d, J=6.3 Hz, 3H), 1.07 (d, J=6.3 Hz, 3H), 1.22 (t, J=6.4 Hz, 6H), 2.06-2.22 (m, 1H), 2.27 (s, 3H), 3.13-3.46 (m, 4H), 4.09-4.23 (m., 2H), 4.51 (d, J=12.1 Hz, 1H), 4.73 (d, J=13.2 Hz, 1H), 7.08 (d, J=7.5 Hz, 1H), 7.13-7.28 (m, 2H), 7.33 (d, J=7.0 Hz, 1H), 7.37-7.47 (m, 1H), 7.56-7.66 (m, 2H), 7.84 (d, J=7.8 Hz, 1H), 8.58 (s, 1H), 8.81 (s, 1H); MS (ESI) m/z 443.0 (M+1)⁺.

Example 1.27

N'-cyano-2-isopropyl-4-(quinoxalin-2-yl)-N-[2-(trifluoromethoxy)phenyl]piperazine-1-carboximidamide ¹H NMR (300 MHz, DMSO-d₆) δ ppm 0.97 (d, J=6.6 Hz, 3H), 1.06 (d, J=6.6 Hz, 3H), 1.99-2.27 (m, 1H), 3.07-3.24 (m, 2H), 3.32 (t, J=12.9 Hz, 1H), 3.76 (bs, 1H), 4.09 (bs, 1H), 4.50 (d, J=12.6 Hz, 1H), 4.65 (d, J=13.2 Hz, 1H), 6.67 (s, 1H), 7.22-7.31 (m, 1H), 7.32-7.41 (m, 3H), 7.46 (t, J=7.8 Hz, 1H), 7.62 (t, J=7.8 Hz, 1H), 7.68 (d, J=7.8 Hz, 1H), 7.92 (d, J=8.6 Hz, 1H), 8.57 (s, 1H); MS (ESI) m/z 484.8 (M+1)⁺.

Example 1.28

N-(3-chlorophenyl)-N'-cyano-2-isopropyl-4-(quinoxalin-2-yl)piperazine-1-carboximidamide ¹H NMR (300 MHz, DMSO-d₆) δ ppm 0.89 (d, J=6.8 Hz, 3H), 1.06 (d, J=6.8 Hz, 3H), 2.02-2.21 (m, 1H), 3.16-3.46 (m, 3H), 4.02-4.18 (m., 2H); 4.52 (d, J=12.4 Hz, 1H), 4.78 (d, J=14.1 Hz, 1H), 7.01-7.19 (m, 3H), 7.28-7.47 (m, 2H), 7.55-7.68 (m, 2H), 7.85 (d, J=8.1 Hz, 1H), 8.80 (s, 1H), 9.07-9.36 (bs, 1H); MS (ESI) m/z 434.8 (M+1)⁺.

Example 1.29

N'-cyano-N-(3-fluoro-2-methylphenyl)-2-isopropyl-4-(quinoxalin-2-yl)piperazine-1-carboximidamide ¹H NMR (300 MHz, CDCl₃) δ ppm 0.94 (d, J=6.4 Hz, 3H), 1.01 (d, J=6.4 Hz, 3H), 2.09-2.22 (m, 1H), 2.27 (s, 3H), 2.95 (bs, 1H), 3.09 (t, J=11.6 Hz, 1H), 3.24 (t, J=15.3 Hz, 1H), 3.50-4.10 (bs, 2H), 4.45 (d, J=13.2 Hz, 1H), 4.54 (d, J=13.8 Hz, 1H), 6.83 (bs, 1H), 6.91-7.02 (m, 2H), 7.19 (q, J=8.3 Hz, 1H), 7.44 (t, J=7.0 Hz, 1H), 7.60 (t, J=7.3 Hz, 1H), 7.67 (d, J=9.1 Hz, 1H), 7.90 (d, J=8.3 Hz, 1H), 8.53 (s, 1H); MS (ESI) m/z 431.8 (M+1)$^+$.

Example 1.30

N-(2-chloro-4-fluorophenyl)-N'-cyano-2-isopropyl-4-(quinoxalin-2-yl)piperazine-1-carboximidamide $^1$H NMR (300 MHz, CDCl$_3$) δ ppm 0.94 (d, J=6.5 Hz, 3H), 1.08 (d, J=6.5 Hz, 3H), 2.05-2.22 (m, 1H), 3.18-3.46 (m, 3H), 4.10-4.26 (m, 2H), 4.51 (d, J=12.5 Hz, 1H), 4.75 (d, J=13.8 Hz, 1H), 7.13-7.28 (m, 1H), 7.32-7.48 (m, 3H), 7.56-7.67 (m, 2H), 7.84 (d, J=8.1 Hz, 1H), 8.80 (s, 1H), 8.97 (bs, 1H); MS (ESI) m/z 452.6 (M+1)$^+$.

Example 1.31

N'-cyano-N-(5-fluoro-2-methylphenyl)-2-isopropyl-4-(quinoxalin-2-yl)piperazine-1-carboximidamide $^1$H NMR (300 MHz, CDCl$_3$) δ ppm 0.96 (d, J=6.5 Hz, 3H), 1.03 (d, J=6.5 Hz, 3H), 2.11-2.24 (m, 1H), 2.31 (s, 3H), 3.01 (bs, 1H), 3.12 (t, J=12.6 Hz, 1H), 3.26 (t, J=15.6 Hz, 1H), 3.66 (bs, 1H), 3.99 (bs, 1H), 4.48 (d, J=12.6 Hz, 1H), 4.58 (d, J=14.8 Hz, 1H), 6.7 (s, 1H), 6.83-6.96 (m, 1H), 7.19-7.31 (t, J=6.7 Hz, 1H), 7.44 (t, J=8.1 Hz, 1H), 7.60 (t, J=8.9 Hz, 1H), 7.67 (d, J=8.6 Hz, 1H), 7.90 (d, J=8.9 Hz, 1H), 8.54 (s, 1H); MS (ESI) m/z 432.8 (M+1)$^+$.

Example 1.32

N'-cyano-N-(4-fluoro-2-methylphenyl)-2-isopropyl-4-(quinoxalin-2-yl)piperazine-1-carboximidamide $^1$H NMR (300 MHz, CDCl$_3$) δ ppm 0.94 (d, J=6.7 Hz, 3H), 1.02 (d, J=6.7 Hz, 3H), 2.08-2.23 (m, 1H), 2.35 (s, 3H), 2.94 (bs, 1H), 3.09 (t, J=13.2 Hz, 1H), 3.23 (t, J=13.6 Hz, 1H), 3.64 (bs, 1H), 4.00 (bs, 1H), 4.46 (d, J=12.6 Hz, 1H), 4.53 (d, J=13.7 Hz, 1H), 6.67 (s, 1H), 6.83-6.94 (t, J=8.9 Hz, 1H), 7.02 (d, J=11.0 Hz, 1H), 7.08-7.16 (m, 1H), 7.45 (t, J=7.0 Hz, 1H), 7.61 (t, J=8.1 Hz, 1H), 7.70 (d, J=9.4 Hz, 1H), 7.90 (d, J=7.8 Hz, 1H), 8.53 (s, 1H); MS (ESI) m/z 432.3 (M+1)$^+$.

Example 1.33

N'-cyano-N-(2-fluoro-6-methylphenyl)-2-isopropyl-4-(quinoxalin-2-yl)piperazine-1-carboximidamide $^1$H NMR (300 MHz, CDCl$_3$) δ ppm 0.94 (d, J=6.6 Hz, 3H), 1.02 (d, J=6.6 Hz, 3H), 2.09-2.21 (m, 1H), 2.39 (s, 3H), 2.79-2.96 (bs, 1H), 3.09 (t, J=11.6 Hz, 1H), 3.27 (t, J=12.9 Hz, 1H); 3.45-3.68 (bs, 1H), 4.11 (bs, 1H), 4.40-4.60 (m, 2H), 6.56 (bs, 1H), 7.02 (t, J=8.9 Hz, 1H), 7.09 (d, J=7.3 Hz, 1H), 7.18-7.25 (m, 1H), 7.45 (t, J=7.3 Hz, 1H), 7.61 (t, J=7.8 Hz, 1H), 7.71 (d, J=8.6 Hz, 1H), 7.91 (d, J=7.5 Hz, 1H), 8.53 (s, 1H); MS (ESI) m/z 432.1 (M+1)$^+$.

Example 1.34

N'-cyano-N-(4,5-difluoro-2-methylphenyl)-2-isopropyl-4-(quinoxalin-2-yl)piperazine-1-carboximidamide $^1$H NMR (300 MHz, CDCl$_3$) δ ppm 0.94 (d, J=6.9 Hz, 3H), 1.07 (d, J=6.9 Hz, 3H), 2.06-2.19 (m, 1H), 2.22 (s, 3H), 3.20-3.45 (m, 3H), 4.09-4.24 (m, 2H), 4.49 (d, J=12.5 Hz, 1H), 4.74 (d, J=13.7 Hz, 1H), 7.14 (q, J=8.1 Hz, 1H), 7.27 (t, J=10.5 Hz, 1H), 7.36-7.47 (m, 1H), 7.55-7.67 (m, 2H), 7.84 (d, J=8.6 Hz, 1H), 8.75 (bs, 1H), 8.80 (s, 1H); MS (ESI) m/z 450.0 (M+1)$^+$.

Example 1.35

N'-cyano-2-isopropyl-N-(2-methylbenzyl)-4-(quinoxalin-2-yl)piperazine-1-carboximidamide $^1$H NMR (300 MHz, DMSO-d$_6$) δ ppm 0.77 (d, J=5.7 Hz, 3H), 1.94-2.12 (m, 1H), 2.31 (s, 3H), 3.11 (t, J=12.1 Hz, 1H), 3.18-3.39 (m, 2H), 3.90 (d, J=14.2 Hz, 1H), 4.01 (d, J=9.7 Hz, 1H), 4.41-4.64 (m, 3H), 4.84 (d, J=14.2 Hz, 1H), 7.11-7.29 (m, 4H), 7.41 (bs, 1H), 7.60 (bs, 2H), 7.74-7.89 (m, 2H), 8.86 (s, 1H).

Example 1.36

N-(3-tert-butyl-1-methyl-1H-pyrazol-5-yl)-N'-cyano-2-isopropyl-4-(quinoxalin-2-yl)piperazine-1-carboximidamide $^1$H NMR (300 MHz, methanol-d) δ ppm 0.89 (d, J=6.8 Hz, 3H), 1.2 (d, J=6.8 Hz, 3H), 1.45 (s, 9H), 2.20-2.30 (m, 1H), 3.30-3.40 (m, 2H), 3.40-3.50 (m, 1H), 3.8 (s, 3H), 4.50-4.74 (m, 3H), 4.85-4.99 (m, 3H), 7.40-7.48 (m, 1H), 7.61-7.68 (m, 1H), 7.69-7.72 (m, 1H), 7.85 (d, J=8 Hz, 1H), 8.75 (s, 1H); MS (ESI) m/z 460.9 (M+1)$^+$.

Example 1.37

N'-cyano-2-isobutyl-N-(2-methylphenyl)-4-(quinoxalin-2-yl)piperazine-1-carboximidamide $^1$H NMR (300 MHz, DMSO-d$_6$) δ ppm 0.78-0.99 (m, 6H), 1.35-1.50 (m, 1H), 1.52-1.68 (m, 2H), 2.33 (s, 3H), 2.95-3.07 (m, 1H), 3.10-3.28 (m, 2H), 3.63-3.81 (bs, 1H), 4.23-4.46 (m, 3H), 7.0-7.11 (m, 2H), 7.12-7.30 (m, 3H), 7.42 (t, J=7.5 Hz, 1H), 7.53-7.70 (m, 2H), 7.89 (d, J=8.6 Hz, 1H), 8.49 (s, 1H); MS (ESI) m/z 428.9 (M+1)$^+$.

Example 1.38

N'-cyano-2-isobutyl-N-(3-methylphenyl)-4-(quinoxalin-2-yl)piperazine-1-carboximidamide $^1$H NMR (300 MHz, CDCl$_3$) δ ppm 0.83-0.99 (m, 6H), 1.47-1.66 (m, 3H), 2.36 (s, 3H), 3.0-3.13 (m, 1H), 3.18-3.32 (m, 2H), 3.76-3.86 (m, 1H), 4.28-4.55 (mn, 3H), 6.86-6.95 (m, 2H), 7.01 (d, J=7.8 Hz; 1H); 7.12 (s, 1H); 7.22-7.32 (m, 1H); 7.44 (t, J=7.8 Hz, 1H), 7.60 (t, J=7.3 Hz, 1H), 7.68 (d, J=3.8 Hz, 1H); 7.92 (d, J=8.6 Hz, 1H); 8.53 (s, 1H); MS (ESI) m/z 428.8 (M+1)$^+$.

Example 1.39

N'-cyano-N-(2-fluorophenyl)-2-isobutyl-4-(quinoxalin-2-yl)piperazine-1-carboximidamide $^1$H NMR (300 MHz, CDCl$_3$) δ ppm 0.92 (d, J=5.6 Hz, 6H), 1.46-1.70 (m, 3H), 3.05-3.42 (m, 4H), 3.75-3.87 (d, J=13.4 Hz, 1H), 4.38 (d, J=14.2 Hz, 2H), 4.50 (d, J=13.2 Hz, 1H); 6.87 (bs, 1H), 7.14-7.26 (m, 4H), 7.46 (t, J=8.1 Hz, 1H); 7.63 (t, J=7.3,1H); 7.70 (d, J=8.6 Hz, 1H), 7.92 (d, J=8.1 Hz, 1H); 8.56 (s, 1H); MS (ESI) m/z 432.4 (M+1)$^+$.

Example 1.40

N'-cyano-N-(3-fluorophenyl)-2-isobutyl-4-(quinoxalin-2-yl)piperazine-1-carboximidamide $^1$H NMR (300 MHz, CDCl$_3$) δ ppm 0.92 (d, J=6.7 Hz, 6H), 1.47-1.69 (m, 3H), 3.12 (t, J=11.6 Hz, 1H), 3.23-3.39 (m, 2H), 3.75-3.88 (bs, 1H), 4.39 (d, J=13.7 Hz, 2H), 4.51 (d, J=7.0 Hz, 1H), 6.80-6.93 (m, 3H), 7.34 (q, J=8.1 Hz, 1H), 7.46 (t, J=7.5 Hz, 2H), 7.62 (t, J=8.3 Hz, 2H), 7.70 (d, J=9.7 Hz, 1H), 7.92 (d, J=8.9 Hz, 1H), 8.55 (s, 1H); MS (ESI) m/z 432.8 (M+1)$^+$.

Example 1.41

N-(2-chlorophenyl)-N'-cyano-2-isobutyl-4-(quinoxalin-2-yl)piperazine-1-carboximidamide $^1$H NMR (300 MHz, CDCl$_3$) δ ppm 0.92 (d, J=5.9 Hz, 6H), 1.45-1.55 (mn, 1H), 1.56-1.69 (m, 2H), 3.16 (t, J=11.6 Hz, 1H), 3.23-3.42 (m, 2H), 3.84 (d, J=14.0 Hz, 1H); 4.28-4.44 (m, 2H), 4.51 (d, J=14.2 Hz, 1H), 6.81-6.91 (bs, 1H), 7.13-7.36 (m, 4H); 7.47 (t, J=8.6 Hz, 2H), 7.63 (t, J=7.8 Hz, 1H), 7.73 (d, J=6.7 Hz, 1H); MS (ESI) m/z 448.3 (M+1)$^+$.

Example 1.42

N'-cyano-2-methyl-N-(2-methylphenyl)-4-(quinoxalin-2-yl)piperazine-1-carboximidamide $^1$H NMR (300 MHz, DMSO-d$_6$) δ ppm 1.22 (d, J=8.8 Hz, 3H), 2.22 (s, 3H), 3.19 (m, 1H), 3.42 (m, 2H), 3.99 (m, 1H), 4.38-4.60 (m, 3H), 7.05-7.28 (m, 4H), 7.41 (m, 1H), 7.62 (d, J=4.4 Hz, 2H), 7.84 (d, J=10.4 Hz, 1H), 8.85 (bs, 1H), 8.94 (bs, 1H); MS (ESI) m/z 386.7 (M+1)$^+$.

Example 1.43

N'-cyano-N-(2-methylphenyl)-8-(quinoxalin-2-yl)-5,8-diazaspiro[3.5]nonane-5-carboximidamide $^1$H NMR (300 MHz, DMSO-d$_6$) δ ppm 1.70-1.82 (m, 1H), 1.86-1.95 (m, 1H), 2.12-2.20 (m, 2H), 2.20-2.30 (m, 2H), 2.26 (s, 3H), 3.40-3.50 (m, 2H), 3.50-3.60 (m, 2H), 4.02 (bs, 2H), 7.10-7.25 (m, 4H), 7.35-7.45 (m, 1H), 7.60-7.72 (m, 2H), 7.80-7.85 (m, 1H), 8.88 (s, 1H), 9.02 (bs, 1H); MS m/z 412.1 (M+1)$^+$; MS (ESI) m/z 412.1 (M+1)$^+$.

Example 1.44

N'-cyano-2-ethyl-N-(2-methylphenyl)-4-(quinoxalin-2-yl)piperazine-1-carboximidamide $^1$H NMR (300 MHz, methanol-di) δ ppm 0.92-1.05 (m, 3H), 1.70-1.78 (m, 2H), 2.32 (s, 3H), 3.20-3.26 (m, 1H), 3.32 (s, 1H), 3.40-3.49 (m, 1H), 4.10-4.20 (m, 1H), 4.35-4.45 (m, 1H), 4.53-4.65 (m, 2H), 7.15-7.25 (m, 4H), 7.40-7.76 (m, 1H), 7.60-7.68 (m, 2H), 7.81-7.88 (m, 1H), 8.68 (s, 1H); MS (ESI) m/z 400.0 (M+1)$^+$.

Example 1.45

N'-cyano-N-(2-methylphenyl)-7-(quinoxalin-2-yl)-4,7-diazaspiro[2.5]octane-4-carboximidamide $^1$H NMR (300 MHz, methanol-di) δ ppm 0.86-1.15 (m, 4H), 2.32 (s, 3H), 3.60-3.70 (m, 2H), 3.82 (bs, 2H), 3.90-3.98 (m, 2H), 6.80 (bs, 1H), 7.03-7.10 (m, 1H), 7.18-7.26 (m, 2H), 7.28-7.33 (m, 1H), 7.40-7.64 (m, 1H), 7.55-7.65 (m, 1H), 7.62-7.68 (m, 1H), 7.85-7.93 (m, 1H); 8.54 (s, 1H); MS (ESI) m/z 398.1 (M+1)$^+$.

Example 1.46

2-tert-butyl-N'-cyano-N-(2-methylphenyl)-4-(quinoxalin-2-yl)piperazine-1-carboximidamide $^1$H NMR (300 MHz, methanol-di) δ ppm 1.04 (s, 9H); 2.26 (s, 3H), 3.60 (m, 1H), 3.78 (m, 2H), 4.20 (m, 1H), 4.30 (m, 1H), 4.40 (m, 1H), 7.08 (m, 1H); 7.16 (m, 2H); 7.24 (m, 1H), 7.46 (m, 1H), 7.64 (m, 1H), 7.72 (m, 1H), 7.86 (m, 1H), 8.70 (s, 1H); MS (ESI) m/z 428.1 (M+1)$^+$.

Example 1.47

2-sec-butyl-N'-cyano-N-(2-methylphenyl)-4-(quinoxalin-2-yl)piperazine-1-carboximidamide $^1$H NMR (300 MHz, DMSO-d$_6$) δ ppm 0.78-0.92 (m, 4H), 0.92-1.06 (m, 2H), 1.08-1.22 (m, 1H), 1.42-1.70 (m, 1H); 1.86 (bs, 1H); 2.24 (s, 3H); 3.14-3.24 (m, 1H), 3.22-3.34 (m, 2H), 4.06-4.16 (m, 2H), 4.50-4.61 (m, 1H), 4.75-4.84 (m, 1H), 7.10-7.28 (m, 4H), 7.35-7.45 (m, 1H), 7.52-7.66 (m, 2H), 7.80-7.90 (m, 1H), 8.86 (s., 1H), 8.92 (bs, 1H); MS (ESI) m/z 428.9 (M+1)$^+$.

Example 1.48

N'-cyano-2-cyclohexyl-N-(2-methylphenyl)-4-(quinoxalin-2-yl)piperazine-1-carboximidamide $^1$H NMR (300 MHz, DMSO-d$_6$) δ ppm 0.90-1.20 (m, 5H), 1.50-1.62 (m, 2H), 1.65-1.78 (m, 3H), 2.00-2.08 (m, 1H), 2.15-2.30 (s, 3H), 3.05-3.08 (m, 2H), 3.27-3.33 (m, 1H), 4.05-3.15 (m, 2H), 4.51- 4.58 (m, 1H), 4.75-4.85 (m, 1H), 7.10-7.26 (m, 4H), 7.35-7.45 (m, 1H), 7.50-7.62 (m, 2H), 7.80-4.88 (m, 1H), 8.84 (bs, 1H), 8.86 (s, 1H); MS (ESI) m/z 454.1 (M+1)$^+$.

Example 1.49

N'-cyano-2-(cyclohexylmethyl)-N-(2-methylphenyl)-4-(quinoxalin-2-yl)piperazine-1-carboximidamide $^1$H NMR (300 MHz, CDCl$_3$) δ ppm 0.82-0.92 (m, 2H), 1.18-1.34 (m, 4H), 1.44-1.51 (m, 1H), 1.55-1.72 (m, 6H), 2.34 (s, 3H), 3.00-3.08 (m, 1H), 3.18-3.24 (m, 2H), 3.65-3.72 (m, 1H), 4.30-4.43 (m, 3H), 6.56 (bs, 1H), 7.02-7.12 (m, 1H), 7.15-7.30 (m, 3H), 7.40-7.48 (m, 1H), 7.55-7.64 (m, 1H), 7.68 (m, 1H), 7.85-7.95 (m, 1H), 8.52 (s, 1H); MS (ESI) m/z 468.5 (M+1)$^+$.

Example 1.50

N'-cyano-4-(6,7-dimethylquinoxalin-2-yl)-2-isopropyl-N-(2-methylphenyl)piperazine-1-carboximidamide $^1$H NMR (300 MHz, methanol-d) δ ppm 1.01-1.16 (m, 6H), 2.15-2.25 (m, 1H), 2.36 (s, 3H), 2.42-3.47 (bs, 6H), 3.16-3.26 (m, 2H), 3.39-3.47 (m, 1H), 4.04-4.28 (m, 2H), 4.48-4.54 (m, 1H), 4.78-4.84 (m, 1H), 7.13-7.29 (m, 4H), 7.47 (s, 1H), 7.61 (1H), 8.62 (bs, 1H); MS (ESI) m/z 442.6 (M+1)$^+$.

Example 1.51

N'-cyano-4-(6,7-difluoroquinoxalin-2-yl)-2-isopropyl-N-(2-methylphenyl)piperazine-1-carboximidamide $^1$H NMR (300 MHz, CDCl$_3$) δ ppm 0.90-1.06 (m, 6H), 2.04-2.18 (m, 1H), 2.36 (s, 3H), 2.86-3.25 (m, 3H), 3.50-3.75 (m, 1H), 3.89-4.06 (m, 1H), 4.36-4.54 (m, 2H), 6.62 (s, 1H), 7.11-7.45 (m, 5H), 7.61-7.66 (m, 1H), 8.46 (s, 1H); MS (ESI) m/z 450.1 (M+1)$^+$.

Example 1.52

N'-cyano-2-isopropyl-N-(2-methylphenyl)-4-(3-methylquinoxalin-2-yl)piperazine-1-carboximidamide $^1$H NMR (300 MHz, methanol-d) δ ppm 0.98-1.07 (m, 6H), 2.34 (s, 3H), 2.47-2.57 (m, 1H), 2.76 (s, 3H), 3.00-3.18 (m, 2H), 3.53-3.62 (m, 1H), 3.82-3.99 (m, 2H), 4.10-4.32 (m, 2H), 7.12-7.29 (m, 4H), 7.56-7.69 (m, 2H), 7.82-7.91 (m, 2H); MS (ESI) m/z 428.4 (M+1)$^+$.

Example 1.53

N'-cyano-2-isopropyl-N-(2-methylphenyl)-4-[3-(trifluoromethyl)quinoxalin-2-yl]piperazine-1-carboximidamide $^1$H NMR (300 MHz, methanol-di) δ ppm 0.98-1.08 (m, 6H), 2.33 (s, 3H), 2.42-2.53 (m, 1H), 3.08-3.18 (m, 1H), 3.52-3.63 (m, 1H), 3.80-4.02 (m, 2H), 4.10-4.30 (m, 2H), 4.80-4.90 (m, 1H), 7.10-7.28 (m, 4H), 7.80-7.85 (m, 1H), 7.89-8.00 (m, 1H), 8.95 (bs, 1H), 9.08 (bs, 1H); MS (ESI) m/z 482.3 (M+1)$^+$.

Example 1.54

N'-cyano-4-(6-fluoroquinoxalin-2-yl)-2-isopropyl-N-(2-methylphenyl)piperazine-1-carboximidamide $^1$H NMR (300 MHz, DMSO-d$_6$) δ ppm 0.77-1.32 (m, 7H), 1.91-2.15 (m, 1H), 2.24 (s, 3H), 3.08-3.20 (m, 2H), 3.94-4.23 (m, 2H), 4.47-4.85 (m, 2H), 7.04-7.30 (m, 4H), 7.46-7.70 (m, 3H), 8.80-9.03 (m, 2H); MS (ESI) m/z 432.0 (M+1)$^+$.

Example 1.55

4-(7-chloroquinoxalin-2-yl)-N'-cyano-2-isopropyl-N-(2-methylphenyl)piperazine-1-carboximidamide $^1$H NMR (300 MHz, DMSO-d$_6$) δ ppm 0.86-1.09 (m, 6H), 1.97-2.09 (m, 1H), 2.24 (s, 3H), 3.13-3.27 (m, 3H), 3.94-4.23 (m, 2H), 4.51-4.88 (m, 2H), 7.04-7.26 (m, 4H), 7.37-7.42 (m, 1H), 7.56 (s, 1H), 7.80-7.86 (m, 1H), 8.86-9.06 (m, 2H); MS (ESI) m/z 448.1 (M+1)$^+$.

Example 1.56

N'-cyano-2-isopropyl-N-(2-methylphenyl)-4-(7-methylquinoxalin-2-yl)piperazine-1-carboximidamide $^1$H NMR (300 MHz, DMSO-d$_6$) δ ppm 0.83-1.07 (m, 6H), 2.01-2.12 (m, 1H), 2.24 (s, 3H), 2.45 (s, 3H), 3.08-3.18 (m, 3H), 3.96-4.21 (m, 2H), 4.50-4.88 (m, 2H), 7.05-7.29 (m, 5H), 7.40 (s, 1H), 7.69-7.75 (m, 1H), 8.72-8.96 (m, 2H); MS (ESI) m/z 448.1 (M+1)$^+$.

Example 1.57

N'-cyano-2-isopropyl-N-(2-methylphenyl)-4-[6-(trifluoromethyl)quinoxalin-2-yl]piperazine-1-carboximidamide $^1$H NMR (300 MHz, DMSO-d$_6$) δ ppm 0.89 (d, J=6.7 Hz, 3H), 1.05 (d, J=6.7 Hz, 3H), 1.99-2.08 (m, 1H), 2.24 (s, 3H), 3.18-3.34 (m, 3H), 4.00-4.21 (m, 2H), 4.58-4.90 (m, 2H), 7.06-7.25 (m, 4H), 774 (bs, 1H), 7.85 (bs, 1H), 8.14 (s, 1H), 8.91 (s, 1H), 9.00 (s, 1H); MS (ESI) m/z 482.2 (M+1)$^+$.

Example 1.58

N'-cyano-4-(6,7-dichloroquinoxalin-2-yl)-2-isopropyl-N-(2-methylphenyl)piperazine-1-carboximidamide $^1$H NMR (300 MHz, methanol-d) δ ppm 0.87 (d, J=7.8 Hz, 3H), 1.04 (d, J=7.8 Hz, 3H), 2.02-2.10 (m, 1H), 2.23 (s, 3H), 3.12-3.30 (m, 3H), 4.08-4.18 (m, 2H), 4.55-4.62 (m, 1H), 4.75-4.83 (m, 1H), 7.05-7.25 (m, 4H), 7.81 (s, 1H), 8.08 (s, 1H), 8.92 (s, 1H); MS (ESI) m/z 481.8 (M+1)$^+$.

Example 1.59

N'-cyano-2-isopropyl-N-(2-methylphenyl)-4-[8-(trifluoromethyl)quinoxalin-2-yl]piperazine-1-carboximidamide $^1$H NMR (300 MHz, methanol-d) δ ppm 1.01 (d, J=7.6 Hz, 3H), 1.13 (d, J=7.6 Hz, 3H), 2.12-2.24 (m, 1H), 2.34 (s, 3H), 3.20-3.43 (m, 3H), 4.05-4.30 (m, 2H), 4.60-4.72 (m, 1H), 4.75-4.90 (m, 1H), 7.13-7.29 (m, 4H), 7.65-7.72 (m, 1H), 7.71-7.76 (m, 1H), 7.80-7.90 (m, 1H), 8.81 (s, 1H); MS (ESI) m/z 482.4 (M+1)$^+$.

Example 1.60

N'-cyano-4-(7-fluoroquinoxalin-2-yl)-2-isopropyl-N-(2-methylphenyl)piperazine-1-carboximidamide $^1$H NMR (300 MHz, methanol-d$_4$) δ ppm 1.04 (d, J=5.6 Hz, 3H), 1.12 (d, J=5.6 Hz, 3H), 2.10-2.20 (m, 1H), 2.31 (s, 3H), 3.20-3.40 (m, 3H), 4.15-4.30 (m, 2H), 4.60-4.70 (m, 1H), 4.75-4.86 (m, 1H), 7.13-7.46 (m, 6H), 7.85-7.92 (m, 1H), 8.76 (s, 1H); MS (ESI) m/z 432.6 (M+1)⁺.

Example 1.61

N'-cyano-2-isopropyl-N-(2-methylphenyl)-4-(quinolin-2-yl)piperazine-1-carboximidamide ¹H NMR (300 MHz, methanol-d) δ ppm 0.95 (d, J=6.9 Hz, 3H), 1.05 (d, J=6.9 Hz, 3H), 2.05-2.15 (m, 1H), 2.27 (s, 3H), 3.10-3.20 (m, 2H), 3.26-3.34 (m, 1H), 4.05-4.16 (m, 2H), 4.40-4.48 (m, 1H), 4.62-4.71 (m, 1H), 7.03.-7.28 (m, 6H), 7.49-7.63 (m, 2H), 7.70 (d, J=8.4 Hz, 1H), 8.03 (d, J=9.2 Hz, 1H), 8.59 (s, 1H); MS (ESI) m/z 481.0 (M+1)⁺.

Example 1.62

N'-cyano-2-isopropyl-N-(2-methylphenyl)-4-(quinazolin-2-yl)piperazine-1-carboximidamide ¹H NMR (300 MHz, DMSO-d₆) δ ppm 0.86 (d, J=7.4 Hz, 3H), 1.03 (d, J=7.4 Hz, 3H), 1.95-2.14 (m, 1H), 2.24 (s, 3H), 3.08-3.20 (m, 3H), 4.05-4.17 (m, 2H), 4.80-4.87 (m, 1H), 5.00-5.10 (m, 1H), 7.05- 7.32 (m, 5H), 7.50 (d, J=8.3 Hz, 1H), 7.74 (t, J=9.0 Hz, 1H), 7.84 (d, J=8.9 Hz, 1H), 8.88 (s, 1H), 9.23 (s, 1H).; MS (ESI) m/z 414.9 (M+1)⁺.

Example 1.63

N'-cyano-2-isopropyl-N-(2-methylphenyl)-4-[6-(morpholin-4-yl)pyrazin-2-yl]piperazine-1-carboximidamide ¹H NMR (300 MHz, CDCl₃) δ ppm 0.80-1.20 (m, 8H), 1.60-1.9-69 (m, 1H), 2.21-3.07 (m, 12H), 3.30-3.37 (m, 2H), 4.46-4.53 (m, 2H), 7.07-7.29 (m, 2H), 7.57 (bs, 1H), 8.07 (bs, 1H), 8.51 (bs, 1H), 8.71 (bs, 1H); MS (ESI) m/z 449.8 (M+1)⁺.

Example 1.64

N'-cyano-4-[4-(cyclohexylamino)-5,6-dimethylpyrimidin-2-yl]-2-isopropyl-N-(2-methylphenyl)piperazine-1-carboximidamide ¹H NMR (300 MHz, DMSO-d₆) δ ppm 0.87 (d, J=7.4 Hz, 3H), 1.08 (d, J=7.4 Hz, 3H), 1.09-1.34 (m, 6H), 1.57-1.76 (m, 3H), 1.81-1.91 (m, 5H), 2.00-2.10 (m, 1H), 2.11 (s, 3H), 2.22 (s, 3H), 2.75-2.85 (m, 2H), 3.02-3.12 (m, 1H), 3.78-4.06 (m, 2H), 4.50-4.62 (m, 1H), 4.70-4.77 (m, 1H), 4.79 (d, J=8.3 Hz, 1H), 7.02-7.25 (m, 4H), 8.79 (bs, 1H); MS (ESI) m/z 489.9 (M+1)⁺.

Example 1.65

N'-cyano-2-isopropyl-N-(2-methylphenyl)-4-(pyrido[2,3-b]pyrazin-6-yl)piperazine-1-carboximidamide ¹H NMR (300 MHz, DMSO-d₆) δ ppm 0.87 (d, J=7.4 Hz, 3H), 1.04 (d, J=7.4 Hz, 3H), 2.00-2.08 (m, 1H), 2.24 (s, 3H), 3.14-3.24 (m, 3H), 4.05-4.15 (m, 2H), 4.55-4.63 (m, 1H), 4.82-4.90 (m, 1H), 7.05- 7.25 (m, 4H), 7.64 (d, J=9.4 Hz, 1H), 8.13 (d, J=9.4 Hz, 1H), 8.57 (s, 1H), 8.86 (s, 1H), 8.90 (bs, 1H); MS (ESI) m/z 415.5 (M+1)⁺.

Example 1.66

N'-cyano-2-isopropyl-N-(2-methylphenyl)-4-(1,8-naphthyridin-2-yl)piperazine-1-carboximidamide ¹H NMR (300 MHz, methanol-d) δ ppm 0.98 (d, J=7.6 Hz, 3H), 1.12 (d, J=7.6 Hz, 3H), 2.17 (m, 1H), 2.33 (s, 3H), 3.19-3.40 (m, 3H), 4.18 (m, 2H), 4.68 (m, 1H), 4.92 (m, 1H), 7.13-7.34 (m, 6H), 8.07 (d, J=8.4 Hz, 1H), 8.19 (d, J=8.4 Hz, 1H), 8.72 (s, 1H); MS (ESI) m/z 414.9 (M+1)⁺.

Example 1.67

(2S)—N'-cyano-4-(6-fluoroquinoxalin-2-yl)-2-isopropyl-N-(2-methylphenyl)piperazine-1-carboximidamide ¹H NMR (300 MHz, CDCl₃) δ ppm 0.95 (d, J=6.5 Hz, 3H); 1.00 (d, J=6.5 Hz, 3H); 2.06-2.21 (m, 1H); 2.37 (s, 3H), 2.83-2.96 (m, 1H); 3.07 (t, J=12.1, 11); 3.21 (t, J=12.9, 1H); 3.46-3.71 (b.s., 1H); 3.89-4.09 (b.s., 1H); 4.32-4.52 (m, 2H); 6.59 (s, 1H); 7.14 (d, J=7.8, 1H); 7.18-7.34 (m, 3H); 7.40 (t, J=8.9, 1H); 7.55 (d, J=8.8, 1H); 7.66 (t, J=7.8, 1H); 8.53 (s, 1H); MS (ESI) m/z 432.8.

Example 1.68

N'-cyano-2-isopropyl-4-(7-methyl-1,8-naphthyridin-2-yl)-N-(2-methylphenyl)piperazine-1-carboximidamide ¹H NMR (300 MHz, methanol-d₄) δ ppm 0.98 (d, J=7.5 Hz, 3H), 1.11 (d, J=7.5 Hz, 3H), 2.11-2.19 (m, 1H), 2.33 (s, 3H), 2.66 (s, 1H), 3.14-3.40 (m, 3H), 4.12-4.22 (m, 2H), 4.60-4.70 (m, 1H), 4.82-4.91 (m, 1H), 7.12-7.30 (m, 6H), 8.00-8.10 (m, 2H); MS (ESI) m/z 428.1 (M+1)⁺.

Example 1.69

N'-cyano-2-isopropyl-4-(1-methyl-1H-benzimidazol-2-yl)-N-(2-methylphenyl)piperazine-1-carboximidamide ¹H NMR (300 MHz, methanol-d₄) δ ppm 1.00-1.15 (m, 6H), 2.34 (s, 3H), 2.60-2.68 (m, 1H), 3.10-3.17 (m, 2H), 3.50-3.65 (m, 2H), 3.67-3.78 (m, 4H), 4.10-4.22 (m, 2H), 7.14-7.30 (m, 6H), 7.37 (d, J=8.3 Hz, 1H), 7.50 (d, J=8.3 Hz, 1H); MS (ESI) m/z 416.2 (M+1)⁺.

Example 1.70

N'-cyano-3-isopropyl-N-(2-methylphenyl)-4-(quinoxalin-2-yl)piperazine-1-carboximidamide ¹H NMR (300 MHz, DMSO-d₆) δ ppm 0.75-0.85 (m, 3H), 1.00-1.14 (m, 3H), 2.14-2.20 (m, 4H), 3.20-3.26 (m, 2H), 3.38 (s, 1H), 4.00-4.12 (m, 1H), 4.20-4.26 (m, 1H), 4.42-4.49 (m, 1H), 4.60-4.65 (m, 1H), 7.00-7.10 (m, 1H), 7.16-7.22 (m, 3H), 7.35-7.45 (m, 1H), 7.60-7.70 (m, 2H), 7.80-7.85 (m, 1H), 8.86 (bs, 1H), 8.88 (bs, 1H); MS (ESI) m/z 414.9 (M+1)⁺.

Example 1.71

(2S)—N-(2-chlorophenyl)-N'-cyano-4-(6-fluoroquinoxalin-2-yl)-2-isopropylpiperazine-1-carboximidamide ¹H NMR (400 MHz, CDCl₃) 0.84 (d, J=6.4 Hz, 3H), 0.94 (d, J=6.4 Hz, 3H), 1.75-1.86 (m, 1H), 3.23-3.28 (m, 1H), 3.42 (t, J=11.0 Hz, 2H), 3.82-3.97 (m, 2H), 4.02-4.16 (m, 2H), 5.79 (bs, 1H), 7.01 (t, J=6.5 Hz, 1H), 7.08 (t, J=11.0 Hz, 1H), 7.21 (d, J=8.9 Hz, 1H), 7.43 (t, J=8.1 Hz, 1H), 7.48 (d, J=9.8 Hz, 1H), 7.72 (d, J=10.0 Hz, 1H), 7.78-7.81 (m, 1H), 7.99 (s, 1H); MS (ESI) m/z 425.6 (M+1)⁺.

Scheme 9: Formation of cyanoguanidines

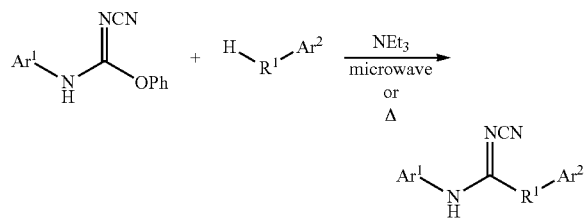

Example 1.72

N'-cyano-2-isopropyl-N-(4-methylpyridin-3-yl)-4-(quinoxalin-2-yl)piperazine-1-carboximidamide

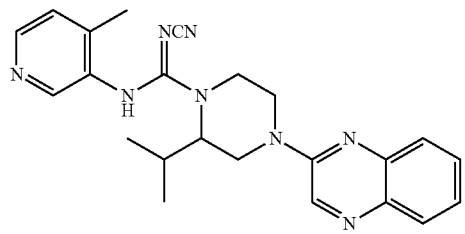

To a mixture of phenyl N'-cyano-N-(4-methylpyridin-3-yl)carbamimidate (Example F1, 500 mg, 1.98 mmol) and 2-(3-isopropylpiperazin-1-yl)quinoxaline (Example G1, 508 mg, 1.98 mmol) was added acetonitrile (2.3 mL) and triethylamine (201 mg, 1.98 mmol). The reaction mixture was stirred in microwave oven (CEM, Discover®-SP with ActiVent®, 300 W maximum) at 110° C. for 3 hours in a pressure vessel. The reaction mixture was cooled down to ambient temperature, ethyl acetate (20 mL) was added, and the organic layer was washed with water and brine. The solvent was removed under reduced pressure, and the residue was purified by silica gel column chromatography eluting with mixture ethyl acetate:hexane (1:1) to afford 140 mg, 17% of the titled compound as a white solid. ¹H NMR (300 MHz, CDCl₃) δ ppm 0.87 (d, J=6.8 Hz, 3H), 1.18 (d, J=6.8 Hz, 3H), 2.19-2.28 (m, 1H), 2.55 (s, 3H), 3.17-3.38 (m, 3H), 4.48-4.56 (m, 1H), 4.70-4.80 (m, 1H), 4.85-4.94 (m, 1H), 5.00-5.10 (m, 1H), 7.32 (d, J=4 Hz, 1H), 7.4 (t, J=7.6 Hz, 1H), 7.59 (t, J=7.6 Hz, 1H), 7.7 (d, J=8.4 Hz, 1H), 7.9 (d, J=8.4 Hz, 1H), 8.21 (d, J=4.4 Hz, 1H), 8.62 (s, 1H); MS (ESI) m/z 415.5 (M+1)⁺.

Example 1.73

N'-cyano-2-isopropyl-N-(2-methylpyridin-3-yl)-4-(quinoxalin-2-yl)piperazine-1-carboximidamide

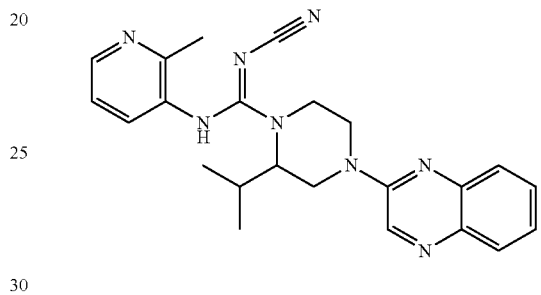

The compound was synthesized according to the procedure described for preparation of N'-cyano-2-isopropyl-N-(4-methylpyridin-3-yl)-4-(quinoxalin-2-yl)piperazine-1-carboximidamide (Example 1.72) making non-critical variations using phenyl N'-cyano-N-(2-methylpyridin-3-yl)carbamimidate (Example F2, 300 mg, 1.19 mmol) instead N'-cyano-N-(4-methylpyridin-3-yl)carbamimidate (Example F1). The product was purified by silica gel column chromatography eluting with mixture ethyl acetate:hexane (1:1) to afford 140 mg, 17% of the titled compound as a yellow solid. ¹H NMR (300 MHz, DMSO-d₆) δ ppm 0.88 (d, J=6.4 Hz, 3H), 1.05 (d, J=6.4 Hz, 3H), 2.00-2.10 (m, 1H), 2.43 (s, 3H), 3.15-3.40 (m, 4H), 4.10-4.25 (m, 2H), 4.50-4.65 (m, 1H), 4.80-4.90 (m, 1H), 7.20-7.30 (m, 1H), 7.35-7.53 (m, 2H), 7.60 (d, J=3.6 Hz, 1H), 7.84 (d, J=8 Hz, 1H), 8.31 (d, J=4 Hz, 1H), 8.88 (s, 1H), 9.09 (bs, 1H); MS (ESI) m/z 415.9 (M+1)⁺.

Scheme 10: Formation of cyanoguanidines

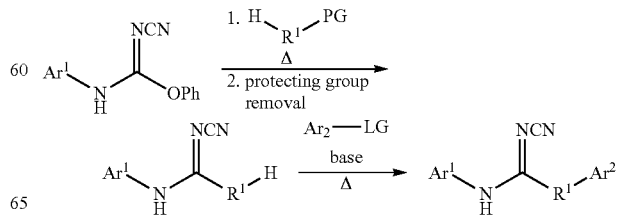

Example 1.74

N'-cyano-N-(2-methylphenyl)-4-(quinoxalin-2-yl)piperazine-1-carboximidamide

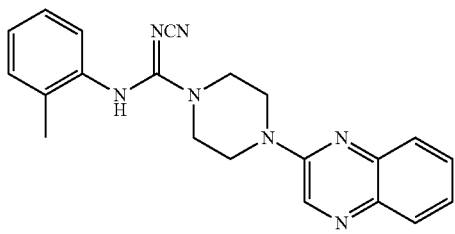

Step A: benzyl 4-[N'-cyano-N-(2-methylphenyl)carbamimidoyl]piperazine-1-carboxylate

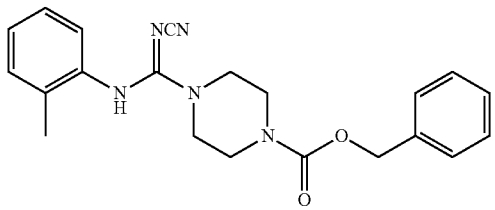

A mixture of phenyl N'-cyano-N-(2-methylphenyl)carbamimidate (Example F3, 1.00 g, 3.98 mmol) and benzyl piperazine-1-carboxylate (0.77 mL, 4.0 mmol) in acetonitrile (22 mL) was heated at about 70° C. After about 16 hours, the reaction was cooled to room temperature and concentrated under reduced pressure. The crude residue was purified via silica gel chromatography eluting with 0-40% dichloromethane/methanol/ammonium hydroxide (90:9:1) in dichloromethane. The product-containing fractions were concentrated to give the title compound (0.90 g, 60%) as a solid after drying under vacuum at about 55° C. $^1$H NMR (400 MHz, DMSO-$d_6$) δ ppm 2.19 (s, 3H), 3.41-3.51 (m, 4H), 3.49-3.59 (m, 4H), 5.10 (s, 2H), 7.05 (d, J=7.7 Hz, 1H), 7.09-7.19 (m, 2H), 7.22 (d, J=7.4 Hz, 1H), 7.27-7.36 (m, 1H), 7.36-7.43 (m, 4H), 8.97 (s, 1H); MS (ESI) m/z 378 (M+H)$^+$;

Step B: N'-cyano-N-(2-methylphenyl)piperazine-1-carboximidamide

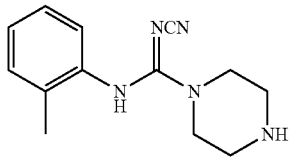

A mixture of benzyl 4-[N'-cyano-N-(2-methylphenyl)carbamimidoyl]piperazine-1-carboxylate (Step A, 0.86 g, 2.3 mmol) and 20 weight % Pd(OH)$_2$ on carbon (0.32 g, 0.46 mmol) was evacuated and purged with nitrogen (3×). Ethanol (20 mL) was added, and the mixture was evacuated and purged with nitrogen (2×). On the third evacuation, the reaction was placed under hydrogen atmosphere via balloon. The reaction was stirred vigorously at room temperature. After about 6 hours, the reaction flask was evacuated under vacuum and purged with nitrogen (3×). The reaction mixture was filtered through a pad of Celite® while washing with CH$_3$OH (15 mL). The filtrate was concentrated under reduced pressure. The crude residue was purified via silica gel chromatography eluting with 0-100% dichloromethane/methanol/ammonium hydroxide (90:9:1) in dichloromethane. The product-containing fractions were concentrated to give the title compound (0.36 g, 65%, ~80% purity). $^1$H NMR (400 MHz, DMSO-$d_6$) δ ppm 2.18 (s, 3H), 2.68-2.75 (m, 4H), 3.39-3.45 (m, 4H), 6.99-7.05 (m, 1H), 7.07-7.24 (m, 3H), 8.81 (s, 1H); MS (ESI) m/z 244 (M+H)$^+$;

Step C: N'-cyano-N-(2-methylphenyl)-4-(quinoxalin-2-yl)piperazine-1-carboximidamide

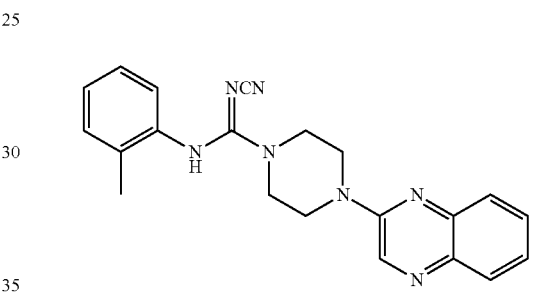

A mixture of N'-cyano-N-(2-methylphenyl)piperazine-1-carboximidamide (Step B, 0.050 g, 0.21 mmol, ~80% purity), 2-chloroquinoxaline (0.037 g, 0.23 mmol), cesium carbonate (0.14 g, 0.43 mmol) and N,N-dimethylformamide (1.5 mL) was heated at about 90° C. The reaction was cooled to room temperature after about 2 hours and then poured into water (10 mL). The resulting pale yellow solid was collected via vacuum filtration. The solid was purified via silica gel chromatography eluting with 0-100% dichloromethane/methanol/ammonium hydroxide (90:9:1) in dichloromethane. The product-containing fraction was concentrated to give the title compound containing ~4 mol % dichloromethane as an excipient (0.043 g, 56%) as a solid. $^1$H NMR (400 MHz, DMSO-$d_6$) δ ppm 2.23 (s, 3H), 3.68-3.73 (m, 4H), 3.84-3.90 (m, 4H), 7.06-7.28 (m, 4H), 7.39-7.47 (m, 1H), 7.60-7.66 (m, 2H), 7.85 (d, J=8.2 Hz, 1H), 8.85 (s, 1H), 9.02 (s, 1H); MS (ESI) m/z 372 (M+H)$^+$.

Scheme 10: Alkylation of cyanoguanidines

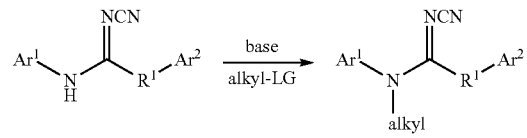

157

Example 1.75

N'-cyano-2-isopropyl-N-methyl-N-(2-methylphenyl)-4-(quinoxalin-2-yl)piperazine-1-carboximidamide

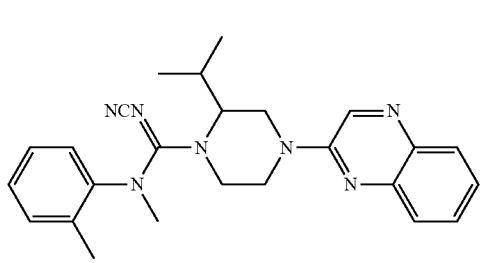

A solution of N'-cyano-2-isopropyl-N-(2-methylphenyl)-4-(quinoxalin-2-yl)piperazine-1-carboximidamide (Example 7.3, 0.3 g, 0.73 mmol) in dimethylamide (10 mL) was treated with sodium hydride (60% oil suspension, 0.046 g, 0.94 mmol). The reaction mixture was stirred at ambient temperature for 1 hour and after that methyl iodide (0.054 mL, 0.87 mmol) was added. The reaction mixture was stirred overnight and then concentrated. The residue was diluted with water (100 mL) and extracted with ethyl acetate (3×30 mL). The crude product was purified by silica gel column chromatography eluting with mixture of ethyl acetate:hexane (1:1) to afford 66 mg, 18% of the titled compound as a white solid. $^1$H NMR (300 MHz, CDCl$_3$) δ ppm 0.93-1.00 (m, 6H), 1.81-1-94 (bs., 1H), 2.04-2.16 (m, 1H), 2.34 (s, 3H), 2.85 (t, J=12.4 Hz, 1H), 3.36 (bs, 3H), 3.58 (t, J=14.0 Hz, 1H), 3.97 (d, J=13.2 Hz, 1H), 4.24 (d, J=13.7 Hz, 1H), 4.42 (d, J=12.6 Hz, 1H), 7.14-7.35 (m, 5H), 7.42 (t, J=7.3 Hz, 1H), 7.58 (t, J=8.3 Hz, 1H), 7.66 (d, J=8.1 Hz, 1H), 7.87 (d, J=7.0 Hz, 1H), 8.43 (s, 1H); MS (ESI) m/z 428.9 (M+1)$^+$.

Scheme 11: Non-cyclic R$^1$ analogs

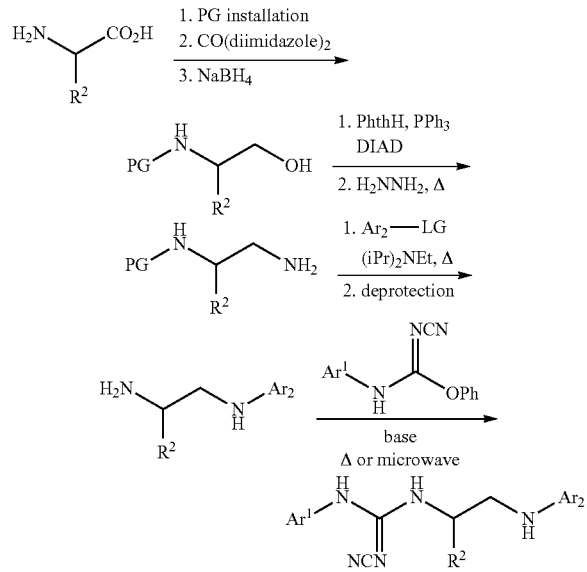

158

Example 2.1

2-cyano-1-(2-methylphenyl)-3-[3-methyl-1-(quinoxalin-2-ylamino)butan-2-yl]guanidine

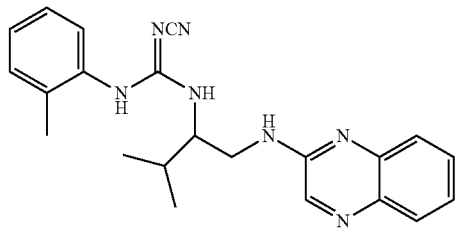

Step A: N-(tert-butoxycarbonyl)valine

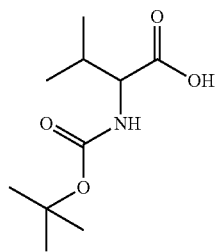

To a solution of valine (25 g, 0.21 mol) in aqueous sodium hydroxide (11.9 g, 0.3 mol; 200 mL) was added a solution of di-tert-butyl dicarbonate (48.9 g, 0.224 mol) in 1,4-dioxane (60 mL). The mixture was stirred at ambient temperature overnight and 2 N hydrochloric acid was added until pH~4-5. The product was extracted with ethyl acetate (3×170 mL). The combined extracts were washed with brine and concentrated to afford 40.3 g, 87% of the titled compound as a yellow solid. $^1$H NMR (300 MHz, DMSO-d$_6$) δ ppm 0.87 (t, J=6.4 Hz, 6H), 1.38 (s, 9H), 2.00-2.10 (m, 1H), 3.75-8.82 (m, 1H), 6.87 (d, J=8 Hz, 1H), 12.42 (bs, 1H).

Step B: tert-butyl (1-hydroxy-3-methylbutan-2-yl)carbamate

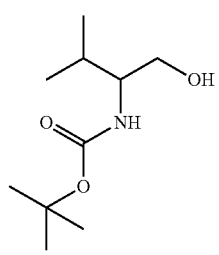

To a stirred solution of N-(tert-butoxycarbonyl)valine (Step A, 7.05 g, 32.4 mmol) in tetrahydrofuran (65 mL) was added 1,1-carbonyldiimidazole (5.25 g, 32.4 mmol), and the reaction mixture was stirred at ambient temperature for 10 minutes. Then a solution of sodium borohydride (1.96 g, 51.8 mmol) in water (32 mL) was added. The resulting solution was stirred at ambient temperature for 12 hours. Then the mixture was diluted with ethyl acetate (200 mL), and the organic layer was separated, washed with 1 N hydrochloric acid (100 mL) and brine (60 mL), dried over Na$_2$SO$_4$, passed through a short pad of SiO$_2$, and concentrated to afford 5.7 g, 86.5% of the titled compound as a white solid. $^1$H NMR (300 MHz, DMSO-d$_6$) δ ppm 0.76-0.90 (m, 6H), 1.38 (s, 9H), 1.73-1.80 (m, 1H), 3.17-3.40 (m, 3H), 4.42 (t, J=5.5 Hz, 1H), 6.36 (m, 1H).

Step C: tert-butyl [1-(1,3-dioxo-1,3-dihydro-2H-isoindol-2-yl)-3-methylbutan-2-yl]carbamate

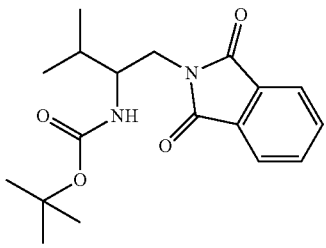 [SMILES: CC(C)C(CN1C(=O)c2ccccc2C1=O)NC(=O)OC(C)(C)C]

Phthalimide (2.74 g, 18.6 mmol) was dissolved in dry tetrahydrofuran (120 mL). Triphenylphosphine (9.76 g, 37.2 mmol) and tert-butyl (1-hydroxy-3-methylbutan-2-yl)carbamate (Step B, 2.52 g, 12.4 mmol) were added. The resulting colorless solution was cooled to 0° C. and stirred under nitrogen. Then diisopropylazodicarboxylate (6.27 g, 31 mmol) was slowly added. The solution was heated to ambient temperature and stirred for 12 hours. Then the reaction mixture was concentrated in vacuo, and the residue was purified with on silica gel column eluting with mixture hexane:ethyl acetate (3:1) to afford 2.7 g, 65% of the titled compound as a white solid. $^1$H NMR (300 MHz, CDCl$_3$) δ ppm 1.03 (t, J=9.2 Hz, 6H), 1.2 (s, 9H), 1.80-1.90 (m, 1H), 3.63-3.96 (m, 3H), 4.50-4.60 (m, 1H), 7.65-7.75 (m, 2H), 7.80-7.90 (m, 2H).

Step D: tert-butyl (1-amino-3-methylbutan-2-yl)carbamate

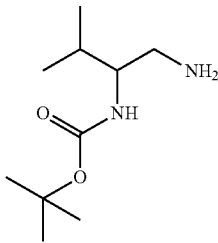

tert-Butyl [1-(1,3-dioxo-1,3-dihydro-2H-isoindol-2-yl)-3-methylbutan-2-yl]carbamate (Step C, 1.60 g, 4.8 mmol) was dissolved in ethanol (40 mL) and hydrazine hydrate (2.1 g, 33.6 mmol) was added. The reaction mixture was refluxed for 45 minutes, cooled and filtered. The solid was washed with diethyl ether. The combined organic solutions were washed with water and concentrated in vacuo to afford a solid. The crude product was precipitated from hexane to afford 0.47 g, 48% of the titled compound as a solid. $^1$H NMR (300 MHz, CDCl$_3$) δ ppm 0.70-0.75 (m, 6H), 1.37 (s, 9H), 1.65-1.74 (m, 1H), 2.40-2.57 (m, 2H), 3.10-3.20 (m, 1H), 6.45-6.50 (m, 1H).

Step E: tert-butyl [3-methyl-1-(quinoxalin-2-ylamino)butan-2-yl]carbamate

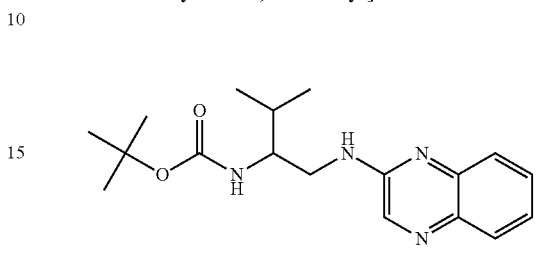

To a solution of 2-chloroquinoxaline (400 mg, 2.43 mmol) in dimethylformamide (30 mL) was added tert-butyl (1-amino-3-methylbutan-2-yl)carbamate (Step D, 491 mg, 2.43 mmol) and diisopropylethylamine (376 mg, 2.91 mmol). The reaction mixture was stirred at 100° C. overnight. The reaction mixture was cooled to ambient temperature and concentrated. The residue was purified by silica gel column chromatography eluting with mixture of ethyl acetate:hexane (1:4) to afford 200 mg, 25% of the titled compound. $^1$H NMR (300 MHz, CDCl$_3$) δ ppm 0.80-1.93 (m, 6H), 1.33 (s, 9H), 1.75-1.82 (m, 1H), 3.25-1.35 (m, 1H), 3.50-3.62 (m, 2H), 6.65-6.71 (m, 1H), 7.25-7.30 (m, 1H), 7.50- 7.82 (m, 3H), 7.74 (d, J=7.6 Hz, 1H), 8.32 (s, 1H).

Step F: 3-methyl-N'-(quinoxalin-2-yl)butane-1,2-diamine dihydrochloride

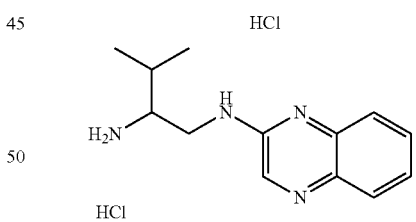

To a solution of tert-butyl [3-methyl-1-(quinoxalin-2-ylamino)butan-2-yl]carbamate (Step E, 200 mg, 0.61 mmol) in 1,4-dioxane (20 mL) was added 3 M hydrochloric acid in 1,4-dioxane (10 mL). The reaction mixture was stirred at ambient temperature overnight and then concentrated to afford 180 mg, 100% of the titled compound as a solid. $^1$H NMR (300 MHz, CDCl$_3$) δ ppm 1.00-1.12 (m, 6H), 2.05-2.15 (m, 1H), 3.30-3.37 (m, 1H), 3.62-3.90 (m, 2H), 7.46 (t, J=7.2 Hz, 1H), 7.66 (t, J=7.2 Hz, 1H), 7.85-7.92 (m, 2H), 8.59 (s, 1H).

Step G: 2-cyano-1-(2-methylphenyl)-3-[3-methyl-1-(quinoxalin-2-ylamino)butan-2-yl]guanidine

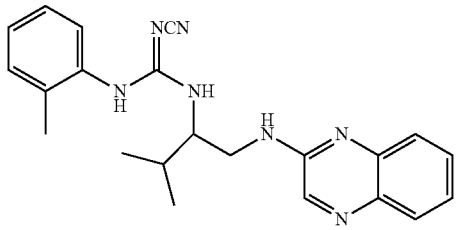

To a mixture of phenyl N'-cyano-N-(2-methylphenyl) carbamimidate (150 mg, 0.59 mmol, prepared using General Procedure F) and 3-methyl-N'-(quinoxalin-2-yl)butane-1,2-diamine dihydrochloride (Step F, 181 mg, 0.59 mmol) was added acetonitrile (10 mL) and triethylamine (181 mg, 1.79 mmol). The reaction mixture was stirred in microwave oven (CEM, Discover®-SP with ActiVent®, 300 W maximum) at 80° C. for 5 hours. The reaction mixture was cooled down to ambient temperature and ethyl acetate (10 mL) was added. The organic solution was washed with water (20 mL) and brine (20 mL). The solvents were removed under reduced pressure, and the residue was purified by silica gel column chromatography eluting with mixture of ethyl acetate:hexane (1:1) to afford 40 mg, 17% of the titled compound as a solid. $^1$H NMR (300 MHz, DMSO-$d_6$) δ ppm 0.95 (m, 6H), 1.90-1.95 (m, 1H), 2.03 (s, 3H), 3.44-3.71 (m, 2H), 3.91 (m, 1H), 6.97-7.16 (m, 4H), 7.32 (t, J=6.8 Hz, 1H), 7.39 (d, J=8 Hz, 1H), 7.5 (t, J=6.8 Hz, 1H), 7.63 (m, 1H), 7.76 (d, J=8 Hz, 1H), 8.33 (s, 1H), 8.61 (s, 1H); MS (ESI) m/z 388.9 (M+1)$^+$.

Scheme 11. Formation of 1,4-diazepane cyanoguanidines

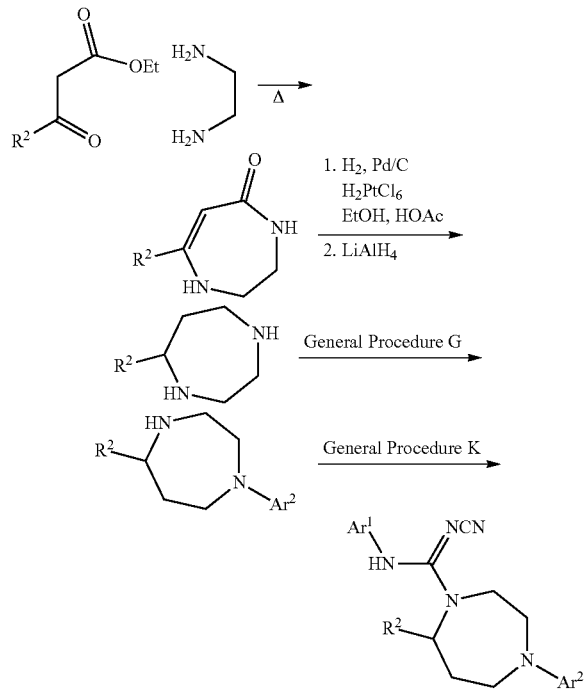

Example 3.1

N'-cyano-7-isopropyl-N-(2-methylphenyl)-4-(quinoxalin-2-yl)-1,4-diazepane-1-carboximidamide

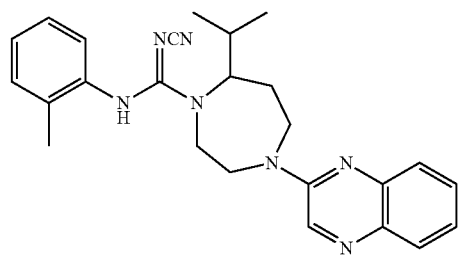

Step A: 7-isopropyl-1,2,3,4-tetrahydro-5H-1,4-diazepin-5-one

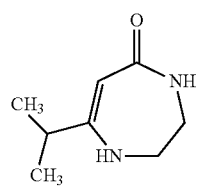

The reaction was carried out at atmospheric pressure in a round-bottomed flask equipped with magnetic stirrer and azeotropic Dean-Stark apparatus. Ethylene diamine (3.73 g, 62.01 mmol, 4.15 mL) was added to ethyl 4-methyl-3-oxopentanoate (1.0 eq., 62.01 mmol, 9.81 g, 10.0 mL) in dry xylene (40 mL). The mixture was stirred at reflux overnight. After cooling to ambient temperature, the precipitate was collected by filtration and washed with xylene, ether, and hexane and dried in vacuo to afford 4.48 g, 47% of the titled compound. $^1$H NMR (300 MHz, CDCl$_3$) δ ppm 1.12 (d, J=6.7 Hz, 6H), 2.27 (d, J=6.7 Hz, 1H), 3.32-3.40 (m, 2H), 3.40-3.50 (m, 2H), 4.55-4.60 (t, J=3.2 Hz, 1H), 6.54 (bs, 1H).

Step B: 7-isopropyl-1,4-diazepan-5-one

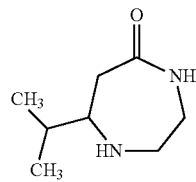

Catalyst (mixture of 10% Pd on charcoal (650 mg) and H$_2$PtCl$_6$ (228 mg)) was added to a solution of 7-isopropyl-1,2,3,4-tetrahydro-5H-1,4-diazepin-5-one (Step A, 3.48 g, 22.58 mmol) in ethanol (100 mL) and acetic acid (5 mL). The reaction mixture was hydrogenated at 50 bar and 80° C. for 24 hours. The reaction mixture was cooled and filtered. The filtrate was concentrated in vacuo to dryness. The oily residue was dispersed in 10% aqueous solution of potassium carbonate (200 mL) and then extracted with chloroform (30 mL). The solvent was removed under reduced pressure to afford 1.08 g, 31% of the titled compound. $^1$H NMR (300 MHz, CDCl$_3$) δ ppm 0.60-0.95 (m, 6H), 1.65-1.70 (m, 1H), 1.19-2.31 (m, 2H), 2.31-2.45 (m, 2H), 2.48-2.74 (m, 1H), 2.75-3.01 (m, 2H), 3.06-3.22 (m, 1H), 7.45 (bs, 1H).

Step C: 5-isopropyl-1,4-diazepane

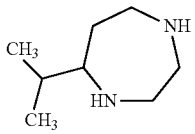

Lithium aluminum hydride (23.48 mmol, 889 mg) was added to a solution of 7-isopropyl-1,4-diazepan-5-one (Step B, 1.08 g, 6.90 mmol) in dry tetrahydrofuran (115 mL). The reaction mixture was stirred at reflux overnight and then cooled down to ambient temperature. 30% Aqueous sodium and potassium tartrate (5 mL) was added dropwise, and the reaction mixture was stirred for 30 minutes. The precipitate was collected by filtration and washed with tetrahydrofuran. The filtrate and washes were combined and concentrated to dryness in vacuo to afford 890 mg, 91% of the titled compound as a yellow oil. MS (ESI) m/z 143.3 (M+1)$^+$.

Step D: 2-(5-isopropyl-1,4-diazepan-1-yl)quinoxaline

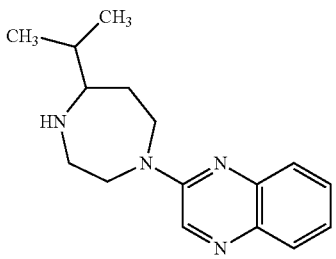 [SMILES: CC(C)C1CCN(c2cnc3ccccc3n2)CCN1]

The compound was synthesized according to the procedure described in the Illustration of General Procedure G (Preparation of 2-(3-isopropylpiperazin-1-yl)quinoxaline, Example G1) making non-critical variations using 5-isopropyl-1,4-diazepane instead of 2-isopropylpiperazine. The titled compound was obtained as a yellow solid 334 mg, 25%. MS (ESI) m/z 271.4 (M+1)$^+$.

Step E: N'-cyano-7-isopropyl-N-(2-methylphenyl)-4-(quinoxalin-2-yl)-1,4-diazepane-1-carboximidamide trifluoroacetate

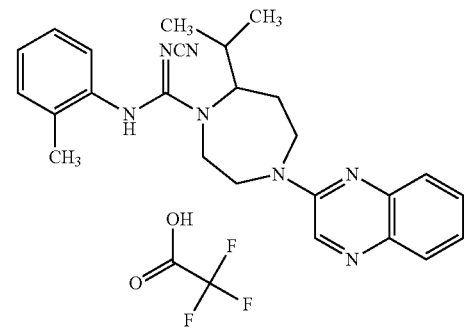

The compound was synthesized according to the procedure described for preparation of N'-cyano-2-isopropyl-N-(2-methylphenyl)-4-(quinoxalin-2-yl)piperazine-1-carboximidamide trifluoroacetate (Illustration of Procedure K, Example 1.3) making non-critical variations using 2-(5-isopropyl-1,4-diazepan-1-yl)quinoxaline instead of 2-(3-isopropylpiperazin-1-yl)quinoxaline. The crude product was purified by HPLC (column: YMC-PACK ODS-AQ C18, 250 mm×20 mm, 10 m; gradient: 20-50% acetonitrile in 0.02% trifluoroacetic acid/water over 15 minutes; 50-100% acetonitrile in 0.02% trifluoroacetic acid/water over 5 minutes; flow rate: 25 mL/minute; temperature: 25° C.) to afford 79 mg, 15% of the titled compound as a trifluoroacetic acid salt as a white solid. $^1$H NMR (300 MHz, DMSO-d$_6$) δ ppm 0.91 (bs, 6H), 1.50-1.93 (m, 1H), 2.07 (s, 3H), 1.93-2.14 (m, 2H), 2.96.-3.68 (m, 8H), 6.43-7.28 (m, 4H), 7.39 (bs, 1H), 7.59 (bs, 2H), 7.83 (bs, 1H), 8.69 (bs, 1H), 8.78 (bs, 1H); MS (ESI) m/z 428.6 (M+1)$^+$.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicants reserve the right to challenge the accuracy and pertinence of the cited references.

Example 1.12

(2R)—N'-cyano-2-isopropyl-N-(2-methylphenyl)-4-(quinoxalin-2-yl)piperazine-1-carboximidamide trifluoroacetate $^1$H NMR (400 MHz, CDCl$_3$) δ ppm 1.04-1.18 (m, 6H), 2.21-2.32 (m, 4H), 3.38-3.54 (m, 3H), 4.44-4.61 (m, 2H), 4.89-5.00 (m, 1H), 7.06 (s, 1H), 7.18-7.31 (m, 5H), 7.44-7.50 (m, 1H), 7.59-7.67 (m, 1H), 7.81-7.85 (m, 1H), 7.90-7.96 (m, 1H), 8.61 (s, 1H); MS (ESI) m/z 406.1 (M+1)$^+$.

Example 1.13

(2S)—N'-cyano-2-isopropyl-N-(2-methylphenyl)-4-(quinoxalin-2-yl)piperazine-1-carboximidamide trifluoroacetate $^1$H NMR (400 MHz, CDCl$_3$) δ ppm 1.04-1.18 (m, 6H), 2.21-2.32 (m, 4H), 3.38-3.54 (m, 3H), 4.44-4.61 (m, 2H), 4.89-5.00 (m, 1H), 7.06 (s, 1H), 7.18-7.31 (m, 5H), 7.44-7.50 (m, 1H), 7.59-7.67 (m, 1H), 7.81-7.85 (m, 1H), 7.90-7.96 (m, 1H), 8.61 (s, 1H); MS (ESI) m/z 406.1 (M+1)$^+$.

What is claimed is:

1. A compound having formula (I), or a pharmaceutically acceptable salt thereof,

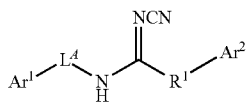
(I)

wherein:

Ar$^1$ is phenyl or monocyclic heteroaryl having a structure corresponding to a formula selected from the group consisting of:

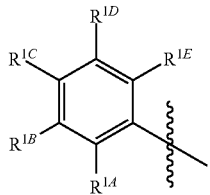
(i-1)

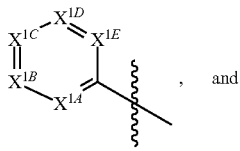
(i-2)

, and

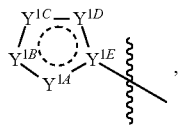
(i-3)

wherein R$^{1A}$ is selected from the group consisting of hydrogen; amino; hydroxy; cyano; fluoro; chloro; bromo; iodo; C$_2$-C$_6$alkenyl; C$_2$-C$_6$alkynyl; C$_1$-C$_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -L$^1$-C(O)—OR$^{1'}$ or -L$^1$-S(O)$_2$R$^{1'}$, wherein L$^1$ is a bond or alkylene, and R$^{1'}$ is hydrogen, C$_1$-C$_6$alkyl or hydroxyalkyl; -L$^2$-O—C(O)—R$^{2'}$, wherein L$^2$ is a bond or alkylene, and R$^{2'}$ is C$_1$-C$_6$alkyl or hydroxyalkyl; -L$^3$-C(O)—NR$^{3'}$R$^{4'}$, wherein L$^3$ is a bond or alkylene, and R$^{3'}$ and R$^{4'}$ are each independently selected from the group consisting of hydrogen, alkyl, and hydroxyalkyl; and -L$^4$-NR$^{5'}$—C(O)—R$^{6'}$, wherein L$^4$ is a bond or alkylene, R$^{5'}$ is hydrogen or alkyl, and R$^{6'}$ is alkyl or hydroxyalkyl; sulfamoyl; N-(alkyl)sulfamoyl; N,N-(dialkyl)sulfamoyl; sulfonamide; alkylthio; and thioalkyl;

R$^{1B}$, R$^{1C}$, R$^{1D}$ and R$^{1E}$ are each independently selected from the group consisting of hydrogen, cyano, halo, alkoxy, amino, alkylamino, dialkylamino, cycloalkyl, heterocyclyl, haloalkoxy, and haloalkyl;

X$^{1A}$ is CR$^{1AX}$ or N; X$^{1B}$ is CR$^{1BX}$ or N; X$^{1C}$ is CR$^{1CX}$ or N; X$^{1D}$ is CR$^{1DX}$ or N and X$^{1E}$ is CR$^{1EX}$ or N respectively; wherein 1, 2 or 3 of X$^{1A}$, X$^{1B}$, X$^{1C}$, X$^{1D}$ and X$^{1E}$ are N; wherein R$^{1AX}$ is C$_1$-C$_6$alkyl; and one of X$^{1B}$ and X$^{1D}$ is N, and the other is CR$^{1BX}$ or CR$^{1DX}$, respectively, wherein R$^{1BX}$ and R$^{1DX}$ are each hydrogen; and R$^{1CX}$ and R$^{1EX}$ are each hydrogen;

Y$^{1A}$ is CR$^{1AY}$, NR$^{1AY}$, N, O or S; Y$^{1B}$ is CR$^{1BY}$, NR$^{1BY}$, N, O or S; Y$^{1C}$ is CR$^{1CY}$, NR$^{1CY}$, N, O or S; and Y$^{1D}$ is CR$^{1DY}$, NR$^{1DY}$, N, O or S respectively; wherein 0, 1, 2, 3 or 4 of Y$^{1A}$, Y$^{1B}$, Y$^{1C}$, and Y$^{1D}$ are NR$^{1AY}$, NR$^{1BY}$, NR$^{1CY}$, or NR$^{1DY}$, respectively or N; wherein 0 or 1 of Y$^{1A}$, Y$^{1B}$, Y$^{1C}$ and Y$^{1D}$ is O or S; Y$^{1E}$ is N or C; wherein 1, 2, 3, or 4 of Y$^{1A}$, Y$^{1B}$, Y$^{1C}$, Y$^{1D}$, and Y$^{1E}$, is NR$^{1AY}$, NR$^{1BY}$, NR$^{1CY}$, NR$^{1DY}$, N, O or S;

R$^{1AY}$, R$^{1BY}$, R$^{1CY}$, and R$^{1DY}$ are each independently selected from the group consisting of hydrogen; amino; hydroxy; cyano; halo; C$_1$-C$_6$alkyl; C$_2$-C$_5$alkenyl; C$_2$-C$_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -L$^1$-C(O)—OR$^{1'}$ or -L$^1$-S(O)$_2$R$^{1'}$, wherein L$^1$ is a bond or alkylene, and R$^{1'}$ is hydrogen, C$_1$-C$_6$alkyl or hydroxyalkyl; -L$^2$-O—C(O)—R$^{2'}$, wherein L$^2$ is a bond or alkylene, and R$^{2'}$ is C$_1$-C$_6$alkyl or hydroxyalkyl; -L$^1$-C(O)—NR$^{3'}$R$^{4'}$, wherein L$^3$ is a bond or alkylene, and R$^{3'}$ and R$^{4'}$ are each independently selected from the group consisting of hydrogen, C$_1$-C$_6$alkyl, and hydroxyalkyl; and -L$^4$-NR$^{5'}$—C(O)—R$^{6'}$, wherein L$^4$ is a bond or alkylene, R$^5$ is hydrogen or C$_1$-C$_6$alkyl, and R$^{6'}$ is C$_1$-C$_6$alkyl or hydroxyalkyl; sulfamoyl; N-(alkyl)sulfamoyl; N,N-(dialkyl)sulfamoyl; sulfonamide; alkylthio; and thioalkyl;

L$^A$ is bond;

R$^1$ is selected from the group consisting of:

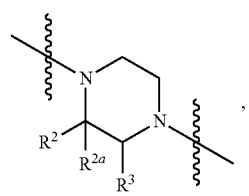
(ii-1)

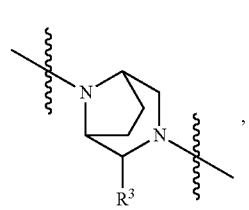
(ii-2)

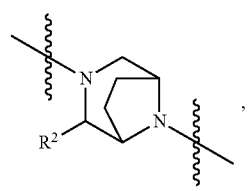
(ii-3)

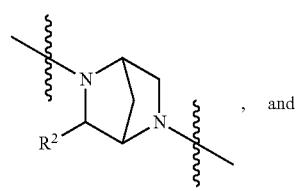
(ii-4)

, and

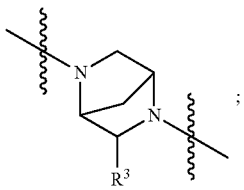
(ii-5)

wherein $R^2$, and $R^3$ are each independently selected from the group consisting of hydrogen, $C_1$-$C_6$alkyl, $C_2$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$-alkyl-; wherein when both $R^2$ and $R^3$ are present, one or both of $R^2$ and $R^3$ are hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, N($R^f$)C(O)O($R^f$), -$L^c$-O—$R^f$, -$L^c$-CN, -$L^c$-N($R^f$)C(O)$R^f$, -$L^1$-CON($R^e$)($R^f$), -$L^c$-C(O)$R^f$, -$L^c$-OC(O)$R^f$, -$L^c$-CO$_2$H, -$L^c$-CO$_2R^f$, -$L^c$-N($R^f$)C(O)N($R^f$)$_2$, -$L^c$-S—$R^f$, -$L^c$-S(O)$_2R^f$, -$L^c$-S(O)$R^f$, - $L^c$-SO$_2$N($R^e$)($R^f$), -$L^c$-N($R^e$)($R^f$), -$L^c$-N($R^f$)S(O)$_2R^f$, and -$L^c$-N($R^f$)C(O)O($R^f$);

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

$R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^f$, at each occurrence, is independently selected from the group consisting of hydrogen, $C_1$-$C_6$alkyl, and $C_1$-$C_6$haloalkyl;

$Ar^2$ is selected from the group consisting of:

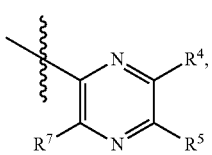
(iii-3)

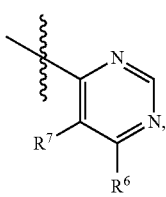
(iii-4)

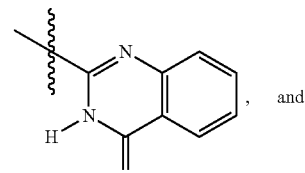
(iii-7)
, and

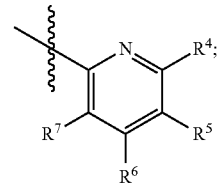
(iii-8)

wherein for (iii-3), $R^4$ and $R^5$, taken together with the atoms to which they are attached, form a fused phenyl optionally substituted with 1, 2, or 3 $C_1$-$C_6$alkyl, halo, or halo$C_1$-$C_6$alkyl; and $R^7$ is hydrogen, $C_1$-$C_6$alkyl, or halo$C_1$-$C_6$alkyl;

wherein for (iii-4), $R^6$ and $R^7$, taken together with the atoms to which they are attached, form a fused phenyl or pyrrolyl;

wherein for (iii-8), $R^4$ and $R^5$, taken together with the atoms to which they are attached, form a fused phenyl, pyridinyl, or pyrazinyl, each optionally substituted with 1, 2, or 3 $C_1$-$C_6$alkyl, halo, or halo$C_1$-$C_6$alkyl; and $R^6$ and $R^7$ are independently hydrogen, $C_1$-$C_6$alkyl, or halo$C_1$-$C_6$alkyl.

2. The compound of claim 1, or a pharmaceutically acceptable salt thereof, wherein $R^{1A}$ is selected from a group consisting of hydrogen, fluoro, chloro, bromo, iodo, haloalkyl and haloalkoxy; and $R^{1B}$, $R^{1C}$, $R^{1D}$ and $R^{1E}$ are each independently selected from a group consisting of hydrogen, halo and haloalkyl.

3. A pharmaceutical composition comprising the compound of claim 1, or a pharmaceutically acceptable salt thereof, and one or more excipients, and optionally one or more additional therapeutic agents.

4. A compound having formula (I), or a pharmaceutically acceptable salt thereof,

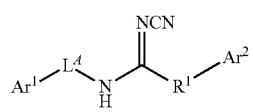
(I)

wherein:

$Ar^1$ is monocyclic heteroaryl having a structure corresponding to a formula selected from the group consisting of:

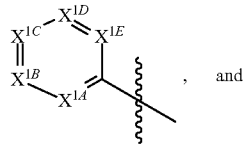
(i-2)
, and

-continued

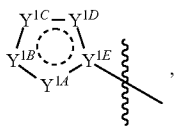
(i-3)

$X^{1A}$ is $CR^{1AX}$ or N; $X^{1B}$ is $CR^{1BX}$ or N; $X^{1C}$ is $CR^{1CX}$ or N; $X^{1D}$ is $CR^{1DX}$ or N; and $X^{1E}$ is $CR^{1EX}$ or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxy; cyano; halo; $C_1$-$C_6$alkyl; $C_2$-$C_6$alkenyl; $C_2$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is selected from the group consisting of hydrogen, $C_1$-$C_6$alkyl and hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^1$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; and -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$R^{1BX}$, $R^{1CX}$, $R^{1DX}$ and $R^{1EX}$ are each hydrogen;

$Y^{1A}$ is $CR^{1AY}$, $NR^{1AY}$, N, O or S; $Y^{1B}$ is $CR^{1BY}$, $NR^{1BY}$, N, O or S; $Y^{1C}$ is $CR^{1CY}$, $NR^{1CY}$, N, O or S; and $Y^{1D}$ is $CR^{1DY}$, $NR^{1DY}$, N, O or S; wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$, and $Y^{1D}$ is O or S;

$Y^{1E}$ is N or C;

wherein 1, 2, 3, or 4 of $Y^{1A}$, $Y^{1B}$, $Y^{1C}$, $Y^{1D}$, and $Y^{1E}$, is $NR^{1AY}$, $NR^{1BY}$, $NR^{1CY}$, $NR^{1DY}$, N, O or S;

$R^{1AY}$, $R^{1BY}$, $R^{1CY}$, and $R^{1DY}$ are each independently selected from the group consisting of hydrogen; amino; hydroxy; cyano; halo; $C_1$-$C_6$alkyl; $C_2$-$C_6$alkenyl; $C_2$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is selected from the group consisting of hydrogen, $C_1$-$C_6$alkyl and hydroxyalkyl; -$L^2$-O—C(O)—$R^{2'}$, wherein $L^2$ is a bond or alkylene, and $R^{2'}$ is $C_1$-$C_6$alkyl or hydroxyalkyl; -$L^1$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; and -$L^4$-$NR^{5'}$—C(O)—$R^{6'}$, wherein $L^4$ is a bond or alkylene, $R^{5'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$L^A$ is bond;

$R^1$ is selected from the group consisting of:

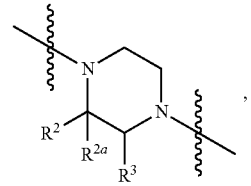
(ii-1)

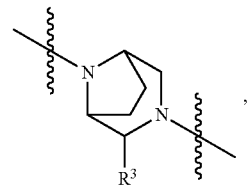
(ii-2)

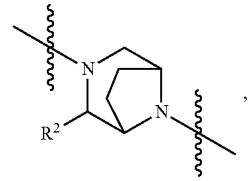
(ii-3)

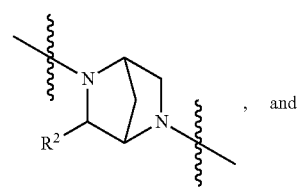
(ii-4)
, and

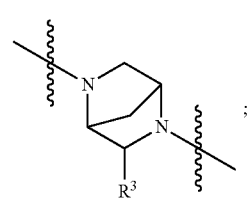
(ii-5)
;

wherein $R^2$, and $R^3$ are each independently selected from the group consisting of hydrogen, $C_1$-$C_6$alkyl, $C_2$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$-alkyl- wherein
when both $R^2$ and $R^3$ are present, one or both of $R^2$ and $R^3$ are hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-CO$_2$H, -$L^c$-CO$_2R^f$, -$L^c$-N($R^f$)C(O)N($R^f$)$_2$, -$L^c$-S—$R^f$, -$L^c$-S(O)$_2R^f$, -$L^c$-S(O)$R^f$, - $L^c$-SO$_2$N($R^e$)($R^f$), -$L^c$-N($R^e$)($R^f$), -$L^c$-N($R^f$)S(O)$_2R^f$, and -$L^c$-N($R^f$)C(O)O($R^f$);

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

R$^e$, at each occurrence, is independently selected form the group consisting of hydrogen, C$_1$-C$_6$alkyl, C$_1$-C$_6$haloalkyl, and C$_3$-C$_8$cycloalkyl, wherein the C$_3$-C$_8$cycloalkyl is optionally substituted with 1, 2, 3, or 4 substituents selected from the group consisting of halogen, oxo, C$_1$-C$_3$alkyl, and C$_1$-C$_3$haloalkyl;

R$^f$, at each occurrence, is independently selected from the group consisting of hydrogen, C$_1$-C$_6$alkyl, and C$_1$-C$_6$haloalkyl;

Ar$^2$ is selected from the group consisting of:

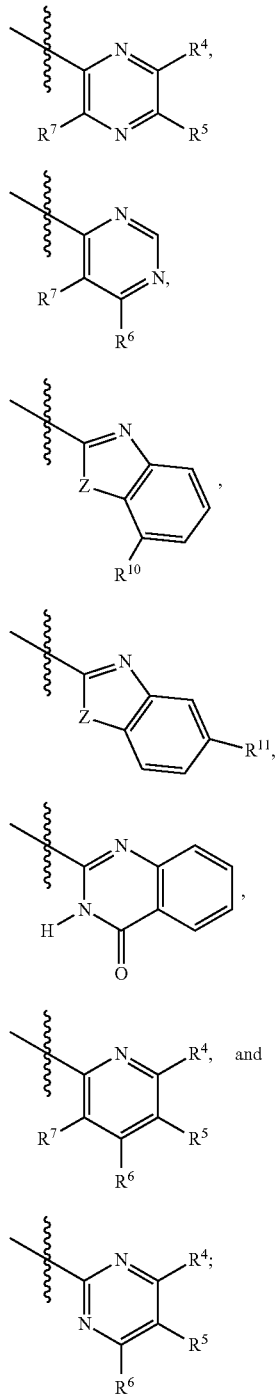

wherein for (iii-3), R$^4$ and R$^5$ are hydrogen and R$^7$ is cyano; or

R$^4$ and R$^7$ are hydrogen and R$^5$ is —CO$_2$CH$_3$; or

R$^4$ is heterocyclyl, and R$^5$ and R$^7$ are hydrogen; or

R$^4$ and R$^5$, taken together with the atoms to which they are attached, form a fused phenyl optionally substituted with 1, 2, or 3 C$_1$-C$_6$alkyl, halo, or haloC$_1$-C$_6$alkyl; and R$^7$ is hydrogen, C$_1$-C$_6$alkyl, or haloC$_1$-C$_6$alkyl;

wherein for (iii-4), R$^6$ and R$^7$, taken together with the atoms to which they are attached, form a fused phenyl or pyrrolyl;

wherein for (iii-5) and (iii-6), Z is selected from the group consisting of O, S, NH, and NCH$_3$;

R$^{10}$ is hydrogen or halogen; and

R$^{11}$ is C$_1$-C$_6$ alkyl;

wherein for (iii-8), R$^4$ and R$^5$, taken together with the atoms to which they are attached, form a fused phenyl, pyridinyl, or pyrazinyl each optionally substituted with 1, 2, or 3 C$_1$-C$_6$alkyl, halo, or haloC$_1$-C$_6$alkyl;

R$^6$ and R$^7$ are each independently hydrogen, C$_1$-C$_6$alkyl, or haloC$_1$-C$_6$alkyl; and wherein for (iii-9), R$^4$ is hydrogen or C$_3$-C$_6$cycloalkylamino, R$^5$ and R$^6$ are independently hydrogen or C$_1$-C$_6$alkyl; or R$^4$ and R$^5$, taken together with the atoms to which they are attached, form a fused phenyl, and R$^6$ is hydrogen.

5. The compound of claim 1, or a pharmaceutically acceptable salt thereof, wherein Ar$^1$ is (i-1):

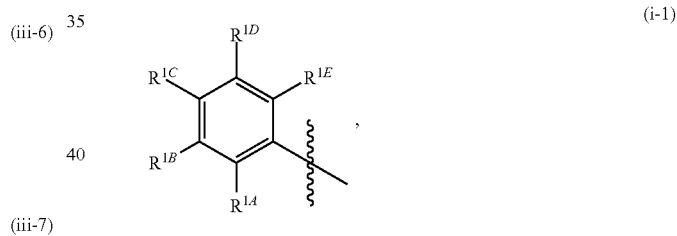

wherein, R$^{1A}$ is selected from the group consisting of hydrogen; fluoro; chloro; C$_1$-C$_6$alkoxy; haloalkyl; and haloalkoxy; and R$^{1B}$, R$^{1C}$, R$^{1D}$ and R$^{1E}$ are each independently hydrogen, halo, or haloalkyl.

6. The compound of claim 4, or a pharmaceutically acceptable salt thereof, wherein Ar$^2$ is

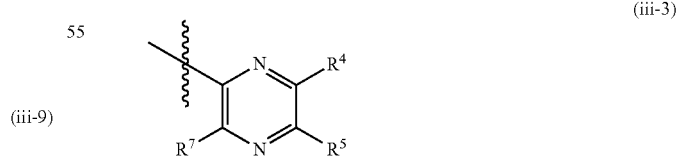

wherein R$^4$ and R$^5$ are hydrogen and R$^7$ is cyano; or

R$^4$ and R$^7$ are hydrogen and R$^5$ is —CO$_2$CH$_3$; or

R$^4$ is heterocyclyl and R$^5$ and R$^7$ are hydrogen.

7. The compound of claim 4, or pharmaceutically acceptable salt thereof, wherein Ar$^2$ is

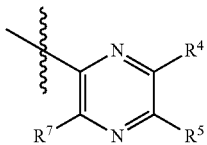

(iii-3)

wherein R⁴ and R⁵, taken together with the atoms to which they are attached, form a fused phenyl optionally substituted with 1, 2, or 3 $C_1$-$C_6$alkyl, halo, or halo$C_1$-$C_6$alkyl; and R⁷ is hydrogen, $C_1$-$C_6$alkyl, or halo$C_1$-$C_6$alkyl.

8. The compound of claim 4, or a pharmaceutically acceptable salt thereof, wherein Ar² is

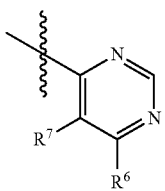

(iii-4)

wherein R⁶ and R⁷, taken together with the atoms to which they are attached, form a fused phenyl or pyrrolyl.

9. The compound of claim 4, or a pharmaceutically acceptable salt thereof, wherein R¹ is (ii-1),

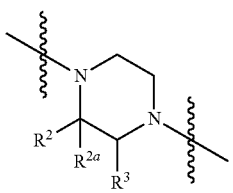

(ii-1)

wherein R² and R³ are each independently selected from the group consisting of hydrogen; $C_1$-$C_6$alkyl; $C_2$-$C_6$alkenyl; haloalkyl; alkynyl; oxoalkyl; hydroxyalkyl; alkoxyalkyl; aminoalkyl; N-alkylaminoalkyl; N,N-dialkylaminoalkyl; thioalkyl; and G¹, G², and G²-alkyl-; G¹ is aryl or heteroaryl, and G² is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—R^f, —CN, —N(R^f)C(O)R^f, —CON(R^e)(R^f), —C(O)R^f, —OC(O)R^f, —CO₂R^f, —N(R^f)C(O)N(R^f)₂, —S—R^f, —S(O)₂R^f, —S(O)R^f, —SO₂N(R^e)(R^f), —N(R^e)(R^f), —N(R^f)S(O)₂R^f, N(R^f)C(O)O(R^f), -L^c-O—R^f, -L^c-CN, -L^c-N(R^f)C(O)R^f, -L^c-CON(R^e)(R^f), -L¹-C(O)R^f, -L^c-OC(O)R^f, -L^c-CO₂H, -L^c-CO₂R^f, -L^c-N(R^f)C(O)N(R^f)₂, -L^c-S—R^f, -L^c-S(O)₂R^f, -L^c-S(O)R^f, -L^c-SO₂N(R^e)(R^f), -L^c- N(R^e)(R^f), -L^c-N(R^f)S(O)₂R^f, and -L^c-N(R^f)C(O)O(R^f);

L^c, at each occurrence, is independently $C_1$-$C_6$alkylene or $C_3$-$C_8$cycloalkyl, wherein L^c at each occurrence, is optionally substituted with 1, 2, 3, or 4 halogen or 1 or 2 hydroxy;

R^e, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl; and R^f, at each occurrence, is independently selected from the group consisting of hydrogen, $C_1$-$C_6$alkyl, and $C_1$-$C_6$haloalkyl.

10. The compound of claim 4, or a pharmaceutically acceptable salt thereof, wherein R¹ is selected from the group consisting of:

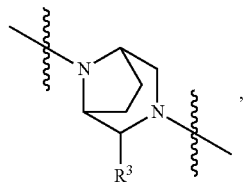

(ii-2)

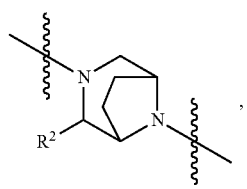

(ii-3)

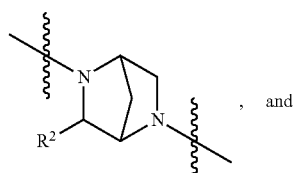

(ii-4)

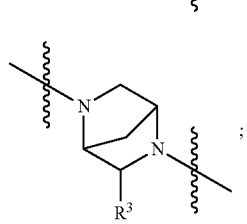

, and (ii-5)

wherein R² and R³ are each independently selected from the group consisting of hydrogen; $C_1$-$C_6$alkyl; $C_2$-$C_6$alkenyl; haloalkyl; alkynyl; oxoalkyl; hydroxyalkyl; alkoxyalkyl; aminoalkyl; N-alkylaminoalkyl; N,N-dialkylaminoalkyl; thioalkyl; and G¹, G², and G²-alkyl-;

G¹ is aryl or heteroaryl, and G² is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—R^f, —CN, —N(R^f)C(O)R^f, —CON(R^e)(R^f), —C(O)R^f, —OC(O)R^f, —CO₂R^f, —N(R^f)C(O)N(R^f)₂, —S—R^f, —S(O)₂R^f, —S(O)R^f, —SO₂N(R^e)(R^f), —N(R^e)(R^f), —N(R^f)S(O)₂R^f, —N(R^f)C(O)O(R^f), -L^c-O—R^f, -L^c-CN, -L^c-N(R^f)C(O)R^f, -L^c-CON(R^e)(R^f), -L^c-C(O)R^f, -L^c-OC(O)R^f, -L^c-CO₂H, -L^c-CO₂R^f, -L^c-N(R^f)C(O)N(R^f)₂, -L^c-S—R^f, -L^c-S(O)₂R^f, -L^c-S(O)R^f, - L^c-SO₂N(R^e)(R^f), -L^c-N(R^e)(R^f), -L^c-N(R^f)S(O)₂R^f, and -L^c-N(R^f)C(O)O(R^f);

L^c, at each occurrence, is independently $C_1$-$C_6$alkylene or $C_3$-$C_8$cycloalkyl, wherein L^c at each occurrence, is optionally substituted with 1, 2, 3, or 4 halogen or 1 or 2 hydroxy;

R$^e$, at each occurrence, is independently selected form the group consisting of hydrogen, C$_1$-C$_6$alkyl, C$_1$-C$_6$haloalkyl, and C$_3$-C$_8$cycloalkyl, wherein the C$_3$-C$_8$cycloalkyl is optionally substituted with 1, 2, 3, or 4 substituents selected from the group consisting of halogen, oxo, C$_1$-C$_3$alkyl, and C$_1$-C$_3$haloalkyl; and R$^f$, at each occurrence, is independently selected from the group consisting of hydrogen, C$_1$-C$_6$alkyl, and C$_1$-C$_6$haloalkyl.

11. A compound having formula (I), or a pharmaceutically acceptable salt thereof,

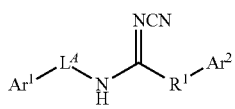
(I)

wherein:

Ar$^1$ is phenyl or monocyclic heteroaryl having a structure corresponding to a formula selected from the group consisting of:

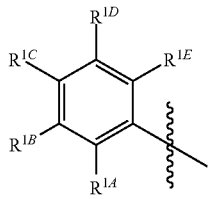
(i-1)

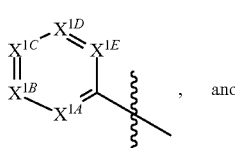
(i-2)

and

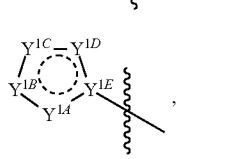
(i-3)

wherein R$^{1A}$ is selected from the group consisting of hydrogen; amino; hydroxy; cyano; halo; C$_1$-C$_6$alkyl; C$_2$-C$_6$alkenyl; C$_2$-C$_6$alkynyl; C$_1$-C$_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -L$^1$-C(O)—OR$^{1'}$ or -L$^1$-S(O)$_2$R$^{1'}$, wherein L$^1$ is a bond or alkylene, and R$^{1'}$ is hydrogen, C$_1$-C$_6$alkyl or hydroxyalkyl; -L$^2$-O—C(O)—R$^{2'}$, wherein L$^2$ is a bond or alkylene, and R$^{2'}$ is C$_1$-C$_6$alkyl or hydroxyalkyl; -L$^3$-C(O)—NR$^{3'}$R$^{4'}$, wherein L$^3$ is a bond or alkylene, and R$^{3'}$ and R$^{4'}$ are each independently selected from the group consisting of hydrogen, alkyl, and hydroxyalkyl; and -L$^4$-NR$^{5'}$—C(O)—R$^{6'}$, wherein L$^4$ is a bond or alkylene, R$^{5'}$ is hydrogen or alkyl, and R$^{6'}$ is alkyl or hydroxyalkyl; sulfamoyl; N-(alkyl)sulfamoyl; N,N-(dialkyl)sulfamoyl; sulfonamide; alkylthio; and thioalkyl;

R$^{1B}$, R$^{1C}$, R$^{1D}$ and R$^{1E}$ are each independently selected from the group consisting of hydrogen, cyano, halo, C$_1$-C$_6$alkyl, alkoxy, amino, alkylamino, dialkylamino, cycloalkyl, heterocyclyl, haloalkoxy, and haloalkyl;

X$^{1A}$ is CR$^{1AX}$ or N; X$^{1B}$ is CR$^{1BX}$ or N; X$^{1C}$ is CR$^{1CX}$ or N; X$^{1D}$ is CR$^{1DX}$ or N; and X$^{1E}$ is CR$^{1EX}$ or N, respectively, wherein 1, 2 or 3 of X$^{1A}$, X$^{1B}$, X$^{1C}$, X$^{1D}$ and X$^{1E}$ are N; wherein R$^{1AX}$ is C$_1$-C$_6$alkyl; and one of X$^{1B}$ and X$^{1D}$ is N, and the other is CR$^{1BX}$ or CR$^{1DX}$, respectively, wherein R$^{1BX}$ and R$^{1DX}$ are each hydrogen; and R$^{1CX}$ and R$^{1EX}$ are each hydrogen;

Y$^{1A}$ is CR$^{1AY}$, NR$^{1AY}$, N, O or S; Y$^{1B}$ is CR$^{1BY}$, NR$^{1BY}$, N, O or S; Y$^{1C}$ is CR$^{1CY}$, NR$^{1CY}$, N, O or S; and Y$^{1D}$ is CR$^{1DY}$, NR$^{1DY}$, N, O or S respectively; wherein 0, 1, 2, 3 or 4 of Y$^{1A}$, Y$^{1B}$, Y$^{1C}$, and Y$^{1D}$ are NR$^{1AY}$, NR$^{1BY}$, NR$^{1CY}$, or NR$^{1DY}$, respectively or N; wherein 0 or 1 of Y$^{1A}$, Y$^{1B}$, Y$^{1C}$, and Y$^{1D}$ is O or S;

Y$^{1E}$ is N or C;

wherein 1, 2, 3, or 4 of Y$^{1A}$, Y$^{1B}$, Y$^{1C}$, Y$^{1D}$, and Y$^{1E}$, is NR$^{1AY}$, NR$^{1BY}$, NR$^{1CY}$, NR$^{1DY}$, N, O or S;

R$^{1AY}$, R$^{1BY}$, R$^{1CY}$, and R$^{1DY}$ are each independently selected from the group consisting of hydrogen; amino; hydroxy; cyano; halo; C$_1$-C$_6$alkyl; C$_2$-C$_6$alkenyl; C$_2$-C$_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -L$^1$-C(O)—OR$^{1'}$ or -L$^1$-S(O)$_2$R$^f$, wherein L$^1$ is a bond or alkylene, and R$^{1'}$ is hydrogen, C$_1$-C$_6$alkyl or hydroxyalkyl; -L$^2$-O—C(O)—R$^{2'}$, wherein L$^2$ is a bond or alkylene, and R$^{2'}$ is C$_1$-C$_6$alkyl or hydroxyalkyl; -L$^3$-C(O)—NR$^{3'}$R$^{4'}$, wherein L$^3$ is a bond or alkylene, and R$^{3'}$ and R$^{4'}$ are each independently selected from the group consisting of hydrogen, C$_1$-C$_6$alkyl, and hydroxyalkyl; and -L$^4$-NR$^{5'}$—C(O)—R$^{6'}$, wherein L$^4$ is a bond or alkylene, R$^{5'}$ is hydrogen or C$_1$-C$_6$alkyl, and R$^{6'}$ is C$_1$-C$_6$alkyl or hydroxyalkyl; sulfamoyl; N-(alkyl)sulfamoyl; N,N-(dialkyl)sulfamoyl; sulfonamide; alkylthio; and thioalkyl;

L$^A$ is a bond;

R$^1$ is selected from the group consisting of:

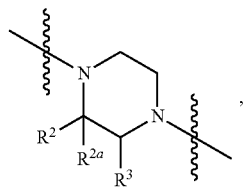
(ii-1)

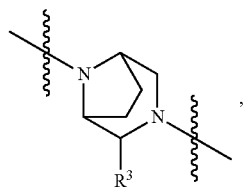
(ii-2)

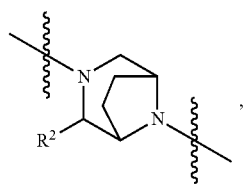
(ii-3)

-continued

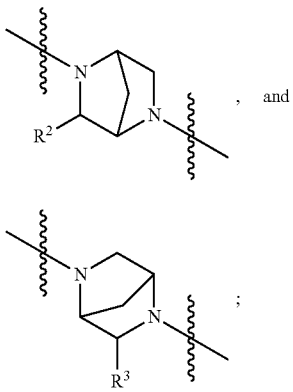

(ii-4)

, and (ii-5)

wherein $R^2$ and $R^3$ are each independently selected from the group consisting of hydrogen, $C_1$-$C_6$alkyl, $C_2$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$-alkyl-; wherein
  when both $R^2$ and $R^3$ are present, one or both of $R^2$ and $R^3$ are hydrogen;
  $G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-CO$_2$H, -$L^c$-CO$_2R^f$, -$L^c$-N($R^f$)C(O)N($R^f$)$_2$, -$L^c$-S—$R^f$, -$L^c$-S(O)$_2R^f$, -$L^c$-S(O)$R^f$, - $L^c$-SO$_2$N($R^e$)($R^f$), -$L^c$-N($R^e$)($R^f$), -$L^c$-N($R^f$)S(O)$_2R^f$, and -$L^c$-N($R^f$)C(O)O($R^f$);
  $L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;
  $R^e$, at each occurrence, is independently selected form the group consisting of hydrogen, $C_1$-$C_6$alkyl, $C_1$-$C_6$haloalkyl, and $C_3$-$C_8$cycloalkyl, wherein the $C_3$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;
  $R^f$, at each occurrence, is independently selected from the group consisting of hydrogen, $C_1$-$C_6$alkyl, and $C_1$-$C_6$haloalkyl;
$Ar^2$ is:

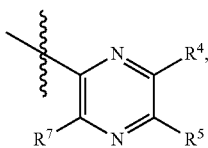

(iii-3)

wherein for (iii-3), $R^4$ and $R^5$, taken together with the atoms to which they are attached, form a fused phenyl substituted with 1, 2, or 3 $C_1$-$C_6$alkyl, halo, or halo$C_1$-$C_6$alkyl; and $R^7$ is hydrogen, $C_1$-$C_6$alkyl, or halo$C_1$-$C_6$alkyl.

12. The compound of claim 11, or a pharmaceutically acceptable salt thereof, wherein
  $R^{1A}$ is selected from the group consisting of hydrogen, $C_1$-$C_6$alkyl, halo, haloalkyl and haloalkoxy; and
  $R^{1A}$, $R^{1C}$, $R^{1D}$ and $R^{1E}$ are each independently selected from a group consisting of hydrogen, $C_1$-$C_6$alkyl, halo and haloalkyl.

13. A compound having formula (II), or a pharmaceutically acceptable salt thereof,

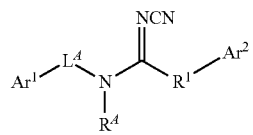

(II)

wherein:
  $Ar^1$ is phenyl or monocyclic heteroaryl having a structure corresponding to a formula selected from the group consisting of:

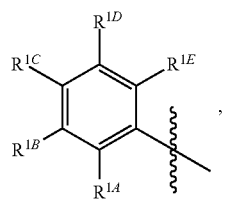

(i-1)

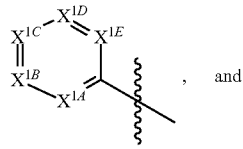

(i-2)

, and

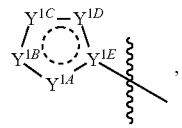

(i-3)

, wherein $R^{1A}$ is selected from the group consisting of hydrogen; amino; hydroxy; cyano; halo; C-$C_6$alkyl; $C_2$-$C_6$alkenyl; $C_2$-$C_6$alkynyl; $C_1$-$C_6$alkoxy; haloalkyl; haloalkoxy; oxoalkyl; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; and -$L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl)sulfamoyl; sulfonamide; alkylthio; and thioalkyl;
  $R^{1B}$, $R^{1C}$, $R^{1D}$ and $R^{1E}$ are each independently selected from the group consisting of hydrogen, cyano, halo, $C_1$-$C_6$alkyl, alkoxy, amino, alkylamino, dialkylamino, cycloalkyl, heterocyclyl, haloalkoxy, and haloalkyl;

$X^{1A}$ is $CR^{1AX}$ or N; $X^{1B}$ is $CR^{1BX}$ or N; $X^{1C}$ is $CR^{1CX}$ or N; $X^{1D}$ is $CR^{1DX}$ or N; and $X^{1E}$ is $CR^{1EX}$ or N; wherein 1, 2 or 3 of $X^{1A}$, $X^{1B}$, $X^{1C}$, $X^{1D}$ and $X^{1E}$ are N; wherein $R^{1AX}$ is selected from the group consisting of hydrogen; amino; hydroxy; cyano; halo; $C_1$-$C_6$alkyl; $C_2$-$C_6$alkenyl; $C_2$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; and -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$R^{1BX}$, $R^{1CX}$, $R^{1DX}$ and $R^{1EX}$ are each independently selected from the group consisting of hydrogen, cyano, halo, $C_1$-$C_6$alkyl, alkoxy: amino, alkylamino, dialkylamino, cycloalkyl, heterocyclyl, haloalkoxy, and haloalkyl;

$Y^{1A}$ is $CR^{1AY}$, $NR^{1AY}$, N, O or S; $Y^{1B}$ is $CR^{1BY}$, $NR^{1BY}$, N, O or S; $Y^{1C}$ is $CR^{1CY}$, $NR^{1CY}$, N, O or S; and $Y^{1D}$ is $CR^{1DY}$, $NR^{1DY}$, N, O or S; respectively, wherein 0, 1, 2, 3 or 4 of $Y^{1A}$, $Y^{1B}$, $Y^{1C}$, and $Y^{1D}$ are $NR^{1AY}$, $NR^{1BY}$, $NR^{1CY}$, or $NR^{1DY}$, respectively or N; wherein 0 or 1 of $Y^{1A}$, $Y^{1B}$, $Y^{1C}$ and $Y^{1D}$ is O or S;

$Y^{1E}$ is N or C;

wherein 1, 2, 3, or 4 of $Y^{1A}$, $Y^{1B}$, $Y^{1C}$, $Y^{1D}$, and $Y^{1E}$, is $NR^{1AY}$, $NR^{1BY}$, $NR^{1CY}$, $NR^{1DY}$, N, O or S;

$R^{1AY}$, $R^{1BY}$, $R^{1CY}$, and $R^{1DY}$ are each independently selected from the group consisting of hydrogen; amino; hydroxy; cyano; halo; $C_1$-$C_6$alkyl; $C_2$-$C_6$alkenyl; $C_2$-$C_6$alkynyl; haloalkyl; haloalkoxy; oxoalkyl; alkoxy; alkylamino; dialkylamino; alkoxyalkyl; aminoalkyl; N-alkylaminoalkyl; N,N-dialkylaminoalkyl; -$L^1$-C(O)—$OR^{1'}$ or -$L^1$-S(O)$_2R^{1'}$, wherein $L^1$ is a bond or alkylene, and $R^{1'}$ is hydrogen, $C_1$-$C_6$alkyl or hydroxyalkyl; -$L^2$-O—C(O)—$R^{2'}$, wherein $L^2$ is a bond or alkylene, and $R^{2'}$ is $C_1$-$C_6$alkyl or hydroxyalkyl; and -$L^3$-C(O)—$NR^{3'}R^{4'}$, wherein $L^3$ is a bond or alkylene, and $R^{3'}$ and $R^{4'}$ are each independently selected from the group consisting of hydrogen, $C_1$-$C_6$alkyl, and hydroxyalkyl; -$L^4$-$NR^{5'}$—C(O)—$R^{6'}$, wherein $L^4$ is a bond or alkylene, $R^{5'}$ is hydrogen or $C_1$-$C_6$alkyl, and $R^{6'}$ is $C_1$-$C_6$alkyl or hydroxyalkyl; sulfamoyl; N-(alkyl)sulfamoyl; N,N-(dialkyl)sulfamoyl; sulfonamide; alkylthio; and thioalkyl;

$L^A$ is a bond;

$R^A$ is $C_1$-$C_6$alkyl, hydroxy$C_1$-$C_6$alkyl or halo$C_1$-$C_6$alkyl;

$R^1$ is selected from the group consisting of:

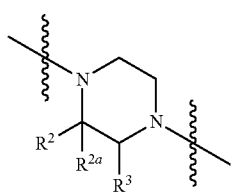

(ii-1)

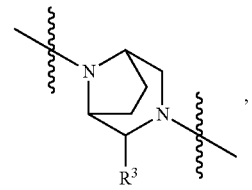

(ii-2)

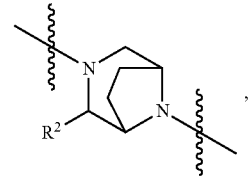

(ii-3)

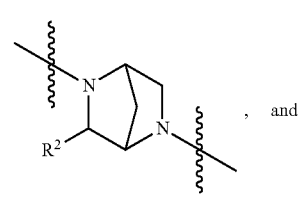

(ii-4)

, and

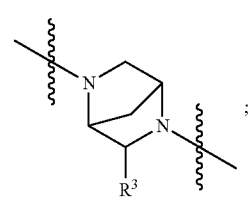

(ii-5)

;

wherein $R^2$ and $R^3$ are each independently selected from the group consisting of hydrogen, $C_1$-$C_6$alkyl, $C_2$-$C_6$alkenyl, haloalkyl, alkynyl, oxoalkyl, hydroxyalkyl, alkoxyalkyl, aminoalkyl, N-alkylaminoalkyl, N,N-dialkylaminoalkyl, thioalkyl, $G^1$, $G^2$, and $G^2$-alkyl-; wherein when both $R^2$ and $R^3$ are present, one or both of $R^2$ and $R^3$ are hydrogen;

$G^1$ is aryl or heteroaryl, and $G^2$ is $C_3$-$C_6$cycloalkyl, wherein the aryl, the heteroaryl and the $C_3$-$C_6$cycloalkyl are optionally substituted with 1, 2, 3, 4, or 5 substituents selected from the group consisting of halogen, $C_1$-$C_6$alkyl, $C_1$-$C_6$haloalkyl, —O—$R^f$, —CN, —N($R^f$)C(O)$R^f$, —CON($R^e$)($R^f$), —C(O)$R^f$, —OC(O)$R^f$, —CO$_2R^f$, —N($R^f$)C(O)N($R^f$)$_2$, —S—$R^f$, —S(O)$_2R^f$, —S(O)$R^f$, —SO$_2$N($R^e$)($R^f$), —N($R^e$)($R^f$), —N($R^f$)S(O)$_2R^f$, N($R^f$)C(O)O($R^f$), -$L^c$-O—$R^f$, -$L^c$-CN, -$L^c$-N($R^f$)C(O)$R^f$, -$L^c$-CON($R^e$)($R^f$), -$L^c$-C(O)$R^f$, -$L^c$-OC(O)$R^f$, -$L^c$-CO$_2$H, -$L^c$-CO$_2R^f$, -$L^c$-N($R^f$)C(O)N($R^f$)$_2$, -$L^c$-S—$R^f$, -$L^c$-S(O)$_2R^f$, -$L^c$-S(O)$R^f$, -$L^c$-SO$_2$N($R^e$)$R^f$), -$L^c$-N($R^e$)($R^f$), -$L^c$-N($R^f$)S(O)$_2R^f$, and -$L^c$-N($R^f$)C(O)O($R^f$);

$L^c$, at each occurrence, is independently $C_1$-$C_6$alkylene or $C_3$-$C_8$cycloalkyl, wherein $L^c$ at each occurrence, is optionally substituted with 1, 2, 3, or 4 halogen or 1 or 2 hydroxy;

$R^e$, at each occurrence, is independently selected form the group consisting of hydrogen, $C_1$-$C_6$alkyl, $C_1$-$C_6$haloalkyl, and $C_1$-$C_6$cycloalkyl, wherein the $C_1$-$C_8$cycloalkyl is optionally substituted with 1, 2, 3, or 4 substituents selected from the group consisting of halogen, oxo, $C_1$-$C_3$alkyl, and $C_1$-$C_3$haloalkyl;

$R^f$, at each occurrence, is independently selected from the group consisting of hydrogen, $C_1$-$C_6$alkyl, and $C_1$-$C_6$haloalkyl;

Ar² is selected from the group consisting of:

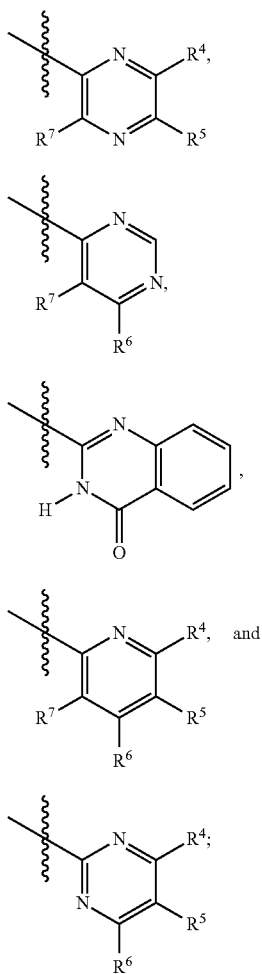

wherein for (iii-3), R⁴ and R⁵, taken together with the atoms to which they are attached, form a fused phenyl optionally substituted with 1, 2, or 3 C₁-C₆alkyl, halo, or haloC₁-C₆alkyl; and R⁷ is hydrogen, C₁-C₆alkyl, or haloC₁-C₆alkyl;
wherein for (iii-4), R⁶ and R⁷, taken together with the atoms to which they are attached, form a fused phenyl or pyrrolyl;
wherein for (iii-8), R⁴ and R⁵, taken together with the atoms to which they are attached, form a fused phenyl, pyridinyl, or pyrazinyl, each optionally substituted with 1, 2, or 3 C₁-C₆alkyl, halo, or haloC₁-C₆alkyl; and R⁶ and R⁷ are independently hydrogen, C₁-C₆alkyl, or haloC₁-C₆alkyl; and
wherein for (iii-9), R⁴ and R⁵ taken together with the atoms to which they are attached, form a fused phenyl, and R⁶ is hydrogen.

14. A compound or a pharmaceutically acceptable salt thereof, wherein the compound is selected from the group consisting of:
N'-cyano-4-(3-cyanopyrazin-2-yl)-2-isopropyl-N-(2-methylphenyl)piperazine-1-carboximidamide;
methyl 5-{4-[N-(2-chlorophenyl)-N'-cyanocarbamimidoyl]-3-isopropylpiperazin-1-yl}pyrazine-2-carboxylate;
N'-cyano-2-isopropyl-N-(2-methylphenyl)-4-(4-oxo-3,4-dihydroquinazolin-2-yl)piperazine-1-carboximidamide;
(2R)—N'-cyano-2-isopropyl-N-(2-methylphenyl)-4-(quinoxalin-2-yl)piperazine-1-carboximidamide;
(2S)—N'-cyano-2-isopropyl-N-(2-methylphenyl)-4-(quinoxalin-2-yl)piperazine-1-carboximidamide;
N-(1,3-benzodioxol-5-yl)-N'-cyano-2-isopropyl-4-(quinoxalin-2-yl)piperazine-1-carboximidamide;
N-(4-chlorophenyl)-N'-cyano-2-isopropyl-4-(quinoxalin-2-yl)piperazine-1-carboximidamide;
N'-cyano-2-isopropyl-N-(4-methylphenyl)-4-(quinoxalin-2-yl)piperazine-1-carboximidamide;
N'-cyano-N-(2,6-dimethylphenyl)-2-isopropyl-4-(quinoxalin-2-yl)piperazine-1-carboximidamide;
N'-cyano-2-isopropyl-N-(2-methoxyphenyl)-4-(quinoxalin-2-yl)piperazine-1-carboximidamide;
N-(2-chlorophenyl)-N'-cyano-2-isopropyl-4-(quinoxalin-2-yl)piperazine-1-carboximidamide;
N'-cyano-N-(3-fluorophenyl)-2-isopropyl-4-(quinoxalin-2-yl)piperazine-1-carboximidamide,
N'-cyano-N-(2-fluorophenyl)-2-isopropyl-4-(quinoxalin-2-yl)piperazine-1-carboximidamide;
N'-cyano-2-isopropyl-N-(3-methylphenyl)-4-(quinoxalin-2-yl)piperazine-1-carboximidamide;
N'-cyano-N-(4-fluorophenyl)-2-isopropyl-4-(quinoxalin-2-yl)piperazine-1-carboximidamide;
N'-cyano-2-isopropyl-4-(quinoxalin-2-yl)-N-[4-(trifluoromethyl)phenyl]piperazine-1-carboximidamide;
N'-cyano-2-isopropyl-4-(quinoxalin-2-yl)-N-[3-(trifluoromethyl)phenyl]piperazine-1-carboximidamide;
N'-cyano-2-isopropyl-N-(2-isopropylphenyl)-4-(quinoxalin-2-yl)piperazine-1-carboximidamide;
N'-cyano-2-isopropyl-4-(quinoxalin-2-yl)-N-[2-(trifluoromethoxy)phenyl]piperazine-1-carboximidamide;
N-(3-chlorophenyl)-N'-cyano-2-isopropyl-4-(quinoxalin-2-yl)piperazine-1-carboximidamide;
N'-cyano-N-(3-fluoro-2-methylphenyl)-2-isopropyl-4-(quinoxalin-2-yl)piperazine-1-carboximidamide;
N-(2-chloro-4-fluorophenyl)-N'-cyano-2-isopropyl-4-(quinoxalin-2-yl)piperazine-1-carboximidamide;
N'-cyano-N-(5-fluoro-2-methylphenyl)-2-isopropyl-4-(quinoxalin-2-yl)piperazine-1-carboximidamide;
N'-cyano-N-(4-fluoro-2-methylphenyl)-2-isopropyl-4-(quinoxalin-2-yl)piperazine-1-carboximidamide;
N'-cyano-N-(2-fluoro-6-methylphenyl)-2-isopropyl-4-(quinoxalin-2-yl)piperazine-1-carboximidamide;
N'-cyano-N-(4,5-difluoro-2-methylphenyl)-2-isopropyl-4-(quinoxalin-2-yl)piperazine-1-carboximidamide;
N'-cyano-2-isopropyl-N-(2-methylbenzyl)-4-(quinoxalin-2-yl)piperazine-1-carboximidamide;
N-(3-tert-butyl-1-methyl-1H-pyrazol-5-yl)-N'-cyano-2-isopropyl-4-(quinoxalin-2-yl)piperazine-1-carboximidamide;
N'-cyano-2-isobutyl-N-(2-methylphenyl)-4-(quinoxalin-2-yl)piperazine-1-carboximidamide;
N'-cyano-2-isobutyl-N-(3-methylphenyl)-4-(quinoxalin-2-yl)piperazine-1-carboximidamide;
N'-cyano-N-(2-fluorophenyl)-2-isobutyl-4-(quinoxalin-2-yl)piperazine-1-carboximidamide;
N'-cyano-N-(3-fluorophenyl)-2-isobutyl-4-(quinoxalin-2-yl)piperazine-1-carboximidamide;
N-(2-chlorophenyl)-N'-cyano-2-isobutyl-4-(quinoxalin-2-yl)piperazine-1-carboximidamide;
N'-cyano-2-methyl-N-(2-methylphenyl)-4-(quinoxalin-2-yl)piperazine-1-carboximidamide;

N'-cyano-N-(2-methylphenyl)-8-(quinoxalin-2-yl)-5,8-diazaspiro[3.5]nonane-5-carboximidamide;
N'-cyano-2-ethyl-N-(2-methylphenyl)-4-(quinoxalin-2-yl)piperazine-1-carboximidamide;
N'-cyano-N-(2-methylphenyl)-7-(quinoxalin-2-yl)-4,7-diazaspiro[2.5]octane-4-carboximidamide;
2-tert-butyl-N'-cyano-N-(2-methylphenyl)-4-(quinoxalin-2-yl)piperazine-1-carboximidamide;
2-sec-butyl-N'-cyano-N-(2-methylphenyl)-4-(quinoxalin-2-yl)piperazine-1-carboximidamide;
N'-cyano-2-cyclohexyl-N-(2-methylphenyl)-4-(quinoxalin-2-yl)piperazine-1-carboximidamide,
N'-cyano-2-(cyclohexylmethyl)-N-(2-methylphenyl)-4-(quinoxalin-2-yl)piperazine-1-carboximidamide;
N'-cyano-4-(6,7-dimethylquinoxalin-2-yl)-2-isopropyl-NV-(2-methylphenyl)piperazine-1-carboximidamide;
N'-cyano-4-(6,7-difluoroquinoxalin-2-yl)-2-isopropyl-N-(2-methylphenyl)piperazine-1-carboximidamide;
N'-cyano-2-isopropyl-N-(2-methylphenyl)-4-(3-methylquinoxalin-2-yl)piperazine-1-carboximidamide;
N'-cyano-2-isopropyl-N-(2-methylphenyl)-4-[3-(trifluoromethyl)quinoxalin-2-yl]piperazine-1-carboximidamide;
N'-cyano-4-(6-fluoroquinoxalin-2-yl)-2-isopropyl-N-(2-methylphenyl)piperazine-1-carboximidamide;
4-(7-chloroquinoxalin-2-yl)-N'-cyano-2-isopropyl-N-(2-methylphenyl)piperazine-1-carboximidamide;
N'-cyano-2-isopropyl-N-(2-methylphenyl)-4-(7-methylquinoxalin-2-yl)piperazine-1-carboximidamide;
N'-cyano-2-isopropyl-N-(2-methylphenyl)-4-[6-(trifluoromethyl)quinoxalin-2-yl]piperazine-1-carboximidamide;
N'-cyano-4-(6,7-dichloroquinoxalin-2-yl)-2-isopropyl-N-(2-methylphenyl)piperazine-1-carboximidamide;
N'-cyano-2-isopropyl-N-(2-methylphenyl)-4-[8-(trifluoromethyl)quinoxalin-2-yl]piperazine-1-carboximidamide;
N'-cyano-4-(7-fluoroquinoxalin-2-yl)-2-isopropyl-N-(2-methylphenyl)piperazine-1-carboximidamide;
N'-cyano-2-isopropyl-N-(2-methylphenyl)-4-(quinolin-2-yl)piperazine-1-carboximidamide;
N'-cyano-2-isopropyl-N-(2-methylphenyl)-4-[6-(morpholin-4-yl)pyrazin-2-yl]piperazine-1-carboximidamide;
N'-cyano-4-[4-(cyclohexylamino)-5,6-dimethylpyrimidin-2-yl]-2-isopropyl-N-(2-methylphenyl)piperazine-1-carboximidamide;
N'-cyano-2-isopropyl-N-(2-methylphenyl)-4-(pyrido[2,3-b]pyrazin-6-yl)piperazine-1-carboximidamide;
N'-cyano-2-isopropyl-N-(2-methylphenyl)-4-(1,8-naphthyridin-2-yl)piperazine-1-carboximidamide;
(2S)—N'-cyano-4-(6-fluoroquinoxalin-2-yl)-2-isopropyl-N-(2-methylphenyl)piperazine-1-carboximidamide;
N'-cyano-2-isopropyl-4-(7-methyl-1,8-naphthyridin-2-yl)-NV-(2-methylphenyl)piperazine-1-carboximidamide;
N'-cyano-2-isopropyl-4-(1-methyl-1H-benzimidazol-2-yl)-N-(2-methylphenyl)piperazine-1-carboximidamide;
N'-cyano-3-isopropyl-N-(2-methylphenyl)-4-(quinoxalin-2-yl)piperazine-1-carboximidamide;
(2S)—N-(2-chlorophenyl)-N'-cyano-4-(6-fluoroquinoxalin-2-yl)-2-isopropylpiperazine-1-carboximidamide;
N'-cyano-2-isopropyl-N-(4-methylpyridin-3-yl)-4-(quinoxalin-2-yl)piperazine-1-carboximidamide;
N'-cyano-2-isopropyl-N-(2-methylpyridin-3-yl)-4-(quinoxalin-2-yl)piperazine-1-carboximidamide;
N'-cyano-N-(2-methylphenyl)-4-(quinoxalin-2-yl)piperazine-1-carboximidamide; and
N'-cyano-2-isopropyl-N-methyl-N-(2-methylphenyl)-4-(quinoxalin-2-yl)piperazine-1-carboximidamide.

15. A method for treating respiratory syncytlal virus infection in a subject, comprising administering to a subject in need thereof a therapeutically effective amount of one or more compounds of any one of claims 1, 14 or 11, or pharmaceutically acceptable salts thereof, optionally in combination with one or more additional therapeutic agents.

16. The method of claim 15, wherein the respiratory syncytlal virus infection is from a respiratory syncytial virus of group A or a respiratory syncytlal virus of group B.

17. The method of claim 15, wherein the respiratory syncytlal virus infection is from a mutant of a respiratory syncytlal virus virus.

18. A method for inhibiting replication of a ribonucleic acid virus, comprising exposing the virus to a therapeutically effective amount of one or more compounds of any one of claims 1, 14 or 11, or pharmaceutically acceptable salts thereof, optionally in combination with one or more additional therapeutic agents.

* * * * *